(12) United States Patent
Bessire et al.

(10) Patent No.: US 12,065,434 B2
(45) Date of Patent: Aug. 20, 2024

(54) METABOLITES OF GLP1R AGONISTS

(71) Applicant: Pfizer Inc., New York, NY (US)

(72) Inventors: Andrew John Bessire, Niantic, CT (US); David James Edmonds, Riehen (CH); David Andrew Griffith, Sudbury, MA (US); Amit Sumant Kalgutkar, Waltham, MA (US); Timothy Frank Ryder, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 17/546,207

(22) Filed: Dec. 9, 2021

(65) Prior Publication Data

US 2022/0213072 A1  Jul. 7, 2022

Related U.S. Application Data

(60) Provisional application No. 63/125,615, filed on Dec. 15, 2020.

(51) Int. Cl.
| | | |
|---|---|---|
| *C07D 405/14* | (2006.01) | |
| *A61K 45/06* | (2006.01) | |
| *C07D 401/14* | (2006.01) | |

(52) U.S. Cl.
CPC ......... *C07D 405/14* (2013.01); *C07D 401/14* (2013.01); *A61K 45/06* (2013.01)

(58) Field of Classification Search
CPC ......... A61K 45/06; A61P 3/10; C07D 401/14; C07D 405/14
See application file for complete search history.

(56) References Cited

U.S. PATENT DOCUMENTS 10,208,019 B2 * 2/2019 Aspnes ................... A61P 15/10
10,676,465 B2    6/2020 Aspnes et al.

FOREIGN PATENT DOCUMENTS

WO    2021/116874    6/2021

OTHER PUBLICATIONS

Hampp et al., "Use of Antidiabetic Drugs in the U.S., 2003-2012", Diabetes Care, vol. 37, pp. 1367-1374 (2014).
Holst, "The Physiology of Glucagon-like Peptide 1", Physiol. Rev., vol. 87, pp. 1409-1439 (2007).
Meier et al., "Glucagon-Like Peptide 1 and Gastric Inhibitory Polypeptide. Potential Applications in Type 2 Diabetes Mellitus", Biodrugs, vol. 17(2), pp. 93-102 (2003).
Meier, "GLP-1 receptor agonists for individualized treatment of type 2 diabetes mellitus", Nat. Rev. Endocrinol., vol. 3, pp. 728-742 (2012).
Vilsboll et al., "Reduced Postprandial Concentrations of Intact Biologically Active Glucagon-Like Peptide 1 in Type 2 Diabetic Patients", Diabetes, vol. 50, pp. 609-613 (2001).

* cited by examiner

*Primary Examiner* — Pancham Bakshi
(74) *Attorney, Agent, or Firm* — Feng Shao

(57) ABSTRACT

The present invention provides compounds of Formula XA-1, XA-2, XA-3, XA-4, XA-5, or XA-6, or metabolites of Compound 1 or metabolites of a compound of Formula I, PA-I, or PA-III, including compositions and salts thereof, which are useful in the prevention and/or treatment of a disease or disorder such as T2DM, obesity, or NASH, as well as analytical methods related to the administration of Compound 1 or a compound of Formula I, PA-1, or PA-III.

21 Claims, 51 Drawing Sheets

\* Both singly- and doubly-charged ions for all metabolites observed in rat hepatocytes > trace level were extracted from the mass data to 10 ppm mass error: m/z 262.0778, 287.0989, 296.1042, 376.1228, 384.1209, 523.1478, 573.1899, 575.2056, 591.2005, 751.2377, 767.2326.

\* Both singly- and doubly-charged ions for all metabolites observed in rat hepatocytes > trace level were extracted from the mass data to 10 ppm mass error: m/z 262.0778, 287.0989, 296.1042, 376.1228, 384.1209, 523.1478, 573.1899, 575.2056, 591.2005, 751.2377, 767.2326.

FIG. 32
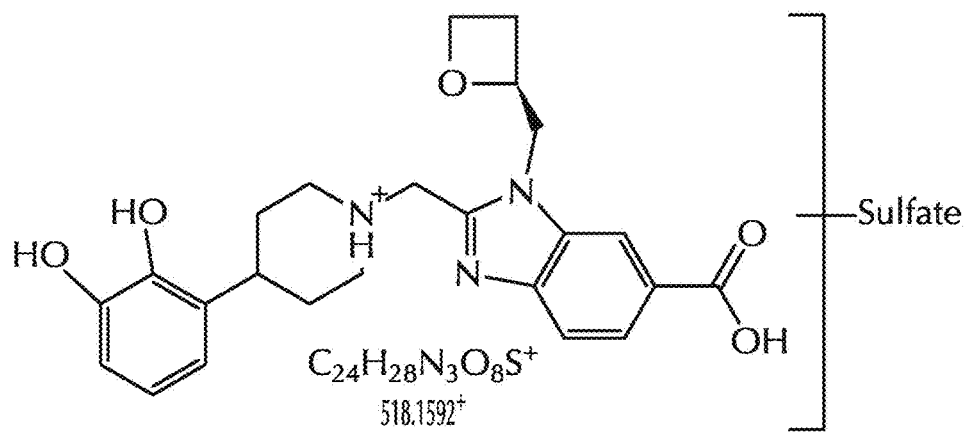
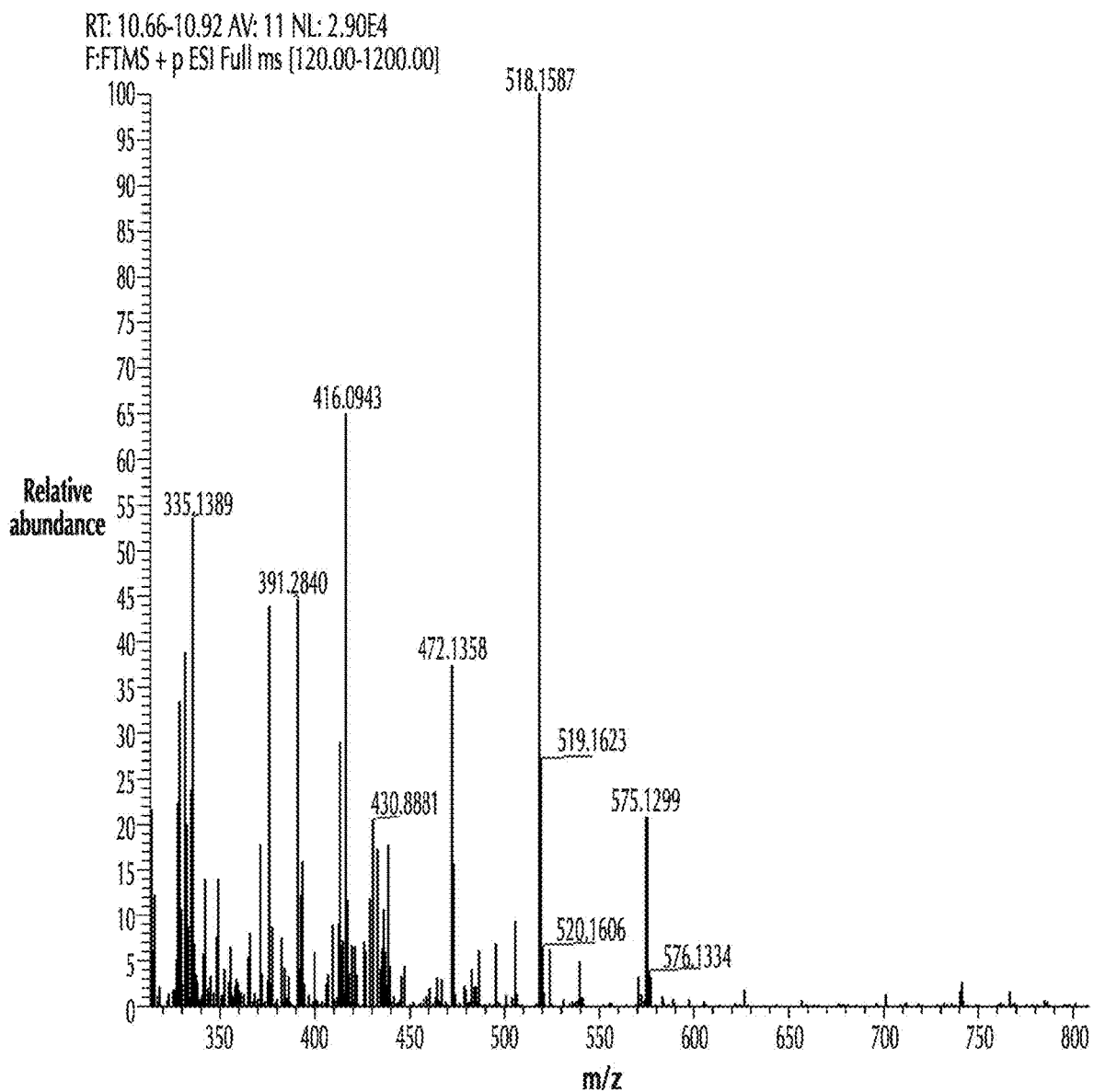

FIG. 41
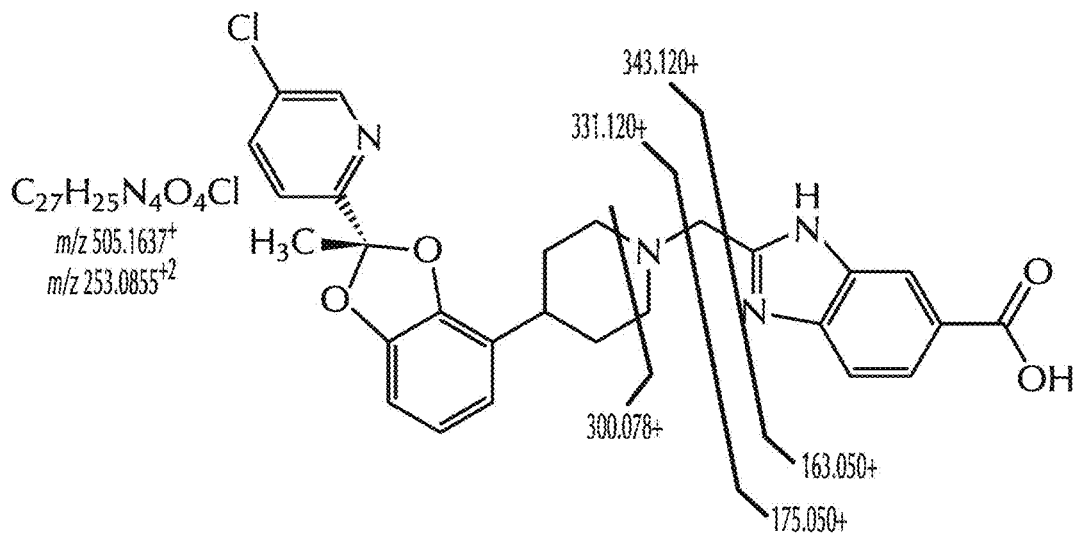
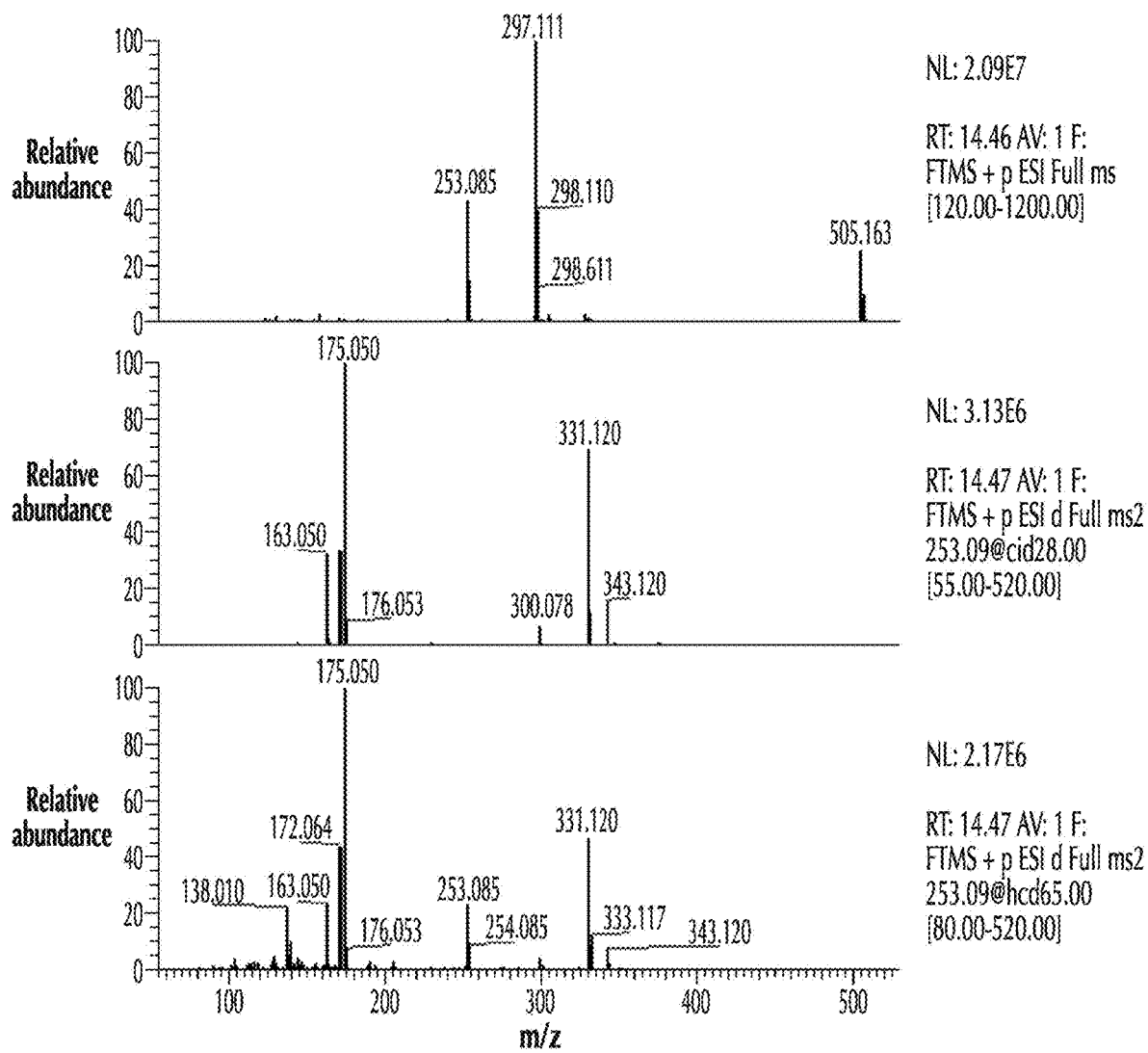

FIG. 44
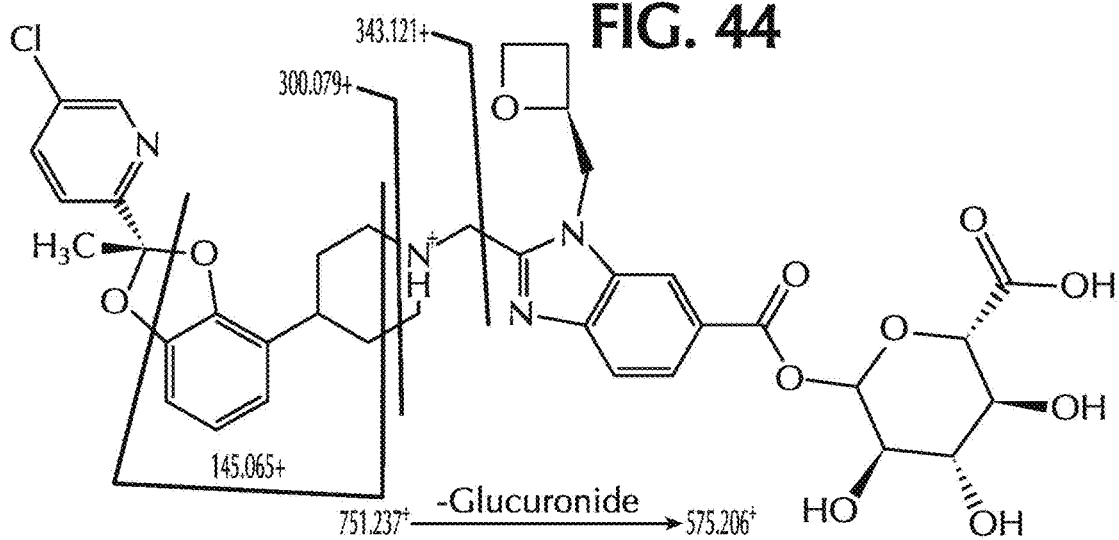
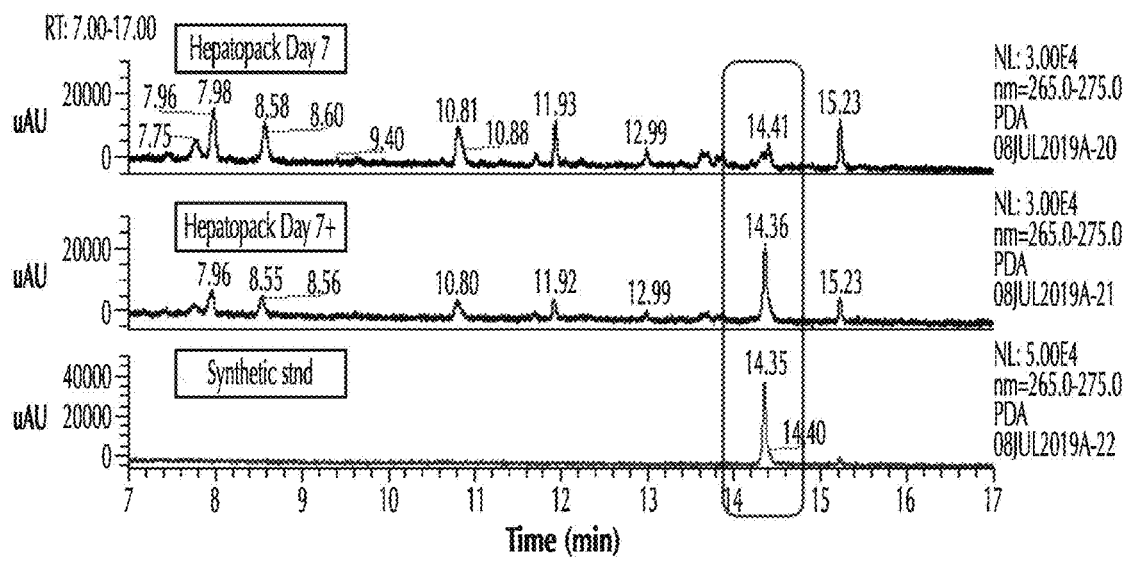
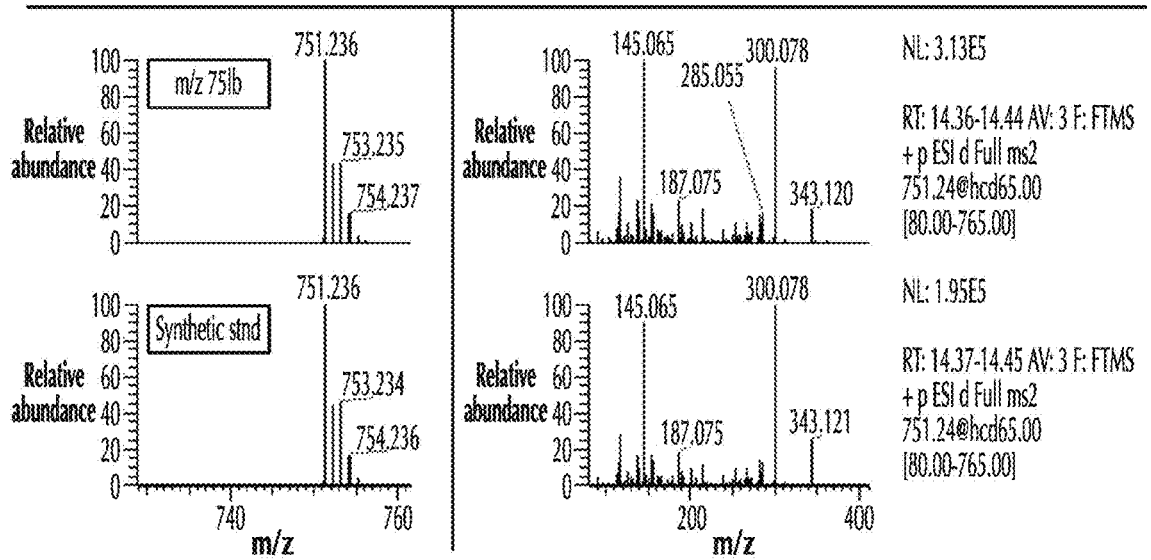

FIG. 45
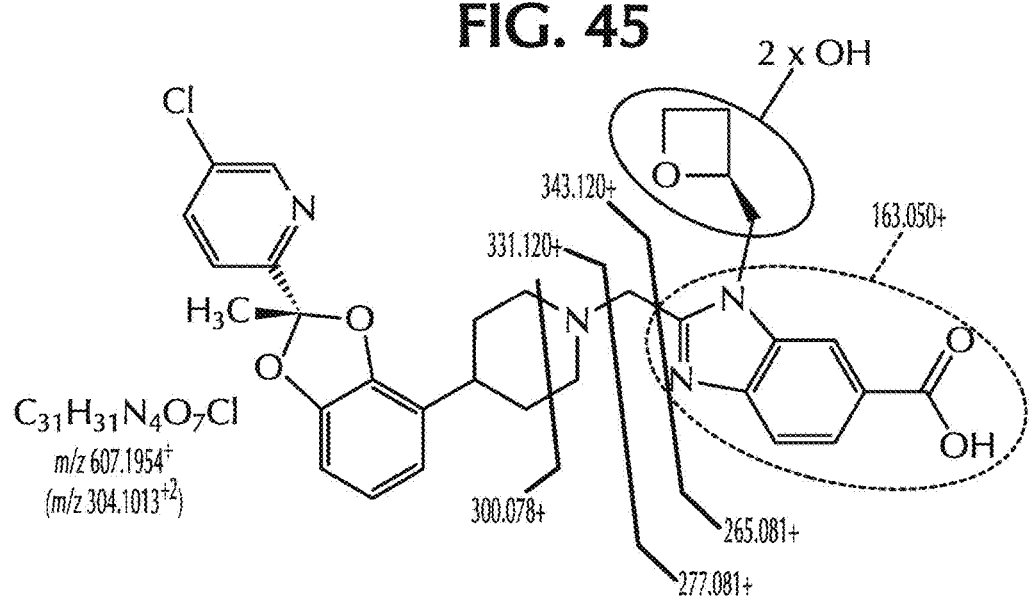
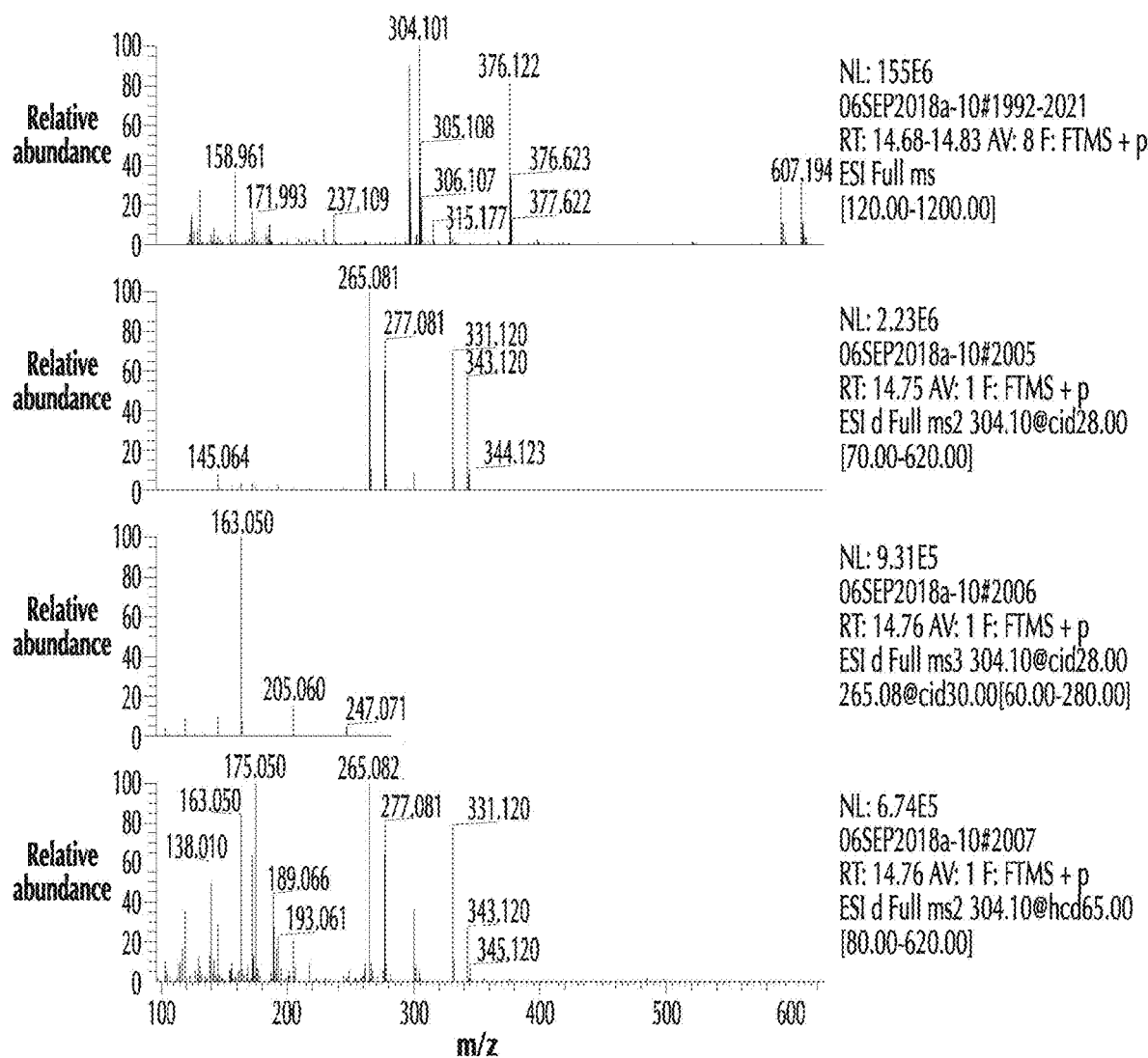

FIG. 47
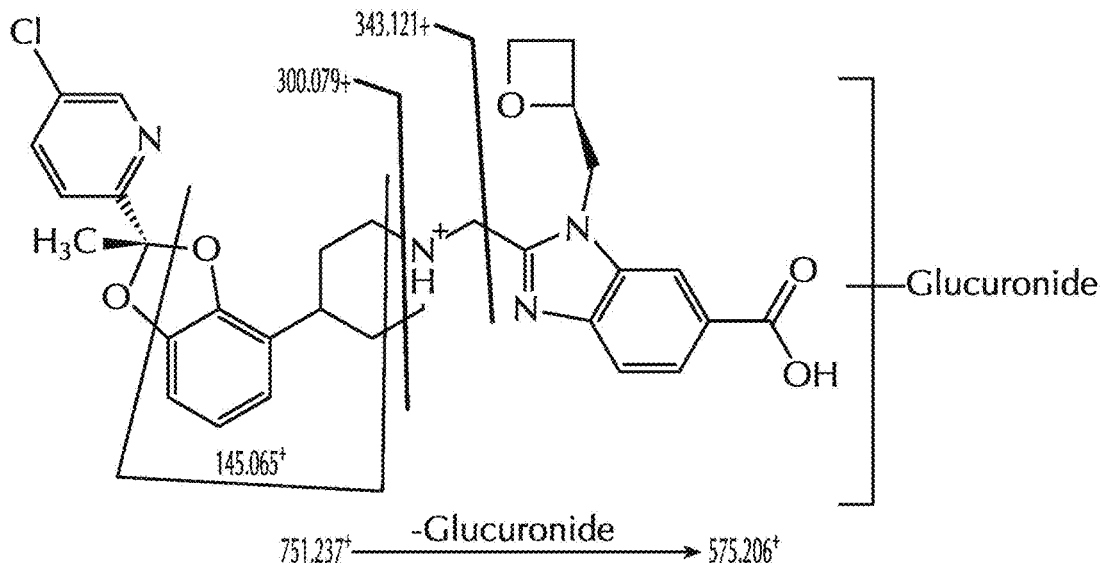
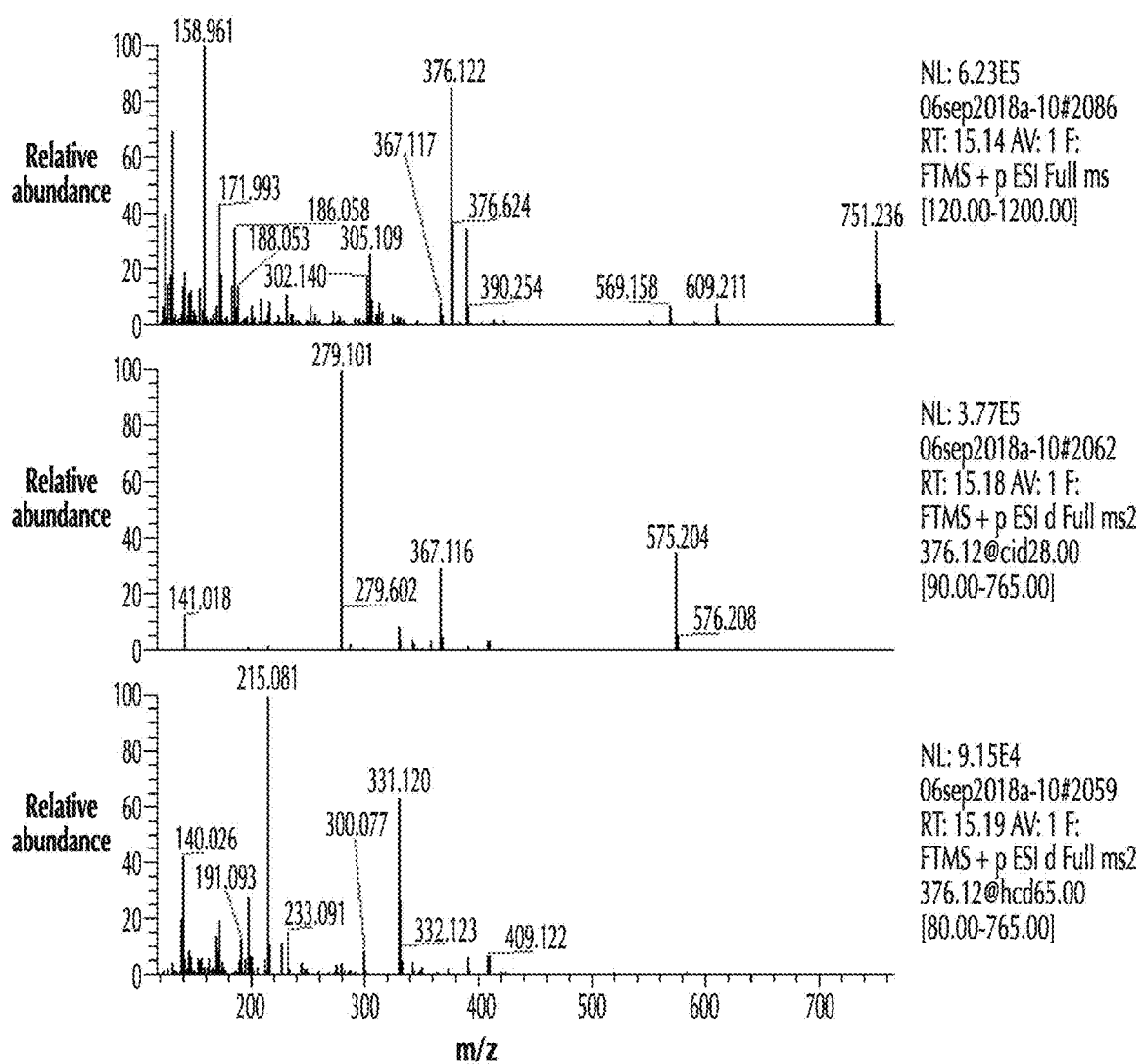

METABOLITES OF GLP1R AGONISTS

This application claims the benefit of priority to U.S. Provisional Patent Application Ser. No. 63/125,615 filed Dec. 15, 2020, the disclosure of which is hereby incorporated by reference in its entirety.

FIELD OF THE INVENTION

The present invention provides metabolites of certain GLP1R agonists, including salts and compositions thereof, which are useful in the prevention and/or treatment of diseases and disorders that are related to the GLP1 receptor as well as analytical methods related to the administration of these GLP1R agonists.

BACKGROUND OF THE INVENTION

Diabetes is a major public health concern because of its increasing prevalence and associated health risks. The disease is characterized by high levels of blood glucose resulting from defects in insulin production, insulin action, or both. Two major forms of diabetes are recognized, Type 1 and Type 2. Type 1 diabetes (T1 D) develops when the body's immune system destroys pancreatic beta cells, the only cells in the body that make the hormone insulin that regulates blood glucose. To survive, people with Type 1 diabetes must have insulin administered by injection or a pump. Type 2 diabetes mellitus (referred to generally as T2DM) usually begins with either insulin resistance or when there is insufficient production of insulin to maintain an acceptable glucose level.

Currently, various pharmacological approaches are available for treating hyperglycemia and subsequently, T2DM (Hampp, C. et al. *Use of Antidiabetic Drugs in the U.S., 2003-2012*, Diabetes Care 2014, 37, 1367-1374). These may be grouped into six major classes, each acting through a different primary mechanism: (A) Insulin secretogogues, including sulphonyl-ureas (e.g., glipizide, glimepiride, glyburide), meglitinides (e.g., nateglidine, repaglinide), dipeptidyl peptidase IV (DPP-IV) inhibitors (e.g., sitagliptin, vildagliptin, alogliptin, dutogliptin, linagliptin, saxogliptin), and glucagon-like peptide-1 receptor (GLP-1R) agonists (e.g., liraglutide, albiglutide, exenatide, lixisenatide, dulaglutide, semaglutide), which enhance secretion of insulin by acting on the pancreatic beta-cells. Sulphonyl-ureas and meglitinides have limited efficacy and tolerability, cause weight gain and often induce hypoglycemia. DPP-IV inhibitors have limited efficacy. Marketed GLP-1R agonists are peptides administered by subcutaneous injection. Liraglutide is additionally approved for the treatment of obesity. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents, and frequent use may also lead to weight gain and carries a risk of hypoglycemia. (F) sodium-glucose linked transporter cotransporter 2 (SGLT2) inhibitors (e.g., dapagliflozin, empagliflozin, canagliflozin, ertugliflozin) inhibit reabsorption of glucose in the kidneys and thereby lower glucose levels in the blood. This emerging class of drugs may be associated with ketoacidosis and urinary tract infections.

However, with the exception of GLP-1R agonists and SGLT2 inhibitors, the drugs have limited efficacy and do not address the most important problems, the declining β-cell function and the associated obesity.

Obesity is a chronic disease that is highly prevalent in modern society and is associated with numerous medical problems including hypertension, hypercholesterolemia, and coronary heart disease. It is further highly correlated with T2DM and insulin resistance, the latter of which is generally accompanied by hyperinsulinemia or hyperglycemia, or both. In addition, T2DM is associated with a two to fourfold increased risk of coronary artery disease. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Although T2DM is most commonly associated with hyperglycemia and insulin resistance, other diseases associated with T2DM include hepatic insulin resistance, impaired glucose tolerance, diabetic neuropathy, diabetic nephropathy, diabetic retinopathy, obesity, dyslipidemia, hypertension, hyperinsulinemia, and nonalcoholic fatty liver disease (NAFLD).

NAFLD is the hepatic manifestation of metabolic syndrome, and is a spectrum of hepatic conditions encompassing steatosis, non-alcoholic steatohepatitis (NASH), fibrosis, cirrhosis and ultimately hepatocellular carcinoma. NAFLD and NASH are considered the primary fatty liver diseases as they account for the greatest proportion of individuals with elevated hepatic lipids. The severity of NAFLD/NASH is based on the presence of lipid, inflammatory cell infiltrate, hepatocyte ballooning, and the degree of fibrosis. Although not all individuals with steatosis progress to NASH, a substantial portion does.

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier, et al. *Biodrugs.* 2003; 17 (2): 93-102).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll T, et al. *Diabetes.* 2001. 50; 609-613).

Holst (*Physiol. Rev.* 2007, 87, 1409) and Meier (*Nat. Rev. Endocrinol.* 2012, 8, 728) describe that GLP-1 receptor agonists, such as GLP-1, liraglutide and exendin-4, have 3 major pharmacological activities to improve glycemic control in patients with T2DM by reducing fasting and postprandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

U.S. Pat. No. 10,208,019 discloses certain GLP1R agonists. For example, 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically salt thereof [such as its 2-amino-2-(hydroxymethyl)propane-1,3-diol salt, also known as its tris salt or its tris(hydroxyethyl)methylamine salt] is a GLP-1R agonist described in U.S. Pat. No. 10,208,019 (see Example 4A-01 of the patent), the disclosure of which is hereby incorporated by reference herein in its entirety for all purposes.

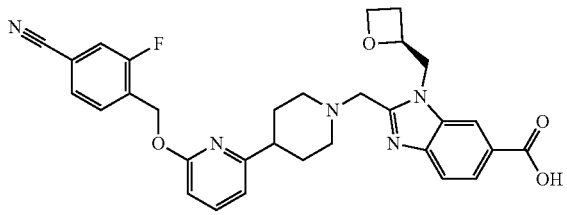 [SMILES: N#Cc1ccc(COc2cccc(C3CCN(Cc4nc5ccc(C(=O)O)cc5n4C[C@@H]4CCO4)CC3)n2)c(F)c1]

2-[(4-{6-[(4-Cyano-2-fluorobenzyl)oxy]pyridin-2-yl}piperidin-1-yl)methyl]-1-[(2S)-oxetan-2-ylmethyl]-1H-benzimidazole-6-carboxylic acid ("Compound 1")

U.S. Pat. No. 10,676,465 discloses certain GLP1R agonists. For example, 2-((4-((S)-2-(5-chloropyridin-2-yl)-2-methylbenzo[d][1,3]dioxol-4-yl)piperidin-1-yl)methyl)-1-(((S)-oxetan-2-yl)methyl)-1H-benzo[d]imidazole-6-carboxylic acid (referred to herein as "Compound 2") is a GLP1R agonist.

Compound 2

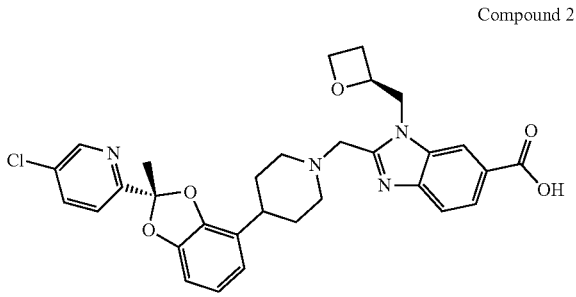 [SMILES: C[C@]1(c2ccc(Cl)cn2)Oc2cccc(C3CCN(Cc4nc5ccc(C(=O)O)cc5n4C[C@@H]4CCO4)CC3)c2O1]

Compound 2 or a pharmaceutically acceptable salt thereof (e.g., in the forms the free acid and as its tris salt) was prepared in Example 10 of U.S. Pat. No. 10,676,465, which is hereby incorporated herein by reference in its entirety. There, Compound 2 was designated as 2-({4-[2-(5-chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2:

DIAST-X2

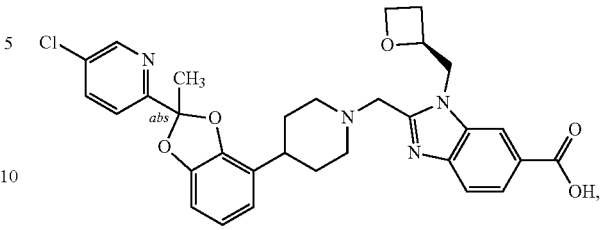

wherein the chiral center on the left part of the compound structure is marked as "abs" to indicate that chiral center has only one stereo-configuration (i.e., not a racemate with respect to that chiral center). In addition, U.S. Pat. No. 10,676,465 discloses an anhydrous crystalline form (designated as Form A) of the tris salt of Compound 2.

There is a continuing need for new and improved GLP1R agonists and for analytical methods related to the administration of GLP1R agonists. The metabolites of Compound 1 (including the salts thereof), as well as their compositions and methods of use described herein, are directed toward fulfilling this need.

SUMMARY OF THE INVENTION

In one embodiment, the present invention provides a compound of Formula XA-1, XA-2, XA-3, XA-4, XA-5, or XA-6:

XA-1

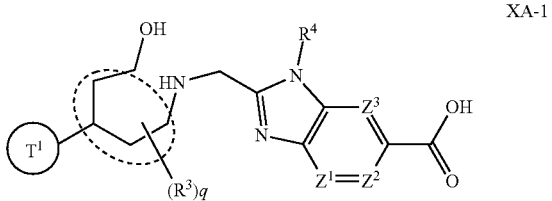

XA-2

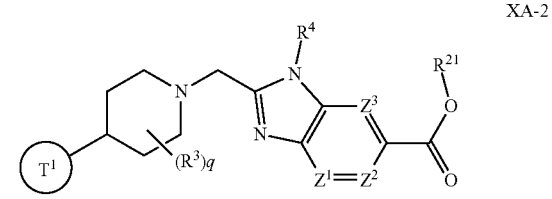

XA-3

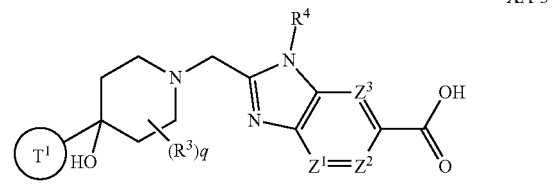

XA-4

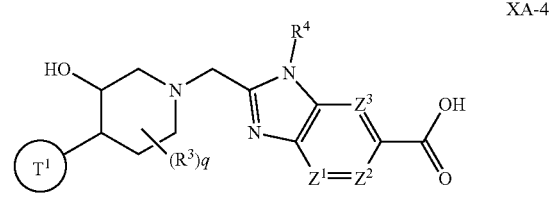

-continued

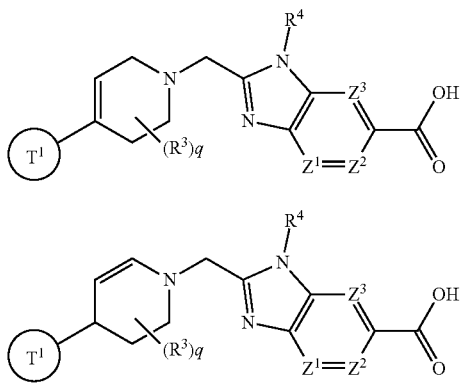

XA-5

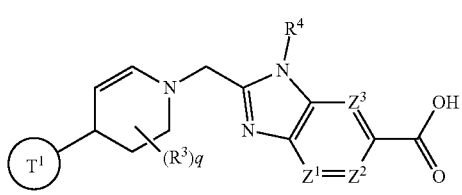

XA-6 or a pharmaceutically acceptable salt thereof, wherein:

Ring $T^1$ is phenyl or pyridinyl, wherein each of the phenyl or pyridinyl is substituted with 1, 2, 3, or 4 independently selected $R^{550}$, wherein each $R^{500}$ is independently F, Cl, —CN, or —OR$^{501}$, or two adjacent $R^{500}$ together form a moiety of —O—CR$^{502}$R$^{503}$—O— that is fused to the phenyl or pyridinyl of Ring $T^1$, and wherein when the phenyl or pyridinyl of ring $T^1$ is not substituted with a moiety of —O—CR$^{502}$R$^{503}$—O—, then it is at least substituted with one —OR$^{501}$;

each $R^{501}$ is independently —C(R$^{504}$R$^{505}$)R$^{506}$;

$R^{502}$ is H or —C$_{1-3}$alkyl, wherein the —C$_{1-3}$alkyl is substituted with 0 to 1 OH;

$R^{503}$ is independently phenyl or a 6-membered heteroaryl, wherein each of the phenyl or pyridinyl is substituted with 0, 1, 2, or 3 independently selected $R^{507}$;

each of $R^{504}$ and $R^{505}$ is H or —C$_{1-3}$alkyl, wherein the —C$_{1-3}$alkyl is substituted with 0 to 1 OH;

each $R^{506}$ is independently phenyl or a 6-membered heteroaryl, wherein each of the phenyl or pyridinyl is substituted with 0, 1, 2, or 3 independently selected $R^{508}$;

each $R^{507}$ is independently halogen, —CN, —C$_{1-3}$alkyl, or —OC$_{1-3}$alkyl, wherein each of the C$_{1-3}$alkyl and OC$_{1-3}$alkyl is substituted with 0 to 3 F atoms;

each $R^{508}$ is independently halogen, —CN, —C$_{1-3}$alkyl, or —OC$_{1-3}$alkyl, wherein each of the C$_{1-3}$alkyl and OC$_{1-3}$alkyl is substituted with 0 to 3 F atoms;

each $R^3$ is independently F, —OH, —CN, —C$_{1-3}$alkyl, —OC$_{1-3}$alkyl, or —C$_{3-4}$cycloalkyl, or 2 $R^3$s may together cyclize to form —C$_{3-4}$spirocycloalkyl, wherein the alkyl of C$_{1-3}$alkyl and OC$_{1-3}$ alkyl, cycloalkyl, or spirocycloalkyl may be substituted as valency allows with 0 to 3 F atoms and with 0 to 1 —OH;

q is 0, 1, or 2;

$R^4$ is —C$_{1-3}$alkyl, —C$_{0-3}$alkylene-C$_{3-6}$cycloalkyl, —C$_{0-3}$alkylene-R$^5$, or —C$_{1-3}$alkylene-R$^6$, wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$;

$R^5$ is a 4- to 6-membered heterocycloalkyl, wherein said heterocycloalkyl may be substituted with 0 to 2 substituents as valency allows independently selected from:

0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;

$R^6$ is a 5- to 6-membered heteroaryl, wherein said heteroaryl may be substituted with 0 to 2 substituents as valency allows independently selected from:

0 to 2 halogens,
0 to 1 substituent selected from —OR$^O$ and —N(R$^N$)$_2$, and
0 to 2 —C$_{1-3}$alkyl, wherein the alkyl may be substituted with 0 to 3 substituents as valency allows independently selected from:
0 to 3 F atoms, and
0 to 1 —OR$^O$;

each R$^O$ is independently H, or —C$_{1-3}$alkyl, wherein C$_{1-3}$alkyl may be substituted with 0 to 3 F atoms;

each R$^N$ is independently H, or —C$_{1-3}$alkyl;

$Z^1$ is CH or N;

$Z^2$ and $Z^3$ are each independently —CR$^Z$ or N, provided that when $Z^1$ or $Z^3$ is N, $Z^2$ is —CR$^Z$;

each R$^Z$ is independently H, F, Cl, or —CH$_3$; and $R^{21}$ is glucuronidation.

In another embodiment, the present invention provides a compound selected from Compounds M2, 574a, 574b, M1, a compound of Formula X, and Compound M4:

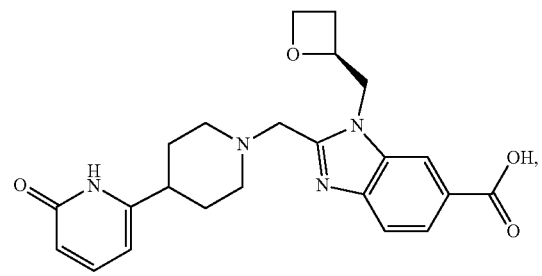

M2

574a

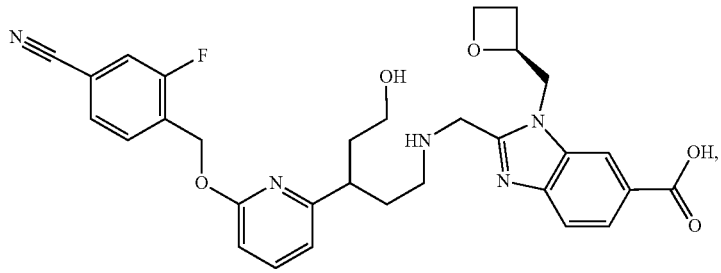

574b

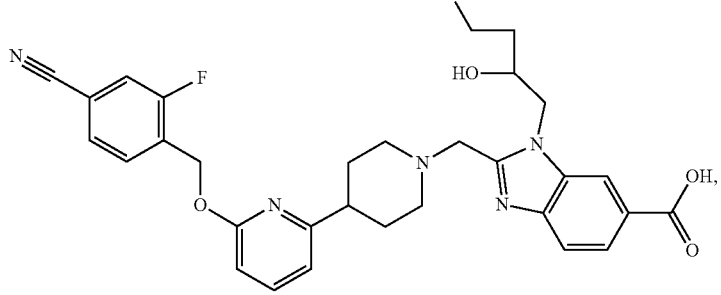

M1

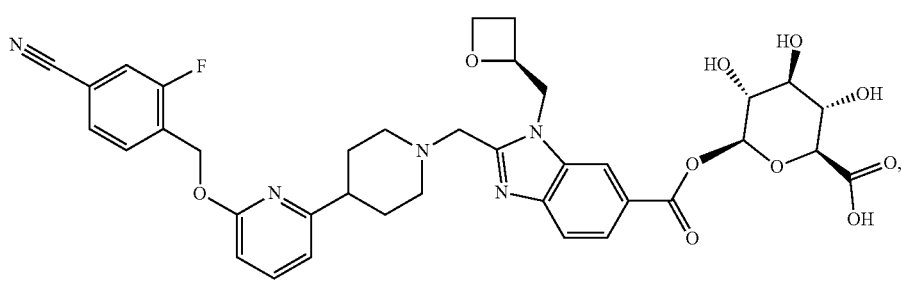

a compound of Formula X

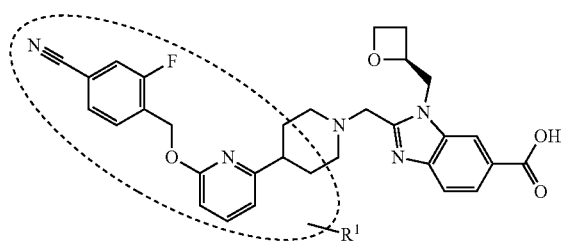

wherein $R^1$ is

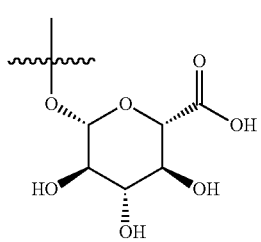 [SMILES: *O[C@@H]1O[C@H](C(=O)O)[C@@H](O)[C@H](O)[C@H]1O]

(i.e. the metabolite is the glucuronic acid conjugation of a hydroxylated Compound 1), and wherein $R^1$ is substituted at the phenyl ring, the pyridine ring, or the part of the piperidine ring within the dotted oval shape (i.e., one of the hydrogen atoms on the phenyl ring, the pyridine ring, or the part of the piperidine ring with the dotted oval shape is replaced by the —O-glucuronic acid conjugation as shown above); and

M4

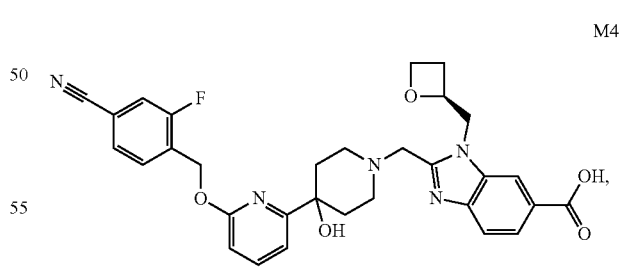

or a pharmaceutically acceptable salt thereof, which is substantially isolated.

The present invention further provides compositions comprising a compound of the invention, or pharmaceutically acceptable salt thereof, and at least one pharmaceutically acceptable carrier.

The present invention further provides preparations comprising a compound of the invention, or a pharmaceutically acceptable salt thereof.

The present invention further provides methods of preventing or treating a disease or disorder in a human by administering to the human a therapeutically effective amount of a compound of the invention, or a pharmaceutically acceptable salt thereof, wherein the disease or disorder is selected from the group consisting of diabetes (including e.g. T1D, T2DM, or pre-diabetes), idiopathic T1D (type 1b), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity, eating disorders, weight gain from use of other agents, excessive sugar craving, dyslipidemia, hyperinsulinemia, NAFLD, NASH, fibrosis, NASH with fibrosis, cirrhosis, hepatocellular carcinoma, cardiovascular disease, atherosclerosis, coronary artery disease, peripheral vascular disease, hypertension, endothelial dysfunction, impaired vascular compliance, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome, and addiction.

The present invention further provides methods of detecting or confirming the administration of Compound 1 to a human, comprising identifying a metabolite of Compound 1 (e.g. a compound of the invention or Compound M3), or a salt thereof, in a biological sample obtained from the human.

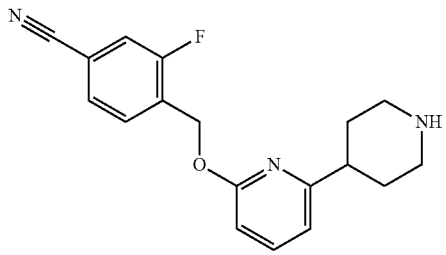 [SMILES: N#Cc1ccc(COc2cccc(C3CCNCC3)n2)c(F)c1]

Structure of Compound M3

The present invention further provides methods of measuring the rate of metabolism of Compound 1 in a patient comprising measuring the amount of a metabolite of Compound 1 (e.g. a compound of the invention or Compound M3), or a salt thereof, in the patient at one or more time points after administration of Compound 1.

The present invention further provides methods of determining the prophylactic or therapeutic response of a patient to Compound 1 in the treatment of a disease or disorder, comprising measuring the amount of a metabolite of Compound 1 (e.g. a compound of the invention or Compound M3), or a salt thereof, in the patient at one or more time points after administration of Compound 1.

The present invention further provides methods of optimizing the dose of Compound 1 for a patient in need of treatment with Compound 1, comprising measuring the amount of a metabolite of Compound 1 (e.g. a compound of the invention or Compound M3), or a salt thereof, in the patient at one or more time points after administration of Compound 1.

BRIEF DESCRIPTION OF THE DRAWINGS

FIG. 32 shows mass spectra and proposed structure of Metabolite m/z 518 (of Compound 2).

FIG. 41 shows mass spectra and proposed structure of Metabolite m/z 505 (of Compound 2).

FIG. 44 shows mass spectra and proposed structure of Metabolite m/z 751b (of Compound 2).

FIG. 45 shows mass spectra and proposed structure of Metabolite m/z 607 (of Compound 2).

FIG. 47 shows mass spectra and proposed structure of Metabolite m/z 751c (of Compound 2).

DETAILED DESCRIPTION

Figure 1:
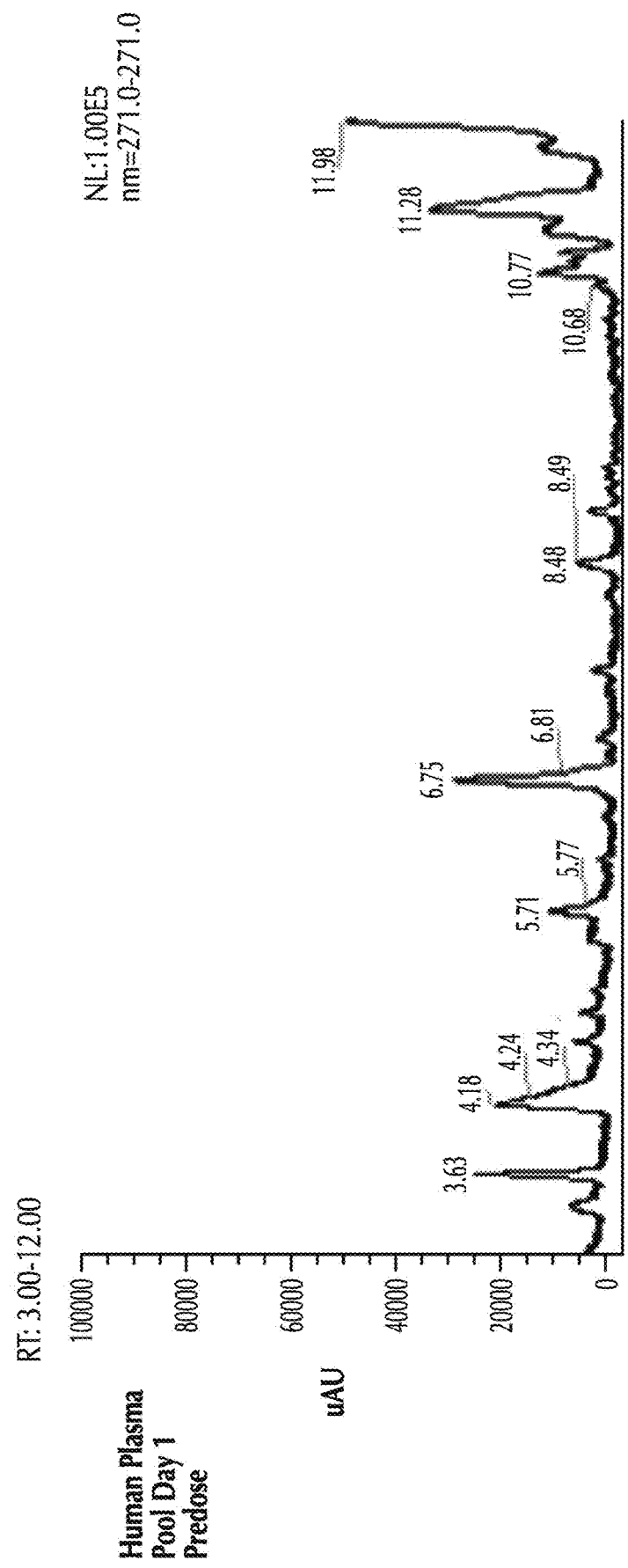
FIG. 1 shows an HPLC/UV chromatogram of pooled plasma extract from patients multiply dosed with Compound 1 (120 mg oral BID, Day 1, pre-dose).
Figure 2:
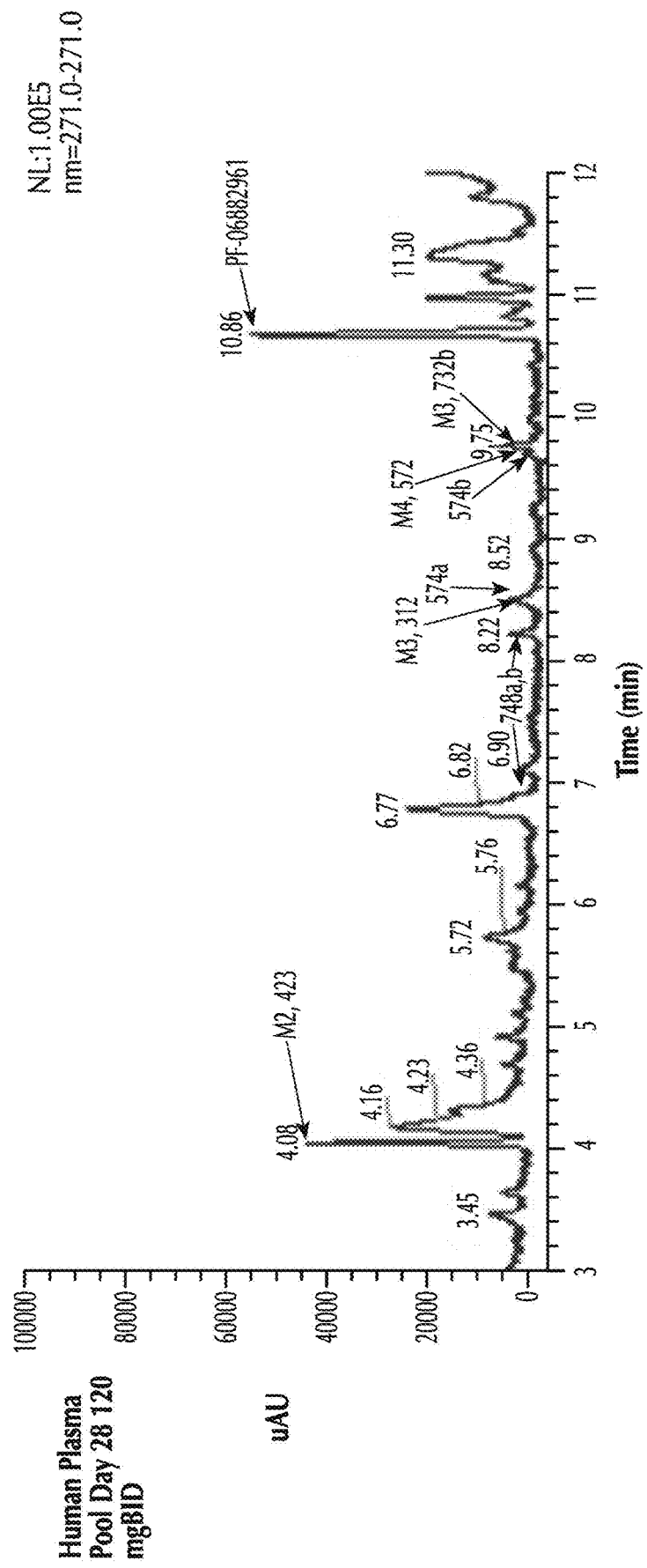
FIG. 2 shows an HPLC/UV chromatogram of pooled plasma extract from patients multiply dosed with Compound 1 (120 mg oral BID, Day 28).

In a first aspect, the present invention provides a compound of Formula XA-1, XA-2, XA-3, XA-4, XA-5, or XA-6:

XA-1

XA-2

XA-3

XA-4

XA-5

XA-6 or a pharmaceutically acceptable salt thereof, wherein:

Ring $T^1$ is phenyl or pyridinyl, wherein each of the phenyl or pyridinyl is substituted with 1, 2, 3, or 4 independently selected $R^{550}$, wherein each $R^{500}$ is independently F, Cl, —CN, or —OR$^{501}$, or two adjacent R$^{500}$ together form a moiety of —O—CR$^{502}$R$^{503}$—O— that is fused to the phenyl or pyridinyl of Ring T$^1$, and wherein when the phenyl or pyridinyl of ring T$^1$ is not substituted with a moiety of —O—CR$^{502}$R$^{503}$—O—, then it is at least substituted with one —OR$^{501}$;

each R$^{501}$ is independently —C(R$^{504}$R$^{505}$)R$^{506}$;

R$^{502}$ is H or —C$_{1-3}$alkyl, wherein the —C$_{1-3}$alkyl is substituted with 0 to 1 OH;

R$^{503}$ is independently phenyl or a 6-membered heteroaryl, wherein each of the phenyl or pyridinyl is substituted with 0, 1, 2, or 3 independently selected R$^{507}$; each of R$^{504}$ and R$^{505}$ is H or —C$_{1-3}$alkyl, wherein the —C$_{1-3}$alkyl is substituted with 0 to 1 OH;

each R$^{506}$ is independently phenyl or a 6-membered heteroaryl, wherein each of the phenyl or pyridinyl is substituted with 0, 1, 2, or 3 independently selected R$^{508}$;

each R$^{507}$ is independently halogen, —CN, —C$_{1-3}$alkyl, or —OC$_{1-3}$alkyl, wherein each of the C$_{1-3}$alkyl and OC$_{1-3}$alkyl is substituted with 0 to 3 F atoms;

each R$^{508}$ is independently halogen, —CN, —C$_{1-3}$alkyl, or —OC$_{1-3}$alkyl, wherein each of the C$_{1-3}$alkyl and OC$_{1-3}$alkyl is substituted with 0 to 3 F atoms;

each R$^3$ is independently F, —OH, —CN, —C$_{1-3}$alkyl, —OC$_{1-3}$alkyl, or —C$_{3-4}$cycloalkyl, or 2 R$^3$s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;

q is 0, 1, or 2;

R$^4$ is —C$_{1-3}$alkyl, —C$_{0-3}$alkylene-C$_{3-6}$cycloalkyl, —C$_{0-3}$alkylene-R$^5$, or —C$_{1-3}$alkylene-R$^6$, wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$;

R$^5$ is a 4- to 6-membered heterocycloalkyl, wherein said heterocycloalkyl may be substituted with 0 to 2 substituents as valency allows independently selected from:

0 to 1 oxo (=O), 0 to 1 —CN, 0 to 2 F atoms, and 0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:

0 to 3 F atoms, 0 to 1-CN, and 0 to 1 —OR$^O$;

R$^6$ is a 5- to 6-membered heteroaryl, wherein said heteroaryl may be substituted with 0 to 2 substituents as valency allows independently selected from:

0 to 2 halogens, 0 to 1 substituent selected from —OR$^O$ and —N(R$^N$)$_2$, and 0 to 2 —C$_{1-3}$alkyl, wherein the alkyl may be substituted with 0 to 3 substituents as valency allows independently selected from:

0 to 3 F atoms, and 0 to 1 —OR$^O$;

each R$^O$ is independently H, or —C$_{1-3}$alkyl, wherein C$_{1-3}$alkyl may be substituted with 0 to 3 F atoms;

each R$^N$ is independently H, or —C$_{1-3}$alkyl;

Z$^1$ is CH or N;

Z$^2$ and Z$^3$ are each independently —CR$^Z$ or N, provided that when Z$^1$ or Z$^3$ is N, Z$^2$ is —CR$^Z$;

each R$^Z$ is independently H, F, C$_1$, or —CH$_3$; and

R$^{21}$ is glucuronidation.

In some embodiments, the present invention provides a compound of Formula XA-1, or a pharmaceutically acceptable salt thereof. A substituent R$^3$, when present (i.e. q is 1 or 2), is substituted on the part of the structure of Formula XA-1 within the dotted oval shape.

In some embodiments, the present invention provides a compound of Formula XA-2, or a pharmaceutically acceptable salt thereof.

In some embodiments, the present invention provides a compound of Formula XA-3, or a pharmaceutically acceptable salt thereof.

In some embodiments, the present invention provides a compound of Formula XA-4, or a pharmaceutically acceptable salt thereof.

In some embodiments, the present invention provides a compound of Formula XA-5, or a pharmaceutically acceptable salt thereof.

In some embodiments, the present invention provides a compound of Formula XA-6, or a pharmaceutically acceptable salt thereof.

In a second aspect, the present invention is directed to metabolites of Compound 1 or a pharmaceutically acceptable salt thereof and uses thereof. In some embodiments, the metabolite results from Compound 1 (or a pharmaceutically acceptable salt thereof) which has undergone (1) glucuronidation (see e.g. Compound M1), (2) O-debenzylation (see e.g. Compound M2), (3) N-dealkylation (see e.g. Compound M3), (4) hydroxylation (see e.g. Compound M4), (5) glucuronic acid conjugation of the hydroxylated-Compound 1 (see e.g. a compound of Formula X—Compound 748a or 748b), (6) oxidation and ring opening of the piperidine ring (see e.g. Compound 574a), or (7) oxidation and ring opening of the oxetane ring (see e.g. Compound 574b), or a combination thereof. In some embodiments, the metabolite is selected from Compounds M1, M2, M3, M4, 574a, 574b, 748a, and 748b.

In some embodiments, the present invention provides Compound M1.

Compound M1

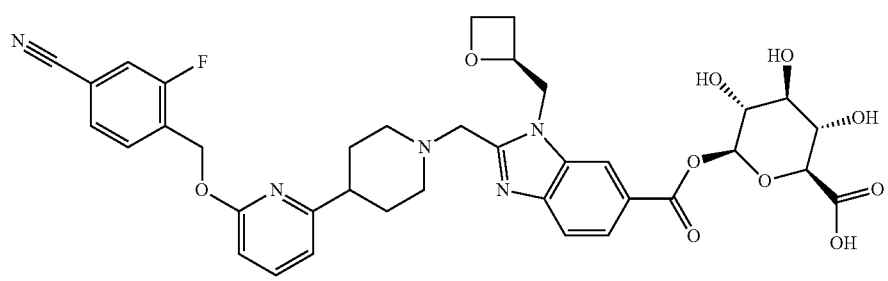

or a pharmaceutically acceptable salt thereof.

In some embodiments, the present invention provides Compound M2, or a pharmaceutically acceptable salt thereof.

Compound M2

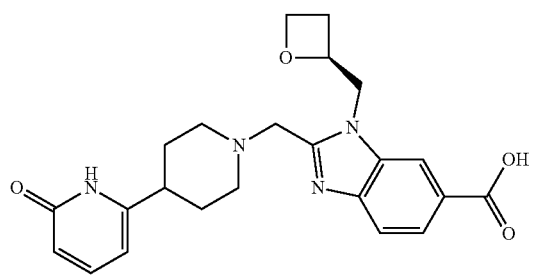

In some embodiments, the present invention provides Compound M3, or a pharmaceutically acceptable salt thereof.

In some embodiments, the present invention provides Compound M4, or a pharmaceutically acceptable salt thereof.

Compound M4

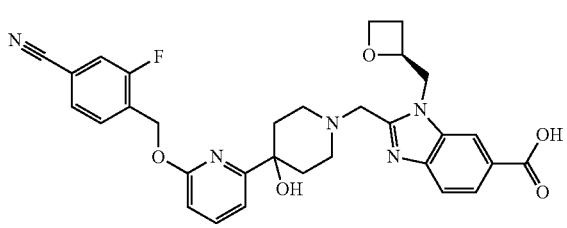

In some embodiments, the present invention provides Compound 574a, or a pharmaceutically acceptable salt thereof.

Compound 574a

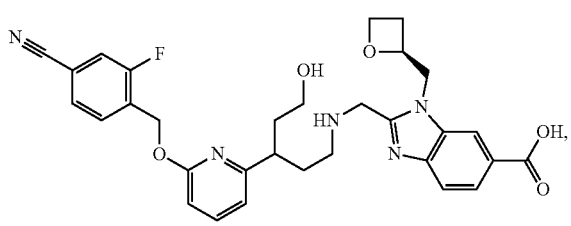

In some embodiments, the present invention provides Compound 574b, or a pharmaceutically acceptable salt thereof.

Compound 574b

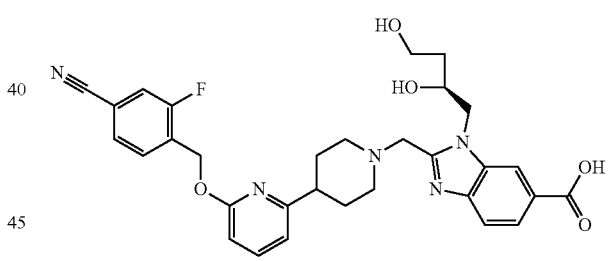

In some embodiments, Compound 574b, or a pharmaceutically acceptable salt thereof is

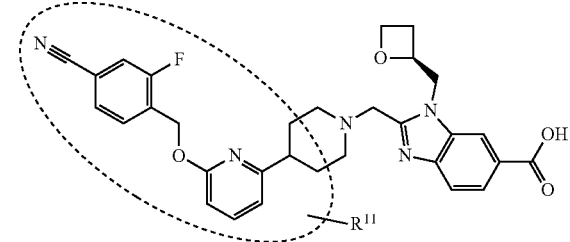

or a pharmaceutically acceptable salt thereof.

In some embodiments, the present invention provides a compound of Formula X

X or a pharmaceutically acceptable salt thereof, wherein R[11] is

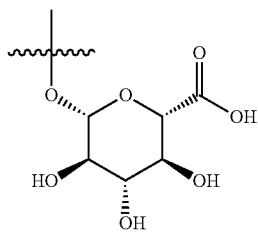 [SMILES: *O[C@@H]1O[C@H](C(=O)O)[C@@H](O)[C@H](O)[C@H]1O]

(i.e. the metabolite is the glucuronic acid conjugation of a hydroxylated Compound 1), and wherein wherein R[1] is substituted at the phenyl ring, the pyridine ring, or the part of the piperidine ring within the dotted oval shape (i.e., one of the hydrogen atoms on the phenyl ring, the pyridine ring, or the part of the piperidine ring with the dotted oval shape is replaced by the —O-glucuronic acid conjugation as shown above). In some further embodiments, the metabolite is Metabolite/Compound 748a, or a pharmaceutically acceptable salt thereof. In other some further embodiments, the metabolite is Metabolite/Compound 748b, or a pharmaceutically acceptable salt thereof. Compound 748a and Compound 748b can be substantially isolated as described herein.

The present invention further includes salts of the metabolites of the invention, such as pharmaceutically acceptable salts. A salt generally refers to a derivative of a disclosed compound wherein the parent compound is modified by converting an existing acid or base moiety to its salt form. A pharmaceutically acceptable salt is one that, within the scope of sound medical judgment, is suitable for use in contact with the tissues of human beings and animals without excessive toxicity, irritation, allergic response, or other problem or complication, commensurate with a reasonable benefit/risk ratio. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid. Lists of suitable salts are found in Remington's Pharmaceutical Sciences, 17 ed., Mack Publishing Company, Easton, Pa., 1985, p. 1418 and Journal of Pharmaceutical Science, 66, 2 (1977), each of which is incorporated herein by reference in its entirety. In one embodiment, the pharmaceutically acceptable salt is a sodium salt.

In some embodiments, the metabolite compounds, or salts thereof, are substantially isolated. By "substantially isolated" is meant that the metabolite compound, or salt thereof, is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the metabolite, or salt thereof. In some embodiments, each of Compounds M1, M2, M3, M4, 574a, and 574b and compounds of Formula X (including e.g. Compounds 748a and 748b) or their salts is substantially isolated. In some embodiments, each of Compounds M1, M2, M4, 574a, and 574b and compounds of Formula X (including e.g. Compounds 748a and 748b) or their salts is substantially isolated.

In some embodiments, one or more of the metabolite compounds, or salts thereof, are prepared by metabolism of Compound 1 or a pharmaceutically salt thereof (for example, in a mammal or a mammalian cell environment); and the metabolite compounds thus prepared are substantially isolated. In some other embodiments, one or more of the metabolite compounds, or salts thereof, are prepared by chemical synthesis other than metabolism of Compound 1 or a pharmaceutically salt thereof (for example, in a mammal or a mammalian cell environment) and the synthesized metabolite compounds are substantially isolated.

A metabolite of the invention, or its salt, can be present in a composition where the composition includes at least one compound other than the metabolite. In some embodiments, the composition includes more than one metabolite of the invention. In some embodiments, the composition comprises one or more metabolites of the invention, or salts thereof, and Compound 1, or a salt thereof. Compositions can be mixtures containing a metabolite of the invention, or salt thereof, and one or more solvents, substrates, carriers, etc. In some embodiments, the composition comprises a metabolite of the invention, or salt thereof, in an amount greater than about 25% by weight. In some embodiments, the composition comprises a metabolite of the invention, or salt thereof, in an amount greater than about 50% by weight. In some embodiments, the composition comprises a metabolite of the invention, or salt thereof, in an amount greater than about 75% by weight. In some embodiments, the composition comprises a metabolite of the invention, or salt thereof, in an amount greater than about 80% by weight. In some embodiments, the composition comprises a metabolite of the invention, or salt thereof, in an amount greater than about 85% by weight. In some embodiments, the composition comprises a metabolite of the invention, or salt thereof, in an amount greater than about 90% by weight. In some embodiments, the composition comprises a metabolite of the invention, or salt thereof, in an amount greater than about 95% by weight.

A preparation of a metabolite of the invention, or salt thereof, can be prepared by chemical synthesis or by isolation of the metabolite from a biological sample. Preparations can have a purity of greater than about 50%, greater than about 60%, greater than about 70%, greater than about 80%, greater than about 90%, or greater than about 95% purity. Purity can be measured by any of conventional means, such as by chromatographic methods or spectroscopic methods like NMR, MS, LC-MS, etc.

The metabolites of the invention are asymmetric (e.g., having one or more stereocenters). All stereoisomers, such as enantiomers and diastereomers, are intended unless otherwise indicated. Methods on how to prepare optically active forms from optically active starting materials are known in the art, such as by resolution of racemic mixtures or by stereoselective synthesis.

Metabolites of the invention also include all isotopes of atoms occurring in the metabolites. Isotopes include those atoms having the same atomic number but different mass numbers. For example, isotopes of hydrogen include tritium and deuterium. In some embodiments, the metabolite includes at least one deuterium.

The term, "compound" or "metabolite," as used herein is meant to include all stereoisomers, geometric isomers, tautomers, and isotopes of the structures depicted.

For example, a compound having the structure of

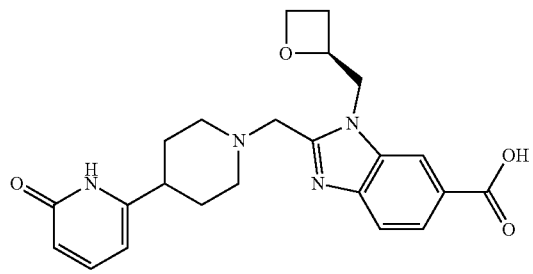 [SMILES: O=C(O)c1ccc2nc(CN3CCC(c4cccc(=O)[nH]4)CC3)n(C[C@@H]3CCO3)c2c1]

also includes its tautomer having the structure of

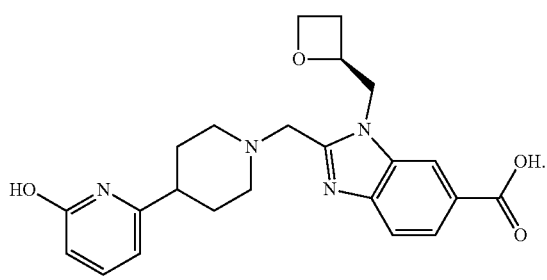 [SMILES: O=C(O)c1ccc2nc(CN3CCC(c4cccc(O)n4)CC3)n(C[C@@H]3CCO3)c2c1]

The term, "metabolite" as used herein is meant to include any and all metabolic derivatives of a parent drug molecule (e.g. Compound 1 or a pharmaceutically acceptable salt thereof), including derivatives that have undergone one or more transformative processes selected from (1) glucuronidation, (2) O-debenzylation, (3) N-dealkylation, (4) hydroxylation, (5) hydroxylation followed by glucuronic acid (or glucuronide) conjugation, (6) oxidation and ring opening of the piperidine ring, (7) oxidation and ring opening of the oxetane ring, (8) dehydrogenation, (9) hydroxylation followed by sulfation or cysteine conjugation, (10) glutathione conjugation, (11) ring opening of the oxetane ring and glutathione conjugation, and (12) cysteine conjugation, or a combination thereof (including a pharmaceutically acceptable salt thereof). In some embodiments, the present invention provides a metabolite of Compound 1 or a pharmaceutically acceptable salt thereof.

As used herein, a cysteine conjugation (or a cysteine adduct) refers to replacing a hydrogen atom of a parent compound with a moiety of

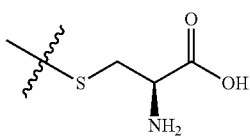 [SMILES: *SC[C@H](N)C(=O)O]

(wherein ⌇ indicates the point of contact of the moiety to the parent compound).

As used herein, a glucuronide conjugation (or a glucuronide adduct, or glucuronidation) of a parent compound refers to replacing a hydrogen atom of the parent compound with a chemical moiety that is glucuronic acid without one of its four alcohol hydroxyl groups, i.e., a moiety having the structure of:

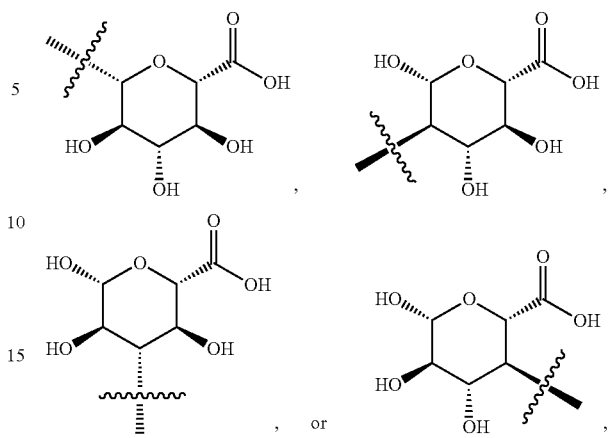

wherein ⌇ indicates the point of contact of the moiety to the parent compound.

As used herein, —O-glucuronidation or —O-glucuronide refers to a moiety of the structure of

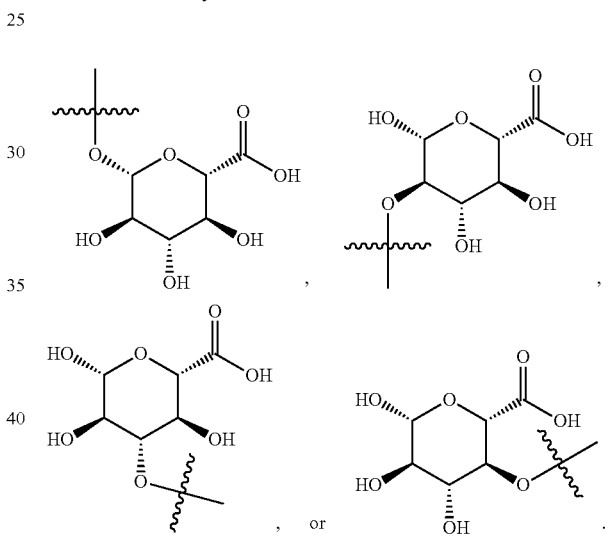

As used herein, a glutathione conjugation (or a glutathione adduct) refers to replacing a hydrogen atom of a parent compound with a moiety of

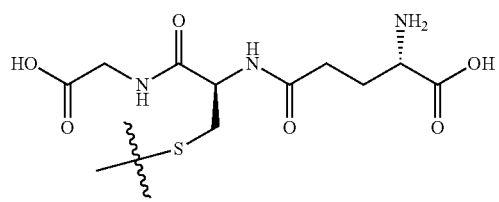 [SMILES: *SC[C@H](NC(=O)CC[C@H](N)C(=O)O)C(=O)NCC(=O)O]

(wherein ⌇ indicates the point of contact of the moiety to the parent compound).

In some embodiments, a metabolite of Compound 1 or a pharmaceutically acceptable salt thereof results from dehydrogenation of the piperidine ring of Compound 1, i.e., a metabolite having the structure of:

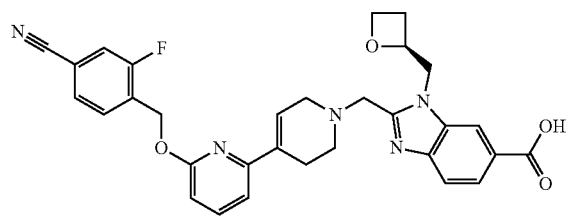

or

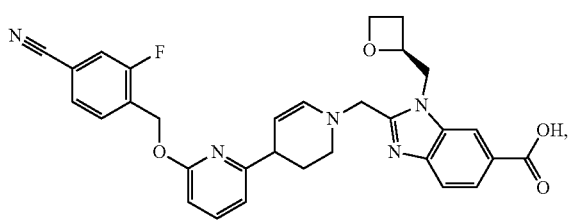

or a pharmaceutically acceptable salt thereof.

In some embodiments, a metabolite of Compound 1 or a pharmaceutically acceptable salt thereof results from hydroxylation followed by sulfation of the piperidine ring of Compound 1, e.g., a metabolite having the structure of:

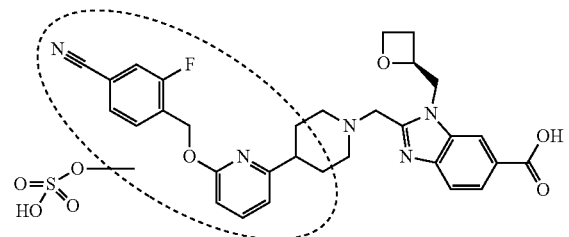

wherein the —O—S(=O)$_2$OH replaces a hydrogen on the part of Compound 1 within the dotted oval shape,
or a pharmaceutically acceptable salt thereof.

Compound 1 can also be considered a prodrug of the metabolites of the invention (e.g., a prodrug of metabolites M1, M2, M4, 748a, 748b, 574a, 574b, and the like) because Compound 1 metabolically transforms upon administration to provide the metabolites of the invention.

Accordingly, Compound 1 can be administered to a human as a means of providing a metabolite of the invention to the human, for example, for preventing or treating a disease or disorder in the human as described herein.

In another aspect, the present of invention provides a metabolite of a compound of Formula I:

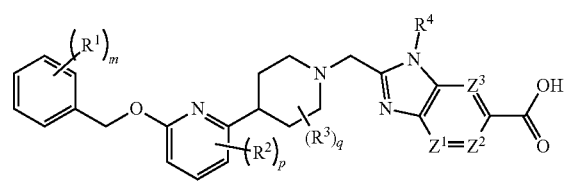

I or a pharmaceutically acceptable salt thereof, wherein
each $R^1$ is independently halogen, —CN, —C$_{1-3}$alkyl, or —OC$_{1-3}$alkyl, wherein the alkyl of C$_{1-3}$alkyl and OC$_{1-3}$alkyl is substituted with 0 to 3 F atoms;

m is 0, 1, 2, or 3;
each $R^2$ is independently F, C$_1$, or —CN;
p is 0, 1 or 2;
each $R^3$ is independently F, —OH, —CN, —C$_{1-3}$alkyl, —OC$_{1-3}$alkyl, or —C$_{3-4}$cycloalkyl, or 2 $R^3$s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;
q is 0, 1, or 2;
$R^4$ is —C$_{1-3}$alkyl, —C$_{0-3}$alkylene-C$_{3-6}$cycloalkyl, —C$_{0-3}$alkylene-R$^5$, or —C$_{1-3}$alkylene-R$^6$, wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, and —N(R$^N$)$_2$, and
wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$,
$R^5$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;
$R^6$ is a 5- to 6-membered heteroaryl, wherein said heteroaryl may be substituted with 0 to 2 substituents as valency allows independently selected from:
0 to 2 halogens,
0 to 1 substituent selected from —OR$^O$ and —N(R$^N$)$_2$, and
0 to 2 —C$_{1-3}$alkyl, wherein the alkyl may be substituted with 0 to 3 substituents as valency allows independently selected from:
0 to 3 F atoms, and
0 to 1 —OR$^O$;
each $R^O$ is independently H, or —C$_{1-3}$alkyl, wherein C$_{1-3}$alkyl may be substituted with 0 to 3 F atoms;
each $R^N$ is independently H, or —C$_{1-3}$alkyl;
$Z^1$ is CH or N;
$Z^2$ and $Z^3$ are each independently —CR$^Z$ or N, provided that when $Z^1$ or $Z^3$ is N, $Z^2$ is —CR$^Z$; and
each $R^Z$ is independently H, F, Cl, or —CH$_3$,
and wherein the metabolite is a derivative of the parent drug molecule (i.e. the compound of Formula I or pharmaceutically acceptable salt thereof), including any of the derivatives that have undergone one or more transformative processes selected from (1) glucuronidation, (2) O-debenzylation, (3) N-dealkylation, (4) hydroxylation, (5) hydroxylation followed by glucuronic acid (or glucuronide) conjugation, (6) oxidation and ring opening of the piperidine ring, (7) oxidation and ring opening of the oxetane ring when $R^4$ is oxetan-2-yl-methyl, (8) dehydrogenation of the piperidine ring, (9) hydroxylation followed by sulfation or cysteine conjugation, (10) glutathione conjugation,

(11) ring opening of the oxetane ring when R⁴ is oxetan-2-yl-methyl and glutathione conjugation, and
(12) cysteine conjugation, or a combination thereof (including a pharmaceutically acceptable salt thereof).

In some embodiments, the present invention provides a compound that is selected from a compound of Formula Mtblt-1

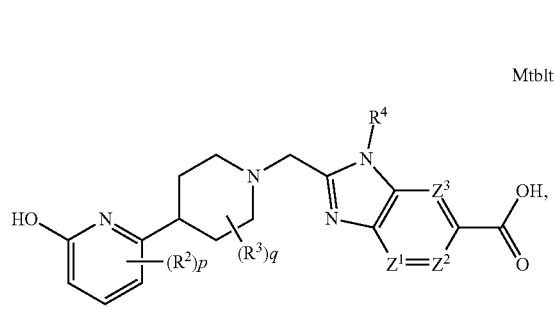

Mtblt-1 a compound of Formula Mtblt-2

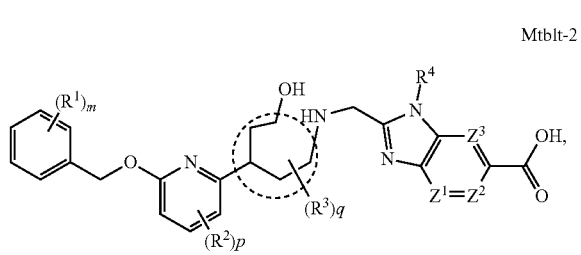

Mtblt-2 a compound of Formula Mtblt-3

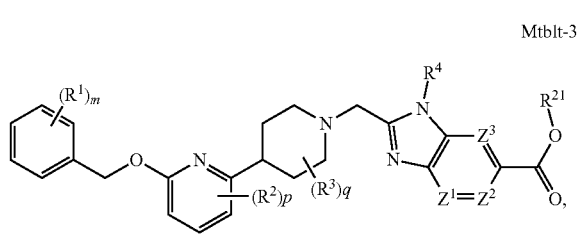

Mtblt-3 a compound of Formula Mtblt-4

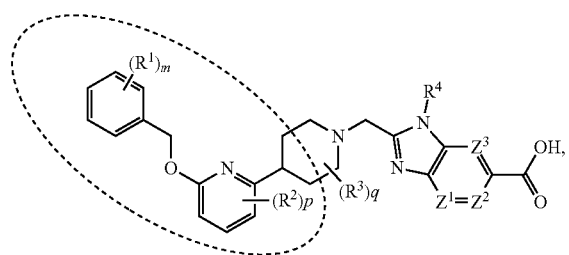

Mtblt-4 a compound of Formula Mtblt-5

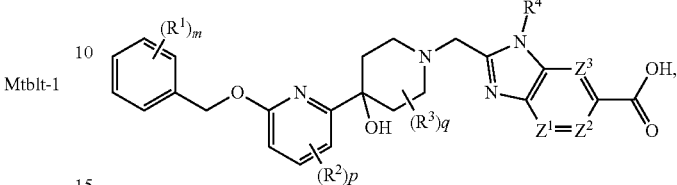

Mtblt-5 a compound of Formula Mtblt-6

Mtblt-6 a compound of Formula Mtblt-7

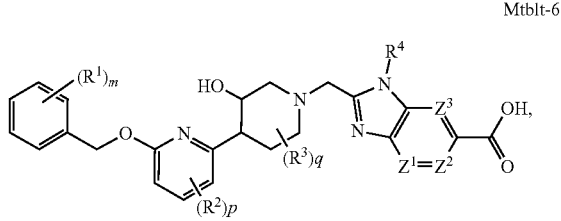

Mtblt-7 a compound of Formula Mtblt-8

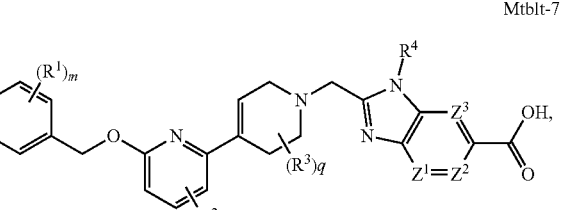

Mtblt-8 a compound of Formula Mtblt-9

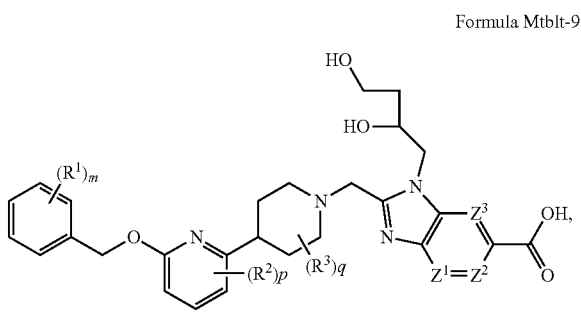

Formula Mtblt-9 or a pharmaceutically acceptable salt thereof, wherein
each $R^1$ is independently halogen, —CN, —$C_{1-3}$alkyl, or —$OC_{1-3}$alkyl, wherein the alkyl of $C_{1-3}$alkyl and $OC_{1-3}$alkyl is substituted with 0 to 3 F atoms;
m is 0, 1, 2, or 3;
each $R^2$ is independently F, $C_1$, or —CN;
p is 0, 1 or 2;
each $R^3$ is independently F, —OH, —CN, —$C_{1-3}$alkyl, —$OC_{1-3}$alkyl, or —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;
q is 0, 1, or 2;
$R^4$ is —$C_{1-3}$alkyl, —$C_{0-3}$alkylene-$C_{3-6}$cycloalkyl, —$C_{0-3}$alkylene-$R^5$, or —$C_{1-3}$alkylene-$R^6$,
wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, and —$N(R^N)_2$, and
wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;
$R^5$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1-CN, and
0 to 1 —$OR^O$;
$R^6$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;

each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$ is CH or N;
$Z^2$ and $Z^3$ are each independently —$CR^Z$ or N, provided that when $Z^1$ or $Z^3$ is N, $Z^2$ is —$CR^Z$;
each $R^Z$ is independently H, F, $C_1$, or —$CH_3$;
$R^{21}$ is glucuronidation; and
$R^{31}$ is —OH, —O—S(=O)$_2$OH, or —O-glucuronidation.

In some embodiments, the present invention provides a compound of Formula Mtblt-1 or a pharmaceutically acceptable salt thereof.

In some embodiments, the present invention provides a compound of Formula Mtblt-2 or a pharmaceutically acceptable salt thereof. A $R^3$ substitution replaces a hydrogen on the phenyl ring, the pyridine ring, or the part of the piperidine ring of Formula Mtblt-2 within the dotted oval shape.

In some embodiments, the present invention provides a compound of Formula Mtblt-3 or a pharmaceutically acceptable salt thereof. In some further embodiments, $R^{21}$ is

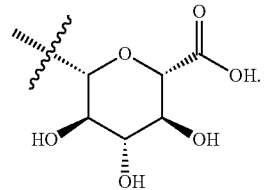

In some embodiments, the present invention provides a compound of Formula Mtblt-4 or a pharmaceutically acceptable salt thereof. The $R^{31}$ substitution replaces a hydrogen on the part of Formula Mtblt-4 within the dotted oval shape. In some further embodiments, $R^{31}$ is —OH. In other further embodiments, $R^{31}$ is —O—S(=O)$_2$OH. In yet other further embodiments, $R^{31}$ is —O-glucuronidation, for example,

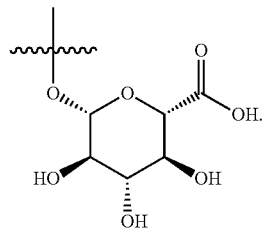 [SMILES: *O[C@@H]1O[C@H](C(=O)O)[C@@H](O)[C@H](O)[C@H]1O]

In some embodiments, the present invention provides a compound of Formula Mtblt-5 or a pharmaceutically acceptable salt thereof.

In some embodiments, the present invention provides a compound of Formula Mtblt-6 or a pharmaceutically acceptable salt thereof.

In some embodiments, the present invention provides a compound of Formula Mtblt-7 or a pharmaceutically acceptable salt thereof.

In some embodiments, the present invention provides a compound of Formula Mtblt-8 or a pharmaceutically acceptable salt thereof.

In some embodiments, the present invention provides a compound of Formula Mtblt-9 or a pharmaceutically acceptable salt thereof.

In some embodiments, one or more of the metabolite compounds, or salts thereof, are prepared by metabolism of its parent compound, e.g., a compound of Formula I or a pharmaceutically salt thereof (for example, in a mammal or a mammalian cell environment); and the metabolite compounds thus prepared are substantially isolated. In some other embodiments, one or more of the metabolite compounds, or salts thereof, are prepared by chemical synthesis other than metabolism of a compound of Formula I or a pharmaceutically salt thereof (for example, in a mammal or a mammalian cell environment) and the synthesized metabolite compounds are substantially isolated. A compound of Formula I or its salt can be prepared, for example, by the methods described in U.S. Pat. No. 10,208,019.

In another aspect, the present invention is directed, in part, to metabolites of Compound 2 or a pharmaceutically acceptable salt thereof and uses thereof. In some embodiments, the present invention provide a metabolite of Compound 2 or a pharmaceutical acceptable salt thereof that results from Compound 2 (or a pharmaceutically acceptable salt thereof) which has undergone (1) ring opening of the benzodioxolane ring to form catechol (see e.g. Metabolite 438); (2) N-dealkylation (see e.g. Metabolite 331, N-dealkylation of the piperidine; or Metabolite 505, N-dealkylation of the benzimidazole ring); (3) hydroxylation (see e.g. Metabolite 591a, 591b, or 591c); (4) glucuronidation (see e.g. Metabolite 751b, Metabolite 751a or 751c); (5) aromatization of the piperidine ring (see e.g. Metabolite 569); (6) dehydrogenation of the piperidine ring (see e.g. Metabolite 573a or 573b); (7) N-oxide formation (see e.g. Metabolite 591); (8) hydroxylation followed by glucuronidation (see e.g. Metabolite 767a, 767b, or 767c); (9) hydroxylation followed by sulfation (see e.g. Metabolite 671); oxidation/hydrolysis and ring opening of the oxetane ring (see e.g. Metabolite 593); (10) cysteine conjugation (see e.g. Metabolite 694); (11) glutathione conjugation; (12) ring opening of the oxetane ring and glutathione conjugation (See e.g. Metabolite 882a and 882b); sulfation of a hydroxyl group; or a combination thereof. In some embodiments, a metabolite of the invention results from bis-hydroxylation (see e.g. Metabolite 607); or a combination of N-dealkylation of the piperidine, hydroxylation, and glucuronidation (see e.g. Metabolite 523); or a combination of ring opening of the benzodioxolane ring to form catechol and sulfation of a hydroxyl group (Metabolite 518). In some embodiments, the metabolite (including a salt thereof) is substantially isolated.

In some embodiments, the present invention provides Metabolite 438

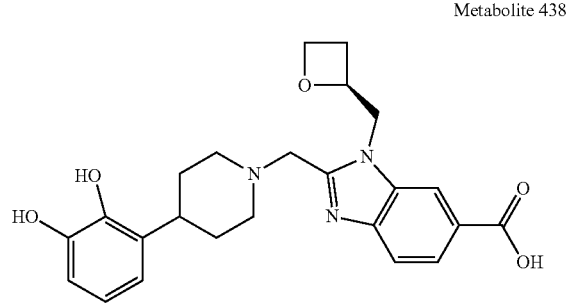 [SMILES: O=C(O)c1ccc2nc(CN3CCC(c4cccc(O)c4O)CC3)n(C[C@@H]3CCO3)c2c1]

Metabolite 438 or a pharmaceutically acceptable salt thereof, which is substantially isolated.

In some embodiments, the present invention provides a compound of Formula X1,

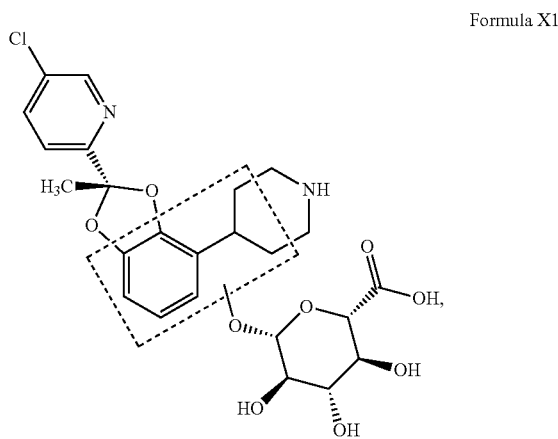

Formula X1 wherein one of the hydrogens on the benzo or piperidine ring within the dotted rectangle is replaced by the —O-glucuronide substitution as shown, or a pharmaceutically acceptable salt thereof, which is substantially isolated. In some further embodiments, the compound of Formula X1 or a pharmaceutically acceptable salt thereof is Metabolite 523 or a pharmaceutically acceptable salt thereof, which is substantially isolated.

In some embodiments, the present invention provides a compound of Formula X2,

Formula X2 wherein one of the hydrogens on the benzo or piperidine ring within the dotted rectangle is replaced by the —O-glucuronide substitution as shown, or a pharmaceutically acceptable salt thereof, which is substantially isolated. In some further embodiments, the compound of Formula X2 or a pharmaceutically acceptable salt thereof is Metabolite 767a or a pharmaceutically acceptable salt thereof, which is substantially isolated.

In some embodiments, the present invention provides a compound of Formula X3:

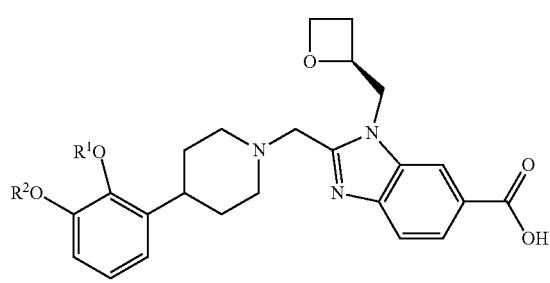

Formula X3 wherein one of $R^1$ and $R^2$ is H, and the other is —S(=O)$_2$OH, or a pharmaceutically acceptable salt thereof, which is substantially isolated. In some further embodiments, the compound of Formula X3 or a pharmaceutically acceptable salt thereof is Metabolite 518 or a pharmaceutically acceptable salt thereof, which is substantially isolated.

In some embodiments, the present invention provides a compound of Formula X4:

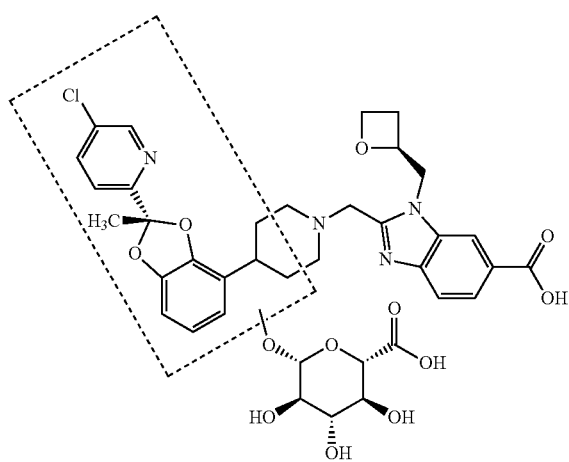

Formula X4 wherein one of the hydrogens on the pyridine, benzo or piperidine ring within the dotted rectangle is replaced by the —O-glucuronide substitution as shown, or a pharmaceutically acceptable salt thereof, which is substantially isolated. In some further embodiments, the compound of Formula X4 or a pharmaceutically acceptable salt thereof is Metabolite 767b or 767c or a pharmaceutically acceptable salt thereof, which is substantially isolated.

In some embodiments, the present invention provides a compound of Formula X5:

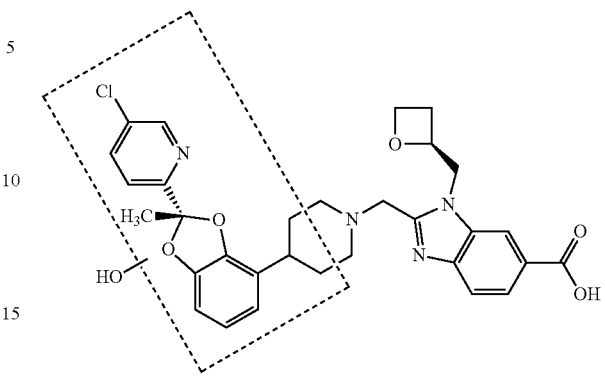

Formula X5 wherein one of the hydrogens on the pyridine, benzo or piperidine ring within the dotted rectangle is replaced by the —OH, or a pharmaceutically acceptable salt thereof, which is substantially isolated. In some further embodiments, the compound of Formula X5 or a pharmaceutically acceptable salt thereof is Metabolite 591a, 591b or 591c or a pharmaceutically acceptable salt thereof, which is substantially isolated.

In some embodiments, the present invention provides a compound of Formula X6:

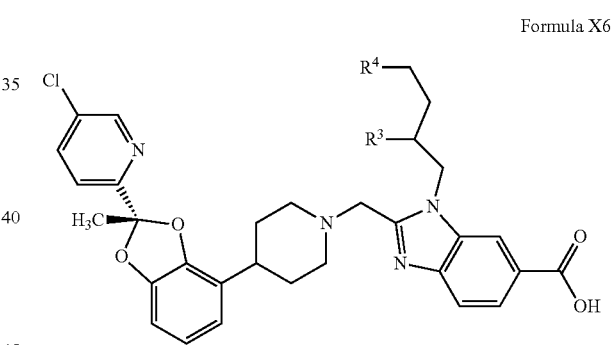

Formula X6 wherein one of $R^3$ and $R^4$ is OH, and the other $R^3$ and $R^4$ is a moiety of

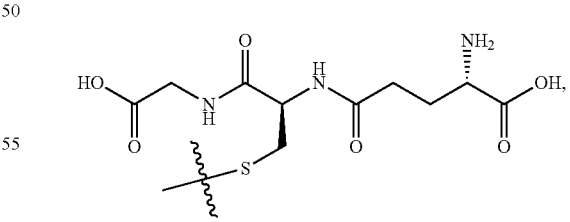

or a pharmaceutically acceptable salt thereof, which is substantially isolated. In some further embodiments, the compound of Formula X1 or a pharmaceutically acceptable salt thereof is Metabolite 882a or 882b or a pharmaceutically acceptable salt thereof, which is substantially isolated.

In some embodiments, the present invention provides a compound of Formula X7:

Formula X7

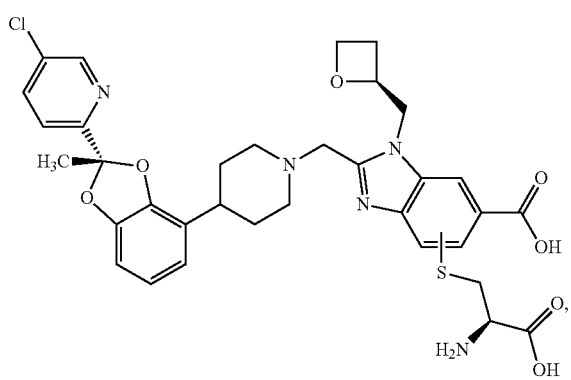

or a pharmaceutically acceptable salt thereof, which is substantially isolated. In some further embodiments, the present invention provides Metabolite 694 or a pharmaceutically acceptable salt thereof, which is substantially isolated.

In some embodiments, the present invention provides a compound of Formula X8:

Formula X8

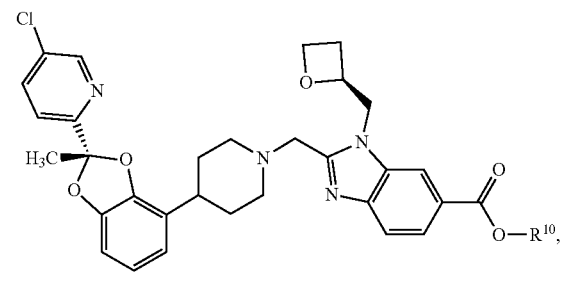

wherein $R^{10}$ is

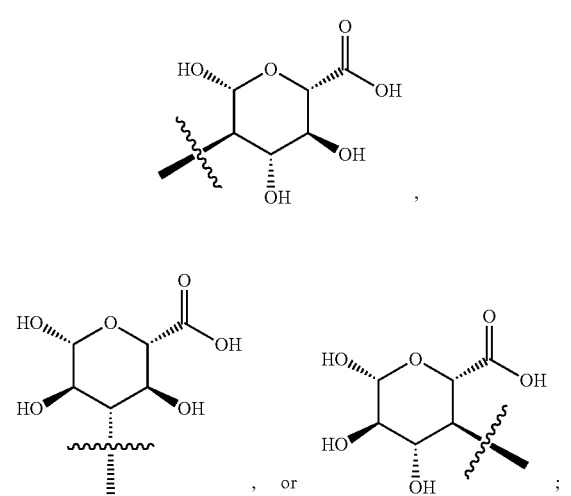

or a pharmaceutically acceptable salt thereof, which is substantially isolated. In some further embodiments, the compound of Formula X8 or a pharmaceutically acceptable salt thereof is Metabolite 751a or 751c or a pharmaceutically acceptable salt thereof, which is substantially isolated.

In some embodiments, the present invention provides Metabolite 505

Metabolite 505

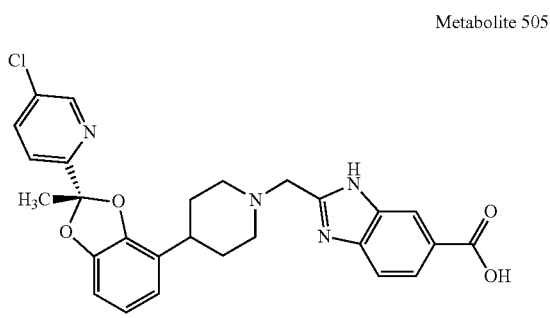 [SMILES: C[C@]1(c2ccc(Cl)cn2)Oc2cccc(C3CCN(Cc4nc5ccc(C(=O)O)cc5[nH]4)CC3)c2O1]

or a pharmaceutically acceptable salt thereof, which is substantially isolated.

In some embodiments, the present invention provides a compound having the formula of

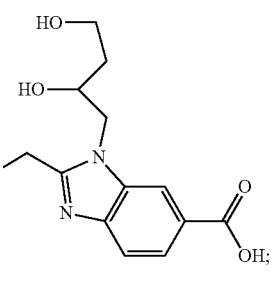

or a pharmaceutically acceptable salt thereof, which is substantially isolated. In some embodiments, the present invention provides Metabolite 593 or a pharmaceutically acceptable salt thereof, which is substantially isolated.

In some embodiments, the present invention provides a compound having the formula of

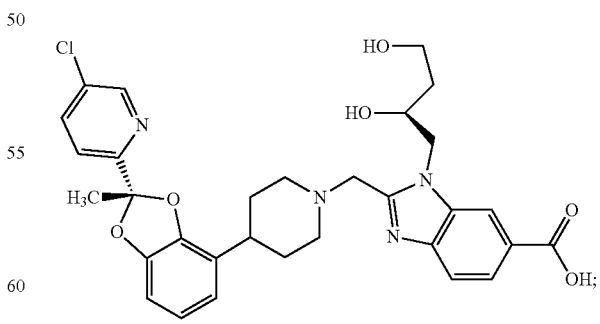

or a pharmaceutically acceptable salt thereof, which is substantially isolated.

In some embodiments, the present invention provides Metabolite 751b:

Metabolite 751b

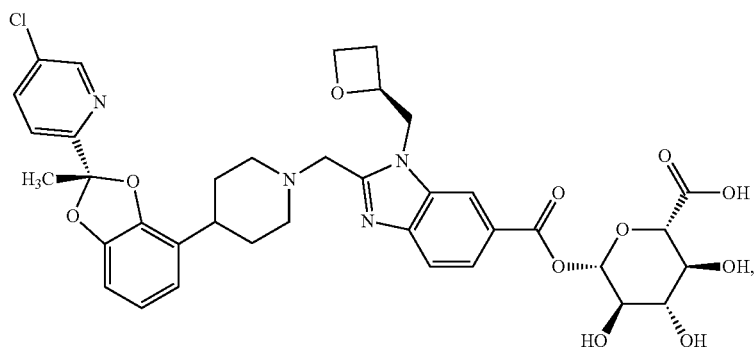

or a pharmaceutically acceptable salt thereof, which is substantially isolated.

In some embodiments, the present invention provides a compound of Formula X9:

Formula X9

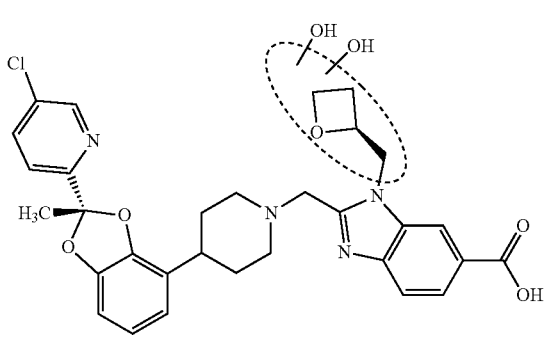

wherein two hydrogens on the moiety within the dotted oval shape are replaced by two —OH groups; or a pharmaceutically acceptable salt thereof, which is substantially isolated. In some further embodiments, the present invention provides Metabolite 607 or a pharmaceutically acceptable salt thereof, which is substantially isolated.

In some embodiments, the present invention provides a compound having the formula of

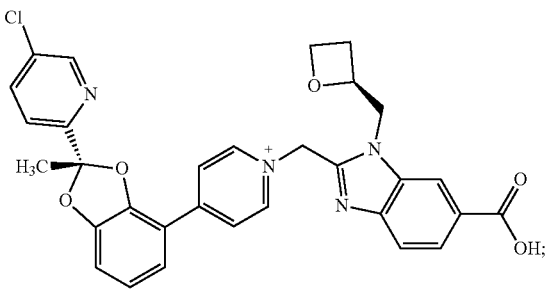

or a pharmaceutically acceptable salt thereof, which is substantially isolated. In some further embodiments, the present invention provides Metabolite 569 or a pharmaceutically acceptable salt thereof, which is substantially isolated.

In some embodiments, the present invention provides a compound having the formula of

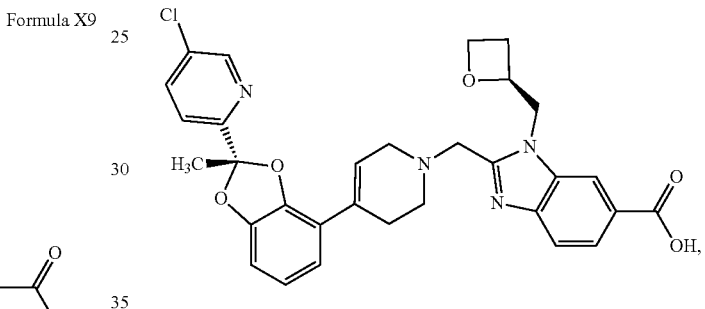

or a pharmaceutically acceptable salt thereof, which is substantially isolated.

In some embodiments, the present invention provides a compound having the formula of

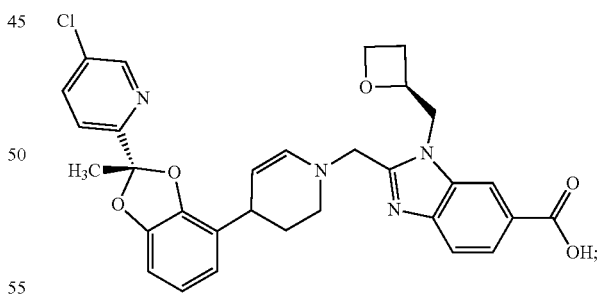

or a pharmaceutically acceptable salt thereof, which is substantially isolated.

In some embodiments, the present invention provides Metabolite 573a, or a pharmaceutically acceptable salt thereof, which is substantially isolated.

In some embodiments, the present invention provides Metabolite 573b, or a pharmaceutically acceptable salt thereof, which is substantially isolated.

In some embodiments, the present invention provides a compound of Formula X10

Formula X10

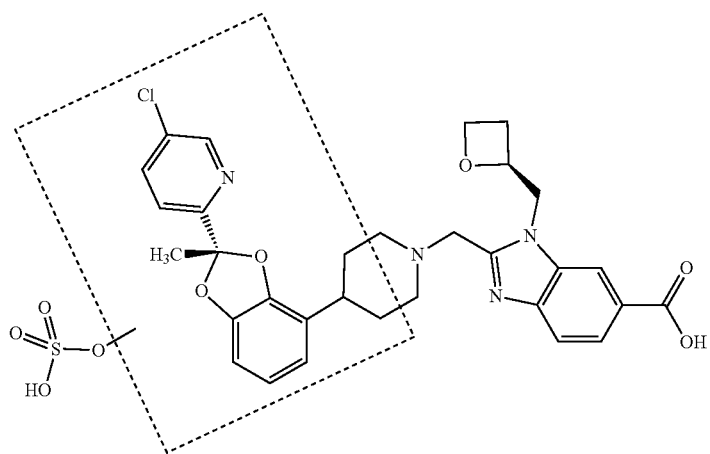

wherein one of the hydrogens on the pyridine, benzo or piperidine ring within the dotted rectangle is replaced by the —OS(=O)₂—OH; or a pharmaceutically acceptable salt thereof, which is substantially isolated. In some further embodiments, the present invention provides Metabolite 671 or a pharmaceutically acceptable salt thereof, which is substantially isolated.

In some embodiments, the present invention provides Metabolite 591d

Metabolite 591d

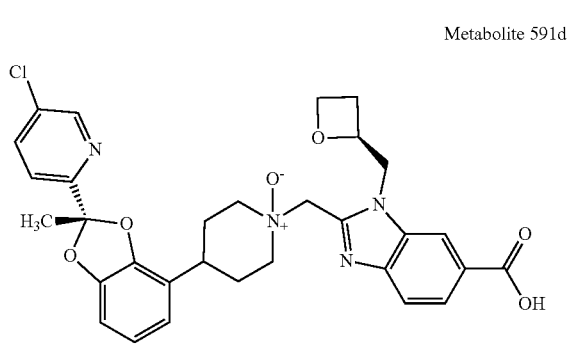 [SMILES: C[C@]1(c2ccc(Cl)cn2)Oc2cccc(C3CC[N+]([O-])(Cc4nc5ccc(C(=O)O)cc5n4C[C@@H]4CCO4)CC3)c2O1]

or a pharmaceutically acceptable salt thereof, which is substantially isolated.

In another aspect, the present of invention provides a metabolite of a compound of Formula PA-I:

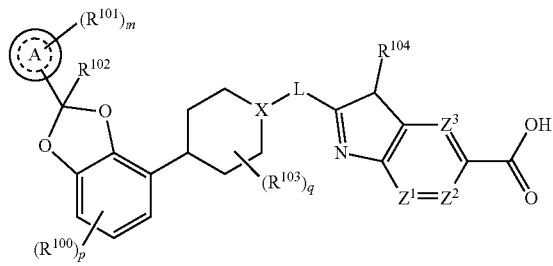

or a pharmaceutically acceptable salt thereof, wherein
$R^{100}$ is F, C₁, or —CN;
p is 0 or 1;

Ring A is phenyl or a 6-membered heteroaryl;
m is 0, 1, 2, or 3;
each $R^{101}$ is independently selected from halogen, —CN, —C$_{1-3}$alkyl, and —OC$_{1-3}$alkyl, wherein the alkyl of C$_{1-3}$alkyl and OC$_{1-3}$alkyl is substituted with 0 to 3 F atoms;
$R^{102}$ is H or —C$_{1-3}$alkyl, wherein alkyl is substituted with 0 to 1 OH;
each $R^{103}$ is independently F, —OH, —CN, —C$_{1-3}$alkyl, —OC$_{1-3}$alkyl, and —C$_{3-4}$cycloalkyl, or 2 R³'s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;
q is 0, 1, or 2;
X-L is N—CH₂, CHCH₂, or cyclopropyl;
Y is CH or N;
$R^{104}$ is —C$_{1-3}$alkyl, —C$_{0-3}$alkylene-C$_{3-6}$cycloalkyl, —C$_{0-3}$alkylene-R$^{105}$, or —C$_{1-3}$alkylene-R$^{106}$, wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, —SO₂—N(R$^N$)₂, —C(O)—N(R$^N$)₂, —N(C=O)(R$^N$), and —N(R$^N$)₂, and
wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)₂,
$R^{105}$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;

$R^{106}$ is a 5- to 6-membered heteroaryl, wherein said heteroaryl may be substituted with 0 to 2 substituents as valency allows independently selected from:

0 to 2 halogens, 0 to 1 substituent selected from —$OR^O$ and —$N(R^N)_2$, and 0 to 2 —$C_{1-3}$alkyl, wherein the alkyl may be substituted with 0 to 3 substituents as valency allows independently selected from:

0 to 3 F atoms, and 0 to 1 —$OR^O$;

each $R^O$ is independently H, or —$C_{1-3}$alkyl, wherein $C_{1-3}$alkyl may be substituted with 0 to 3 F atoms;

each $R^N$ is independently H, or —$C_{1-3}$alkyl;

$Z^1$, $Z^2$, and $Z^3$ are each —$CR^Z$, or one of $Z^1$, $Z^2$, and $Z^3$ is N and the other two are —$CR^Z$; and each $R^Z$ is independently H, F, Cl, or —$CH_3$, and wherein the metabolite is a derivative of the parent drug molecule (i.e. the compound of Formula PA-I or pharmaceutically acceptable salt thereof), including any of the derivatives that have undergone one or more transformative processes selected from (1) ring opening of the benzodioxolane ring to form catechol; (2) N-dealkylation (e.g. N-dealkylation of the piperidine wherein X is N; or N-dealkylation of the benzimidazole ring); (3) hydroxylation; (4) glucuronidation; (5) aromatization of the piperidine ring wherein X is N; (6) dehydrogenation of the piperidine ring wherein X is N; (7) N-oxide formation wherein X is N; (8) hydroxylation followed by glucuronidation; (9) hydroxylation followed by sulfation; (10) oxidation/hydrolysis and ring opening of the oxetane ring wherein $R^{104}$ is oxetan-2-yl-methyl; (11) cysteine conjugation; (12) glutathione conjugation; (13) ring opening of the oxetane ring and glutathione conjugation wherein $R^{104}$ is oxetan-2-yl-methyl; (14) sulfation of a hydroxyl group; or a combination thereof.

In some embodiments, the present invention provides a compound selected from:

a compound of Formula Y1

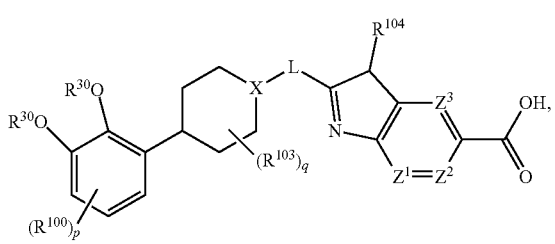

a compound of Formula Y2

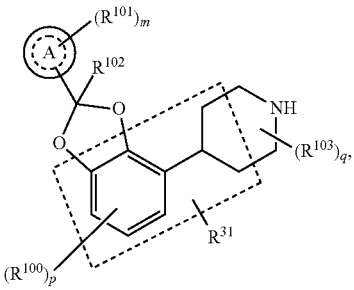

a compound of Formula Y3

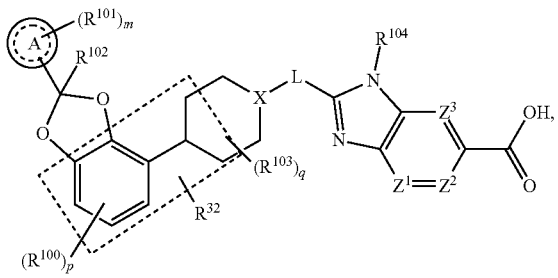

a compound of Formula Y4

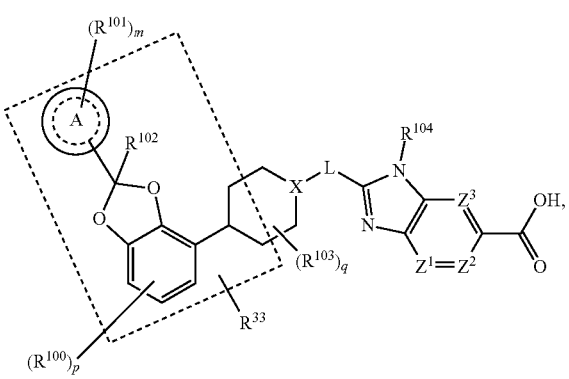

a compound of Formula Y5

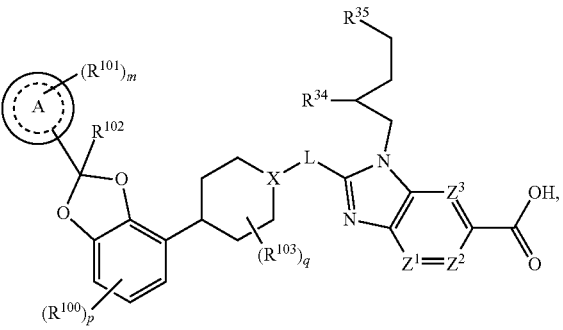

a compound of Formula Y6
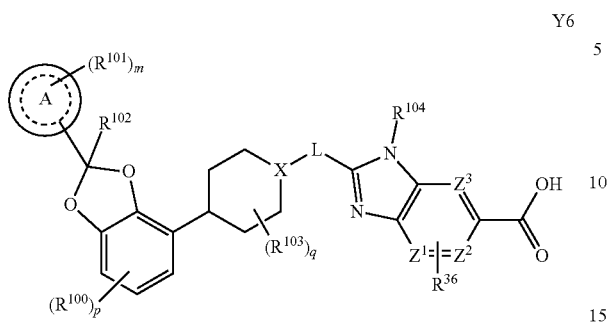
a compound of Formula Y7
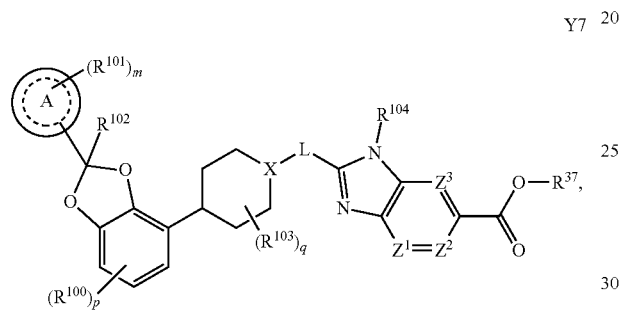
a compound of Formula Y8
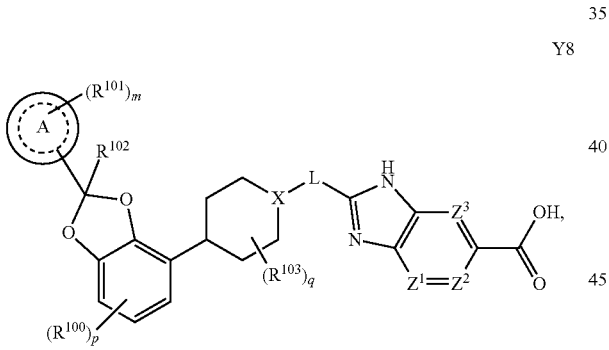
a compound of Formula Y9
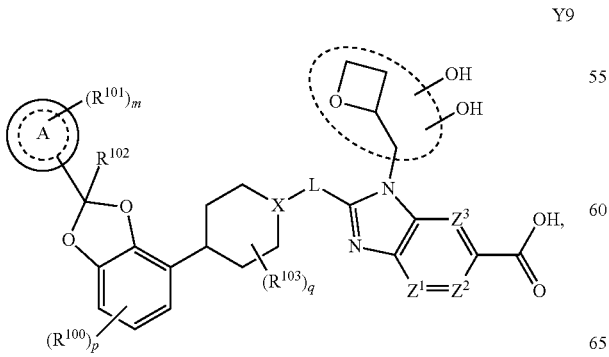
a compound of Formula Y10
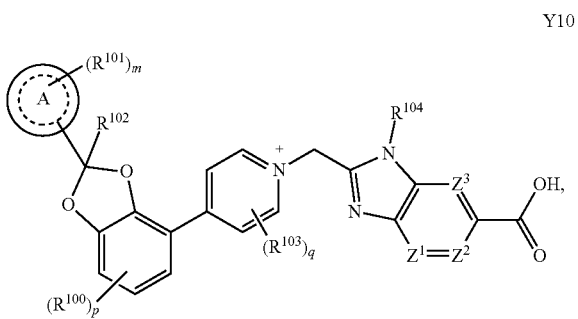
a compound of Formula Y11
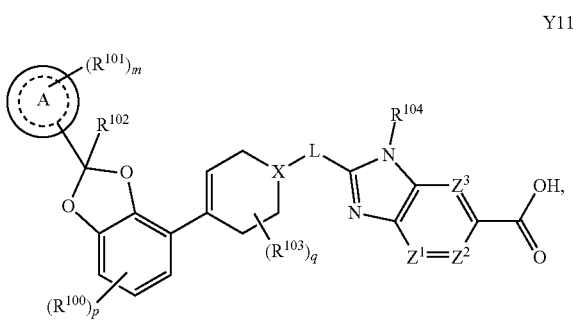
a compound of Formula Y12
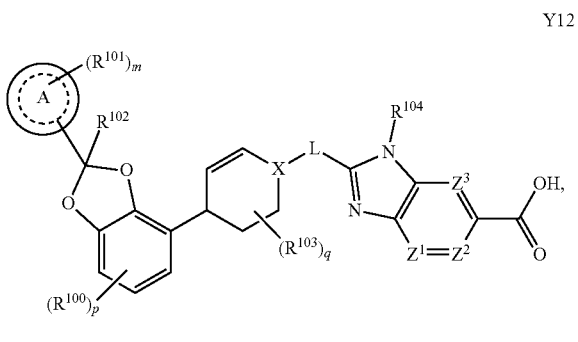
and
a compound of Formula Y13
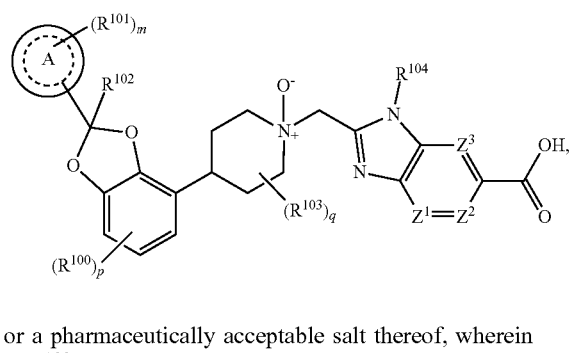
or a pharmaceutically acceptable salt thereof, wherein
$R^{100}$ is F, $C_1$, or —CN;
p is 0 or 1;

Ring A is phenyl or a 6-membered heteroaryl;
m is 0, 1, 2, or 3;
each $R^{101}$ is independently selected from halogen, —CN, —$C_{1-3}$alkyl, and —$OC_{1-3}$alkyl, wherein the alkyl of $C_{1-3}$alkyl and $OC_{1-3}$alkyl is substituted with 0 to 3 F atoms;
$R^{102}$ is H or —$C_{1-3}$alkyl, wherein alkyl is substituted with 0 to 1 OH;
each $R^{103}$ is independently F, —OH, —CN, —$C_{1-3}$alkyl, —$OC_{1-3}$alkyl, and —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;
q is 0, 1, or 2;
X-L is N—$CH_2$, $CHCH_2$, or cyclopropyl;
Y is CH or N;
$R^{104}$ is —$C_{1-3}$alkyl, —$C_{0-3}$alkylene-$C_{3-6}$cycloalkyl, —$C_{0-3}$alkylene-$R^{105}$, or —$C_{1-3}$alkylene-$R^{106}$,
wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, —$SO_2$—N$(R^N)_2$, —C(O)—$N(R^N)_2$, —$N(C=O)(R^N)$, and —$N(R^N)_2$, and
wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;
$R^{105}$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1-CN, and
0 to 1 —$OR^O$;
$R^{106}$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;
each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$, $Z^2$, and $Z^3$ are each —$CR^Z$, or
one of $Z^1$, $Z^2$, and $Z^3$ is N and the other two are —$CR^Z$; and
each $R^Z$ is independently H, F, $C_1$, or —$CH_3$,
and wherein
each of $R^{30}$ is H, or one of $R^{30}$ is H and the other is —$S(=O)_2OH$;
$R^{31}$ is —O-glucuronide;

$R^{32}$ is —O-glucuronide;
$R^{33}$ is —OH, —O-glucuronide, or —O—$S(=O)_2OH$;
each of $R^{34}$ and $R^{35}$ is OH, or one of $R^{34}$ and $R^{35}$ is OH, and the other $R^3$ and $R^4$ is a moiety of

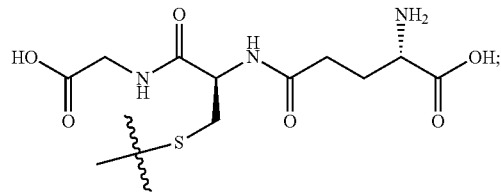 [SMILES: *SC[C@H](NC(=O)CC[C@H](N)C(=O)O)C(=O)NCC(=O)O]

$R^{36}$ is a moiety of

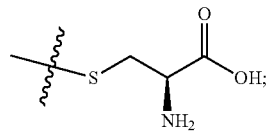 [SMILES: *SC[C@H](N)C(=O)O]

and
$R^{37}$ is —O-glucuronide.
In some embodiments, the present invention provides a compound of Formula Y1 or a pharmaceutically acceptable salt thereof. In some further embodiments, each of $R^{30}$ is H. In other further embodiments, one $R^{30}$ is H and the other is —$S(=O)_2OH$.
In some embodiments, the present invention provides a compound of Formula Y2 or a pharmaceutically acceptable salt thereof. The $R^{31}$ substitution replaces a hydrogen on the part of Formula Y2 within the dotted rectangle shape. In some further embodiments, $R^{31}$ is a moiety having the structure of

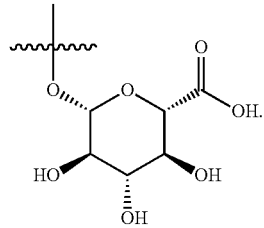 [SMILES: *O[C@@H]1O[C@H](C(=O)O)[C@@H](O)[C@H](O)[C@H]1O]

In some embodiments, the present invention provides a compound of Formula Y3 or a pharmaceutically acceptable salt thereof. The $R^{32}$ substitution replaces a hydrogen on the part of Formula Y3 within the dotted rectangle shape. In some further embodiments, $R^{32}$ is a moiety having the structure of

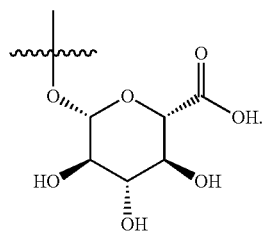 [SMILES: *O[C@@H]1O[C@H](C(=O)O)[C@@H](O)[C@H](O)[C@H]1O]

In some embodiments, the present invention provides a compound of Formula Y4 or a pharmaceutically acceptable salt thereof. The $R^{33}$ substitution replaces a hydrogen on the part of ring A, the benzo or the 6-membered ring comprising the variable X within the dotted rectangle shape. In some embodiments, $R^{33}$ is —OH. In some other embodiments, $R^{33}$ is —O—S(=O)$_2$OH. In yet other embodiments, $R^{33}$ is —O-glucuronide, for example, a moiety having the structure of

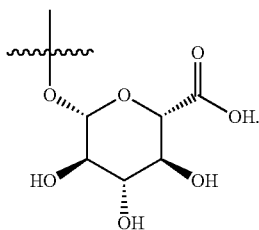 [SMILES: *O[C@@H]1O[C@H](C(=O)O)[C@@H](O)[C@H](O)[C@H]1O]

In some embodiments, the present invention provides a compound of Formula Y5 or a pharmaceutically acceptable salt thereof. In some embodiments, each of $R^{34}$ and $R^{35}$ is OH. In some other embodiments, one of $R^{34}$ and $R^{35}$ is OH, and the other $R^3$ and $R^4$ is a moiety of

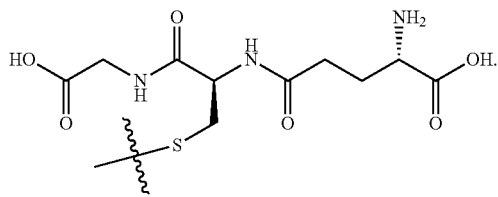 [SMILES: *SC[C@H](NC(=O)CC[C@H](N)C(=O)O)C(=O)NCC(=O)O]

In some embodiments, the present invention provides a compound of Formula Y6 or a pharmaceutically acceptable salt thereof.

In some embodiments, the present invention provides a compound of Formula Y7 or a pharmaceutically acceptable salt thereof. In some further embodiments, $R^{37}$ is a moiety having the structure of

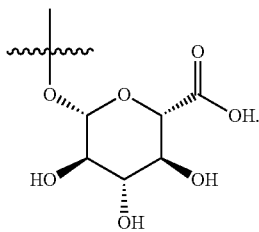 [SMILES: *O[C@@H]1O[C@H](C(=O)O)[C@@H](O)[C@H](O)[C@H]1O]

In some embodiments, the present invention provides a compound of Formula Y8 or a pharmaceutically acceptable salt thereof.

In some embodiments, the present invention provides a compound of Formula Y9 or a pharmaceutically acceptable salt thereof. Both of the OH groups are substituted on the part within the dotted oval shape.

In some embodiments, the present invention provides a compound of Formula Y10 or a pharmaceutically acceptable salt thereof.

In some embodiments, the present invention provides a compound of Formula Y11 or a pharmaceutically acceptable salt thereof.

In some embodiments, the present invention provides a compound of Formula Y12 or a pharmaceutically acceptable salt thereof.

In some embodiments, the present invention provides a compound of Formula Y13 or a pharmaceutically acceptable salt thereof.

In some embodiments, the present of invention provides a metabolite of a compound of Formula PA-III:

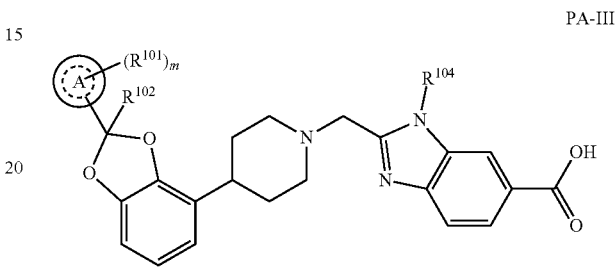

PA-III or a pharmaceutically acceptable salt thereof, wherein
Ring A is phenyl or a 6-membered heteroaryl;
m is 0, 1, 2, or 3;
each $R^{101}$ is independently selected from halogen, —CN, —C$_{1-3}$alkyl, and —OC$_{1-3}$alkyl, wherein the alkyl of C$_{1-3}$alkyl and OC$_{1-3}$alkyl is substituted with 0 to 3 F atoms;
$R^{102}$ is H or —C$_{1-3}$alkyl, wherein alkyl is substituted with 0 to 1 OH;
$R^{104}$ is —C$_{1-3}$alkyl, —C$_{0-3}$alkylene-C$_{3-6}$cycloalkyl, —C$_{0-3}$alkylene-R$^{105}$, or —C$_{1-3}$alkylene-R$^{106}$,
wherein said alkyl may be substituted as valency allows with 0 to 3 substituents independently selected from 0 to 3 F atoms and 0 to 1 substituent selected from —C$_{0-1}$alkylene-CN, —C$_{0-1}$alkylene-OR$^O$, —SO$_2$—N(R$^N$)$_2$, —C(O)—N(R$^N$)$_2$, —N(C=O)(R$^N$), and —N(R$^N$)$_2$, and
wherein said alkylene and cycloalkyl may be independently substituted as valency allows with 0 to 2 substituents independently selected from 0 to 2 F atoms and 0 to 1 substituent selected from —C$_{0-1}$alkylene-CN, —C$_{0-1}$alkylene-OR$^O$, and —N(R$^N$)$_2$,
$R^{105}$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —C$_{1-3}$alkyl and —OC$_{1-3}$alkyl, wherein the alkyl of C$_{1-3}$alkyl and OC$_{1-3}$alkyl may be substituted with 0 to 3 substituents as valency allows independently selected from:
0 to 3 F atoms,
0 to 1 —CN, and
0 to 1 —OR$^O$;
$R^{106}$ is a 5- to 6-membered heteroaryl, wherein said heteroaryl may be substituted with 0 to 2 substituents as valency allows independently selected from:
0 to 2 halogens, 0 to 1 substituent selected from —OR$^O$ and —N(R$^N$)$_2$, and 0 to 2 —C$_{1-3}$alkyl, wherein the alkyl may be substituted with 0 to 3 substituents as valency allows independently selected from:
  0 to 3 F atoms, and
  0 to 1 —OR$^O$;

each R$^O$ is independently H, or —C$_{1-3}$alkyl, wherein C$_{1-3}$alkyl may be substituted with 0 to 3 F atoms;

each R$^N$ is independently H, or —C$_{1-3}$alkyl;

Z$^1$, Z$^2$, and Z$^3$ are each —CR$^Z$, or one of Z$^1$, Z$^2$, and Z$^3$ is N and the other two are —CR$^Z$; and each R$^Z$ is independently H, F, C$_1$, or —CH$_3$, and wherein the metabolite is a derivative of the parent drug molecule (i.e. the compound of Formula PA-III or pharmaceutically acceptable salt thereof), including any of the derivatives that have undergone one or more transformative processes selected from (1) ring opening of the benzodioxolane ring to form catechol; (2) N-dealkylation (e.g. N-dealkylation of the piperidine; or N-dealkylation of the benzimidazole ring); (3) hydroxylation; (4) glucuronidation; (5) aromatization of the piperidine ring; (6) dehydrogenation of the piperidine ring; (7) N-oxide formation; (8) hydroxylation followed by glucuronidation; (9) hydroxylation followed by sulfation; (10) oxidation/hydrolysis and ring opening of the oxetane ring wherein R$^{104}$ is oxetan-2-yl-methyl; (11) cysteine conjugation; (12) glutathione conjugation; (13) ring opening of the oxetane ring and glutathione conjugation wherein R$^{104}$ is oxetan-2-yl-methyl; (14) sulfation of a hydroxyl group; or a combination thereof.

In some embodiments, the present invention provides a compound selected from a compound of Formula Z1

Z1

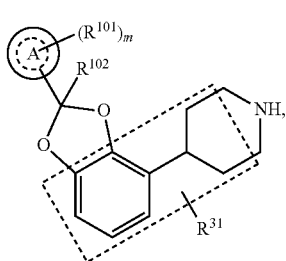

a compound of Formula Z2

Z2

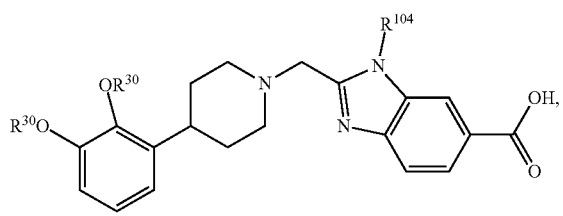

a compound of Formula Z3

Z3

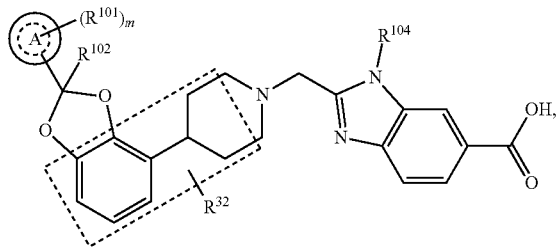

a compound of Formula Z4

Z4

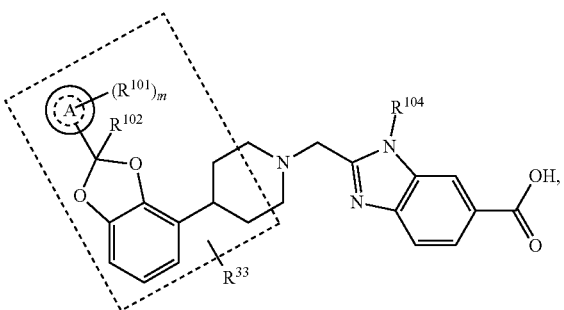

a compound of Formula Z5

Z5

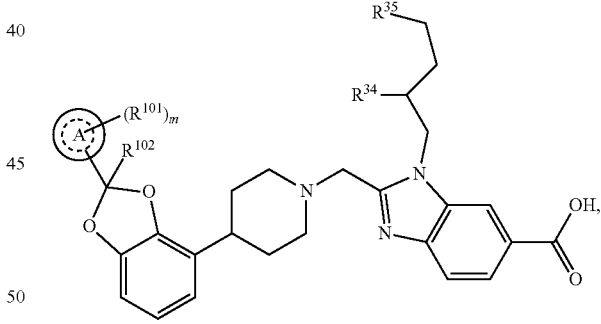

a compound of Formula Z6

Z6

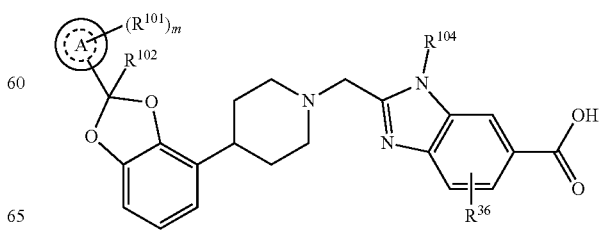

a compound of Formula Z7

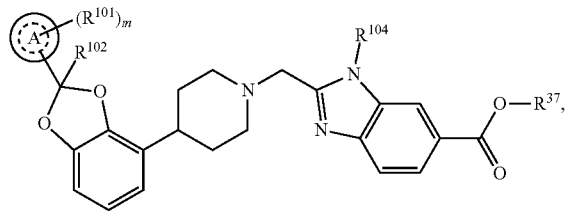

a compound of Formula Z8

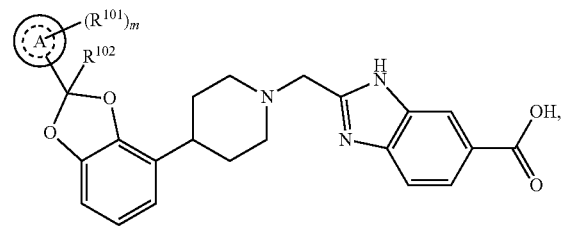

a compound of Formula Z9

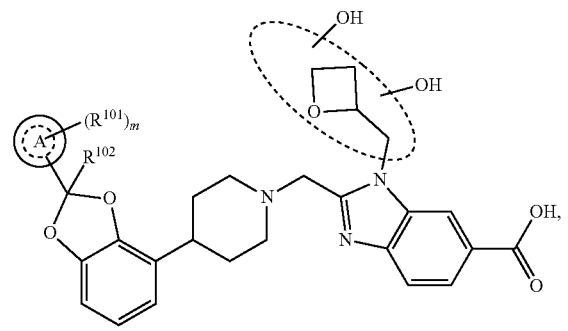

a compound of Formula Z10

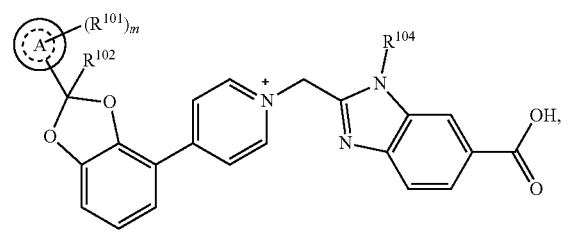

a compound of Formula Z11

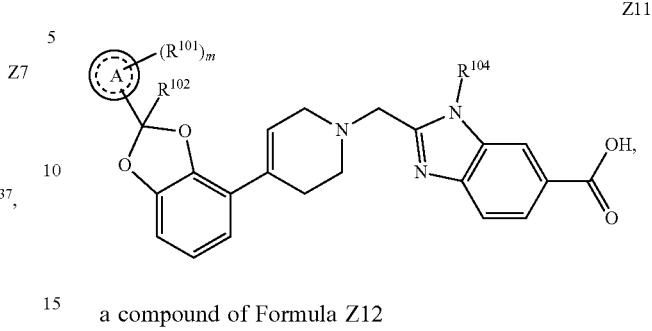

a compound of Formula Z12

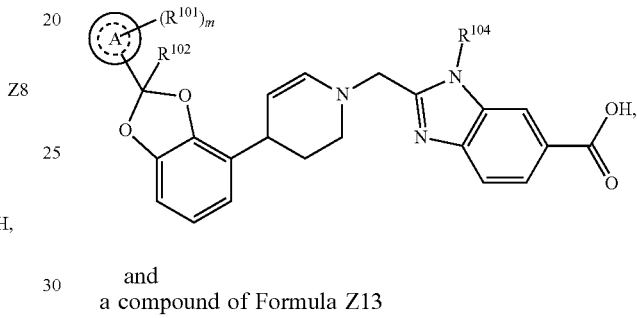

and
a compound of Formula Z13

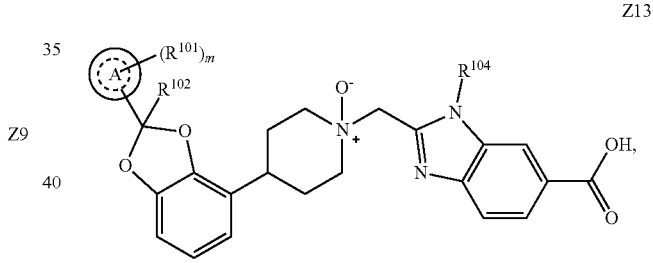

or a pharmaceutically acceptable salt thereof, wherein
$R^{100}$ is F, $C_1$, or —CN;
p is 0 or 1;
Ring A is phenyl or a 6-membered heteroaryl;
m is 0, 1, 2, or 3;
each $R^{101}$ is independently selected from halogen, —CN, —$C_{1-3}$alkyl, and —$OC_{1-3}$alkyl, wherein the alkyl of $C_{1-3}$alkyl and $OC_{1-3}$alkyl is substituted with 0 to 3 F atoms;
$R^{102}$ is H or —$C_{1-3}$alkyl, wherein alkyl is substituted with 0 to 1 OH;
$R^{104}$ is —$C_{1-3}$alkyl, —$C_{0-3}$alkylene-$C_{3-6}$cycloalkyl, —$C_{0-3}$alkylene-$R^{105}$, or —$C_{1-3}$alkylene-$R^{106}$,
wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, —$SO_2$—N$(R^N)_2$, —C(O)—N$(R^N)_2$, —N(C=O)($R^N$), and —N$(R^N)_2$, and
wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —N$(R^N)_2$, $R^{105}$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1-CN, and
0 to 1 —$OR^O$;
$R^{106}$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;
each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$, $Z^2$, and $Z^3$ are each —$CR^Z$, or
one of $Z^1$, $Z^2$, and $Z^3$ is N and the other two are —$CR^Z$; and
each $R^Z$ is independently H, F, $C_1$, or —$CH_3$,
and wherein
each of $R^{30}$ is H, or one of $R^{30}$ is H and the other is —$S(=O)_2OH$;
$R^{31}$ is —O-glucuronide;
$R^{32}$ is —O-glucuronide;
$R^{33}$ is —OH, —O-glucuronide, or —O—$S(=O)_2OH$;
each of $R^{34}$ and $R^{35}$ is OH, or one of $R^{34}$ and $R^{35}$ is OH, and the other $R^3$ and $R^4$ is a moiety of

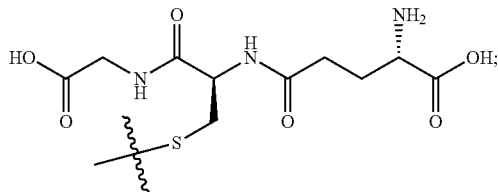 [SMILES: *SC[C@H](NC(=O)CC[C@H](N)C(=O)O)C(=O)NCC(=O)O]

$R^{36}$ is a moiety of

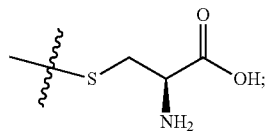

and
$R^{37}$ is —O-glucuronide.

In some embodiments, the present invention provides a compound of Formula Z1 or a pharmaceutically acceptable salt thereof. In some further embodiments, each of $R^{30}$ is H. In other further embodiments, one $R^{30}$ is H and the other is —$S(=O)_2OH$.

In some embodiments, the present invention provides a compound of Formula Z2 or a pharmaceutically acceptable salt thereof. The $R^{31}$ substitution replaces a hydrogen on the part of Formula Y2 within the dotted rectangle shape. In some further embodiments, $R^{31}$ is a moiety having the structure of

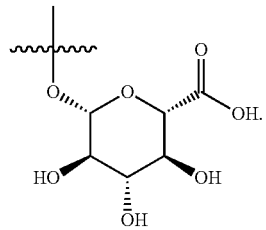 [SMILES: *O[C@@H]1O[C@H](C(=O)O)[C@@H](O)[C@H](O)[C@H]1O]

In some embodiments, the present invention provides a compound of Formula Z3 or a pharmaceutically acceptable salt thereof. The $R^{32}$ substitution replaces a hydrogen on the part of Formula Z3 within the dotted rectangle shape. In some further embodiments, $R^{32}$ is a moiety having the structure of

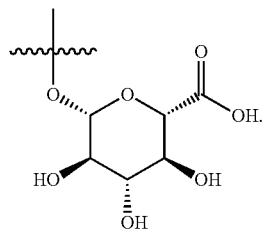 [SMILES: *O[C@@H]1O[C@H](C(=O)O)[C@@H](O)[C@H](O)[C@H]1O]

In some embodiments, the present invention provides a compound of Formula Z4 or a pharmaceutically acceptable salt thereof. The $R^{33}$ substitution replaces a hydrogen on the part of ring A, the benzo or the piperidine ring within the dotted rectangle shape. In some embodiments, $R^{33}$ is —OH. In some other embodiments, $R^{33}$ is —O—$S(=O)_2OH$. In yet other embodiments, $R^{33}$ is —O-glucuronide, for example, a moiety having the structure of

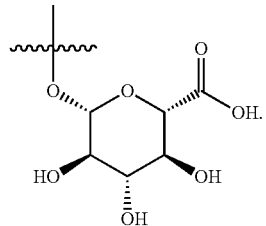 [SMILES: *O[C@@H]1O[C@H](C(=O)O)[C@@H](O)[C@H](O)[C@H]1O]

In some embodiments, the present invention provides a compound of Formula Z5 or a pharmaceutically acceptable salt thereof. In some embodiments, each of $R^{34}$ and $R^{35}$ is OH. In some other embodiments, one of $R^{34}$ and $R^{35}$ is OH, and the other $R^3$ and $R^4$ is a moiety of

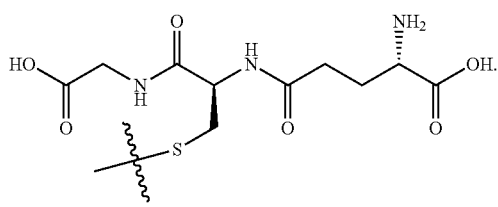 [SMILES: *SC[C@H](NC(=O)CC[C@H](N)C(=O)O)C(=O)NCC(=O)O]

In some embodiments, the present invention provides a compound of Formula Z6 or a pharmaceutically acceptable salt thereof.

In some embodiments, the present invention provides a compound of Formula Z7 or a pharmaceutically acceptable salt thereof. In some further embodiments, $R^{37}$ is a moiety having the structure of

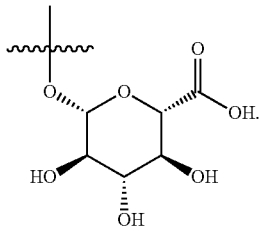 [SMILES: *O[C@@H]1O[C@H](C(=O)O)[C@@H](O)[C@H](O)[C@H]1O]

In some embodiments, the present invention provides a compound of Formula Z8 or a pharmaceutically acceptable salt thereof.

In some embodiments, the present invention provides a compound of Formula Z9 or a pharmaceutically acceptable salt thereof. Both of the OH groups are substituted on the part within the dotted oval shape.

In some embodiments, the present invention provides a compound of Formula Z10 or a pharmaceutically acceptable salt thereof.

In some embodiments, the present invention provides a compound of Formula Z11 or a pharmaceutically acceptable salt thereof.

In some embodiments, the present invention provides a compound of Formula Z12 or a pharmaceutically acceptable salt thereof.

In some embodiments, the present invention provides a compound of Formula Z13 or a pharmaceutically acceptable salt thereof.

In a further embodiment of a compound of any one of Formula Y2 to Y13 and Formula Z2 to Z13, or a pharmaceutically acceptable salt thereof, ring A is a phenyl ring.

In a further embodiment of a compound of any one of Formula Y2 to Y13 and Formula Z2 to Z13, or a pharmaceutically acceptable salt thereof, ring A is a pyridine ring.

In some embodiments, one or more of the metabolite compounds, or salts thereof, are prepared by metabolism of its parent compound, e.g., a compound of Formula PA-I or PA-III or a pharmaceutically salt thereof (for example, in a mammal or a mammalian cell environment); and the metabolite compounds thus prepared are substantially isolated. In some other embodiments, one or more of the metabolite compounds, or salts thereof, are prepared by chemical synthesis other than metabolism of a compound of Formula PA-I or PA-III or a pharmaceutically salt thereof (for example, in a mammal or a mammalian cell environment) and the synthesized metabolite compounds are substantially isolated. A compound of Formula PA-I or PA-III or its salt can be prepared, for example, by the methods described in U.S. Pat. No. 10,676,465.

The term "alkyl", as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl and hexyl.

The term "alkylene", as used herein, means a straight or branched chain divalent hydrocarbon group of formula —$C_nH_{2n}$—. Non-limiting examples include ethylene, and propylene.

The term "cycloalkyl", as used herein, means a cyclic, monovalent hydrocarbon group of formula —$C_nH_{(2n-1)}$ containing at least three carbon atoms. Non-limiting examples include cyclopropyl, cyclobutyl, cyclopentyl and cyclohexyl.

The term "halogen", as used herein, refers to fluoride, chloride, bromide, or iodide.

The term "heterocycloalkyl", as used herein, refers to a cycloalkyl group in which one or more of the ring methylene groups (—$CH_2$—) has been replaced with a group selected from —O—, —S— or nitrogen, wherein the nitrogen may provide a point of attachment or may be substituted as provided within each embodiment. Where nitrogen provides a point of attachment, a structural drawing of a heterocycloalkyl would have an hydrogen on said nitrogen. Generally, the heterocycloalkyl may be substituted with 0 to 2 substituents as valency allows independently selected from oxo, —CN, halogen, alkyl and —Oalkyl and the alkyl may be further substituted. One will note that when there is 0 substitution, the heterocycloalkyl is unsubstituted.

The term "heteroaryl", as used herein, refers to a monocyclic aromatic hydrocarbon containing from 5 to 6 carbon atoms in which at least one of the ring carbon atoms has been replaced with a heteroatom selected from oxygen, nitrogen and sulfur. Such a heteroaryl group may be attached through a ring carbon atom or, where valency permits, through a ring nitrogen atom. Generally, the heteroaryl may be substituted with 0 to 2 substituents as valency allows independently selected from halogen, OH, alkyl, O-alkyl, and amino (e.g., $NH_2$, NHalkyl, N(alkyl)$_2$), and the alkyl may be further substituted. One will note that when there is 0 substitution, the heteroaryl is unsubstituted.

As used herein, a wavy line, "⁓" denotes a point of attachment of a substituent to another group.

As used herein, when a bond to a substituent is shown to cross a ring (or a bond connecting two atoms in a ring), then such substituent may be bonded to any of the ring-forming atoms in that ring that are substitutable (i.e., any ring forming atom that is bonded to one or more hydrogen atoms), unless otherwise specified or otherwise implicit from the context. For example, as shown in Formula Mt-1 below, $R^3$ may be bonded to any ring-forming carbon atom of the piperidine ring that is substitutable (i.e., any one of the carbon ring-forming atoms of the piperidine ring). For another example, as shown in Moiety Mt-2 below, $R^3$ may be bonded to any ring-forming carbon atom of the piperidine ring that is substitutable (i.e., any one of the carbon atoms of a —$CH_2$—$CH_2$— group of the piperidine ring); but not on the ring-forming carbon atom of the piperidine ring that is bonded to the OH group because that ring-forming carbon is not substitutable.

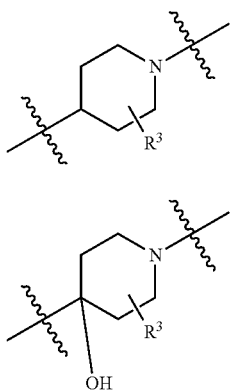

Mt-1

Mt-2

The present invention further includes a pharmaceutical composition comprising a compound (or a metabolite) of the invention, or pharmaceutically acceptable salt thereof, and at least one pharmaceutically acceptable carrier. In some further embodiments, the compound (or the metabolite) of the invention or pharmaceutically acceptable salt thereof is present in the composition in an amount greater than about 0.01%, 0.05%, 0.08%, 0.1%, 0.5%, or 1.0% by weight As used herein, "pharmaceutically acceptable carrier" is meant to refer to any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Methods

The present invention further relates to a method of preventing or treating a disease or disorder in a human by administering to the human a therapeutically effective amount of a metabolite of the invention, or a pharmaceutically acceptable salt thereof, wherein the disease or disorder is selected from the group consisting of T1D, T2DM, pre-diabetes, idiopathic T1D, LADA, EOD, YOAD, MODY, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, sleep apnea, obesity, eating disorders, weight gain from use of other agents, excessive sugar craving, dyslipidemia, hyperinsulinemia, NAFLD, NASH, fibrosis, NASH with fibrosis, cirrhosis, hepatocellular carcinoma, cardiovascular disease, atherosclerosis, coronary artery disease, peripheral vascular disease, hypertension, endothelial dysfunction, impaired vascular compliance, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, Polycystic Ovary Syndrome, and addiction. The human may have or be at risk of having the disease or disorder.

The term "treating", "treat", or "treatment" in connection with a disease or disorder as used herein embraces palliative treatment, including reversing, relieving, alleviating, eliminating, or slowing the progression of the disease or disorder, or one or more symptoms of the disease or disorder, or any tissue damage associated with one or more symptoms of the disease or disorder.

The term "prevention" or "preventing" in connection with a disease or disorder refers to delaying or forestalling the onset or development of the disease or disorder a period of time from minutes to indefinitely. The term also includes prevention of the appearance of symptoms of the disease or disorder. The term further includes reducing risk of developing the disease or disorder.

The terms "effective amount" or "therapeutically effective amount" refer to an amount of a metabolite according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a metabolite according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Administration of the metabolites of the invention, or their pharmaceutically acceptable salts, can be carried out via any of the accepted modes of administration of agents for serving similar utilities. The pharmaceutical compositions of the invention can be prepared by combining a metabolite of the invention, or a pharmaceutically acceptable salt thereof, with an appropriate pharmaceutically acceptable carrier and, in specific embodiments, are formulated into preparations in solid, semi solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral, sublingual, buccal, rectal, vaginal, and intranasal. In one embodiment, pharmaceutical compositions of the invention are tablets. In another embodiment, pharmaceutical compositions of the invention are injection (intramuscular (IM) or intraperitoneal (IP)). Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000).

The composition to be administered will, in any event, contain a therapeutically effective amount of a compound of the invention, or a pharmaceutically acceptable salt thereof, for treatment of a disease or disorder of interest in accordance with the teachings described herein.

The present invention further relates to a method of detecting or confirming the administration of Compound 1 to a patient comprising identifying a metabolite of Compound 1 (e.g. a metabolite of the invention or Compound M3), or salt thereof, in a biological sample obtained from the patient. In some embodiments, the biological sample is derived from plasma, urine, or feces.

The present invention further relates to a method of measuring the rate of metabolism of Compound 1 in a patient comprising measuring the amount of a metabolite, or salt thereof, in the patient at one or more time points after administration of Compound 1.

The present invention further relates to a method of determining the prophylactic or therapeutic response of a patient to Compound 1 in the treatment of a disease or disorder comprising measuring the amount of a metabolite of Compound 1 (e.g. a metabolite of the invention or compound M3), or salt thereof, in the patient at one or more time points after administration of Compound 1.

The present invention further relates to a method of optimizing the dose of Compound 1 for a patient in need of treatment with Compound 1 comprising measuring the amount of a metabolite of Compound 1 (including, e.g. a metabolite of the invention or compound M3) or salt thereof, in the patient at one or more time points after administration of Compound 1. The amount of metabolite may be indicative of the rate at which the patient metabolizes Compound 1. Patients who metabolize Compound 1 more quickly or more effectively than other patients may form higher amounts of metabolite and potentially require higher doses of Compound 1, or additional doses, compared with patients who metabolize Compound 1 more slowly. Patients who metabolize Compound 1 less quickly or less effectively than other patients may form lower amounts of metabolite and potentially require lower doses of Compound 1, or fewer doses, compared with patients who metabolize Compound 1 more quickly. Accordingly, the method of optimizing the dose of Compound 1 may further include determining whether the measured amounts of metabolite are higher or lower than average, and adjusting the dosage of Compound 1 accordingly.

Measuring the amount of metabolite, or salt thereof, in a patient can be carried out by obtaining a biological sample from the patient and measuring the amount of metabolite, or salt thereof, in the sample. In some embodiments, the sample is blood. In other embodiments, the sample is plasma. In other embodiments, the sample is urine. In other embodiments, the sample is feces.

The term "patient" is meant to refer to a human or another mammal such as laboratory animals and household pets (e.g., cats, dogs, swine, cattle, sheep, goats, horses, rabbits), and non-domestic animals such as non-human primates, mammalian wildlife, and the like, that are in need of therapeutic or preventative treatment for a disease or disorder described herein.

Combination Therapies One or more additional pharmaceutical agents can be used in combination with the compounds, salts, and compositions of the present invention for preventing or treating a disease or disorder described herein, e.g., in a human patient. In some embodiments, the composition of the invention further comprises one or more additional therapeutic agents. In some embodiments, the composition of the invention further comprises one to three additional therapeutic agents.

In one embodiment, the compounds of this invention are administered with an antidiabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this invention are administered with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this invention are administered with an agent to treat NASH including but not limited to PF-05221304, an FXR agonist (e.g., obeticholic acid), a PPAR a/δ agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037MO), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

In some embodiments, a DGAT2 inhibitor (used in the combination of the invention) is one selected from those described in U.S. Pat. No. 10,071,992, the disclosure of which is hereby incorporated herein by reference in its entirety. In some embodiment, a DGAT2 inhibitor (used in the combination of the invention) is selected from:
(S)-2-(5-((3-Ethoxy-5-fluoropyridin-2-yl)oxy)pyridin-3-yl)-N-(tetrahydrofuran-3-yl)pyrimidine-5-carboxamide;
N-(2-cyanopropan-2-yl)-2-(5-((3-ethoxypyridin-2-yl)oxy)pyridin-3-yl)pyrimidine-5-carboxamide;
2-(5-((3-ethoxypyridin-2-yl)oxy)pyridin-3-yl)-N-(3-methyl-1,1-dioxidotetrahydrothiophen-3-yl)pyrimidine-5-carboxamide;
2-(5-((3-ethoxypyridin-2-yl)oxy)pyridin-3-yl)-N-(1-hydroxy-2-methylpropan-2-yl)pyrimidine-5-carboxamide;
(S)-2-(5-((3-ethoxypyridin-2-yl)oxy)pyridin-3-yl)-N-(tetrahydrofuran-3-yl)pyrimidine-5-carboxamide;
(S)-2-(5-((3-ethoxypyridin-2-yl)oxy)pyridin-3-yl)-N-(3-(hydroxymethyl)tetrahydrofuran-3-yl)pyrimidine-5-carboxamide;
(R)-2-(5-((3-ethoxypyridin-2-yl)oxy)pyridin-3-yl)-N-(3-(hydroxymethyl)tetrahydrofuran-3-yl)pyrimidine-5-carboxamide;
2-(5-((3-ethoxypyridin-2-yl)oxy)pyridin-3-yl)-N-(2-methyl-1-(methylsulfonyl)propan-2-yl)pyrimidine-5-carboxamide;
(S)-2-(5-((3-(2-fluoroethoxy)pyridin-2-yl)oxy)pyridin-3-yl)-N-(tetrahydrofuran-3-yl)pyrimidine-5-carboxamide;
3-(5-((3-ethoxypyridin-2-yl)oxy)pyridin-3-yl)-N-(1-hydroxy-2-methylpropan-2-yl)-1,2,4-triazine-6-carboxamide;
N-(1,3-dihydroxy-2-methylpropan-2-yl)-2-(5-((3-ethoxypyridin-2-yl)oxy)pyridin-3-yl)pyrimidine-5-carboxamide;
(S)-3-(5-((3-ethoxypyridin-2-yl)oxy)pyridin-3-yl)-N-(tetrahydrofuran-3-yl)-1,2,4-triazine-6-carboxamide;
N-(1,1-dioxidotetrahydrothiophen-3-yl)-2-(5-((3-ethoxypyridin-2-yl)oxy)pyridin-3-yl)pyrimidine-5-carboxamide;
(R)-2-(5-((3-ethoxypyridin-2-yl)oxy)pyridin-3-yl)-N-(tetrahydrofuran-3-yl)pyrimidine-5-carboxamide; and
2-(5-((3-ethoxypyrazin-2-yl)oxy)pyridin-3-yl)-N-(1-hydroxy-2-methylpropan-2-yl)pyrimidine-5-carboxamide,
or a pharmaceutically acceptable salt thereof.

In some embodiment, a DGAT2 inhibitor (used in the combination of the invention) is
(R)-2-(5-((3-ethoxypyridin-2-yl)oxy)pyridin-3-yl)-N-(3-(hydroxymethyl)tetrahydrofuran-3-yl)pyrimidine-5-carboxamide;
(S)-2-(5-((3-ethoxypyridin-2-yl)oxy)pyridin-3-yl)-N-(tetrahydrofuran-3-yl)pyrimidine-5-carboxamide; or
(S)-2-(5-((3-ethoxypyridin-2-yl)oxy)pyridin-3-yl)-N-(3-(hydroxymethyl)tetrahydrofuran-3-yl)pyrimidine-5-carboxamide,
or a pharmaceutically acceptable salt thereof.

In some embodiment, a DGAT2 inhibitor (used in the combination of the invention) is
(S)-2-(5-((3-ethoxypyridin-2-yl)oxy)pyridin-3-yl)-N-(tetrahydrofuran-3-yl)pyrimidine-5-carboxamide,

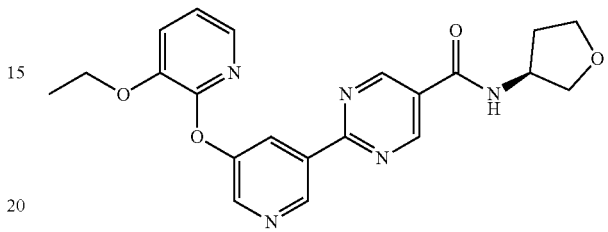

or a pharmaceutically acceptable salt thereof.

In certain embodiments, a metabolite disclosed herein, or a pharmaceutically acceptable salt thereof, is combined with two, three, four or more additional therapeutic agents. The two, three four or more additional therapeutic agents can be different therapeutic agents selected from the same class of therapeutic agents, or they can be selected from different classes of therapeutic agents.

When different components/APIs (active pharmaceutical ingredients) in a combination of the present invention are administered together, such administration is simultaneous. In some embodiments, simultaneous administration of drug combinations is used. For a separate administration, each component/API may be administered in any order and each of them can be administered in an independent frequency or dose regimen. In some embodiments, such administration be oral. In some embodiments, such administration can be oral and simultaneous. When different components/APIs are administered separately (including, for example, sequentially), the administration of each may be by the same or by different methods. In some embodiments, administration of one component/API is oral but administration of another component/API is not oral (for example, is injectable).

In certain embodiments, when a metabolite disclosed herein is combined with one or more additional therapeutic agents as described above, the components of the composition are administered as a simultaneous or separate (e.g. sequential) regimen. When administered sequentially, the combination may be administered in two or more administrations.

In certain embodiments, a metabolite disclosed herein is combined with one or more additional therapeutic agents in a unitary dosage form for simultaneous administration to a patient, for example as a solid dosage form for oral administration (e.g., a fixed dose combination tablet).

In certain embodiments, a metabolite disclosed herein is administered with one or more additional therapeutic agents. Co-administration of a metabolite disclosed herein, or a pharmaceutically acceptable salt thereof, with one or more additional therapeutic agents generally refers to simultaneous or separate (e.g. sequential) administration of a compound disclosed herein and one or more additional therapeutic agents, such that therapeutically effective amounts of the metabolite and one or more additional therapeutic agents are both present in the body of the patient.

Co-administration includes administration of unit dosages of the metabolites disclosed herein before or after administration of unit dosages of one or more additional therapeutic agents, for example, administration of the metabolites disclosed herein within seconds, minutes, or hours of the administration of one or more additional therapeutic agents. For example, in some embodiments, a unit dose of a metabolite disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a metabolite disclosed herein within seconds or minutes. In some embodiments, a unit dose of a metabolite disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a metabolite disclosed herein.

Pharmaceutical Formulations and Dosage Forms

The pharmaceutical compositions disclosed herein can be prepared by methodologies well known in the pharmaceutical art. For example, in certain embodiments, a pharmaceutical composition intended to be administered by injection can prepared by combining a metabolite of the invention with sterile, distilled water so as to form a solution. In some embodiments, a surfactant is added to facilitate the formation of a homogeneous solution or suspension.

Surfactants are compounds that non-covalently interact with the compound of the invention so as to facilitate dissolution or homogeneous suspension of the compound in the aqueous delivery system.

The metabolites of the invention, or their pharmaceutically acceptable salts, can be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1: Investigation of Metabolism of Compound 1 (in the Form of its Tris Salt) in a Clinical Study Study Design and Objectives The metabolism of Compound 1 (dosed in the form of its tris salt) was investigated in humans. A primary objective of this study was to gain a preliminary assessment of the human metabolites of Compound 1 using plasma after repeat dosing (multi-dose). Plasma samples from nine human subjects following oral administration of 120 mg BID for 28 days in a clinical study were examined for metabolites.

Materials and Methods

Plasma Sample Preparation

Individual subject's plasma (from nine human subjects with 120 mg BID dose Day 28) were pooled in proportion to the time period represented by each to yield a pool for profiling that was representative of the AUC (0-12 hr) according to the method of Hamilton et al. [Hamilton R A, Garnett W R, Kline B J. Determination of a mean valproic acid serum level by assay of a single pooled sample. Clin Pharmacol Ther 1981; 29(3):408-13] Pooled plasma time points were first prepared by aliquoting equal amounts (1.0 mL) of plasma from each subject prior to making a single Hamilton pool. Blank plasma pools were made by taking equal aliquots of predose samples. To a 2 mL aliquot of each pooled plasma sample was added 6 mL of acetonitrile and then mixed. Protein precipitated samples were centrifuged for 5 minutes at 2000×g and the supernatants were transferred to other clean 15 mL centrifuge tubes. Samples were dried using an evaporative centrifuge set to 37° C. Samples were reconstituted using 0.2 mL of 5:95 acetonitrile:water and analyzed by HPLC/UV/MS.

HPLC/UV/MS Sample Analysis

Reconstituted samples were analyzed by positive ion HPLC/UV/MS using a Thermo Orbitrap Elite mass spectrometer operating in positive ion electrospray mode. Xcalibur software version 3.0.63 was used to control the HPLC/UV/MS system. Full scan data were collected at 15,000 resolution. Data dependent product ion scans of the two most intense ions found in the full scan were obtained at 15,000 resolution. The dynamic exclusion function was used with a 10 second exclusion duration after 3 successive product ion scans with an early exclusion if the precursor ion fell below a signal to noise ratio of 20. The HPLC system consisted of an Accela quaternary solvent delivery pump, an Accela autoinjector, an Accela PDA Plus photodiode array detector (Thermo Electron Corporation). Chromatography was performed on a Phenomenex Kinetex column (2.1 mm×100 mm, 2.6 µm) at 45° C. using a HotSleeve column heater (Analytical Sales and Services). The mobile phase was composed of 0.1% formic acid in water (solvent A) and acetonitrile (solvent B). The solvent delivery gradient program was as follows:

| Time min | % A | % B | Flow Rate (µL/min) |
|---|---|---|---|
| 0.0 | 95 | 5 | 400 |
| 0.5 | 95 | 5 | 400 |
| 16.0 | 45 | 55 | 400 |
| 18.0 | 5 | 95 | 400 |
| 19.0 | 5 | 95 | 400 |
| 19.1 | 95 | 5 | 400 |
| 20.0 | 95 | 5 | 400 |

Results and Analyses

The biotransformation of Compound 1 was studied in the human plasma samples from the Day 28 120 mg BID multiple dose group. An examination of the HPLC/UV (FIG. 1) and mass spectra of Compound 1 was used to determine metabolic pathways and metabolite structures. A total of 8 metabolites were observed in plasma (see table below). O-debenzylation to Metabolite/Compound M2 was the major circulating metabolite. Seven additional minor metabolites observed in circulation were a single hydroxylation (Compound M4), oxidation and ring opening of the piperidine ring (Compound 574a), oxidation and ring opening of the oxetane ring (Compound 574b), N-dealkylation (Compound M3), acyl glucuronide (Compound M1), and two O-glucuronides (Compounds 748a and 748b). Each of the minor metabolites individually represented less than 10% of the total circulating drug related material based on UV response.

| Compound identification number | m/z | $T_r$ (min) | Plasma Extracts |
| --- | --- | --- | --- |
| M2 | 423.2027 | 4.05 | +++ |
| 748a | 748.2625 | 6.90 | + |
| 748b | 748.2625 | 8.25 | + |
| M3 | 312.1507 | 8.50 [1] | + |
| 574a | 574.2460 | 8.50 [1] | + |
| 574b | 574.2460 | 9.70 | + |
| M4 | 572.2304 | 9.75 [2] | + |
| M1 | 732.2675 | 9.75 [2] | + |
| Compound 1 | 556.2355 | 10.65 | +++ |

+: Detected by Mass Spectrometry and Minor UV Peak
++: Detected by Mass Spectrometry and Moderate UV Peak
+++: Detected by Mass Spectrometry and Major UV Peak
[1]: UV Peaks of M3 and 574a are not Resolved.
[2]: UV Peaks of M4 and M1 are not Resolved.

A. Compound 1 (m/z 556.2355 Theoretical; m/z 556.2355 Observed).

Figure 3:
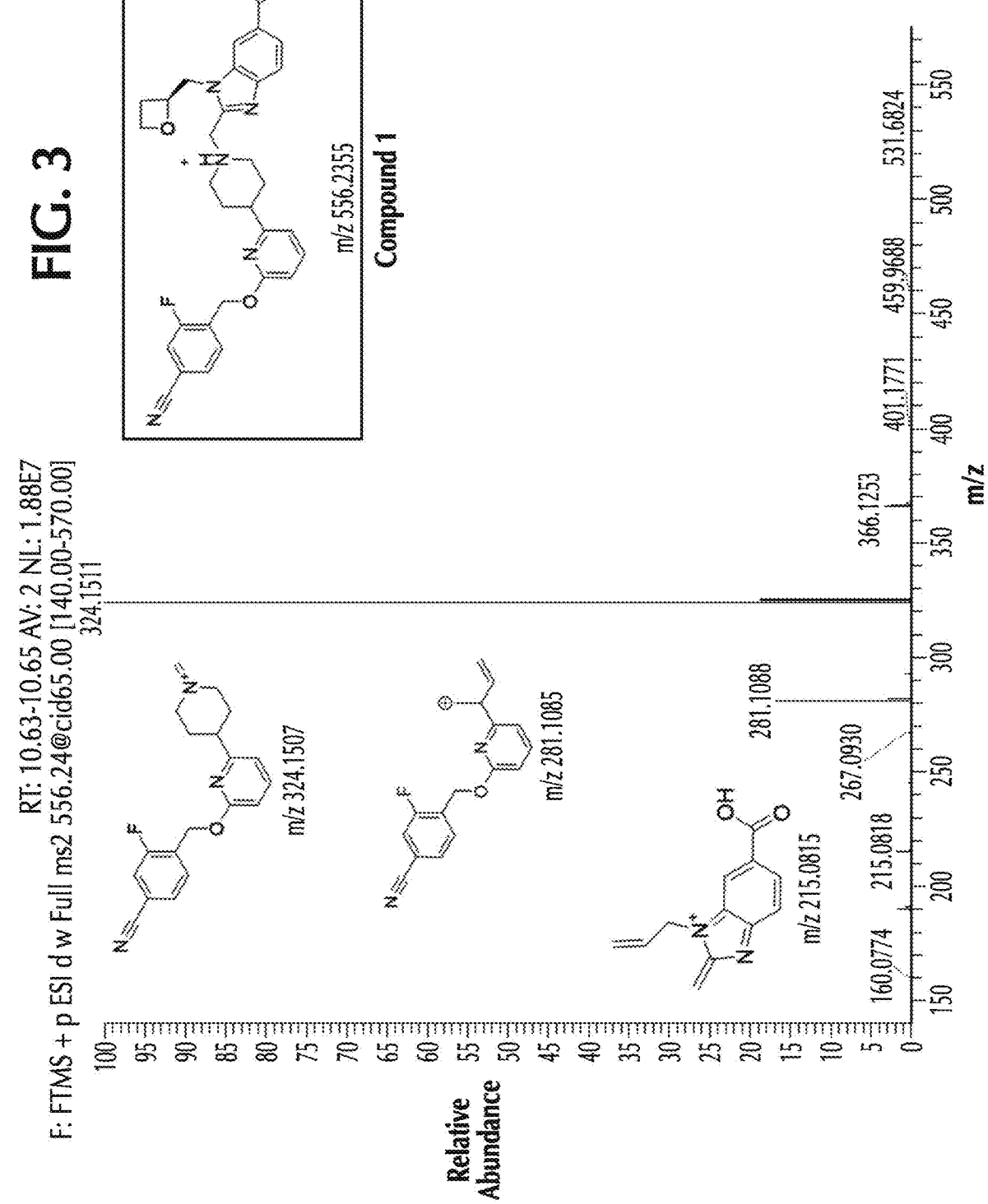
FIG. 3 shows product ion scan of m/z 556.2355 in pooled human plasma from patients multiply dosed with Compound 1 (120 mg oral BID, Day 28). Tr=10.65 min
Figure 4:
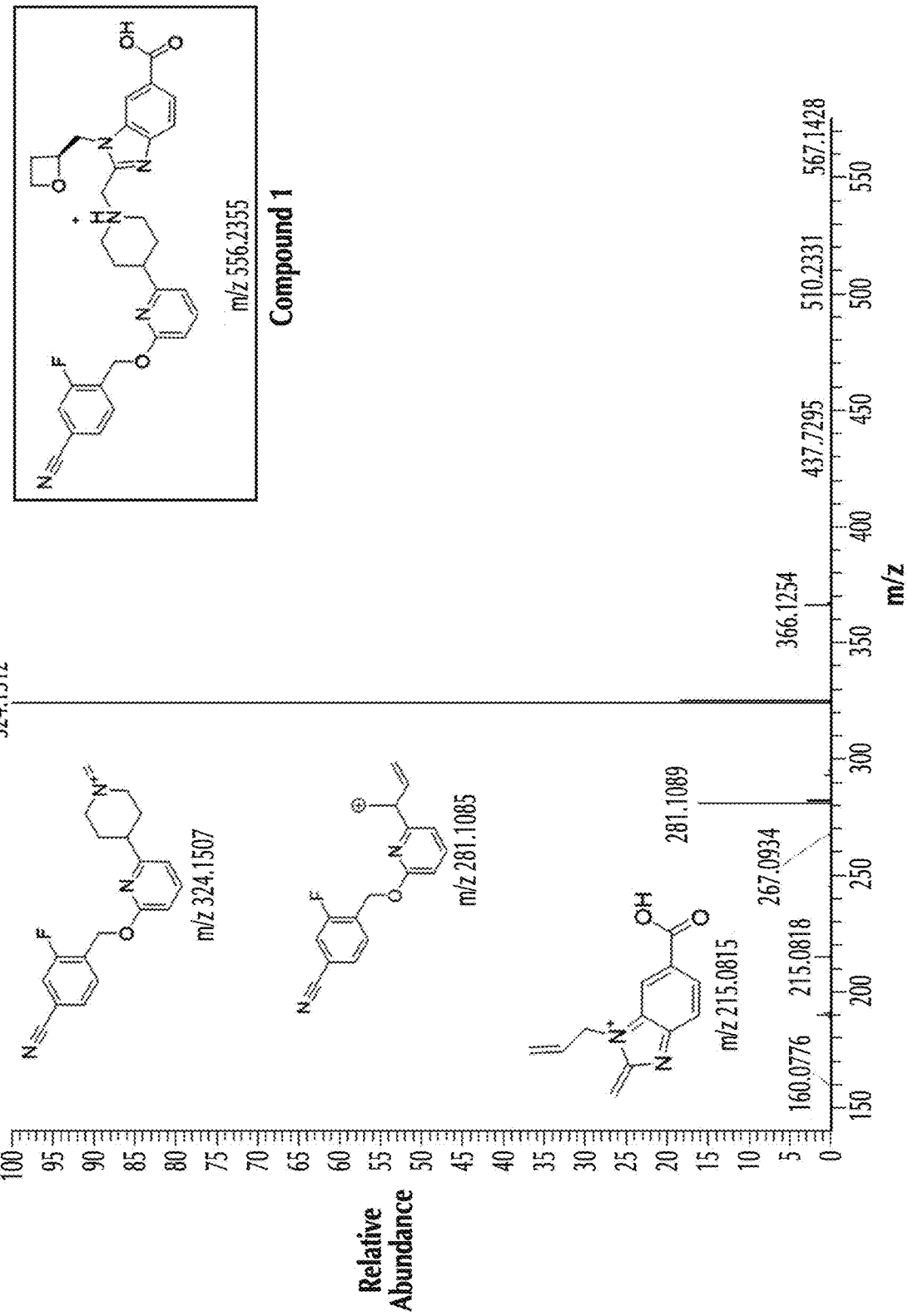
FIG. 4 shows product ion spectrum of m/z 556.2355 for synthetic standard Compound 1. Tr=10.65 min

Compound 1 had a retention time of ~10.65 min on HPLC in human plasma and has a protonated molecular ion at m/z 556.2355. Its $MS^2$ product ion spectrum (Tandem mass spectrometry) for m/z 556 showed diagnostic fragment ions at m/z 324, 281, and 215 (FIG. 3). The ion at m/z 324 resulted from the neutral loss of the (S)-1-(oxetan-2-ylmethyl)-1H-benzo[d]imidazole-6-carboxylic acid moiety. The ion at m/z 281 resulted from cleavage of the piperidine ring with charge retention on the 4-(((6-(but-3-en-2-yl)pyridin-2-yl)oxy)methyl)-3-fluorobenzonitrile moiety. The ion at m/z 215 resulted from charge retention on the (S)-2-methyl-1-(oxetan-2-ylmethyl)-1H-benzo[d]imidazole-6-carboxylic acid moiety followed by a neutral loss of methanol from the oxetane ring. The product ion spectrum of Compound 1 in human plasma is comparable to the product ion spectrum of a synthetic standard Compound 1 (FIG. 4).

Compound 1

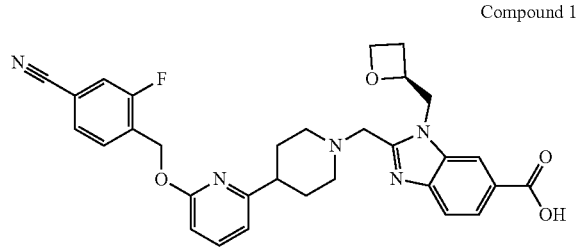 [SMILES: N#Cc1ccc(COc2cccc(C3CCN(Cc4nc5ccc(C(=O)O)cc5n4C[C@@H]4CCO4)CC3)n2)c(F)c1]

B. Metabolite/Compound M2 (423, m/z 423.2027 Theoretical; m/z 423.2031 Observed).

Figure 5:
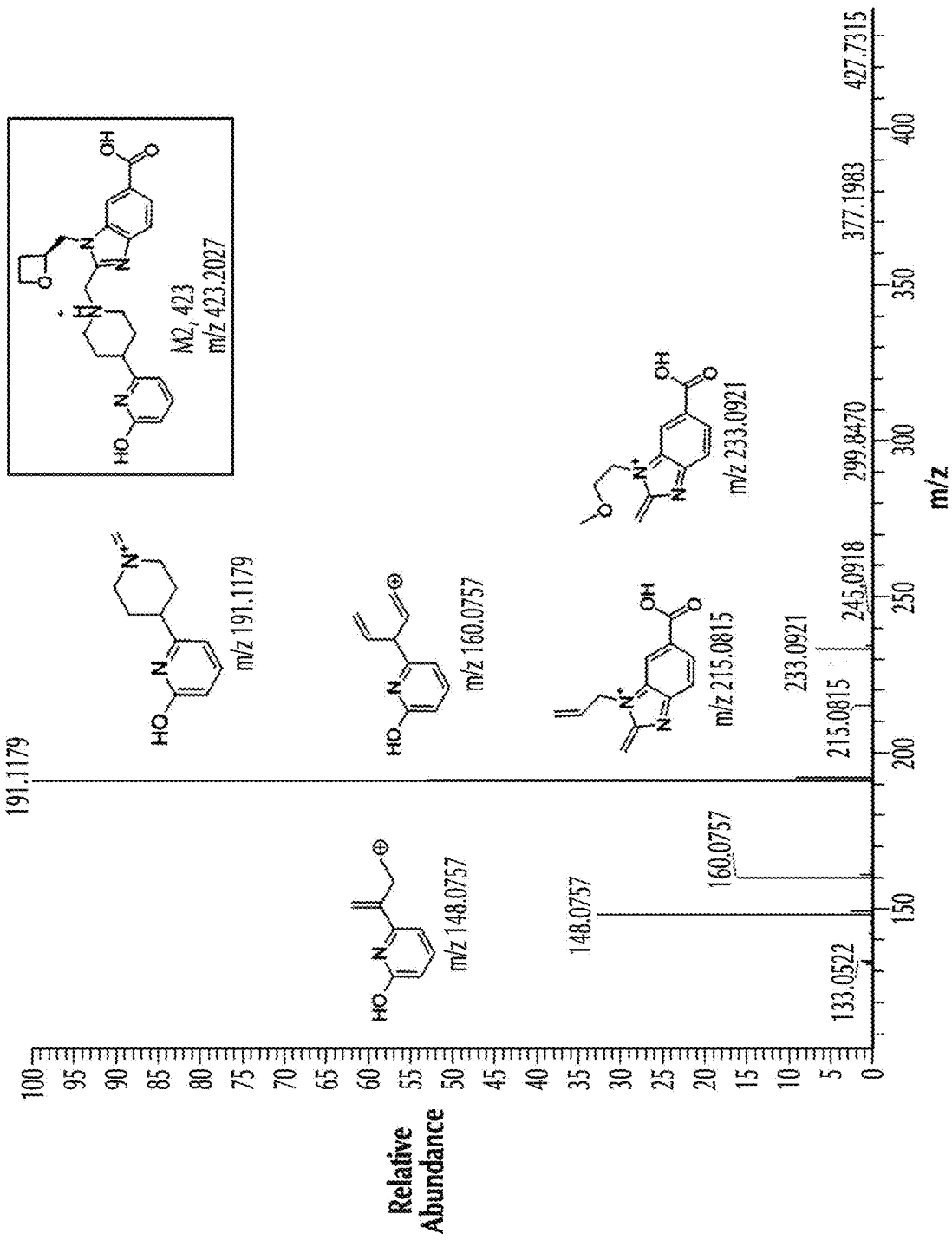
FIG. 5 shows product ion scan of Metabolite M2 at m/z 423.2027 in human plasma pool extract of patients dosed with Compound 1 (Day 28 120 mg oral BID). $T_r$=4.05 min
Figure 6:
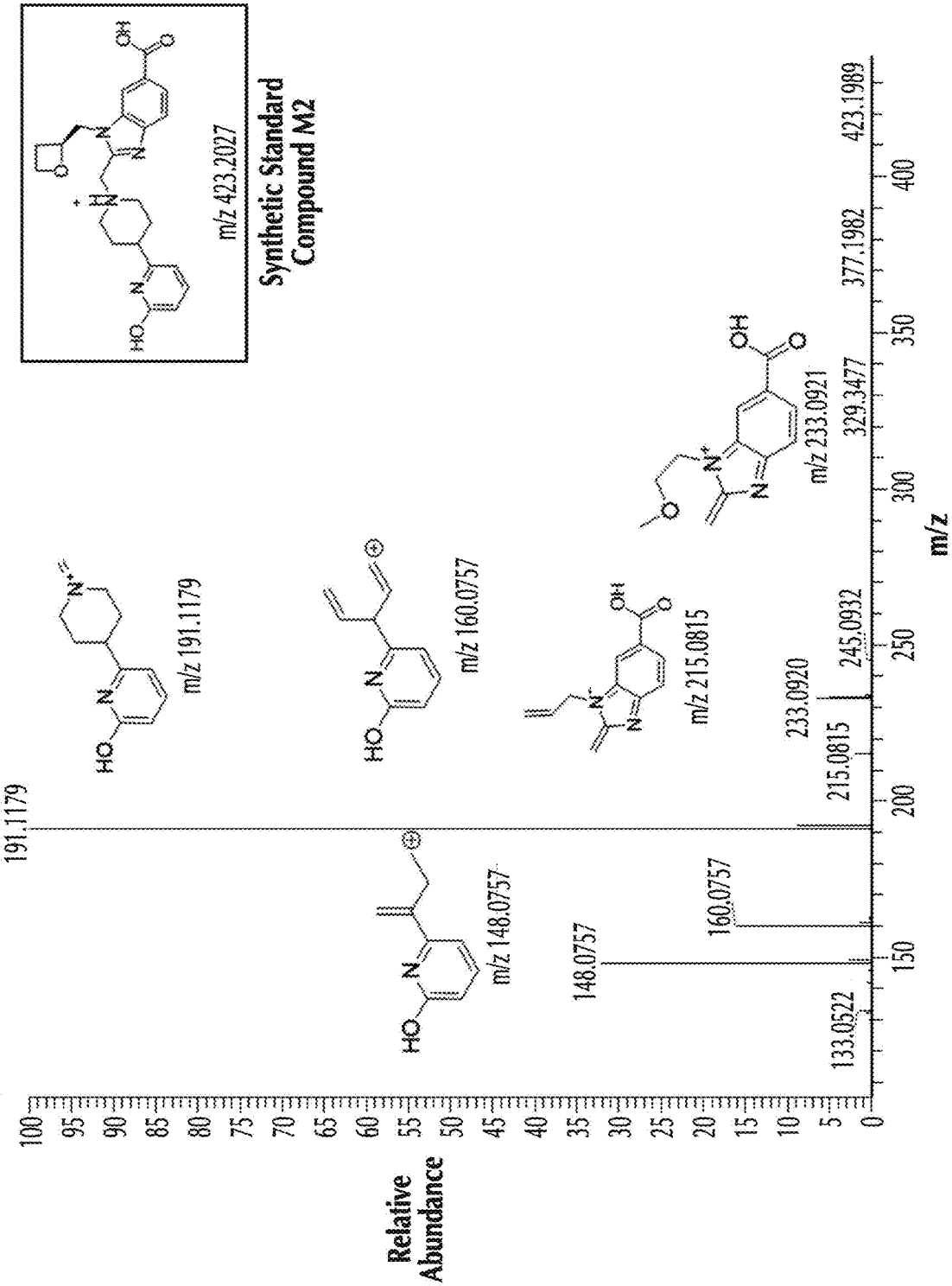
FIG. 6 shows product ion scan at m/z 423.2027 for Synthetic Standard Compound M2. Tr=4.05 min

Metabolite/Compound M2 was observed as a major metabolite in human plasma. Metabolite M2 had a retention time of ~4.05 min on HPLC and a protonated molecular ion at m/z 423.2031, which was 133 Da less than Compound 1, suggesting a loss of the 3-fluoro-4-methylbenzonitrile moiety. The product ion spectrum for M2 contained the fragment ions at m/z 233, 215, 191, 160, and 148 (FIG. 5). The ions at m/z 191 and 148, which were both 133 Da less that parent ions 324 and 281, are consistent with the loss of the 3-fluoro-4-methylbenzonitrile moiety. The ion at m/z 215, which was observed in the parent spectrum, also resulted in charge retention on the (S)-2-methyl-1-(oxetan-2-ylmethyl)-1H-benzo[d]imidazole-6-carboxylic acid moiety followed by a neutral loss of methanol from the oxetane ring. Metabolite/Compound M2 was compared to a synthetic standard Compound M2 and was found to have the same retention time and product ion spectrum (FIG. 6).

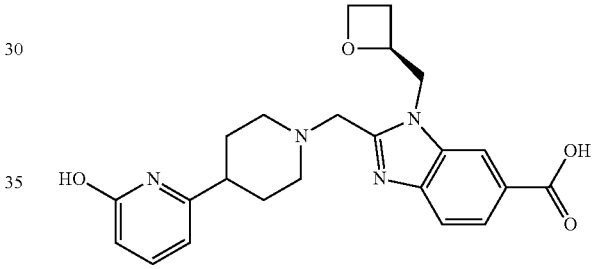

M2, Chemical Name: (S)-2-((4-(6-hydroxypyridin-2-yl)piperidin-1-yl)methyl)-1-(oxetan-2-ylmethyl)-1H-benzo[d]imidazole-6-carboxylic acid C. Metabolite 748a (m/z 748.2625 Theoretical; m/z 748.2628 Observed)

Figure 7:
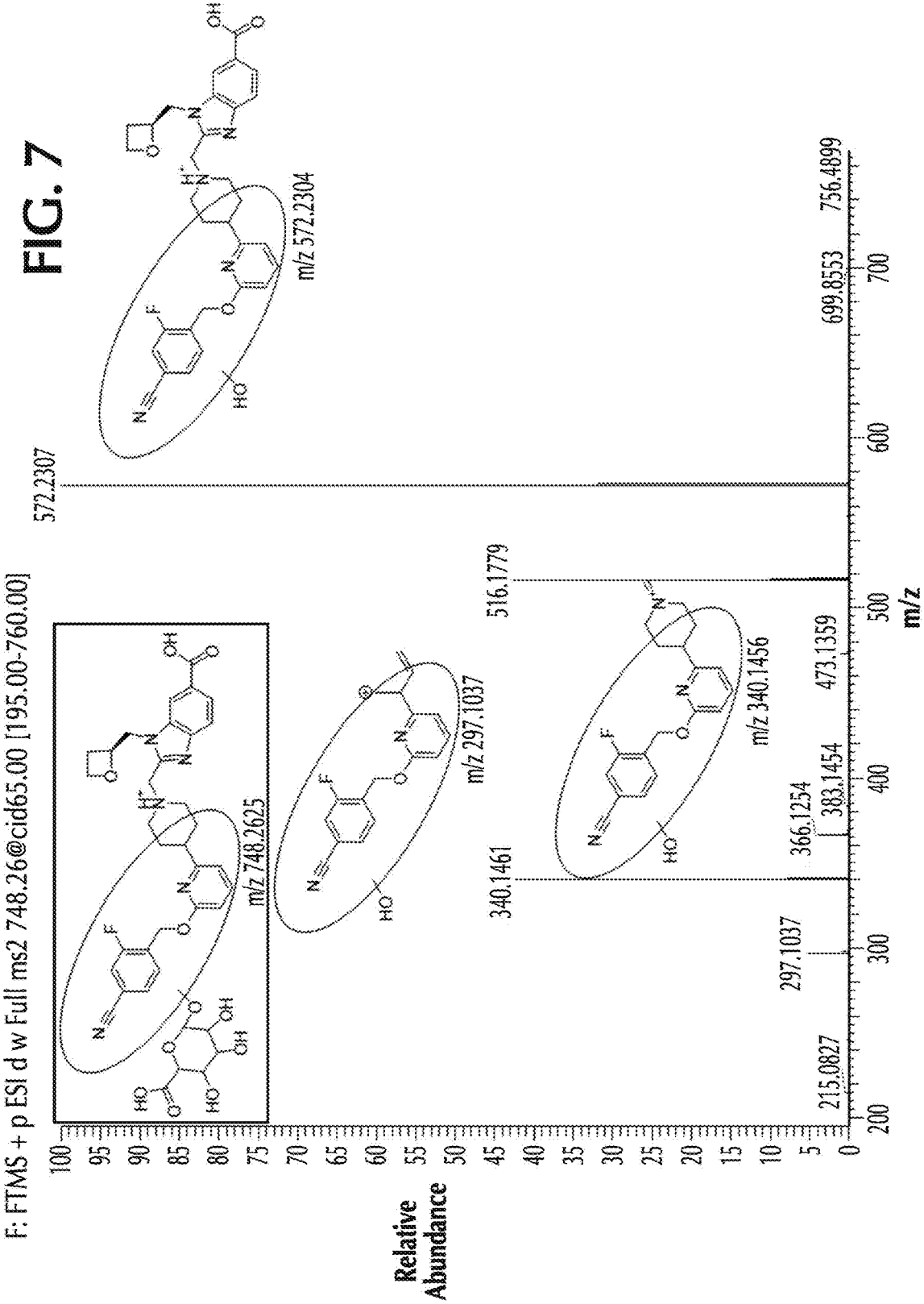
FIG. 7 shows product ion scan of Metabolite 748a at m/z 748.2625 in human plasma pool extract of patients dosed with Compound 1 (Day 28 120 mg oral BID). $T_r$=6.9 min

Metabolite/Compound 748a was observed as a minor metabolite in human plasma. It had a retention time of ~6.90 min on HPLC and a protonated molecular ion at m/z 748.2628, which was 192 Da greater than Compound 1, suggesting a hydroxylation followed by glucuronidation. The product ion spectrum for 748a contained the fragment ions at m/z 572, 340, and 297 (FIG. 7). The ion at m/z 572 can be attributed to the neutral loss of glucuronic acid. The ion at m/z 297, which was 16 Da greater than m/z 281 observed in the parent spectrum, suggests oxidation occurred on the 4-(((6-(but-3-en-2-yl)pyridin-2-yl)oxy)methyl)-3-fluorobenzonitrile moiety. This information indicates that the proposed structure of 748a resulted from O-glucuronidation of hydroxylated Compound 1.

Compound 748a

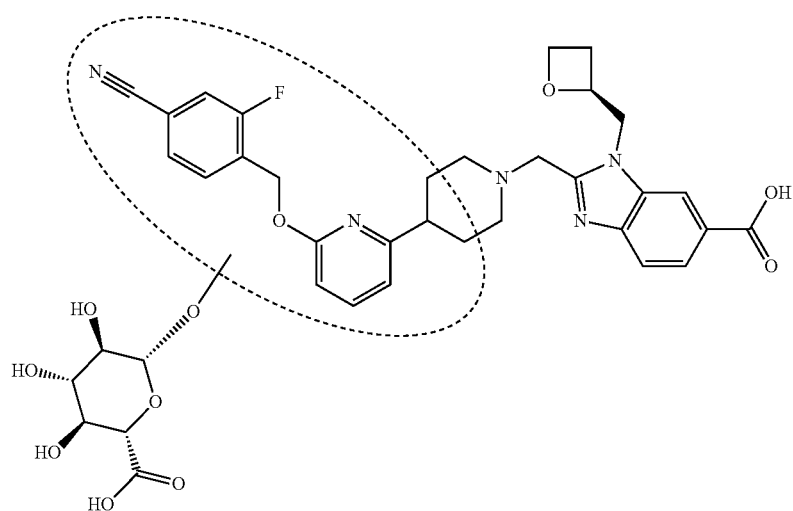

D. Metabolite 748b (m/z 748.2625 Theoretical; m/z 748.2636 Observed)

Figure 8:
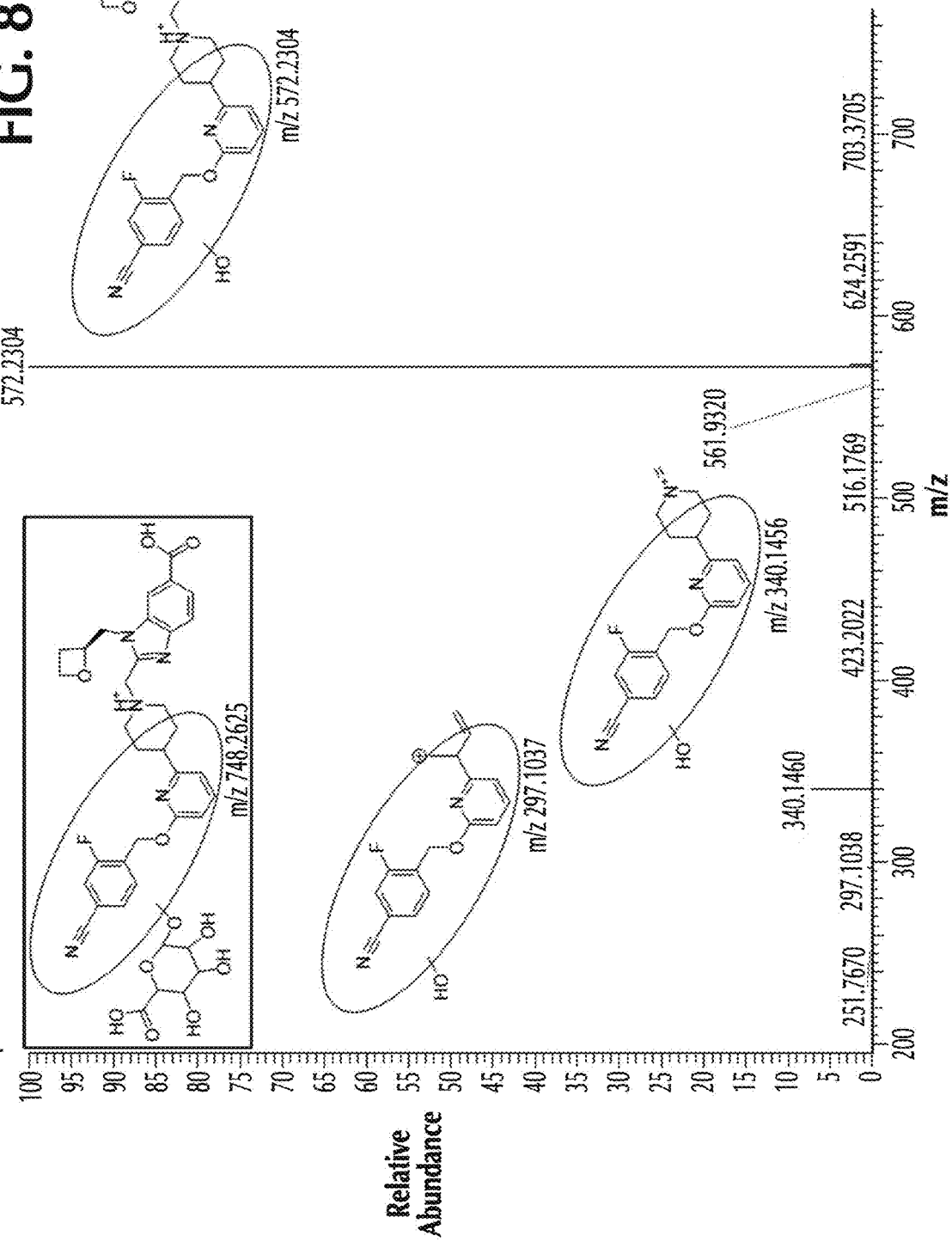
FIG. 8 shows product ion scan of Metabolite 748b at m/z 748.2625 in human plasma pool extract of patients dosed with Compound 1 (Day 28 120 mg oral BID). $T_r$=8.25 min

Metabolite/Compound 748b was observed as a minor metabolite in human plasma. It had a retention time of ~8.25 min on HPLC and a protonated molecular ion at m/z 748.2636, which was 192 Da greater than Compound 1, suggesting a hydroxylation followed by glucuronidation. The product ion spectrum for 748b contained the fragment ions at m/z 572, 340, and 297 (FIG. 8). The ion at m/z 572 can be attributed to the neutral loss of glucuronic acid. The ion at m/z 297, which 16 Da greater than m/z 281 observed in the parent spectrum, suggests oxidation occurred on the 4-(((6-(but-3-en-2-yl)pyridin-2-yl)oxy)methyl)-3-fluorobenzonitrile moiety. This information indicates that the proposed structure of 748b resulted from O-glucuronidation of hydroxylated Compound 1.

E. Metabolite M3 (m/z 312.1507 Theoretical; m/z 312.1510 Observed).

Figure 9:
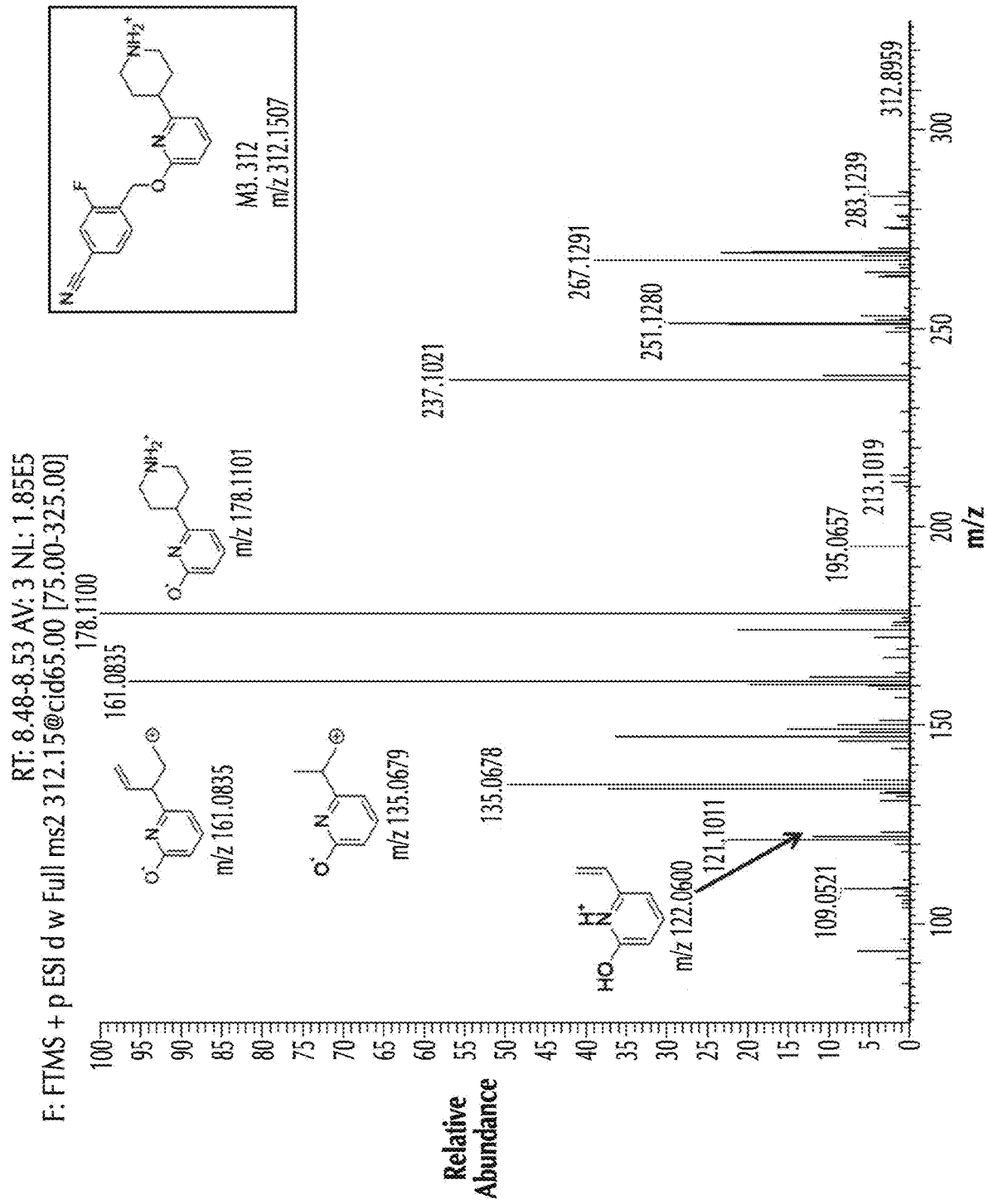
FIG. 9 shows product ion scan of Metabolite M3 at m/z 312.1507 in human plasma pool extract of patients dosed with Compound 1 (Day 28 120 mg oral BID). $T_r$=8.5 min FIG. 10 product ion scan at m/z 312.1507 for Synthetic Standard Compound M3. Tr=8.50 min.
Figure 10:
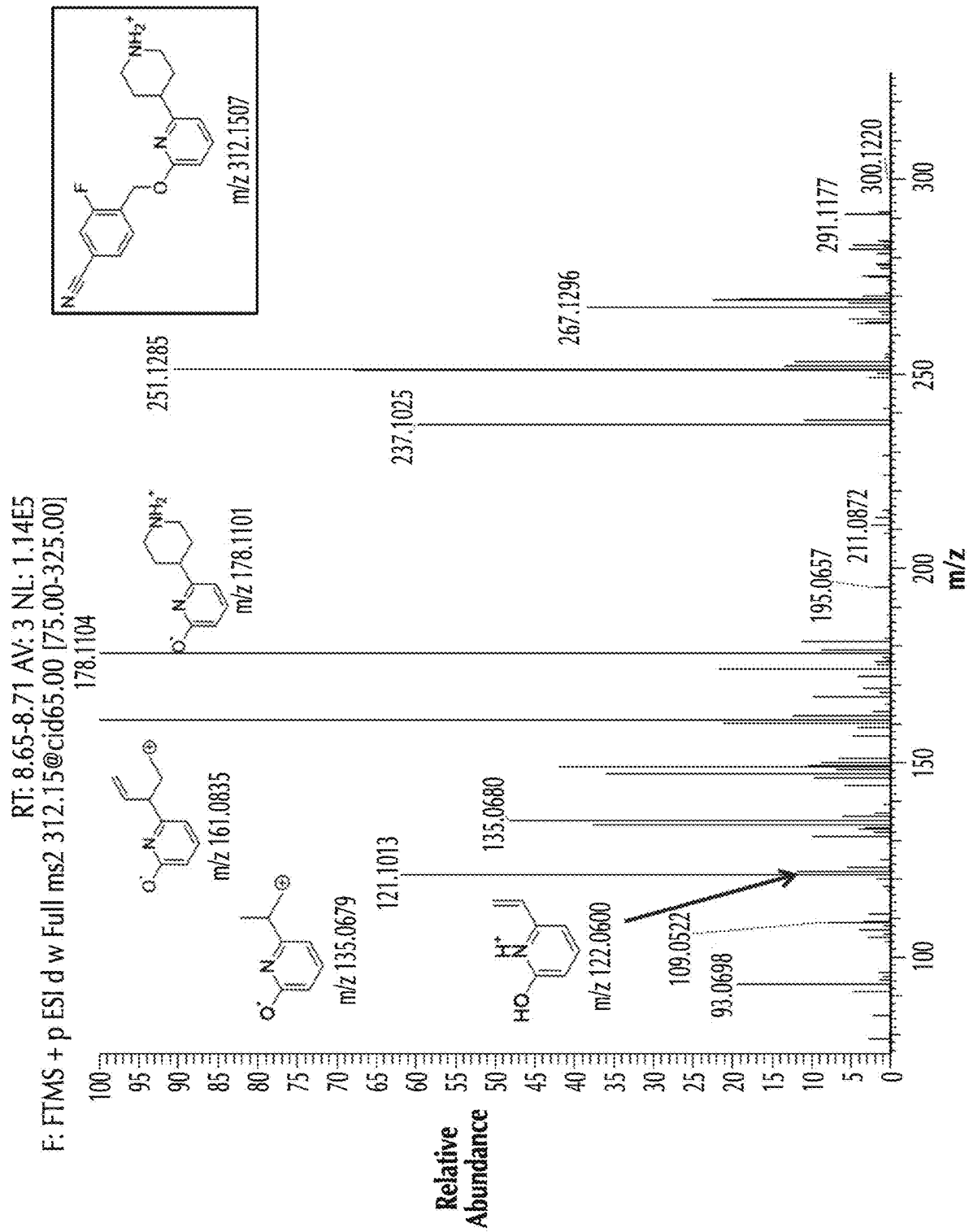

Metabolite/Compound M3 was observed as a minor metabolite in human plasma. It had a retention time of ~8.50 min on HPLC and a protonated molecular ion at m/z 312.1510, which was 244 Da less than Compound 1, suggested a loss of the (S)-2-methyl-1-(oxetan-2-ylmethyl)-1H-benzo[d]imidazole-6-carboxylic acid moiety. The product ion spectrum for M3 contained the fragment ions at m/z 178, 161, 135, and 122 (FIG. 9). The ion at m/z 178 is attributed to the loss of 3-fluoro-4-methylbenzonitrile with charge retention as a radical cation on the 6-(piperidin-4-yl)pyridin-2-ol moiety. The ion at m/z 122 is attributed to charge retention on the 6-vinylpyridin-2-ol moiety. Metabolite M3 was compared to synthetic standard Compound M3 and was found to have the same retention time and product ion spectrum (FIG. 10).

Compound 748b

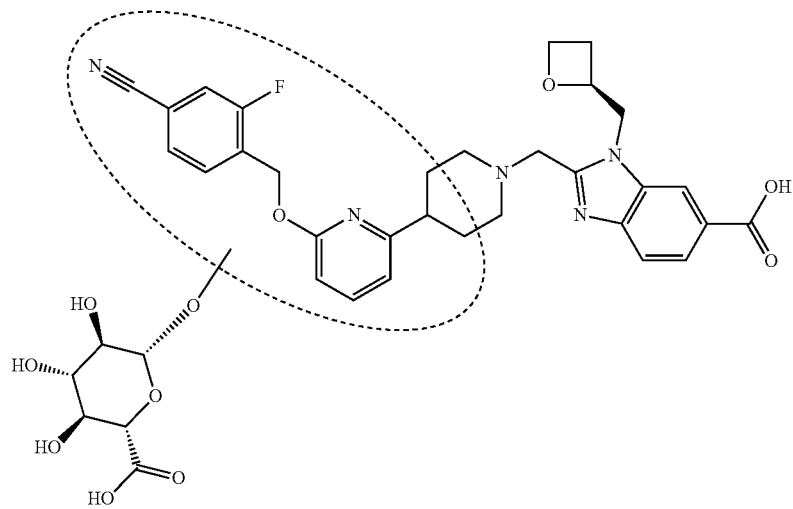

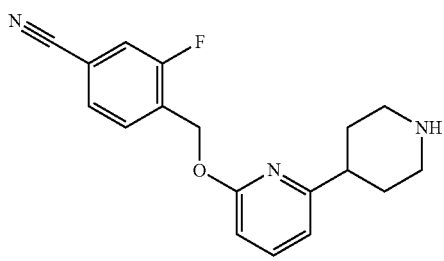 [SMILES: N#Cc1ccc(COc2cccc(C3CCNCC3)n2)c(F)c1]

Metabolite/Compound M3, Chemical Name:
3-fluoro-4-(((6-(piperidin-4-yl)pyridin-2-yl)oxy)methyl)benzonitrile F. Metabolite 574a (m/z 574.2460 Theoretical; m/z 574.2463 Observed).

Figure 11:
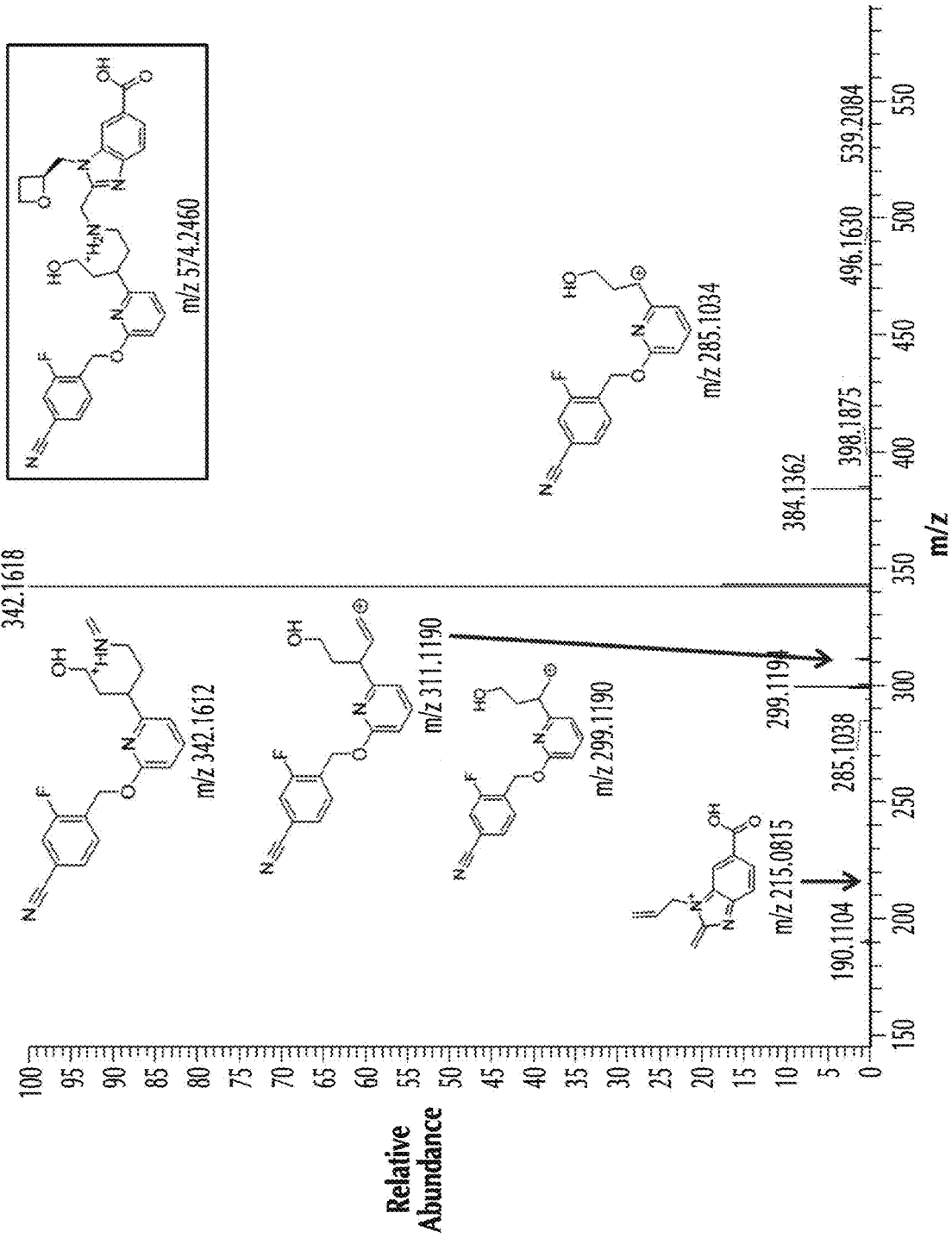
FIG. 11 shows product ion scan of Metabolite 574a at m/z 574.2460 in human plasma pool extract of patients dosed with Compound 1 (Day 28 120 mg oral BID). Tr=8.50 min

Metabolite 574a was observed as a minor metabolite in human plasma. It had a retention time of ~8.50 min on HPLC and a protonated molecular ion at m/z 574.2463, which was 18 Da greater than Compound 1. The product ion spectrum for 574a contained fragment ions at m/z 342, 311, 299, 285, and 215 (FIG. 11). The ion at m/z 342 resulted from the neutral loss of the unchanged (S)-1-(oxetan-2-ylmethyl)-1H-benzo[d]imidazole-6-carboxylic acid moiety. The ion at m/z 299 resulted from cleavage of the piperidine ring with charge retention on the 4-(((6-(but-3-en-2-yl)pyridin-2-yl)oxy)methyl)-3-fluorobenzonitrile moiety. The ions at m/z 342 and 299 were both 18 Da greater than their respective ions m/z 324 and 281 of the parent compound suggested oxidation and ring opening of the piperidine ring. The ion at m/z 215, which was observed in the parent compound, resulted from charge retention on the (S)-2-methyl-1-(oxetan-2-ylmethyl)-1H-benzo[d]imidazole-6-carboxylic acid moiety followed by a neutral loss of methanol from the oxetane ring. This information indicates that the proposed structure of 574a resulted from oxidation and ring opening of the piperidine ring of Compound 1.

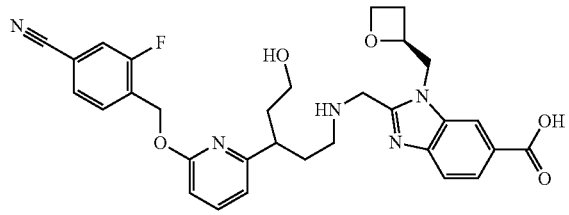 [SMILES: N#Cc1ccc(COc2cccc(C(CCO)CCNCc3nc4ccc(C(=O)O)cc4n3C[C@@H]3CCO3)n2)c(F)c1]

Compound/Metabolite 574a, Chemical Name:
2-(((3-(6-((4-cyano-2-fluorobenzyl)oxy)pyridin-2-yl)-5-hydroxypentyl)amino)methyl)-1-(((S)-oxetan-2-yl)methyl)-1H-benzo[d]imidazole-6-carboxylic acid G. Metabolite 574b (m/z 574.2460 Theoretical; m/z 574.2465 Observed).

Figure 12:
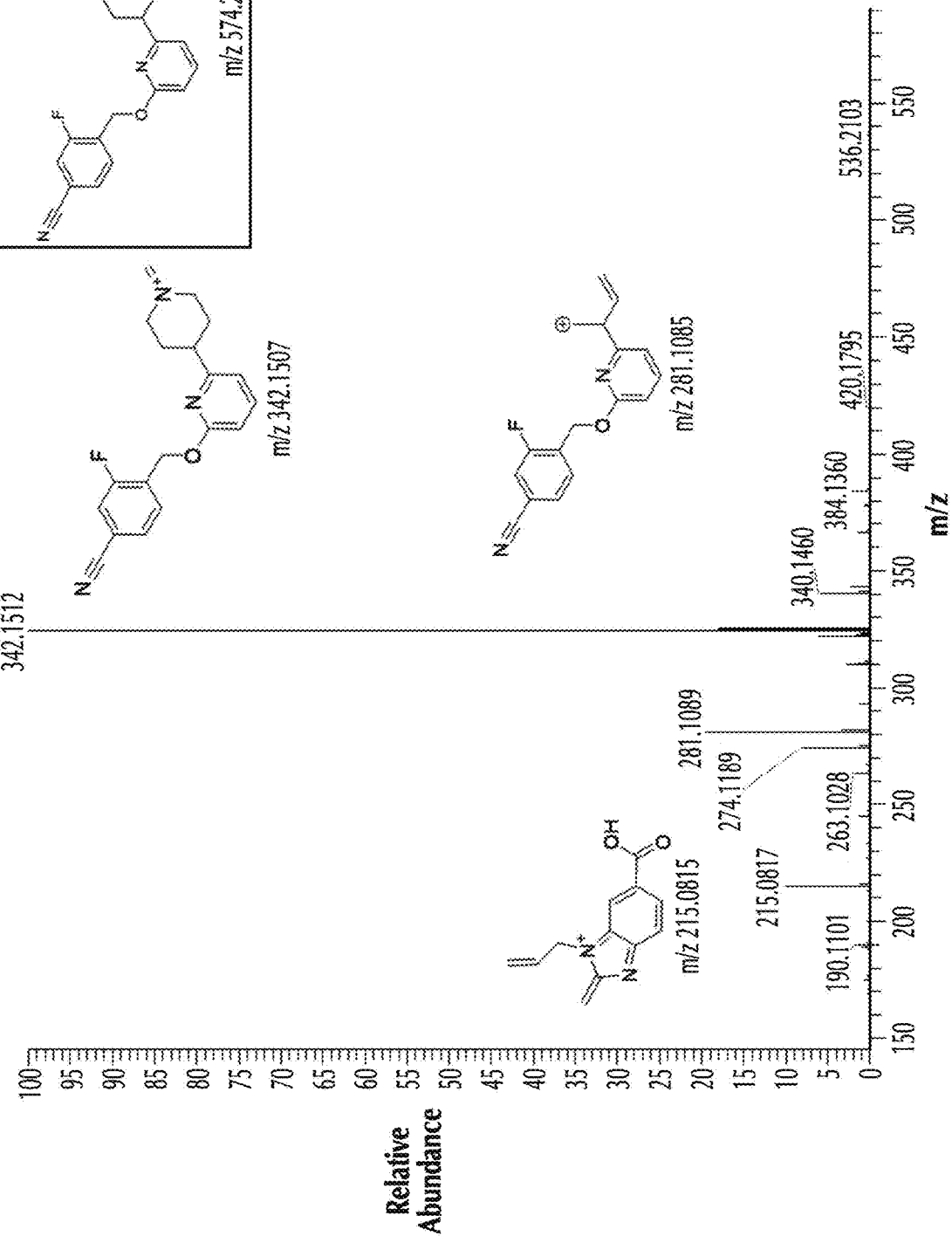
FIG. 12 shows product ion scan of Metabolite 574b at m/z 574.2460 in human plasma pool extract of patients dosed with Compound 1 (Day 28 120 mg oral BID). Tr=9.7 min

Metabolite 574b was observed as a minor metabolite in human plasma. It had a retention time of ~9.70 min on HPLC and a protonated molecular ion at m/z 574.2465, which was 18 Da greater than Compound 1. The product ion spectrum for m/z 574 contained the fragment ions at m/z 324, 281, and 215 (FIG. 12). The ion at m/z 324, which was the same as parent, suggested no modification of the 3-fluoro-4-(((6-(1-methylpiperidin-4-yl)pyridin-2-yl)oxy)methyl)benzonitrile moiety. The ion at m/z 215, which was also the same as parent, suggested no modification of the (S)-2-methyl-1-(oxetan-2-ylmethyl)-1H-benzo[d]imidazole-6-carboxylic acid moiety. This information indicates that the proposed structure of 574b resulted from oxidation and ring opening of the oxetane ring of Compound 1.

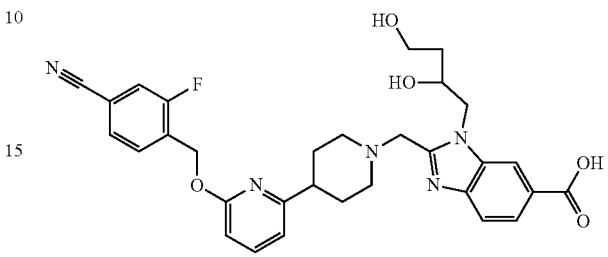

Compound/Metabolite 574b, Chemical Name:
2-((4-(6-((4-cyano-2-fluorobenzyl)oxy)pyridin-2-yl)piperidin-1-yl)methyl)-1-(2,4-dihydroxybutyl)-1H-benzo[d]imidazole-6-carboxylic acid While not wishing to be bound by any particular theory, it is believed that Metabolite 574b is

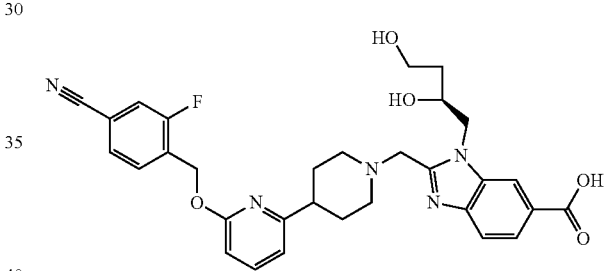

Chemical Name: (S)-2-((4-(6-((4-cyano-2-fluorobenzyl)oxy)pyridin-2-yl)piperidin-1-yl)methyl)-1-(2,4-dihydroxybutyl)-1H-benzo[d]imidazole-6-carboxylic acid H. Metabolite M4 (m/z 572.2304 Theoretical; m/z 572.2298 Observed).

Figure 13:
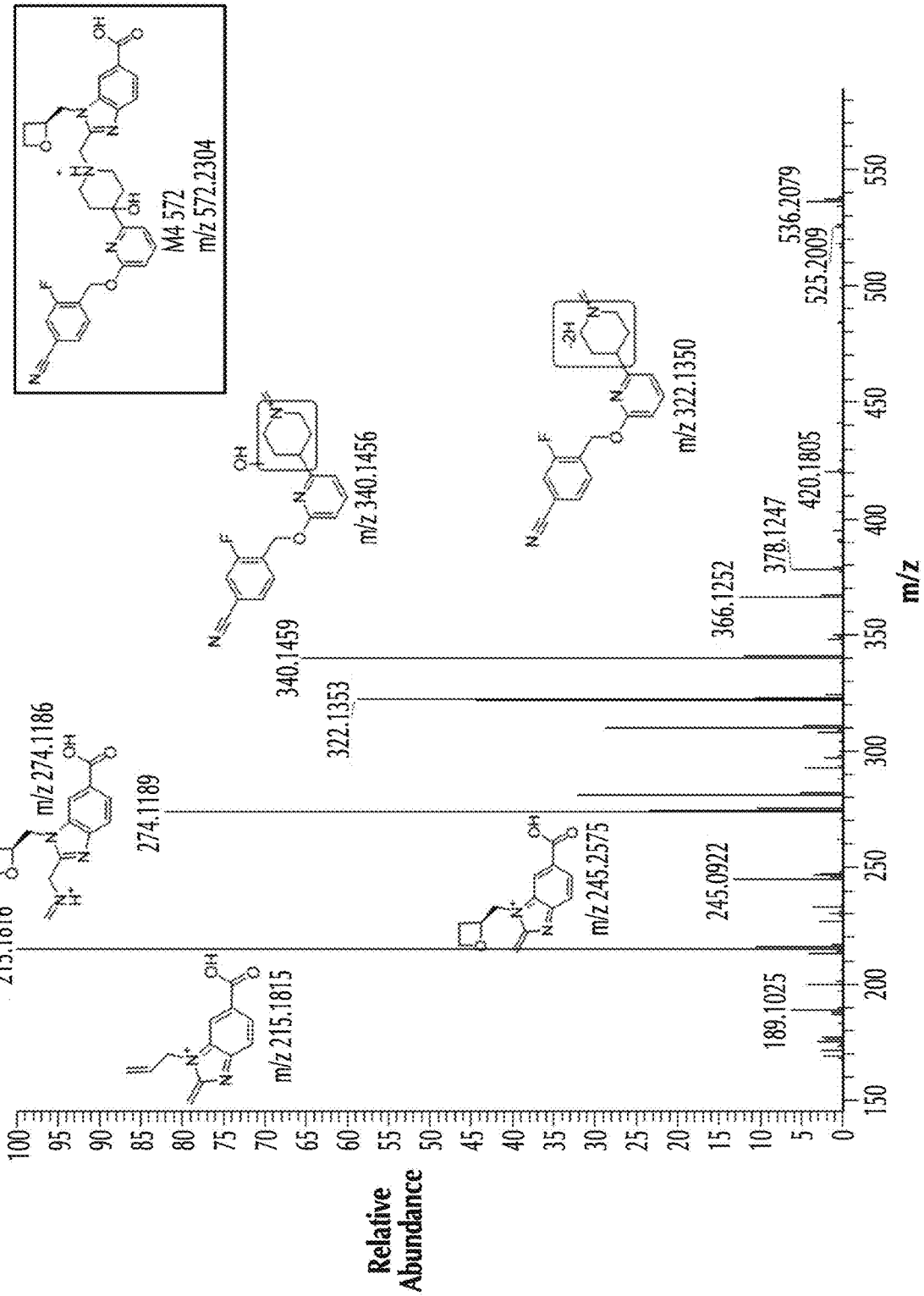
FIG. 13 shows product ion scan of Metabolite M4 at m/z 572.2304 in human plasma pool extract of patients dosed with Compound 1 (Day 28 120 mg oral BID). $T_r$=9.75 min
Figure 14:
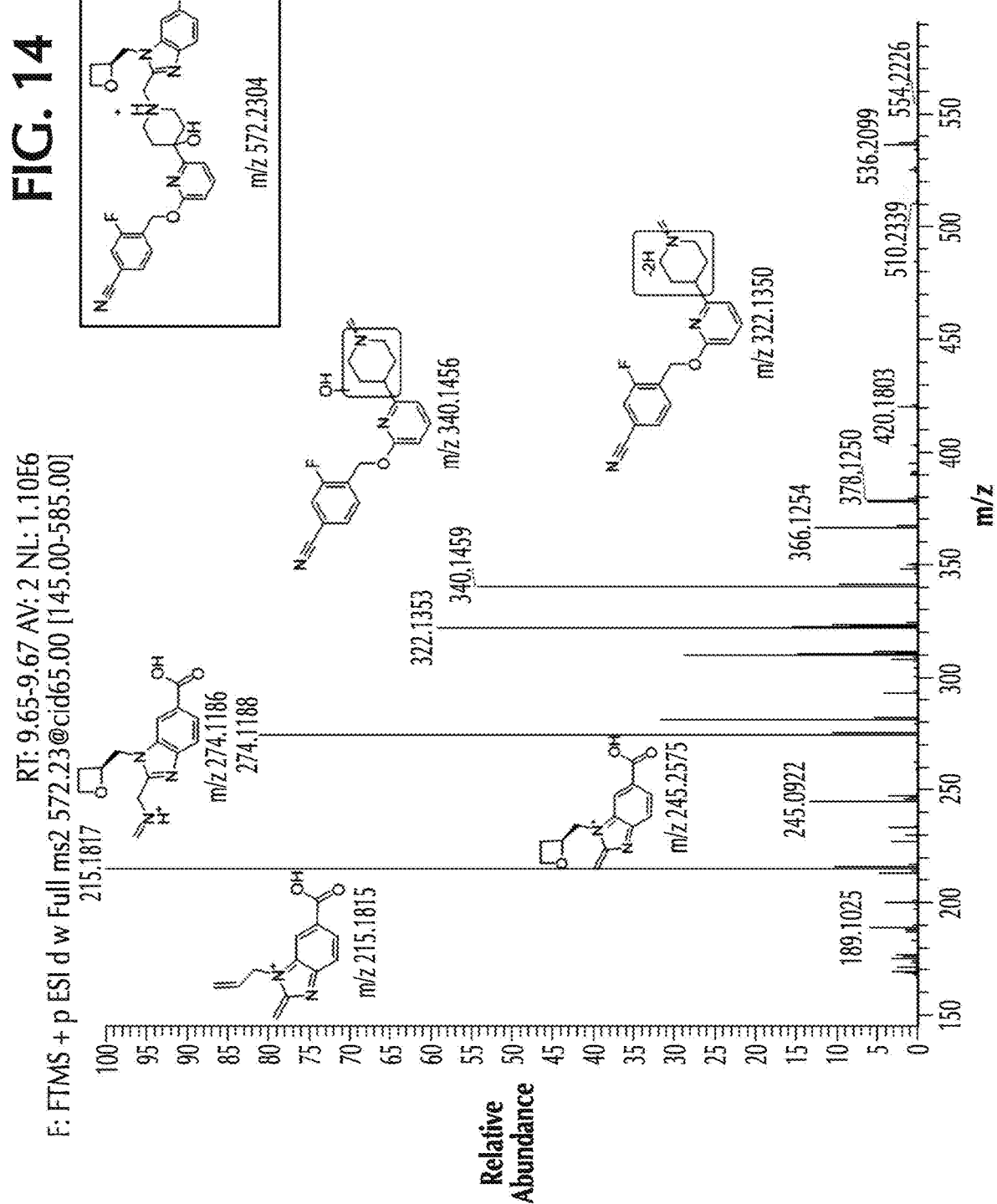
FIG. 14 shows product ion scan of a Standard Compound M4 (see Example 2 for preparation). $T_r$=9.75 min

Metabolite M4 was observed as a minor metabolite in human plasma. It had a retention time of ~9.75 min on HPLC and a protonated molecular ion at m/z 572.2298, which was 16 Da greater than Compound 1. The product ion spectrum for m/z 572 contained the fragment ions at m/z 340, 322, 274, 245, and 215 (FIG. 13). The ion at m/z 340, which is 16 Da greater than parent ion m/z 324, suggested hydroxylation occurred on the 3-fluoro-4-(((6-(1-methylpiperidin-4-yl)pyridin-2-yl)oxy)methyl)benzonitrile moiety. The ion at m/z 322 resulted from a neutral loss of water from fragment ion m/z 340. This suggests hydroxylation occurred on an aliphatic carbon in the piperidine ring. The ion at m/z 215, which was observed in the parent compound, resulted from charge retention on the (S)-2-methyl-1-(oxetan-2-ylmethyl)-1H-benzo[d]imidazole-6-carboxylic acid moiety followed by a neutral loss of methanol from the oxetane ring. Metabolite M4 was compared to a standard Compound M4 (See Example 2) and was found to have the same retention time and product ion spectrum (FIG. 14).

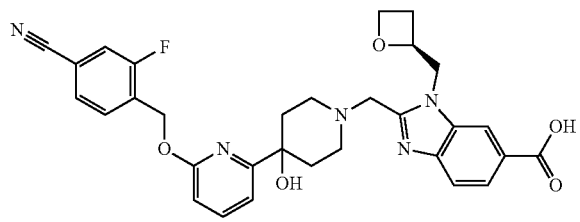 [SMILES: N#Cc1ccc(COc2cccc(C3(O)CCN(Cc4nc5ccc(C(=O)O)cc5n4C[C@@H]4CCO4)CC3)n2)c(F)c1]

Compound/Metabolite M4, Chemical Name: (S)-2-((4-(6-((4-cyano-2-fluorobenzyl)oxy)pyridin-2-yl)-4-hydroxypiperidin-1-yl)methyl)-1-(oxetan-2-ylmethyl)-1H-benzo[d]imidazole-6-carboxylic acid Metabolite M1 (732b, m/z 732.2675 Theoretical; m/z 732.2681 Observed).

Figure 15:
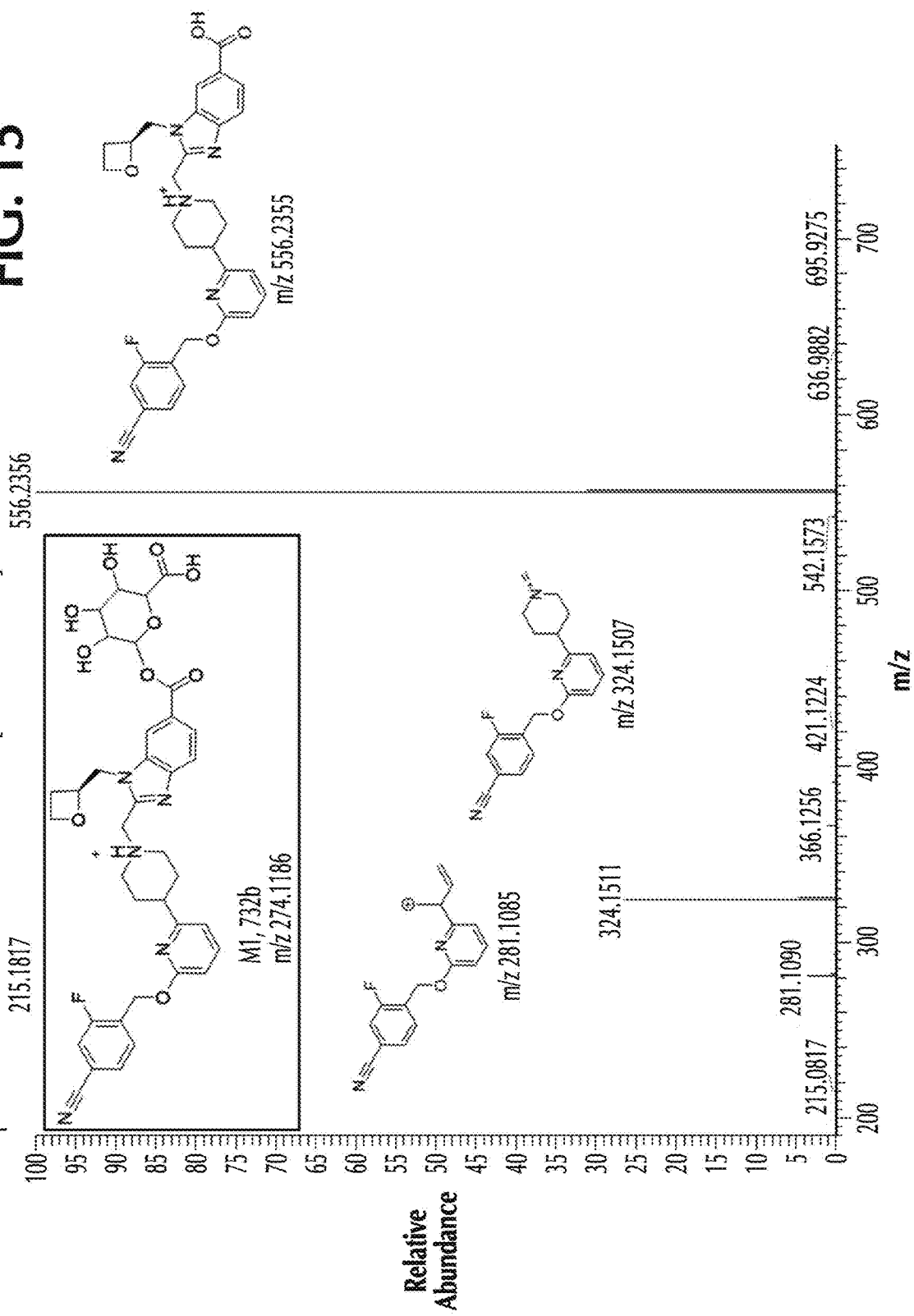
FIG. 15 shows product ion scan of Metabolite M1 at m/z 732.27 in human plasma pool extract of patients dosed with Compound 1 (Day 28 120 mg oral BID). Tr=9.75 min FIG. 16. shows product ion scan of m/z 732.2675 for Synthetic Standard Compound M1. Tr=9.75 min
Figure 16:
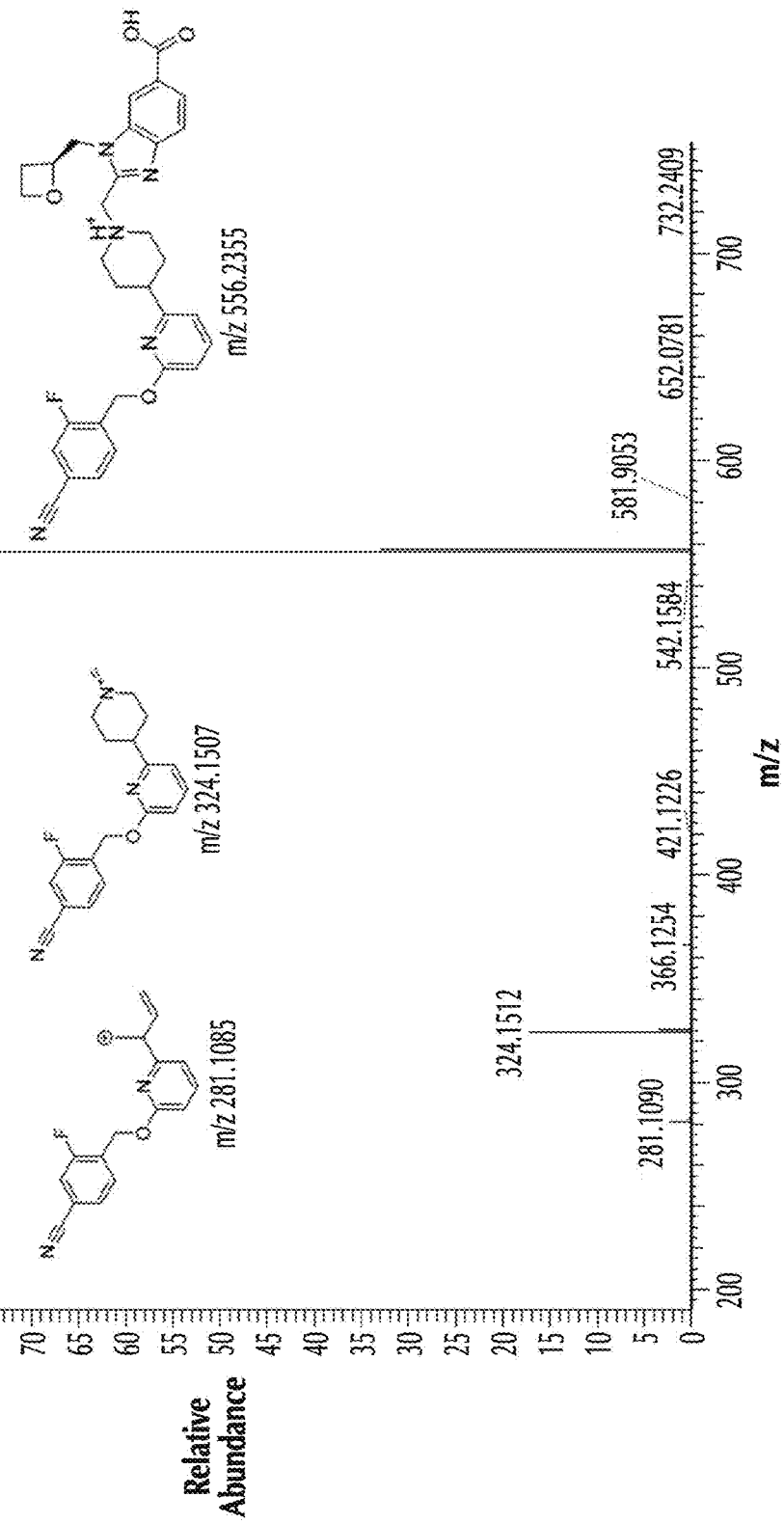
Figure 17:
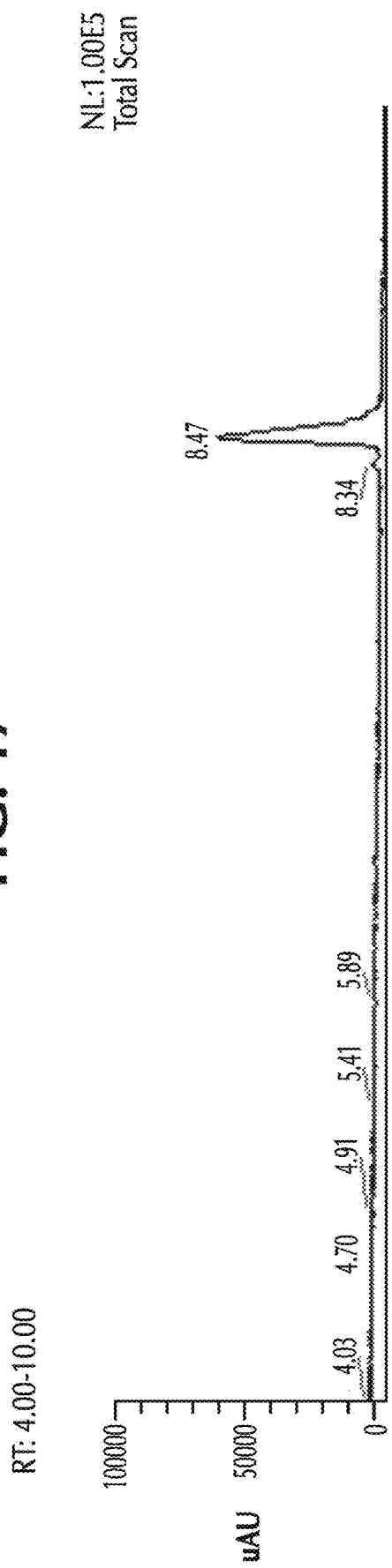
FIG. 17 shows HPLC/UV chromatogram of the fraction that contains of Metabolite M4 in Example 2.
Figure 18:
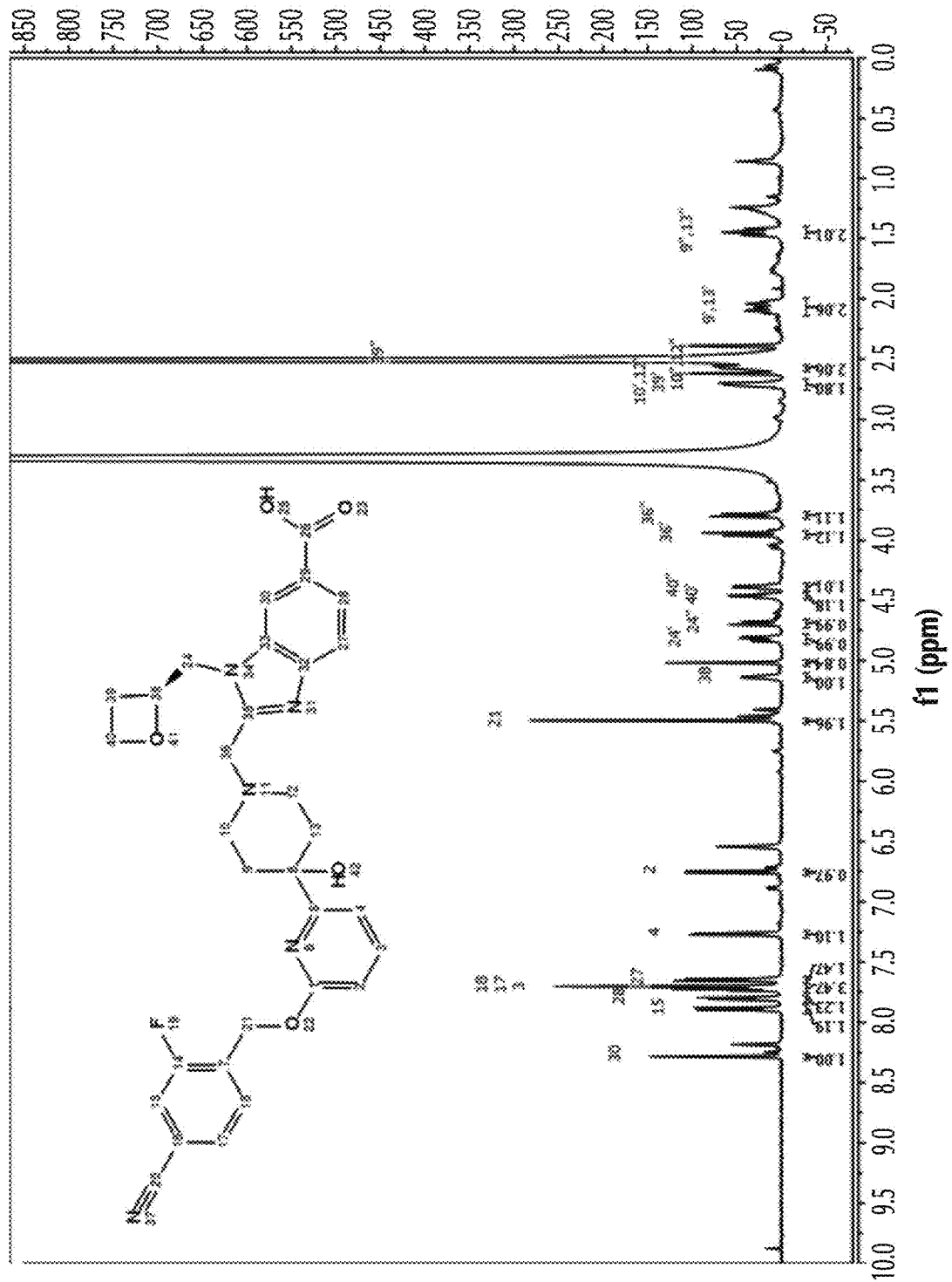
FIG. 18 shows a representative $^1$H NMR spectrum of Metabolite M4.
Figure 19:
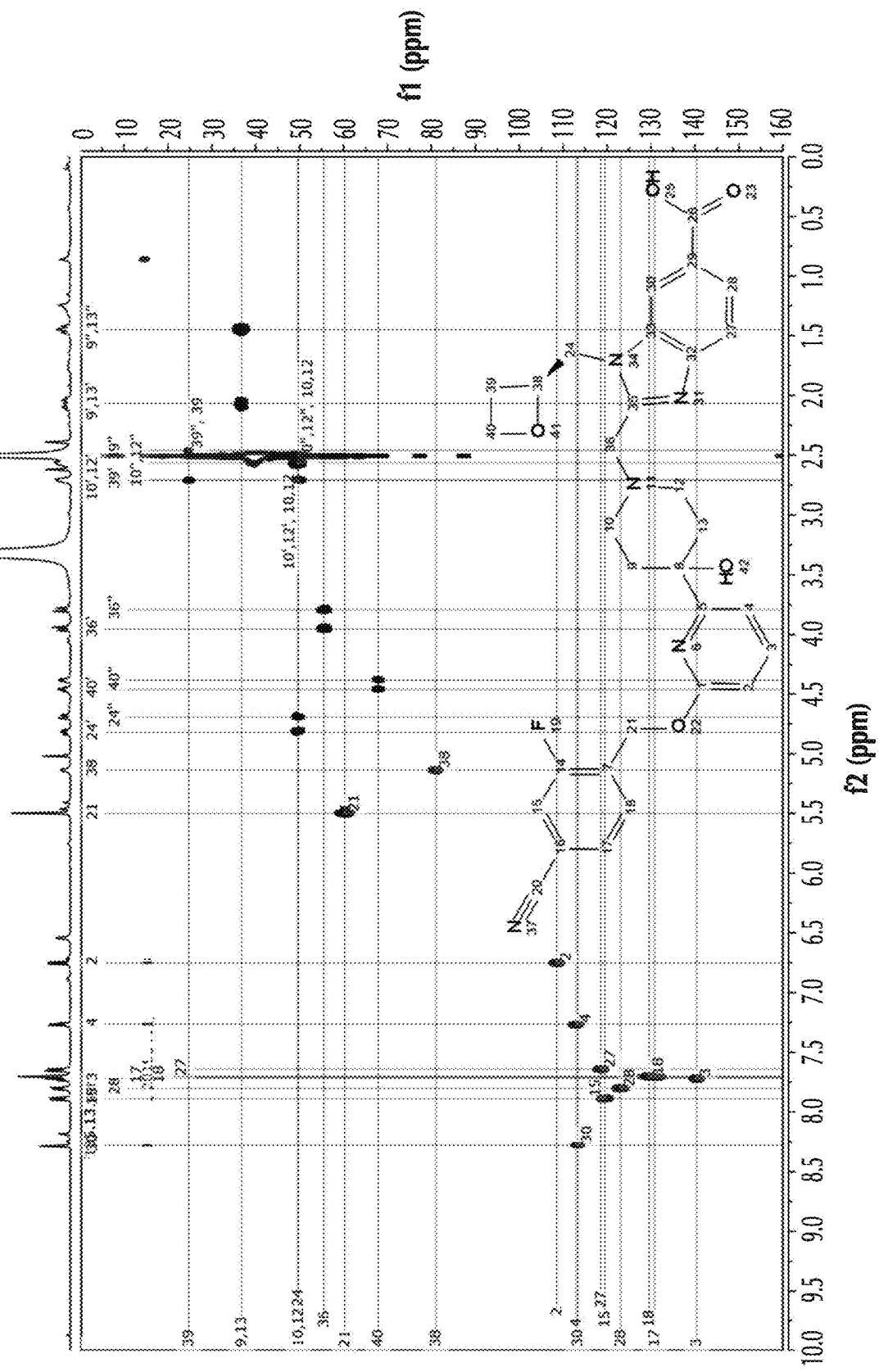
FIG. 19 shows a representative HSQC NMR spectrum of Metabolite M4.

Metabolite M1 was observed as a minor metabolite in human plasma. It had a retention time of ~9.75 min on HPLC and a protonated molecular ion at m/z 732.2681, which was 176 Da greater than Compound 1, suggesting direct glucuronidation. The product ion spectrum for m/z 732 contained the fragment ions at m/z 556, 324, and 281 (FIG. 15). The ion at m/z 556, which was the same as the parent protonated molecular ion, can be attributed to the neutral loss of glucuronic acid. The ion at m/z 324 resulted from the neutral loss of glucuronic acid followed by the loss of the (S)-1-(oxetan-2-ylmethyl)-1H-benzo[d]imidazole-6-carboxylic acid moiety. The ion at m/z 281 resulted from the neutral loss of glucuronide acid followed by cleavage of the piperidine ring with charge retention on the 4-(((6-(but-3-en-2-yl)pyridin-2-yl)oxy)methyl)-3-fluorobenzonitrile moiety. Metabolite M1 was compared to synthetic standard M1 and was found to have the same retention time and product ion spectrum (FIG. 16).

Sample Preparation

CYP3A4 (Panvera Lot #20814) was used. One 40 mL incubation was prepared: Phosphate buffer (0.1 M pH7.4) was aliquoted into a 250 mL Erlenmeyer flask followed by $MgCl_2$, CYP3A4, and tris salt of Compound 1. Incubation was started by adding NADPH. After 2 hours, incubation was protein precipitated with 40 mL of acetonitrile. Incubations were divided into two parts and each part was concentrated using an evaporative centrifuge at 37° C. to approximately 20 mL and then combined. Formic acid (0.5 mL) was added to the combined sample and was diluted to 40 mL with water. Sample was centrifuged for 30 minutes at 40000×g to further remove precipitate.

| Total Volume for reaction: | 40 ml (reaction volume) | Final concentration |
|---|---|---|
| phosphate buffer (0.1M pH 7.4): | 32040 µl | |
| NADPH | 4000 µL (13 mM stock) | 1.3 mM |
| $MgCl_2$ | 800 µl (165 mM stock) | 3.3 mM |
| CYP3A4: | 2000 µL | 2.0 mg/mL |
| Compound 1 (tris salt) | 160 µL (5.0 mM) | 20.0 µM |

Column Loading:

The diluted sample was manually injected (~3 mL) into a 5 mL sample loop onto the HPLC system.

Fraction Collection:

Analytical column was connected to Waters Acquity HPLC system connected to a Thermo Velos HPLC/MS system splitting approximately 10% of the post column flow to the mass spectrometer and 90% of the flow to a LEAP PAL HTS-XT fraction collector collecting 20 second fractions into 96 deep well plates with glass inserts for about 100 minutes.

Semi-prep HPLC/MS Conditions:

Sample loaded analytical column was connected to a Waters Acquity HPLC system connected to a Thermo Velos HPLC/MS system splitting approximately 10% of the post column flow to the mass spectrometer and 90% of the flow

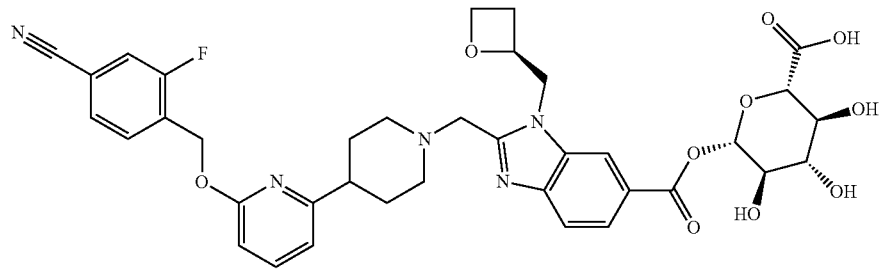 [SMILES: N#Cc1ccc(COc2cccc(C3CCN(Cc4nc5ccc(C(=O)O[C@@H]6O[C@H](C(=O)O)[C@@H](O)[C@H](O)[C@H]6O)cc5n4C[C@@H]4CCO4)CC3)n2)c(F)c1]

Compound/Metabolite M1, Chemical Name: (2S,3S,4S,5R,6S)-6-((2-((4-(6-((4-cyano-2-fluorobenzyl)oxy)pyridin-2-yl)piperidin-1-yl)methyl)-1-(((S)-oxetan-2-yl)methyl)-1H-benzo[d]imidazole-6-carbonyl)oxy)-3,4,5-trihydroxytetrahydro-2H-pyran-2-carboxylic acid Example 2. Metabolite M4 Scale Up (In Vitro Incubation of Compound 1 with CYP3A4)

Compound 1 (in its tris salt form) was incubated with rhCYP3A4 and metabolites were isolated. Metabolite M4 was isolated and also submitted for NMR analyses.

to a LEAP PAL HTS-XT fraction collector. Separation was performed on a Phenomenex Luna C18 10.0×250 mm 10 µm HPLC column. HPLC conditions were:

| Time min | % A | % B | Flow Rate (µL/min) |
|---|---|---|---|
| 0.0 | 80 | 20 | 2.0 |
| 6.0 | 80 | 20 | 2.0 |
| 60 | 50 | 50 | 2.0 |
| 90 | 5.0 | 95 | 2.0 |
| 99 | 5.0 | 95 | 2.0 |

-continued

| Time min | % A | % B | Flow Rate (µL/min) |
|---|---|---|---|
| 100 | 80 | 20 | 2.0 |
| 110 | 80 | 20 | 2.0 |

A: 0.1% Formic acid in water
B: Acetonitrile

Fractions were analyzed by HPLC/MS to determine metabolite of interest and purity. Final fractions containing the isolated metabolite were combined and concentrated to dryness using an evaporative centrifuge set to 37° C. Sample was reconstituted using DMSO-D6 (~0.1 mM) prior to NMR analysis.

HPLC/MS Conditions for Analyzing Individual Fractions

Individual fraction samples were analyzed by positive ion HPLC/UV/MS using a Thermo Orbitrap Elite mass spectrometer operating in positive ion electrospray mode. Xcalibur software version 3.0.63 was used to control the HPLC/MS system. Full scan data were collected at 15,000 resolution. Data dependent product ion scans of the two most intense ions found in the full scan were obtained at 15,000 resolution. The dynamic exclusion function was used with a 10 second exclusion duration after 3 successive product ion scans with an early exclusion if the precursor ion fell below a signal to noise of 20. The HPLC system consisted of an Accela quaternary solvent delivery pump, an Accela autoinjector, a Surveyor PDA Plus photodiode array detector (Thermo Electron Corporation), and a Hot Sleeve column heater (Analytical Sales & Products). Chromatography was performed on a Phenomenex Kinetex column (2.1 mm×100 mm, 2.6 µm) at 45° C. The mobile phase was composed of 0.1% formic acid in water (solvent A) and acetonitrile (solvent B). The solvent delivery gradient program was as follows:

| Time min | % A | % B | Flow Rate (mL/min) |
|---|---|---|---|
| 0.0 | 95 | 5 | 400 |
| 0.5 | 95 | 5 | 400 |
| 11.0 | 55 | 45 | 400 |
| 13.0 | 5 | 95 | 400 |
| 14.0 | 5 | 95 | 400 |
| 14.1 | 95 | 5 | 400 |
| 15.0 | 95 | 5 | 400 |

NMR Sample Analysis

Isolated sample was reconstituted in DMSO-$d_6$ "100%" (Cambridge Isotope Laboratories, Andover, MA) and placed in a 1.7 mm NMR tube in a dry argon atmosphere. The $^1$H and $^{13}$C spectra were referenced using residual DMSO-$d_6$ ($^1$H δ=2.50 ppm relative to TMS, δ=0.00, $^{13}$C δ=39.50 ppm relative to TMS, 5=0.00). NMR spectra were recorded on a Bruker Avance 600 MHz (Bruker BioSpin Corporation, Billerica, MA) controlled by Topspin V3.1 and equipped with a 1.7 mm TCI Cryo probe. 1D spectra were recorded using an approximate sweep width of 8400 Hz and a total recycle time of approximately 7 s. The resulting time-averaged free induction decays were transformed using an exponential line broadening of 1.0 Hz to enhance signal to noise. The 2D data were recorded using the standard pulse sequences provided by Bruker. At minimum a 1K×128 data matrix was acquired using a minimum of 2 scans and 16 dummy scans with a spectral width of 10000 Hz in the f2 dimension. The 2D data sets were zero-filled to at least 1 k data point. Post-acquisition data processing was performed with either Topspin V2.0.

Analyses

Among other things, one fraction of interest isolated by Semi-prep HPLC/MS fraction (designated as Fraction 135) was analyzed and determined to have the following structure based on its NMR data and MS data. This single hydroxylated metabolite was used as a standard in Example 1.

Metabolite M4

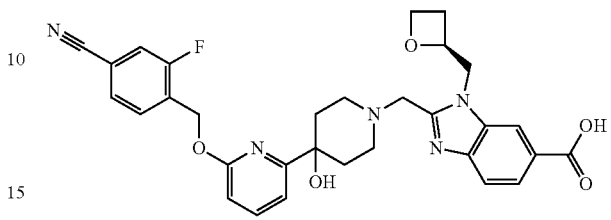

A representative product ion scan/spectrum, HPLC/UV Chromatogram, $^1$H NMR and HSQC NMR spectra are shown in FIGS. 14, 17, 18, and 19 respectively.

Example 2. Form 2 of 1,3-dihydroxy-2-(hydroxymethyl)propan-2-aminium salt of Compound 2

Preparation of Form 2 of 1,3-dihydroxy-2-(hydroxymethyl)propan-2-aminium salt of Compound 2

Compound 2 and its tris salt [i.e. 1,3-dihydroxy-2-(hydroxymethyl)propan-2-aminium salt] can be prepared by the methods disclosed in U.S. Pat. No. 10,676,465 (see Example 10 therein).

Compound 2 (49.7 mg) was mixed with methanol (0.828 mL) in a vial and heated to 50° C. A stock solution of Tris (30.25 µL, 3M) was then added and the resultant mixture was cooled to room temperature slowly. The mixture was then allowed to slowly evaporate at room temperature (the vial was placed in a fume hood and the cap slightly cracked to allow for solvent evaporation). Crystals of tris salt of Compound 2 formed by slow evaporation in the methanol/water mixed solvent (and this crystalline form is designated as Form 2).

Single Crystal X-Ray Analysis.

A sample of Form 2 of tris salt of Compound 2 was tested for single crystal analysis. Data collection was performed on a Bruker D8 Venture diffractometer at room temperature. Data collection consisted of omega and phi scans.

The structure was solved by intrinsic phasing using SHELX software suite in the Monoclinic class space group $P2_1$. The structure was subsequently refined by the full-matrix least squares method. All non-hydrogen atoms were found and refined using anisotropic displacement parameters.

Terminal ring (C1-C2-C3-C4-C5-Cl1) was disordered. A disorder model was tested for this group, but did not refine satisfactorily. CIF_Check module generated level "A" based on above mentioned segment.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Figure 20:
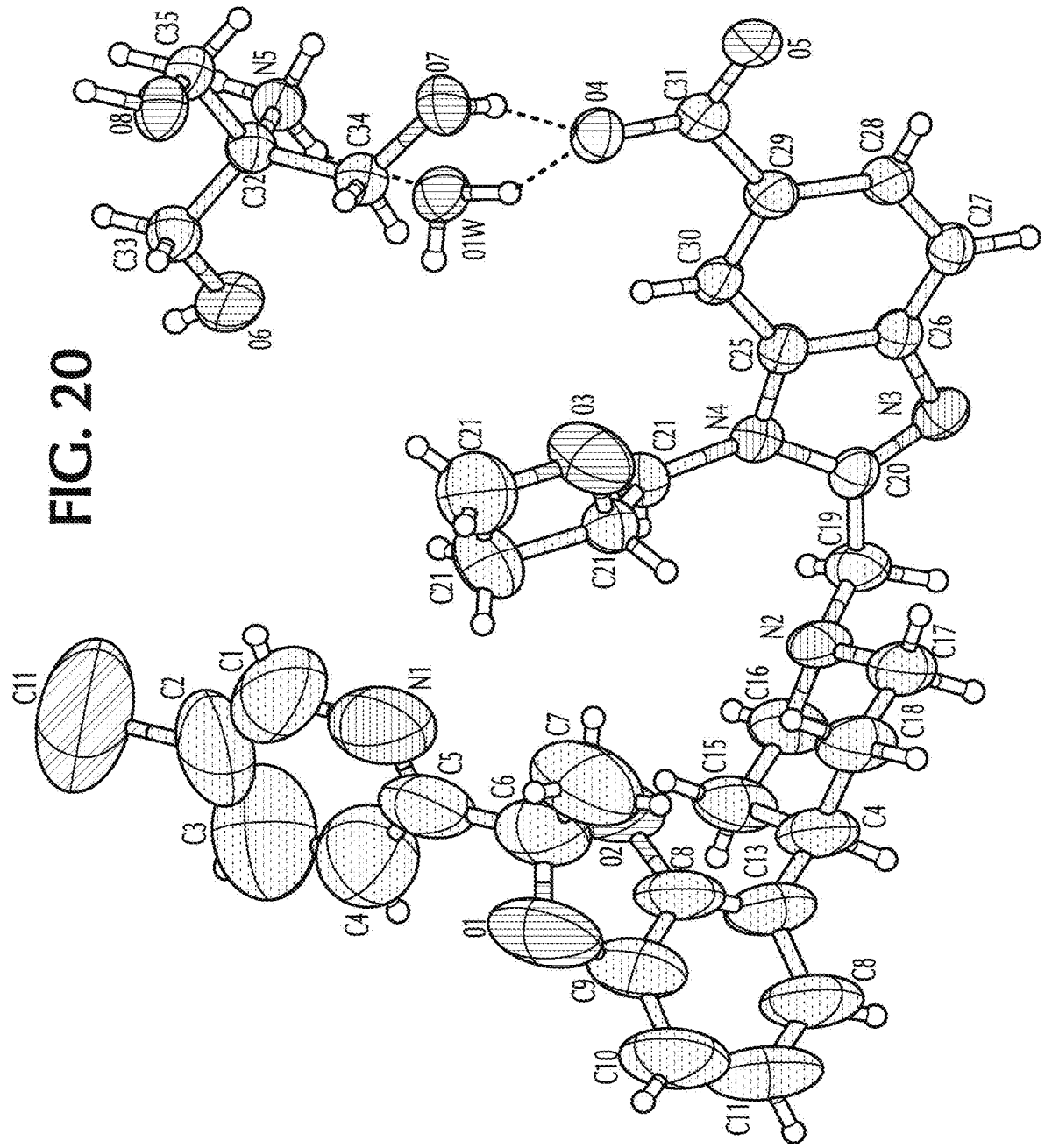
FIG. 20 shows an illustrative single crystal structure of a monohydrate crystalline form (Form 2) of tris salt of Compound 2.

TRIS salt was confirmed because of proton transfer from O5 to N5. Additionally, the structure contained one water molecule (and thus monohydrate). Analysis of the absolute structure using likelihood methods (Hooft 2008) was performed using PLATON (Spek 2010), with the known stereochemistry information of C22 (and thus, the stereochemistry information of C6 was determined). The refined structure was plotted using the SHELXTL plotting package (FIG. 20). According to the refined structure, Form 2 is a monohydrate of tris salt of Compound 2, the structure of which can be represented as shown below:

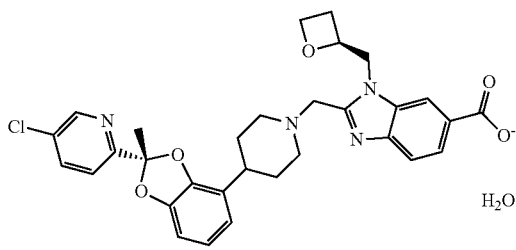

-continued

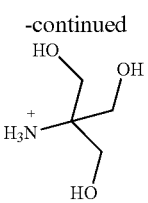

The final R-index was 6.6%. A final difference Fourier revealed no missing or misplaced electron density.

Pertinent crystal, data collection and refinement are summarized in Table E2-1. Atomic coordinates, bond lengths, bond angles and displacement parameters are listed in tables E2-2 to E2-4.

TABLE E2-1

Crystal data and structure refinement for Form 2.

| | |
|---|---|
| Empirical formula | C35 H44 Cl N5 O9 |
| Formula weight | 714.20 |
| Temperature | 296(2) K |
| Wavelength | 1.54178 Å |
| Crystal system | Monoclinic |
| Space group | $P2_1$ |
| Unit cell dimensions | a = 12.944(4) Å    □ = 90°. |
| | b = 6.1938(16) Å    □ = 91.731(16)°. |
| | c = 24.777(7) Å    □ = 90°. |
| Volume | 1985.5(9) Å$^3$ |
| Z | 2 |
| Density (calculated) | 1.195 Mg/m$^3$ |
| Absorption coefficient | 1.311 mm$^{-1}$ |
| F(000) | 756 |
| Crystal size | 0.500 × 0.060 × 0.020 mm$^3$ |
| Theta range for data collection | 3.416 to 58.358°. |
| Index ranges | −14 <= h <= 14, −6 <= k <= 6, −25 <= l <= 26 |
| Reflections collected | 22149 |
| Independent reflections | 5405 [R(int) = 0.0849] |
| Completeness to theta = 58.358° | 96.9% |
| Absorption correction | Empirical |
| Refinement method | Full-matrix least-squares on F$^2$ |
| Data/restraints/parameters | 5405/9/476 |
| Goodness-of-fit on F$^2$ | 1.074 |
| Final R indices [I >2sigma(I)] | R1 = 0.0659, wR2 = 0.1680 |
| R indices (all data) | R1 = 0.0821, wR2 = 0.1786 |
| Absolute structure parameter | 0.12 (6) |
| Extinction coefficient | n/a |
| Largest diff. peak and hole | 0.301 and −0.346 e·Å$^{-3}$ |

TABLE E2-2

Atomic coordinates (× 10$^4$) and equivalent isotropic displacement parameters (Å$^2$ × 10$^3$) for Form 2.

| | x | y | z | U(eq) |
|---|---|---|---|---|
| Cl (1) | 2581 (4) | 11780 (30) | 6569 (4) | 378 (7) |
| N (1) | 5044 (11) | 8410 (30) | 6117 (5) | 175 (5) |
| C (1) | 4152 (16) | 9050 (60) | 6370 (8) | 225 (12) |
| C (2) | 3718 (14) | 10890 (60) | 6277 (12) | 219 (13) |
| C (3) | 4300 (30) | 12470 (60) | 5989 (14) | 286 (17) |
| C (4) | 5186 (17) | 11870 (40) | 5789 (11) | 227 (10) |
| C (5) | 5581 (10) | 9900 (20) | 5840 (5) | 126 (4) |
| N (2) | 9326 (3) | 11743 (8) | 7589 (2) | 54 (1) |
| N (3) | 10176 (3) | 8565 (8) | 8754 (2) | 52 (1) |
| N (4) | 8507 (3) | 8823 (7) | 8496 (2) | 47 (1) |
| N (5) | 3667 (3) | 3409 (8) | 9569 (2) | 49 (1) |
| O (1) | 6700 (8) | 10298 (17) | 5094 (3) | 151 (3) |
| O (2) | 7372 (5) | 10295 (14) | 5994 (2) | 122 (2) |
| O (3) | 6798 (5) | 6442 (10) | 7818 (2) | 103 (2) |
| O (4) | 6517 (3) | 2465 (7) | 9413 (2) | 62 (1) |
| O (5) | 7791 (3) | 641 (7) | 9848 (2) | 64 (1) |

TABLE E2-2-continued

Atomic coordinates (× 10⁴) and equivalent isotropic displacement parameters (Å² × 10³) for Form 2.

|       | x         | y          | z        | U(eq)   |
|-------|-----------|------------|----------|---------|
| O (6) | 3401 (3)  | 5679 (7)   | 8537 (2) | 75 (1)  |
| O (7) | 4901 (3)  | 86 (6)     | 9094 (2) | 62 (1)  |
| O (8) | 2255 (3)  | −731 (6)   | 8733 (2) | 61 (1)  |
| C (6) | 6593 (9)  | 9250 (20)  | 5626 (4) | 118 (3) |
| C (7) | 6806 (13) | 6880 (20)  | 5590 (7) | 167 (5) |
| C (8) | 8023 (8)  | 11410 (16) | 5654 (3) | 98 (3)  |
| C (9) | 7637 (10) | 11460 (20) | 5116 (3) | 116 (3) |
| C (10)| 8078 (12) | 12520 (30) | 4692 (4) | 142 (4) |
| C (11)| 8984 (13) | 13550 (30) | 4828 (4) | 155 (5) |
| C (12)| 9410 (9)  | 13510 (20) | 5362 (3) | 128 (4) |
| C (13)| 8937 (7)  | 12450 (16) | 5800 (3) | 96 (3)  |
| C (14)| 9378 (6)  | 12511 (14) | 6388 (3) | 83 (2)  |
| C (15)| 8732 (6)  | 13879 (13) | 6775 (3) | 82 (2)  |
| C (16)| 9212 (6)  | 13926 (11) | 7362 (3) | 75 (2)  |
| C (17)| 9980 (5)  | 10417 (12) | 7242 (2) | 71 (2)  |
| C (18)| 9549 (6)  | 10275 (14) | 6651 (3) | 83 (2)  |
| C (19)| 9680 (4)  | 11785 (10) | 8170 (2) | 58 (1)  |
| C (20)| 9472 (4)  | 9706 (9)   | 8468 (2) | 48 (1)  |
| C (21)| 7527 (4)  | 9701 (10)  | 8270 (2) | 55 (1)  |
| C (22)| 7151 (4)  | 8630 (12)  | 7742 (2) | 65 (2)  |
| C (23)| 6088 (7)  | 9320 (20)  | 7521 (4) | 112 (3) |
| C (24)| 5793 (8)  | 7010 (30)  | 7585 (5) | 145 (5) |
| C (25)| 8600 (4)  | 6993 (9)   | 8828 (2) | 46 (1)  |
| C (26)| 9649 (4)  | 6850 (9)   | 8990 (2) | 46 (1)  |
| C (27)| 9995 (4)  | 5194 (10)  | 9341 (2) | 50 (1)  |
| C (28)| 9282 (4)  | 3703 (10)  | 9519 (2) | 48 (1)  |
| C (29)| 8227 (4)  | 3843 (9)   | 9353 (2) | 45 (1)  |
| C (30)| 7881 (4)  | 5488 (9)   | 8998 (2) | 45 (1)  |
| C (31)| 7460 (4)  | 2181 (9)   | 9559 (2) | 46 (1)  |
| C (32)| 3324 (4)  | 2306 (9)   | 9042 (2) | 47 (1)  |
| C (33)| 2752 (4)  | 3898 (9)   | 8662 (2) | 57 (1)  |
| C (34)| 4280 (4)  | 1420 (9)   | 8750 (2) | 52 (1)  |
| C (35)| 2607 (4)  | 435 (10)   | 9209 (2) | 54 (1)  |
| O (1W)| 5386 (3)  | 6086 (7)   | 9518 (2) | 62 (1)  |

U(eq) is defined as one third of the trace of the orthogonalized $U^{ij}$ tensor.

TABLE E2-3

Bond lengths [Å] and angles [°] for Form 2.

| Cl(1)-C(2)   | 1.75 (2)   | C(3)-C(4)     | 1.32 (3)   |
|--------------|------------|---------------|------------|
| N(1)-C(5)    | 1.356 (17) | C(3)-H(3)     | 0.9300     |
| N(1)-C(1)    | 1.39 (3)   | C(4)-C(5)     | 1.33 (2)   |
| C(1)-C(2)    | 1.29 (4)   | C(4)-H(4)     | 0.9300     |
| C(1)-H(1)    | 0.9300     | C(5)-C(6)     | 1.483 (18) |
| C(2)-C(3)    | 1.43 (4)   | N(2)-C(16)    | 1.469 (9)  |
| N(2)-C(17)   | 1.473 (8)  | C(11)-C(12)   | 1.418 (16) |
| N(2)-C(19)   | 1.498 (7)  | C(11)-H(11)   | 0.9300     |
| N(3)-C(20)   | 1.340 (7)  | C(12)-C(13)   | 1.422 (12) |
| N(3)-C(26)   | 1.399 (7)  | C(12)-H(12)   | 0.9300     |
| N(4)-C(20)   | 1.368 (6)  | C(13)-C(14)   | 1.548 (11) |
| N(4)-C(25)   | 1.403 (7)  | C(14)-C(18)   | 1.544 (11) |
| N(4)-C(21)   | 1.475 (7)  | C(14)-C(15)   | 1.545 (10) |
| N(5)-C(32)   | 1.528 (7)  | C(14)-H(14)   | 0.9800     |
| N(5)-H(5X)   | 0.97 (3)   | C(15)-C(16)   | 1.565 (10) |
| N(5)-H(5Y)   | 0.98 (3)   | C(15)-H(15A)  | 0.9700     |
| N(5)-H(5Z)   | 0.99 (3)   | C(15)-H(15B)  | 0.9700     |
| O(1)-C(9)    | 1.410 (14) | C(16)-H(16A)  | 0.9700     |
| O(1)-C(6)    | 1.479 (13) | C(16)-H(16B)  | 0.9700     |
| O(2)-C(8)    | 1.392 (10) | C(17)-C(18)   | 1.554 (10) |
| O(2)-C(6)    | 1.486 (12) | C(17)-H(17A)  | 0.9700     |
| O(3)-C(22)   | 1.445 (9)  | C(17)-H(17B)  | 0.9700     |
| O(3)-C(24)   | 1.450 (12) | C(18)-H(18A)  | 0.9700     |
| O(4)-C(31)   | 1.274 (6)  | C(18)-H(18B)  | 0.9700     |
| O(5)-C(31)   | 1.261 (7)  | C(19)-C(20)   | 1.512 (8)  |
| O(6)-C(33)   | 1.426 (7)  | C(19)-H(19A)  | 0.9700     |
| O(6)-H(6Z)   | 0.99 (3)   | C(19)-H(19B)  | 0.9700     |
| O(7)-C(34)   | 1.420 (7)  | C(21)-C(22)   | 1.534 (9)  |
| O(7)-H(7Z)   | 0.99 (3)   | C(21)-H(21A)  | 0.9700     |
| O(8)-C(35)   | 1.445 (7)  | C(21)-H(21B)  | 0.9700     |
| O(8)-H(8Z)   | 0.97 (3)   | C(22)-C(23)   | 1.527 (10) |
| C(6)-C(7)    | 1.50 (2)   | C(22)-H(22)   | 0.9800     |

TABLE E2-3-continued

Bond lengths [Å] and angles [°] for Form 2.

| | | | |
|---|---|---|---|
| C(7)-H(7A) | 0.9600 | C(23)-C(24) | 1.493 (19) |
| C(7)-H(7B) | 0.9600 | C(23)-H(23A) | 0.9700 |
| C(7)-H(70) | 0.9600 | C(23)-H(23B) | 0.9700 |
| C(8)-C(13) | 1.386 (13) | C(24)-H(24A) | 0.9700 |
| C(8)-C(9) | 1.410 (12) | C(24)-H(24B) | 0.9700 |
| C(9)-C(10) | 1.376 (16) | C(25)-C(30) | 1.391 (7) |
| C(10)-C(11) | 1.371 (18) | C(25)-C(26) | 1.406 (7) |
| C(10)-H(10) | 0.9300 | C(26)-C(27) | 1.410 (8) |
| C(27)-C(28) | 1.386 (8) | N(1)-C(5)-C(6) | 118.0 (13) |
| C(27)-H(27) | 0.9300 | C(16)-N(2)-C(17) | 110.1 (5) |
| C(28)-C(29) | 1.416 (7) | C(16)-N(2)-C(19) | 112.0 (5) |
| C(28)-H(28) | 0.9300 | C(17)-N(2)-C(19) | 113.9 (5) |
| C(29)-C(30) | 1.411 (8) | C(20)-N(3)-C(26) | 106.8 (4) |
| C(29)-C(31) | 1.528 (7) | C(20)-N(4)-C(25) | 106.9 (4) |
| C(30)-H(30) | 0.9300 | C(20)-N(4)-C(21) | 127.5 (5) |
| C(32)-C(33) | 1.538 (8) | C(25)-N(4)-C(21) | 125.3 (4) |
| C(32)-C(35) | 1.549 (8) | C(32)-N(5)-H(5X) | 118 (3) |
| C(32)-C(34) | 1.552 (7) | C(32)-N(5)-H(5Y) | 106 (3) |
| C(33)-H(33A) | 0.9700 | H(5X)-N(5)-H(5Y) | 107 (5) |
| C(33)-H(33B) | 0.9700 | C(32)-N(5)-H(5Z) | 117 (4) |
| C(34)-H(34A) | 0.9700 | H(5X)-N(5)-H(5Z) | 90 (5) |
| C(34)-H(34B) | 0.9700 | H(5Y)-N(5)-H(5Z) | 118 (5) |
| C(35)-H(35A) | 0.9700 | C(9)-O(1)-C(6) | 107.0 (7) |
| C(35)-H(35B) | 0.9700 | C(8)-O(2)-C(6) | 104.8 (7) |
| O(1W)-H(1WX) | 0.99 (3) | C(22)-O(3)-C(24) | 90.2 (8) |
| O(1W)-H(1WY) | 1.00 (3) | C(33)-O(6)-H(6Z) | 110 (5) |
| C(5)-N(1)-C(1) | 119 (2) | C(34)-O(7)-H(7Z) | 110 (4) |
| C(2)-C(1)-N(1) | 122 (2) | C(35)-O(8)-H(8Z) | 113 (4) |
| C(2)-C(1)-H(1) | 118.8 | O(1)-C(6)-C(5) | 107.9 (9) |
| N(1)-C(1)-H(1) | 118.8 | O(1)-C(6)-O(2) | 106.1 (9) |
| C(1)-C(2)-C(3) | 117 (2) | C(5)-C(6)-O(2) | 104.7 (9) |
| C(1)-C(2)-Cl(1) | 125 (3) | O(1)-C(6)-C(7) | 110.7 (11) |
| C(3)-C(2)-Cl(1) | 117 (3) | C(5)-C(6)-C(7) | 116.9 (13) |
| C(4)-C(3)-C(2) | 118 (3) | O(2)-C(6)-C(7) | 109.8 (10) |
| C(4)-C(3)-H(3) | 120.8 | C(6)-C(7)-H(7A) | 109.5 |
| C(2)-C(3)-H(3) | 120.8 | C(6)-C(7)-H(7B) | 109.5 |
| C(3)-C(4)-C(5) | 124 (3) | H(7A)-C(7)-H(7B) | 109.5 |
| C(3)-C(4)-H(4) | 118.0 | C(6)-C(7)-H(7C) | 109.5 |
| C(5)-C(4)-H(4) | 118.0 | H(7A)-C(7)-H(7C) | 109.5 |
| C(4)-C(5)-N(1) | 118.2 (17) | H(7B)-C(7)-H(7C) | 109.5 |
| C(4)-C(5)-C(6) | 123.8 (15) | C(13)-C(8)-O(2) | 126.8 (7) |
| O(2)-C(8)-C(9) | 112.3 (9) | C(13)-C(8)-C(9) | 120.9 (8) |
| C(10)-C(9)-C(8) | 126.1 (12) | N(2)-C(17)-C(18) | 112.6 (5) |
| C(10)-C(9)-O(1) | 126.1 (10) | N(2)-C(17)-H(17A) | 109.1 |
| C(8)-C(9)-O(1) | 107.8 (8) | C(18)-C(17)-H(17A) | 109.1 |
| C(11)-C(10)-C(9) | 113.9 (10) | N(2)-C(17)-H(17B) | 109.1 |
| C(11)-C(10)-H(10) | 123.0 | C(18)-C(17)-H(17B) | 109.1 |
| C(9)-C(10)-H(10) | 123.0 | H(17A)-C(17)-H(17B) | 107.8 |
| C(10)-C(11)-C(12) | 121.8 (11) | C(14)-C(18)-C(17) | 113.0 (6) |
| C(10)-C(11)-H(11) | 119.1 | C(14)-C(18)-H(18A) | 109.0 |
| C(12)-C(11)-H(11) | 119.1 | C(17)-C(18)-H(18A) | 109.0 |
| C(11)-C(12)-C(13) | 123.9 (12) | C(14)-C(18)-H(18B) | 109.0 |
| C(11)-C(12)-H(12) | 118.1 | C(17)-C(18)-H(18B) | 109.0 |
| C(13)-C(12)-H(12) | 118.1 | H(18A)-C(18)-H(18B) | 107.8 |
| C(8)-C(13)-C(12) | 113.4 (8) | N(2)-C(19)-C(20) | 113.6 (5) |
| C(8)-C(13)-C(14) | 123.1 (6) | N(2)-C(19)-H(19A) | 108.8 |
| C(12)-C(13)-C(14) | 123.5 (9) | C(20)-C(19)-H(19A) | 108.8 |
| C(18)-C(14)-C(15) | 107.6 (5) | N(2)-C(19)-H(19B) | 108.8 |
| C(18)-C(14)-C(13) | 114.8 (7) | C(20)-C(19)-H(19B) | 108.8 |
| C(15)-C(14)-C(13) | 114.0 (7) | H(19A)-C(19)-H(19B) | 107.7 |
| C(18)-C(14)-H(14) | 106.6 | N(3)-C(20)-N(4) | 111.7 (5) |
| C(15)-C(14)-H(14) | 106.6 | N(3)-C(20)-C(19) | 125.4 (5) |
| C(13)-C(14)-H(14) | 106.6 | N(4)-C(20)-C(19) | 122.8 (5) |
| C(14)-C(15)-C(16) | 112.4 (6) | N(4)-C(21)-C(22) | 114.3 (5) |
| C(14)-C(15)-H(15A) | 109.1 | N(4)-C(21)-H(21A) | 108.7 |
| C(16)-C(15)-H(15A) | 109.1 | C(22)-C(21)-H(21A) | 108.7 |
| C(14)-C(15)-H(15B) | 109.1 | N(4)-C(21)-H(21B) | 108.7 |
| C(16)-C(15)-H(15B) | 109.1 | C(22)-C(21)-H(21B) | 108.7 |
| H(15A)-C(15)-H(15B) | 107.9 | H(21A)-C(21)-H(21B) | 107.6 |
| N(2)-C(16)-C(15) | 111.7 (6) | O(3)-C(22)-C(23) | 91.5 (6) |
| N(2)-C(16)-H(16A) | 109.3 | O(3)-C(22)-C(21) | 112.8 (5) |
| C(15)-C(16)-H(16A) | 109.3 | C(23)-C(22)-C(21) | 116.3 (7) |
| N(2)-C(16)-H(16B) | 109.3 | O(3)-C(22)-H(22) | 111.6 |
| C(15)-C(16)-H(16B) | 109.3 | C(23)-C(22)-H(22) | 111.6 |
| H(16A)-C(16)-H(16B) | 107.9 | C(21)-C(22)-H(22) | 111.6 |
| C(24)-C(23)-H(23A) | 114.4 | C(24)-C(23)-C(22) | 85.5 (8) |
| C(22)-C(23)-H(23A) | 114.4 | C(33)-C(32)-C(35) | 111.2 (4) |
| C(24)-C(23)-H(23B) | 114.4 | N(5)-C(32)-C(34) | 110.0 (4) |

TABLE E2-3-continued

Bond lengths [Å] and angles [°] for Form 2.

| | | | |
|---|---|---|---|
| C(22)-C(23)-H(23B) | 114.4 | C(33)-C(32)-C(34) | 108.5 (4) |
| H(23A)-C(23)-H(23B) | 111.5 | C(35)-C(32)-C(34) | 110.7 (4) |
| O(3)-C(24)-C(23) | 92.7 (8) | O(6)-C(33)-C(32) | 110.6 (4) |
| O(3)-C(24)-H(24A) | 113.2 | O(6)-C(33)-H(33A) | 109.5 |
| C(23)-C(24)-H(24A) | 113.2 | C(32)-C(33)-H(33A) | 109.5 |
| O(3)-C(24)-H(24B) | 113.2 | O(6)-C(33)-H(33B) | 109.5 |
| C(23)-C(24)-H(24B) | 113.2 | C(32)-C(33)-H(33B) | 109.5 |
| H(24A)-C(24)-H(24B) | 110.5 | H(33A)-C(33)-H(33B) | 108.1 |
| C(30)-C(25)-N(4) | 132.2 (4) | O(7)-C(34)-C(32) | 111.7 (4) |
| C(30)-C(25)-C(26) | 121.4 (5) | O(7)-C(34)-H(34A) | 109.3 |
| N(4)-C(25)-C(26) | 106.4 (4) | C(32)-C(34)-H(34A) | 109.3 |
| N(3)-C(26)-C(25) | 108.2 (5) | O(7)-C(34)-H(34B) | 109.3 |
| N(3)-C(26)-C(27) | 131.3 (4) | C(32)-C(34)-H(34B) | 109.3 |
| C(25)-C(26)-C(27) | 120.5 (5) | H(34A)-C(34)-H(34B) | 107.9 |
| C(28)-C(27)-C(26) | 118.6 (4) | O(8)-C(35)-C(32) | 109.4 (4) |
| C(28)-C(27)-H(27) | 120.7 | O(8)-C(35)-H(35A) | 109.8 |
| C(26)-C(27)-H(27) | 120.7 | C(32)-C(35)-H(35A) | 109.8 |
| C(27)-C(28)-C(29) | 120.8 (5) | O(8)-C(35)-H(35B) | 109.8 |
| C(27)-C(28)-H(28) | 119.6 | C(32)-C(35)-H(35B) | 109.8 |
| C(29)-C(28)-H(28) | 119.6 | H(35A)-C(35)-H(35B) | 108.2 |
| C(30)-C(29)-C(28) | 120.7 (5) | H(1WX)-O(1W)-H(1WY) | 104 (6) |
| C(30)-C(29)-C(31) | 119.8 (4) | | |
| C(28)-C(29)-C(31) | 119.5 (5) | | |
| C(25)-C(30)-C(29) | 118.0 (4) | | |
| C(25)-C(30)-H(30) | 121.0 | | |
| C(29)-C(30)-H(30) | 121.0 | | |
| O(5)-C(31)-O(4) | 124.9 (5) | | |
| O(5)-C(31)-C(29) | 119.1 (4) | | |
| O(4)-C(31)-C(29) | 116.0 (5) | | |
| N(5)-C(32)-C(33) | 111.0 (4) | | |
| N(5)-C(32)-C(35) | 105.5 (4) | | |

Symmetry transformations used to generate equivalent atoms:

TABLE E2-4

Anisotropic displacement parameters ($Å^2 \times 10^3$) for Form 2. The anisotropic displacement factor exponent takes the form: $-2\pi^2[\, h^2 a^{*2} U^{11} + \ldots + 2\, h\, k\, a^*\, b^*\, U^{12}\,]$

| | $U^{11}$ | $U^{22}$ | $U^{33}$ | $U^{23}$ | $U^{13}$ | $U^{12}$ |
|---|---|---|---|---|---|---|
| Cl(1) | 135(3) | 610(20) | 393(10) | −72(14) | 34(5) | 33(7) |
| N(1) | 154(10) | 208(13) | 161(9) | 50(10) | −32(8) | −41(10) |
| C(1) | 108(12) | 390(40) | 175(15) | 30(20) | −3(11) | −59(18) |
| C(2) | 99(11) | 320(40) | 230(20) | −30(20) | −48(12) | 48(16) |
| C(3) | 180(20) | 280(40) | 390(40) | −50(30) | 0(30) | 60(30) |
| C(4) | 167(16) | 169(18) | 350(30) | 60(20) | 34(17) | 21(14) |
| C(5) | 127(9) | 134(10) | 113(7) | 39(7) | −32(6) | −16(8) |
| N(2) | 60(3) | 46(3) | 56(2) | 3(2) | 10(2) | −2(2) |
| N(3) | 46(2) | 56(3) | 55(2) | −4(2) | 2(2) | −13(2) |
| N(4) | 40(2) | 52(3) | 51(2) | 1(2) | 2(2) | −3(2) |
| N(5) | 43(2) | 46(3) | 58(3) | −5(2) | 2(2) | 2(2) |
| O(1) | 184(8) | 173(8) | 92(4) | 21(5) | −40(5) | −9(7) |
| O(2) | 115(4) | 173(7) | 77(3) | 35(4) | −21(3) | −36(5) |
| O(3) | 103(4) | 95(4) | 108(4) | −3(3) | −39(3) | −16(3) |
| O(4) | 38(2) | 60(3) | 87(3) | 6(2) | −1(2) | −8(2) |
| O(5) | 48(2) | 64(3) | 79(3) | 19(2) | 3(2) | −6(2) |
| O(6) | 69(3) | 48(2) | 109(3) | 14(2) | 17(2) | 3(2) |
| O(7) | 44(2) | 48(2) | 92(3) | −2(2) | −3(2) | 4(2) |
| O(8) | 42(2) | 52(2) | 90(3) | −11(2) | 1(2) | −7(2) |
| C(6) | 127(8) | 135(10) | 91(6) | 3(6) | −21(6) | −10(7) |
| C(7) | 185(13) | 125(11) | 189(13) | 22(10) | −43(10) | 0(10) |
| C(8) | 122(7) | 109(7) | 63(4) | 27(4) | 13(4) | 2(6) |
| C(9) | 151(9) | 126(8) | 70(5) | 15(5) | −16(5) | 3(7) |
| C(10) | 184(12) | 177(12) | 65(5) | 24(6) | 1(6) | 4(10) |
| C(11) | 203(13) | 186(13) | 79(6) | 45(7) | 33(7) | −10(12) |
| C(12) | 157(9) | 158(10) | 70(5) | 32(6) | 16(5) | −10(8) |
| C(13) | 117(7) | 106(6) | 67(4) | 14(4) | 24(4) | −3(6) |
| C(14) | 97(5) | 92(5) | 61(4) | 19(4) | 13(3) | −7(4) |
| C(15) | 106(5) | 58(4) | 82(4) | 8(4) | 5(4) | 13(4) |
| C(16) | 92(5) | 53(3) | 79(4) | 0(3) | 6(4) | 6(4) |
| C(17) | 77(4) | 71(4) | 67(4) | 10(3) | 16(3) | 17(4) |
| C(18) | 102(5) | 84(5) | 64(4) | −4(4) | 27(4) | 23(4) |
| C(19) | 57(3) | 55(4) | 61(3) | 3(3) | 2(3) | −9(3) |
| C(20) | 39(3) | 55(3) | 48(3) | −7(2) | 1(2) | −6(2) |
| C(21) | 45(3) | 58(4) | 61(3) | 2(3) | 2(2) | 4(3) |
| C(22) | 50(3) | 82(5) | 61(3) | 5(3) | −2(3) | −1(3) |
| C(23) | 76(5) | 148(10) | 110(6) | 14(6) | −29(5) | 6(6) |
| C(24) | 84(6) | 196(14) | 152(9) | 15(10) | −36(6) | −32(8) |
| C(25) | 40(3) | 55(3) | 43(2) | −3(2) | 2(2) | 0(2) |
| C(26) | 37(2) | 53(3) | 46(2) | −7(3) | 2(2) | −3(2) |
| C(27) | 34(2) | 63(4) | 52(3) | −5(3) | −3(2) | −3(2) |
| C(28) | 44(3) | 57(3) | 44(2) | 1(3) | −4(2) | −4(3) |
| C(29) | 42(3) | 53(3) | 41(2) | −3(2) | 1(2) | −4(2) |
| C(30) | 36(2) | 53(3) | 47(2) | 0(2) | 4(2) | −5(2) |
| C(31) | 45(3) | 48(3) | 46(3) | −1(3) | 3(2) | −1(2) |
| C(32) | 36(2) | 47(3) | 57(3) | 0(2) | 1(2) | −1(2) |
| C(33) | 48(3) | 47(3) | 76(3) | 1(3) | 3(3) | 4(3) |
| C(34) | 41(3) | 50(3) | 66(3) | −5(3) | 4(2) | −2(2) |
| C(35) | 42(3) | 53(3) | 67(3) | −3(3) | 5(2) | −4(3) |
| O(1W) | 52(2) | 54(2) | 80(3) | 4(2) | 5(2) | −2(2) |

Calculated/Simulated PXRD Data.

Figure 21:
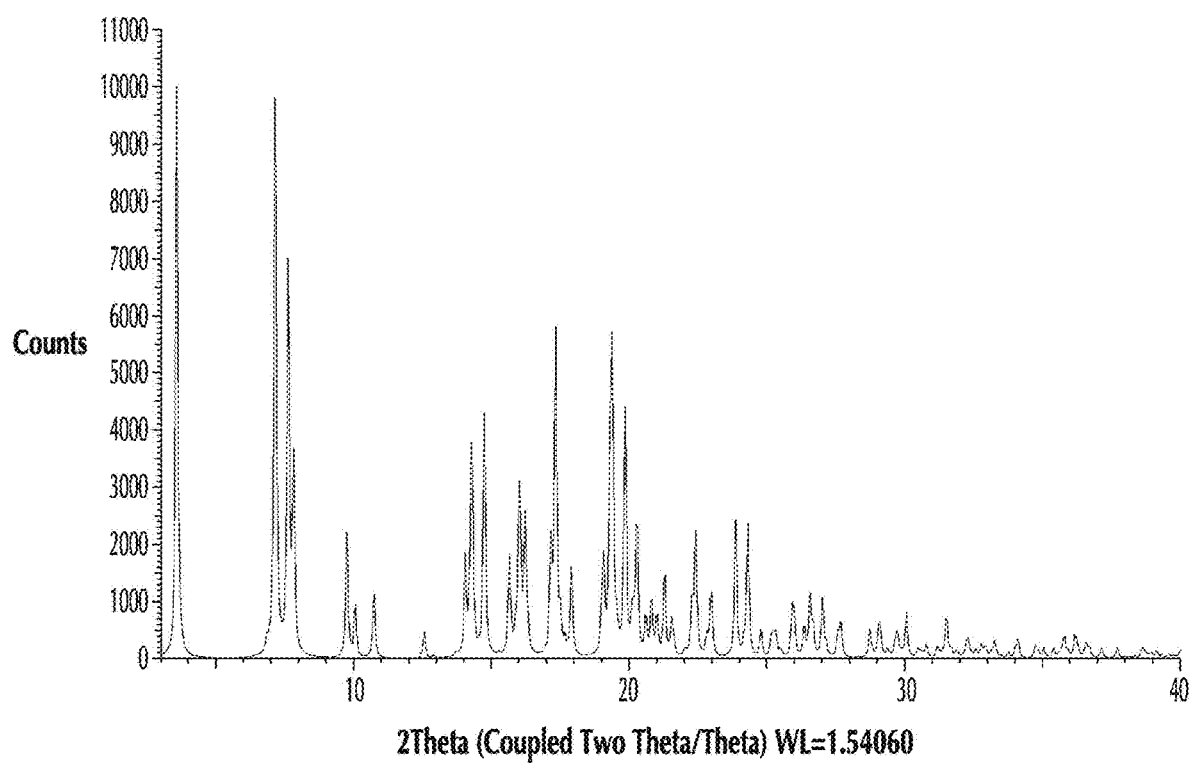
FIG. 21 shows a calculated/simulated PXRD pattern of Form 2 of tris salt of Compound 2 based on the information from its single crystal X-ray data analysis.

Using the information obtained by Single Crystal X-Ray Analysis herein above, PXRD peak positions and intensity for Form 2 can be calculated/simulated (See FIG. 21, using Bruker DIFFRAC.EVA version 5.0.0.22). A list of calculated/simulated PXRD diffraction peaks expressed in terms of the degree 2θ and relative intensities with a relative intensity of 3.0% for Form 2 is provided below.

TABLE E2-5

Calculated PXRD peak positions and intensity for Form 2.

| Angle 2-Theta ° | Relative Intensity % |
|---|---|
| 3.6 | 100% |
| 7.1 | 96% |
| 7.6 | 69% |
| 7.8 | 37% |
| 9.7 | 22% |
| 10.0 | -9% |
| 10.7 | 11% |
| 12.5 | -5% |
| 14.0 | 18% |
| 14.3 | 37% |
| 14.7 | 42% |
| 15.6 | 18% |
| 16.0 | 31% |
| 16.2 | 25% |
| 17.3 | 57% |
| 17.9 | 15% |
| 19.0 | 19% |
| 19.4 | 57% |
| 19.8 | 42% |
| 20.2 | 23% |
| 20.6 | -7% |
| 20.8 | 10% |
| 21.0 | -7% |
| 21.3 | 14% |
| 21.5 | -6% |
| 22.4 | 21% |
| 22.9 | 11% |
| 23.8 | 24% |
| 24.3 | 23% |
| 24.8 | -4% |
| 25.9 | -9% |
| 26.4 | -5% |
| 26.6 | 11% |
| 27.0 | 10% |
| 28.7 | -5% |
| 29.1 | -6% |
| 29.7 | -4% |
| 30.0 | -8% |
| 31.5 | -7% |
| 32.3 | -3% |
| 34.1 | -3% |
| 35.8 | -4% |
| 36.2 | -4% |

Example 3. Form 3 of Tris Salt of Compound 2

Preparation of Form 3 of Tris Salt of Compound 2 (Slurry to Slurry Conversion)

The anhydrous form Form A of tris salt of Compound 2 (1.177 grams) was added to a 50 mL EasyMax® reactor. A mixed solvent of acetonitrile and water (27.9 mL acetonitrile and 2.4 mL water) was then added. The resulting mixture (a slurry) was stirred with overhead paddle stirring at room temperature (about 25° C.) over two days. The mixture was then cooled to 0° C. and stirred for about 1 hour. Then the mixture was filtered by suction filtration through filter paper and the solid collected (cake) was rinsed with 2-3 mL cold acetonitrile (0° C.) twice. The resulting cake was air-dried on the funnel for one hour. The cake/funnel was transferred to a vacuum oven for further drying (50° C./~22 in Hg vacuum, with slight nitrogen bleed). After about hours 1.115 gm of white solid was obtained (designed as Form 3).

Alternative Preparation of Form 3 of Compound 2, 1,3-dihydroxy-2-(hydroxymethyl)propan-2-aminium salt Alternatively, single crystals of Form 3 of tris salt of Compound 2 were prepared by vapor diffusion of acetonitrile into a saturated solution of Compound 2, 1,3-dihydroxy-2-(hydroxymethyl)propan-2-aminium salt in acetonitrile/15% water (v/v).

Single Crystal X-Ray Analysis.

A sample of Form 3 of tris salt of Compound 2 was tested for single crystal X-ray analysis. Data collection was performed on a Bruker D8 Venture diffractometer at room temperature on a representative crystal. Data collection consisted of omega and phi scans.

The structure was solved by intrinsic phasing using SHELX software suite (SHELXTL, Version 5.1, Bruker-AXS, 1997) in the Monoclinic space group P2₁. The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (See R. W. W. Hooft et al. *J. Appl. Cryst.* (2008). 41. 96-103) was performed using PLATON (See A. L. Spek, J. Appl. Cryst. 2003, 36, 7-13). Assuming the sample submitted is enantiopure, the absolute structure (with stereochemistry information on the two chiral centers) was assigned.

Figure 22:
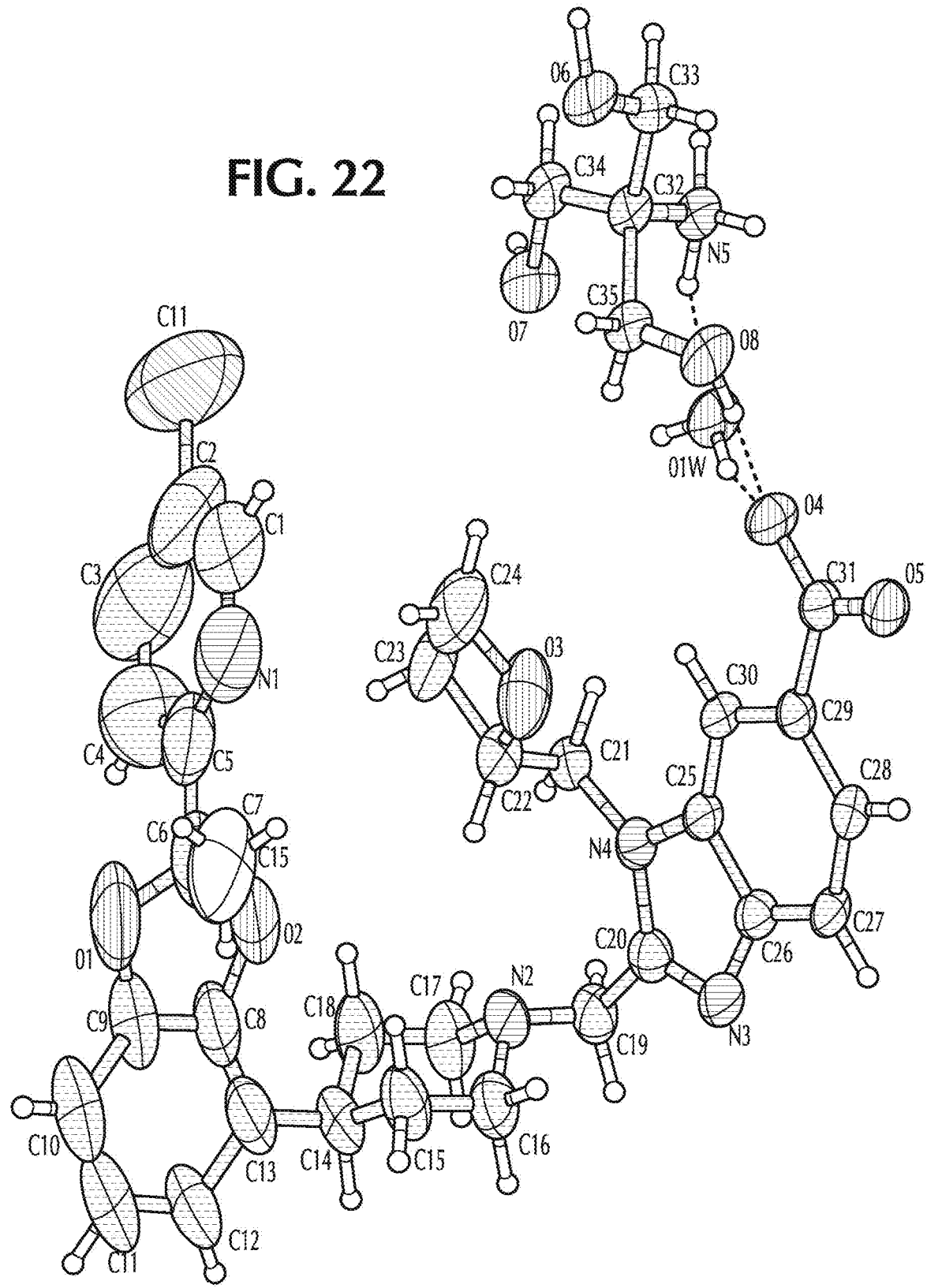
FIG. 22 shows an illustrative single crystal structure of a monohydrate crystalline form (Form 3) of tris salt of Compound 2.

The final R-index was 5.1%. A final difference Fourier revealed no missing or misplaced electron density. The refined structure was plotted using the SHELXTL plotting package (SHELXTL, Version 5.1, BrukerAXS, 1997) (FIG. 22). The absolute configuration was determined by the method of Flack (See H. D. Flack, *Acta Cryst.* 1983, A39, 867-881). According to the refined structure, Form 3 is a monohydrate of tris salt of Compound 2:

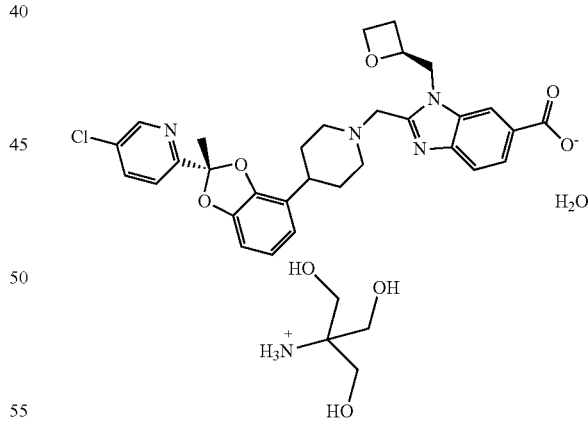

and a chemical name for this hydrate form (including stereochemistry information) is: 2-({4-[(2S)-2-(5-Chloro-pyridin-2-yl)-2-methyl-1,3-benzodioxol-4-yl]piperidin-1-yl}methyl)-1-[(2S)-oxetan-2-ylmethyl]-1H-benzimidazole-6-carboxylate, 1,3-dihydroxy-2-(hydroxymethyl)propan-2-aminium salt, monohydrate.

Pertinent crystal, data collection and refinement are summarized in Table E3-1. Atomic coordinates, bond lengths, bond angles and displacement parameters are listed in tables E3-2 to E3-4.

TABLE E3-1

Crystal data and structure refinement for Form 3.

| | |
|---|---|
| Empirical formula | C35 H44 Cl N5 O9 |
| Formula weight | 714.20 |
| Temperature | 296(2) K |
| Wavelength | 1.54178 Å |
| Crystal system | Monoclinic |
| Space group | P21 |
| Unit cell dimensions | a = 12.8892(5) Å   α = 90°. |
| | b = 6.1536(3) Å   β = 91.835(2)°. |
| | c = 23.9167(10) Å   γ = 90°. |
| Volume | 1895.98(14) Å$^3$ |
| Z | 2 |
| Density (calculated) | 1.251 Mg/m$^3$ |
| Absorption coefficient | 1.373 mm$^{-1}$ |
| F(000) | 756 |
| Crystal size | 0.780 × 0.100 × 0.040 mm$^3$ |
| Theta range for data collection | 3.431 to 72.528°. |
| Index ranges | −12 <= h <= 15, −7 <= k <= 7, −29 <= l <= 29 |
| Reflections collected | 16800 |
| Independent reflections | 6869 [R(int) = 0.0523] |
| Completeness to theta = 67.679° | 98.0% |
| Absorption correction | Empirical |
| Refinement method | Full-matrix least-squares on F$^2$ |
| Data/restraints/parameters | 6869/9/476 |
| Goodness-of-fit on F2 | 1.043 |
| Final R indices [I > 2sigma(I)] | R1 = 0.0508, wR2 = 0.1434 |
| R indices (all data) | R1 = 0.0542, wR2 = 0.1482 |
| Absolute structure parameter | 0.06(3) |
| Extinction coefficient | n/a |
| Largest diff. peak and hole | 0.260 and −0.321 e•Å$^{-3}$ |

TABLE E3-2

Atomic coordinates (×10$^4$) and equivalent isotropic displacement parameters (Å$^2$ × 10$^3$) for Form 3. U(eq) is defined as one third of the trace of the orthogonalized U$^{ij}$ tensor.

| | x | y | z | U(eq) |
|---|---|---|---|---|
| Cl(1) | 2582(2) | 9965(16) | 6603(2) | 325(4) |
| N(1) | 5060(6) | 6766(14) | 6129(3) | 148(2) |
| N(2) | 9316(2) | 10129(4) | 7585(1) | 49(1) |
| N(3) | 10186(2) | 6949(4) | 8750(1) | 48(1) |
| N(4) | 8505(2) | 7208(4) | 8496(1) | 44(1) |
| N(5) | 3669(2) | 1786(4) | 9568(1) | 47(1) |
| O(1) | 6678(4) | 8716(10) | 5096(2) | 131(2) |
| O(2) | 7358(3) | 8701(8) | 6001(1) | 104(1) |
| O(3) | 6794(3) | 4812(6) | 7825(1) | 92(1) |
| O(4) | 6522(2) | −848(4) | 9422(1) | 58(1) |
| O(5) | 7796(2) | −981(4) | 9855(1) | 60(1) |
| O(6) | 2262(2) | −2325(4) | 8721(1) | 56(1) |
| O(7) | 3425(2) | 4070(4) | 8536(1) | 69(1) |
| O(8) | 4910(2) | −1536(3) | 9093(1) | 58(1) |
| O(1W) | 5392(2) | 4478(4) | 9523(1) | 58(1) |
| O(1) | 4178(9) | 7380(30) | 6380(4) | 185(5) |
| O(2) | 3714(8) | 9290(40) | 6315(6) | 190(6) |
| O(3) | 4194(12) | 10740(30) | 6016(7) | 229(7) |
| O(4) | 5148(9) | 10270(20) | 5778(6) | 186(6) |
| C(5) | 5568(5) | 8290(13) | 5846(2) | 113(2) |
| O(6) | 6587(5) | 7667(12) | 5634(2) | 107(2) |
| O(7) | 6794(7) | 5276(14) | 5590(4) | 150(3) |
| O(8) | 8020(4) | 9821(9) | 5659(2) | 87(1) |
| O(9) | 7605(5) | 9845(11) | 5117(2) | 104(2) |
| O(10) | 8072(7) | 10888(14) | 4692(2) | 126(2) |
| O(11) | 8964(7) | 11915(15) | 4824(2) | 131(2) |
| O(12) | 9397(5) | 11903(12) | 5359(2) | 107(2) |
| O(13) | 8917(4) | 10851(8) | 5804(2) | 81(1) |
| O(14) | 9376(3) | 10911(7) | 6388(2) | 73(1) |
| O(15) | 9545(3) | 8656(7) | 6648(1) | 73(1) |
| O(16) | 9983(3) | 8811(6) | 7242(1) | 64(1) |
| O(17) | 9203(3) | 12329(6) | 7363(2) | 68(2) |
| O(18) | 8725(4) | 12292(6) | 6778(2) | 76(2) |
| O(19) | 9678(2) | 10173(5) | 8169(1) | 54(1) |
| O(20) | 9475(2) | 8082(5) | 8466(1) | 46(1) |
| O(21) | 7529(2) | 8089(5) | 8276(1) | 49(1) |
| O(22) | 7147(3) | 7018(7) | 7745(1) | 61(1) |
| O(23) | 6068(3) | 7712(11) | 7537(2) | 94(2) |
| O(24) | 5782(5) | 5437(16) | 7594(3) | 128(2) |
| O(25) | 8603(2) | 5376(5) | 8831(1) | 42(1) |
| O(26) | 9655(2) | 5244(5) | 8988(1) | 43(1) |
| O(27) | 10003(2) | 3558(5) | 9340(1) | 46(1) |
| O(28) | 9287(2) | 2076(5) | 9519(1) | 46(1) |
| O(29) | 8228(2) | 2223(5) | 9355(1) | 42(1) |
| O(30) | 7882(2) | 3870(5) | 9003(1) | 42(1) |
| O(31) | 7462(2) | −548(5) | 9563(1) | 45(1) |
| O(32) | 3329(2) | −681(4) | 9035(1) | 43(1) |
| O(33) | 2609(2) | −1171(5) | 9201(1) | 51(1) |
| O(34) | 2769(2) | 2309(5) | 8659(1) | 54(1) |
| O(35) | 4294(2) | −−179(5) | 8747(1) | 49(1) |

TABLE E3-3

Bond lengths [Å] and angles [°] for Form 3.

| | |
|---|---|
| Cl(1)-C(2) | 1.684(13) |
| N(1)-C(5) | 1.340(10) |
| N(1)-C(1) | 1.355(16) |
| N(2)-C(16) | 1.454(4) |
| N(2)-C(19) | 1.458(4) |
| N(2)-C(17) | 1.460(4) |
| N(3)-C(20) | 1.322(4) |
| N(3)-C(26) | 1.385(4) |
| N(4)-C(20) | 1.365(4) |
| N(4)-C(25) | 1.386(4) |
| N(4)-C(21) | 1.454(4) |
| N(5)-C(32) | 1.496(4) |
| N(5)-H(5X) | 0.95(2) |
| N(5)-H(5Y) | 0.98(2) |
| N(5)-H(5Z) | 0.97(2) |
| O(1)-C(9) | 1.382(8) |
| O(1)-C(6) | 1.446(7) |
| O(2)-C(8) | 1.385(6) |
| O(2)-C(6) | 1.452(7) |
| O(3)-C(22) | 1.446(5) |
| O(3)-C(24) | 1.451(7) |
| O(4)-C(31) | 1.261(3) |
| O(5)-C(31) | 1.241(4) |
| O(6)-C(33) | 1.410(4) |
| O(6)-H(6Y) | 0.95(2) |
| O(7)-C(34) | 1.411(4) |
| O(7)-H(7Y) | 0.96(3) |
| O(8)-C(35) | 1.405(4) |
| O(8)-H(8Y) | 0.97(2) |
| O(1W)-H(1WX) | 0.97(2) |
| O(1W)-H(1WY) | 0.96(2) |
| C(1)-C(2) | 1.33(2) |
| C(1)-H(1) | 0.9300 |
| C(2)-C(3) | 1.31(2) |
| C(3)-C(4) | 1.401(17) |
| C(3)-H(3) | 0.9300 |
| O(4)-C(5) | 1.343(14) |
| C(4)-H(4) | 0.9300 |
| C(5)-C(6) | 1.473(10) |
| C(6)-C(7) | 1.500(12) |
| C(7)-H(7A) | 0.9600 |
| C(7)-H(7B) | 0.9600 |
| C(7)-H(7C) | 0.9600 |
| C(8)-C(13) | 1.354(7) |
| C(8)-C(9) | 1.387(6) |
| C(9)-C(10) | 1.359(9) |
| C(10)-C(11) | 1.340(11) |
| C(10)-H(10) | 0.9300 |
| C(11)-C(12) | 1.379(9) |
| C(11)-H(11) | 0.9300 |
| C(12)-C(13) | 1.405(6) |
| C(12)-H(12) | 0.9300 |

TABLE E3-3-continued

Bond lengths [Å] and angles [°] for Form 3.

| | |
|---|---|
| C(13)-C(14) | 1.499(6) |
| C(14)-C(18) | 1.532(6) |
| C(14)-C(15) | 1.534(6) |
| C(14)-H(14) | 0.9800 |
| C(15)-C(16) | 1.514(5) |
| C(15)-H(15A) | 0.9700 |
| C(15)-H(15B) | 0.9700 |
| C(16)-H(16A) | 0.9700 |
| C(16)-H(16B) | 0.9700 |
| C(17)-C(18) | 1.510(5) |
| C(17)-H(17A) | 0.9700 |
| C(17)-H(17B) | 0.9700 |
| C(18)-H(18A) | 0.9700 |
| C(18)-H(18B) | 0.9700 |
| C(19)-C(20) | 1.496(4) |
| C(19)-H(19A) | 0.9700 |
| C(19)-H(19B) | 0.9700 |
| C(21)-C(22) | 1.500(4) |
| C(21)-H(21A) | 0.9700 |
| C(21)-H(21B) | 0.9700 |
| C(22)-C(23) | 1.522(5) |
| C(22)-H(22) | 0.9800 |
| C(23)-C(24) | 1.455(11) |
| C(23)-H(23A) | 0.9700 |
| C(23)-H(23B) | 0.9700 |
| C(24)-H(24A) | 0.9700 |
| C(24)-H(24B) | 0.9700 |
| C(25)-C(30) | 1.385(4) |
| C(25)-C(26) | 1.398(4) |
| C(26)-C(27) | 1.400(4) |
| C(27)-C(28) | 1.376(4) |
| C(27)-H(27) | 0.9300 |
| C(28)-C(29) | 1.411(4) |
| C(28)-H(28) | 0.9300 |
| C(29)-C(30) | 1.384(4) |
| C(29)-C(31) | 1.521(4) |
| C(30)-H(30) | 0.9300 |
| C(32)-C(34) | 1.514(4) |
| C(32)-C(33) | 1.530(4) |
| C(32)-C(35) | 1.536(4) |
| C(33)-H(33A) | 0.9700 |
| C(33)-H(33B) | 0.9700 |
| C(34)-H(34A) | 0.9700 |
| C(34)-H(34B) | 0.9700 |
| C(35)-H(35A) | 0.9700 |
| C(35)-H(35B) | 0.9700 |
| C(5)-N(1)-C(1) | 117.3(11) |
| C(16)-N(2)-C(19) | 111.9(3) |
| C(16)-N(2)-C(17) | 111.4(3) |
| C(19)-N(2)-C(17) | 110.9(3) |
| C(20)-N(3)-C(26) | 105.5(2) |
| C(20)-N(4)-C(25) | 106.5(2) |
| C(20)-N(4)-C(21) | 128.1(3) |
| C(25)-N(4)-C(21) | 125.1(2) |
| C(32)-N(5)-H(5X) | 105(2) |
| C(32)-N(5)-H(5Y) | 112(2) |
| H(5X)-N(5)-H(5Y) | 104(3) |
| C(32)-N(5)-H(5Z) | 111(2) |
| H(5X)-N(5)-H(5Z) | 115(3) |
| H(5Y)-N(5)-H(5Z) | 109(3) |
| C(9)-O(1)-C(6) | 106.8(4) |
| C(8)-O(2)-C(6) | 106.5(4) |
| C(22)-O(3)-C(24) | 89.1(4) |
| C(33)-O(6)-H(6Y) | 107(2) |
| C(34)-O(7)-H(7Y) | 105(3) |
| C(35)-O(8)-H(8Y) | 105(3) |
| H(1WX)-O(1W)-H(1WY) | 117(3) |
| C(2)-C(1)-N(1) | 125.3(13) |
| C(2)-C(1)-H(1) | 117.4 |
| N(1)-C(1)-H(1) | 117.4 |
| C(3)-C(2)-C(1) | 116.5(13) |
| C(3)-C(2)-Cl(1) | 119.2(17) |
| C(1)-C(2)-Cl(1) | 124.3(17) |
| C(2)-C(3)-C(4) | 121.4(16) |
| C(2)-C(3)-H(3) | 119.3 |
| C(4)-C(3)-H(3) | 119.3 |
| C(5)-C(4)-C(3) | 119.4(13) |
| C(5)-C(4)-H(4) | 120.3 |
| C(3)-C(4)-H(4) | 120.3 |
| N(1)-C(5)-C(4) | 119.7(9) |
| N(1)-C(5)-C(6) | 116.6(7) |
| C(4)-C(5)-C(6) | 123.7(7) |
| O(1)-C(6)-O(2) | 105.6(5) |
| O(1)-C(6)-C(5) | 106.8(5) |
| O(2)-C(6)-C(5) | 106.1(5) |
| O(1)-C(6)-C(7) | 110.9(7) |
| O(2)-C(6)-C(7) | 110.6(6) |
| C(5)-C(6)-C(7) | 116.3(7) |
| C(6)-C(7)-H(7A) | 109.5 |
| C(6)-C(7)-H(7B) | 109.5 |
| H(7A)-C(7)-H(7B) | 109.5 |
| C(6)-C(7)-H(7C) | 109.5 |
| H(7A)-C(7)-H(7C) | 109.5 |
| H(7B)-C(7)-H(7C) | 109.5 |
| C(13)-C(8)-O(2) | 128.3(4) |
| C(13)-C(8)-C(9) | 122.4(4) |
| O(2)-C(8)-C(9) | 109.3(5) |
| C(10)-C(9)-O(1) | 128.0(5) |
| C(10)-C(9)-C(8) | 122.5(7) |
| O(1)-C(9)-C(8) | 109.6(5) |
| C(11)-C(10)-C(9) | 116.4(6) |
| C(11)-C(10)-H(10) | 121.8 |
| C(9)-C(10)-H(10) | 121.8 |
| C(10)-C(11)-C(12) | 122.3(6) |
| C(10)-C(11)-H(11) | 118.8 |
| C(12)-C(11)-H(11) | 118.8 |
| C(11)-C(12)-C(13) | 122.0(7) |
| C(11)-C(12)-H(12) | 119.0 |
| C(13)-C(12)-H(12) | 119.0 |
| C(8)-C(13)-C(12) | 114.5(4) |
| C(8)-C(13)-C(14) | 123.9(3) |
| C(12)-C(13)-C(14) | 121.6(5) |
| C(13)-C(14)-C(18) | 112.0(4) |
| C(13)-C(14)-C(15) | 113.8(4) |
| C(18)-C(14)-C(15) | 109.1(3) |
| C(13)-C(14)-H(14) | 107.2 |
| C(18)-C(14)-H(14) | 107.2 |
| C(15)-C(14)-H(14) | 107.2 |
| C(16)-C(15)-C(14) | 111.6(3) |
| C(16)-C(15)-H(15A) | 109.3 |
| C(14)-C(15)-H(15A) | 109.3 |
| C(16)-C(15)-H(15B) | 109.3 |
| C(14)-C(15)-H(15B) | 109.3 |
| H(15A)-C(15)-H(15B) | 108.0 |
| N(2)-C(16)-C(15) | 110.8(3) |
| N(2)-C(16)-H(16A) | 109.5 |
| C(15)-C(16)-H(16A) | 109.5 |
| N(2)-C(16)-H(16B) | 109.5 |
| C(15)-C(16)-H(16B) | 109.5 |
| H(16A)-C(16)-H(16B) | 108.1 |
| N(2)-C(17)-C(18) | 110.9(3) |
| N(2)-C(17)-H(17A) | 109.5 |
| C(18)-C(17)-H(17A) | 109.5 |
| N(2)-C(17)-H(17B) | 109.5 |
| C(18)-C(17)-H(17B) | 109.5 |
| H(17A)-C(17)-H(17B) | 108.1 |
| C(17)-C(18)-C(14) | 111.0(3) |
| C(17)-C(18)-H(18A) | 109.4 |
| C(14)-C(18)-H(18A) | 109.4 |
| C(17)-C(18)-H(18B) | 109.4 |
| C(14)-C(18)-H(18B) | 109.4 |
| H(18A)-C(18)-H(18B) | 108.0 |
| N(2)-C(19)-C(20) | 112.5(2) |
| N(2)-C(19)-H(19A) | 109.1 |
| C(20)-C(19)-H(19A) | 109.1 |
| N(2)-C(19)-H(19B) | 109.1 |
| C(20)-C(19)-H(19B) | 109.1 |
| H(19A)-C(19)-H(19B) | 107.8 |
| N(3)-C(20)-N(4) | 112.7(2) |
| N(3)-C(20)-C(19) | 124.6(3) |
| N(4)-C(20)-C(19) | 122.6(3) |
| N(4)-C(21)-C(22) | 113.6(2) |
| N(4)-C(21)-H(21A) | 108.8 |
| C(22)-C(21)-H(21A) | 108.8 |
| N(4)-C(21)-H(21B) | 108.8 |
| C(22)-C(21)-H(21B) | 108.8 |

TABLE E3-3-continued

Bond lengths [Å] and angles [°] for Form 3.

| | |
|---|---|
| H(21A)-C(21)-H (21B) | 107.7 |
| O(3)-C(22)-C(21) | 113.4(3) |
| O(3)-C(22)-C(23) | 91.1(4) |
| C(21)-C(22)-C(23) | 115.1(3) |
| O(3)-C(22)-H(22) | 111.9 |
| C(21)-C(22)-H(22) | 111.9 |
| C(23)-C(22)-H(22) | 111.9 |
| C(24)-C(23)-C(22) | 86.1(4) |
| C(24)-C(23)-H(23A) | 114.3 |
| C(22)-C(23)-H(23A) | 114.3 |
| C(24)-C(23)-H(23B) | 114.3 |
| C(22)-C(23)-H(23B) | 114.3 |
| H(23A)-C(23)-H (23B) | 111.5 |
| O(3)-C(24)-C(23) | 93.6(4) |
| O(3)-C(24)-H(24A) | 113.0 |
| C(23)-C(24)-H(24A) | 113.0 |
| O(3)-C(24)-H(24B) | 113.0 |
| C(23)-C(24)-H(24B) | 113.0 |
| H(24A)-C(24)-H (24B) | 110.4 |
| C(30)-C(25)-N(4) | 131.7(2) |
| C(30)-C(25)-C(26) | 122.5(2) |
| N(4)-C(25)-C(26) | 105.8(2) |
| N(3)-C(26)-C(25) | 109.5(2) |
| N(3)-C(26)-C(27) | 131.0(2) |
| C(25)-C(26)-C(27) | 119.6(2) |
| C(28)-C(27)-C(26) | 118.3(2) |
| C(28)-C(27)-H(27) | 120.9 |
| C(26)-C(27)-H(27) | 120.9 |
| C(27)-C(28)-C(29) | 121.6(3) |
| C(27)-C(28)-H(28) | 119.2 |
| C(29)-C(28)-H(28) | 119.2 |
| C(30)-C(29)-C(28) | 120.4(2) |
| C(30)-C(29)-C(31) | 119.7(2) |
| C(28)-C(29)-C(31) | 119.8(2) |
| C(29)-C(30)-C(25) | 117.7(2) |
| C(29)-C(30)-H(30) | 121.2 |
| C(25)-C(30)-H(30) | 121.2 |
| O(5)-C(31)-O(4) | 125.1(3) |
| O(5)-C(31)-C(29) | 118.7(2) |
| O(4)-C(31)-C(29) | 116.2(2) |
| N(5)-C(32)-C(34) | 109.1(2) |
| N(5)-C(32)-C(33) | 106.4(2) |
| C(34)-C(32)-C(33) | 111.4(2) |
| N(5)-C(32)-C(35) | 108.6(2) |
| C(34)-C(32)-C(35) | 109.8(2) |
| C(33)-C(32)-C(35) | 111.5(2) |
| O(6)-C(33)-C(32) | 110.1(2) |
| O(6)-C(33)-H(33A) | 109.6 |
| C(32)-C(33)-H(33A) | 109.6 |
| O(6)-C(33)-H(33B) | 109.6 |
| C(32)-C(33)-H(33B) | 109.6 |
| H(33A)-C(33)-H(33B) | 108.2 |
| O(7)-C(34)-C(32) | 110.8(2) |
| O(7)-C(34)-H(34A) | 109.5 |
| C(32)-C(34)-H(34A) | 109.5 |
| O(7)-C(34)-H(34B) | 109.5 |
| C(32)-C(34)-H(34B) | 109.5 |
| H(34A)-C(34)-H(34B) | 108.1 |
| O(8)-C(35)-C(32) | 113.0(2) |
| O(8)-C(35)-H(35A) | 109.0 |
| C(32)-C(35)-H(35A) | 109.0 |
| O(8)-C(35)-H(35B) | 109.0 |
| C(32)-C(35)-H(35B) | 109.0 |
| H(35A)-C(35)-H(35B) | 107.8 |

Symmetry transformations used to generate equivalent atoms:

TABLE E3-4

Anisotropic displacement parameters (Å² × 10³) for Form 3. The anisotropic displacement factor exponent takes the form:
$-2\pi^2[ h^2 a^{*2} U^{11} + \ldots + 2 h k a^* b^* U^{12} ]$

| | $U^{11}$ | $U^{22}$ | $U^{33}$ | $U^{23}$ | $U^{13}$ | $U^{12}$ |
|---|---|---|---|---|---|---|
| Cl(1) | 121(2) | 543(11) | 312(4) | −88(7) | 38(2) | 21(4) |
| N(1) | 123(5) | 171(6) | 147(5) | 38(5) | −24(4) | −23(5) |
| N(2) | 56(1) | 44(1) | 49(1) | 0(1) | 9(1) | −3(1) |
| N(3) | 38(1) | 55(1) | 51(1) | −4(1) | 1(1) | −8(1) |
| N(4) | 38(1) | 48(1) | 47(1) | −1(1) | 2(1) | −2(1) |
| N(5) | 38(1) | 50(1) | 54(1) | −6(1) | 2(1) | 1(1) |
| O(1) | 160(4) | 152(4) | 77(2) | 20(2) | −31(2) | −19(4) |
| O(2) | 101(2) | 141(3) | 70(2) | 29(2) | −13(2) | −25(2) |
| O(3) | 100(2) | 84(2) | 89(2) | −4(2) | −30(2) | −16(2) |
| O(4) | 37(1) | 59(1) | 79(1) | 6(1) | 1(1) | −7(1) |
| O(5) | 45(1) | 62(1) | 71(1) | 19(1) | 2(1) | −5(1) |
| O(6) | 38(1) | 53(1) | 77(1) | −11(1) | 2(1) | −7(1) |
| O(7) | 61(1) | 48(1) | 99(2) | 13(1) | 14(1) | 2(1) |
| O(8) | 42(1) | 46(1) | 85(1) | −6(1) | −4(1) | 3(1) |
| O(1W) | 48(1) | 54(1) | 72(1) | 3(1) | 1(1) | −2(1) |
| C(1) | 113(6) | 286(17) | 154(7) | 53(10) | −9(5) | −33(9) |
| C(2) | 95(6) | 277(19) | 196(10) | −10(11) | −40(6) | 5(9) |
| C(3) | 156(10) | 233(16) | 296(18) | −36(15) | −1(11) | 77(12) |
| C(4) | 162(8) | 142(8) | 258(12) | 43(9) | 36(8) | 6(7) |
| C(5) | 112(4) | 126(5) | 98(3) | 30(3) | −33(3) | −22(4) |
| C(6) | 114(4) | 120(4) | 85(3) | 17(3) | −22(3) | −12(3) |
| C(7) | 167(7) | 114(5) | 167(7) | 21(5) | −30(5) | −7(5) |
| C(8) | 107(3) | 98(3) | 55(2) | 17(2) | 5(2) | 6(3) |
| C(9) | 140(5) | 110(4) | 62(2) | 9(2) | −8(2) | 2(4) |
| C(10) | 172(6) | 147(6) | 60(2) | 18(3) | 0(3) | 1(5) |
| C(11) | 180(7) | 148(6) | 68(3) | 32(3) | 31(3) | −4(6) |
| C(12) | 126(4) | 127(4) | 71(2) | 30(3) | 24(3) | −4(4) |
| C(13) | 96(3) | 90(3) | 59(2) | 14(2) | 15(2) | 4(2) |
| C(14) | 79(2) | 83(2) | 59(2) | 15(2) | 14(2) | −5(2) |
| C(15) | 92(3) | 76(3) | 53(2) | 0(2) | 20(2) | 23(2) |
| C(16) | 68(2) | 65(2) | 60(2) | 7(2) | 14(1) | 16(2) |
| C(17) | 86(2) | 45(2) | 72(2) | 2(2) | 1(2) | 2(2) |
| C(18) | 98(3) | 55(2) | 73(2) | 10(2) | 0(2) | 12(2) |
| C(19) | 54(2) | 51(2) | 57(1) | −3(1) | 3(1) | −10(1) |
| C(20) | 44(1) | 50(1) | 45(1) | −5(1) | 5(1) | −7(1) |
| C(21) | 40(1) | 56(2) | 52(1) | 2(1) | 4(1) | 5(1) |
| C(22) | 50(2) | 78(2) | 53(2) | 1(2) | −1(1) | 1(2) |
| C(23) | 64(2) | 132(5) | 85(3) | 5(3) | −22(2) | 11(3) |
| C(24) | 79(3) | 170(7) | 134(4) | 16(5) | −36(3) | −38(4) |
| C(25) | 36(1) | 50(1) | 40(1) | −2(1) | 1(1) | 0(1) |
| C(26) | 35(1) | 52(1) | 41(1) | −8(1) | 2(1) | −7(1) |
| C(27) | 31(1) | 63(2) | 44(1) | −4(1) | −4(1) | −3(1) |
| C(28) | 40(1) | 58(2) | 38(1) | 3(1) | −2(1) | 1(1) |
| C(29) | 36(1) | 52(1) | 38(1) | −3(1) | 2(1) | −4(1) |
| C(30) | 31(1) | 53(1) | 44(1) | 1(1) | 0(1) | −3(1) |
| C(31) | 36(1) | 53(2) | 45(1) | −2(1) | 3(1) | −3(1) |
| C(32) | 35(1) | 44(1) | 51(1) | −4(1) | −1(1) | −2(1) |
| C(33) | 39(1) | 52(2) | 62(2) | 0(1) | 6(1) | −3(1) |
| C(34) | 43(1) | 50(2) | 68(2) | 0(1) | 1(1) | 2(1) |
| C(35) | 38(1) | 50(2) | 58(1) | −7(1) | 4(1) | −1(1) |

Acquisition of Powder X-Ray Diffraction (PXRD) Data for Form 3 of Compound 2, 1,3-dihydroxy-2-(hydroxymethyl)propan-2-aminium salt (Also Known as Form 3 of Monohydrate of Tris Salt of Compound 2)

A sample of Form 3 (e.g., the white solid of the tris salt of Compound 2 prepared according to the method described herein) was submitted for PXRD analysis and found to be a crystalline material (which is designated as Form 3).

Powder X-ray diffraction analysis was conducted using a Bruker AXS D8 Endeavor diffractometer equipped with a Cu radiation source (K-α average). The divergence slit was set at 15 mm continuous illumination. Diffracted radiation was detected by a PSD-Lynx Eye detector, with the detector PSD opening set at 2.99 degrees. The X-ray tube voltage and amperage were set to 40 kV and 40 mA respectively. Data was collected in the Theta-Theta goniometer at the Cu wavelength from 3.0 to 40.0 degrees 2-Theta using a step size of 0.00999 degrees and a step time of 1.0 second. The antiscatter screen was set to a fixed distance of 1.5 mm. Samples were rotated at 15/min during collection. Samples were prepared by placing them in a silicon low background sample holder and rotated during collection. Data were collected using Bruker DIFFRAC Plus software and analysis was performed by EVA diffract plus software. The sample holder used in a particular experiment is given by a code-name within the filename: DW=Deep well holder, SD=small divot holder and FP=Flat plate holder.

Figure 23:
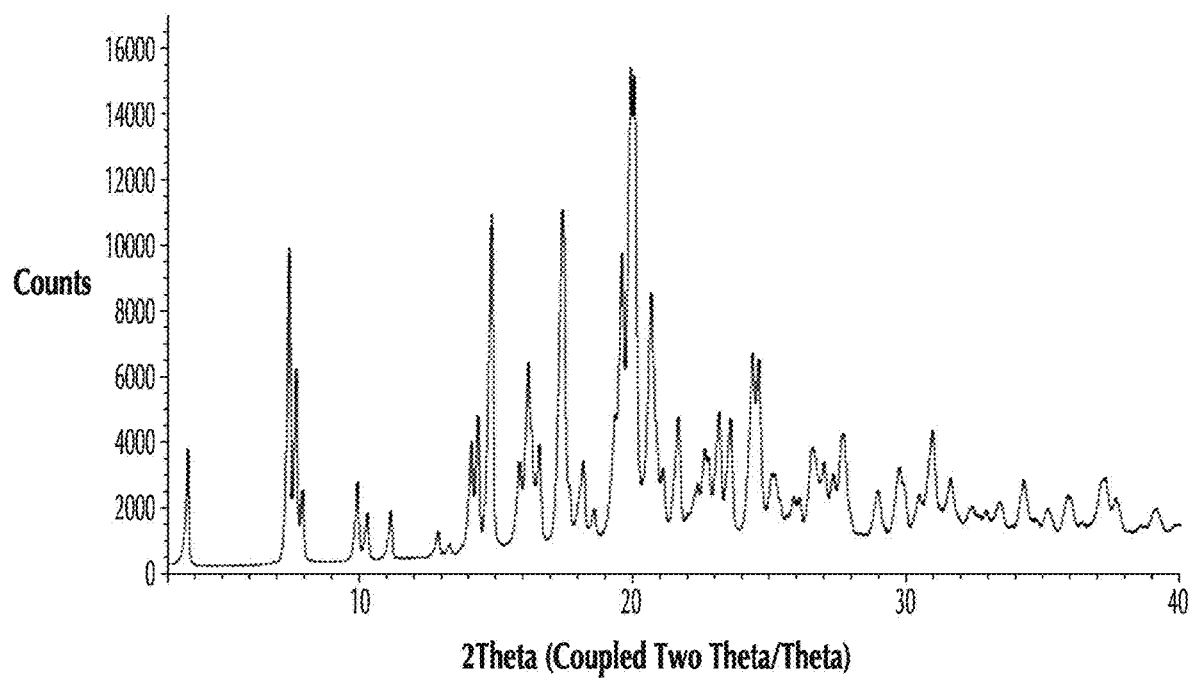
FIG. 23 shows an observed powder X-ray diffraction pattern for Form 3 of tris salt of Compound 2 carried out on a Bruker AXS D8 Endeavor diffractometer equipped with a Cu radiation source.

The PXRD data file was not processed prior to peak searching. Using the peak search algorithm in the EVA software, peaks selected with a threshold value of 1 and a width value of 0.3 were used to make preliminary peak assignments. The output of automated assignments was visually checked to ensure validity and adjustments were manually made if necessary. Peaks with relative intensity of 3% were generally chosen. The peaks which were not resolved or were consistent with noise were not selected. A typical error associated with the peak position from PXRD stated in USP up to +/−0.2° 2-Theta (USP-941). Form 3 has a PXRD pattern substantially the same as that shown in FIG. 23. A list of PXRD diffraction peaks expressed in terms of the degree 2θ and relative intensities with a relative intensity of 3.0% from a sample of Form 3 is provided below.

TABLE E3-5

PXRD Peaks and Relative Intensities of Form 3

| Degrees 2θ (Angle) ± 0.2° 2θ | Relative Intensity |
|---|---|
| 3.7* | 16% |
| 7.4* | 45% |
| 7.7 | 28% |
| 7.9 | 10% |
| 9.9* | 11% |
| 10.2 | -7% |
| 11.1* | -7% |
| 12.8 | -3% |
| 14.1 | 16% |
| 14.3 | 20% |
| 14.8* | 49% |
| 15.8 | 12% |
| 16.1 | 27% |
| 16.6 | 14% |
| 17.4 | 48% |
| 18.2* | 12% |
| 18.6 | -4% |
| 19.6 | 42% |
| 19.9* | 100% |
| 20.0 | 98% |
| 20.6* | 36% |
| 21.6 | 18% |
| 23.1 | 18% |
| 23.5* | 17% |
| 24.3* | 39% |
| 24.6* | 25% |
| 25.9 | -5% |
| 26.1 | -5% |
| 26.6 | 12% |
| 27.0 | 11% |
| 27.3 | -8% |
| 27.7 | 14% |
| 28.9 | -7% |
| 30.5 | -5% |
| 30.9 | 15% |
| 31.6 | -8% |
| 34.2 | -8% |
| 35.2 | -4% |
| 35.9 | -5% |
| 37.2 | -7% |

Solid State NMR Analysis of Form 3 of Tris Salt of Compound 2 (Monohydrate)

Solid state NMR (ssNMR) analysis was conducted on a CPMAS probe positioned into a Bruker-BioSpin Avance III 500 MHz ($^1$H frequency) NMR spectrometer. A sample of Form 3 of 1,3-Dihydroxy-2-(hydroxymethyl)propan-2-aminium Salt of Compound 2, monohydrate was packed into a 4 mm rotor. A magic angle spinning rate of 15.0 kHz was used.

$^{13}$C ssNMR spectrum was collected using a proton decoupled cross-polarization magic angle spinning (CP-MAS) experiment. A phase modulated proton decoupling field of 80-90 kHz was applied during spectral acquisition. The cross-polarization contact time was set to 2 ms and the recycle delay of 3-8 seconds. The number of scans was adjusted to obtain an adequate signal to noise ratio, with 2048 scans being collected for each API. The $^{13}$C chemical shift scale was referenced using a $^{13}$C CPMAS experiment on an external standard of crystalline adamantane, setting its up-field resonance to 29.5 ppm.

Figure 24:
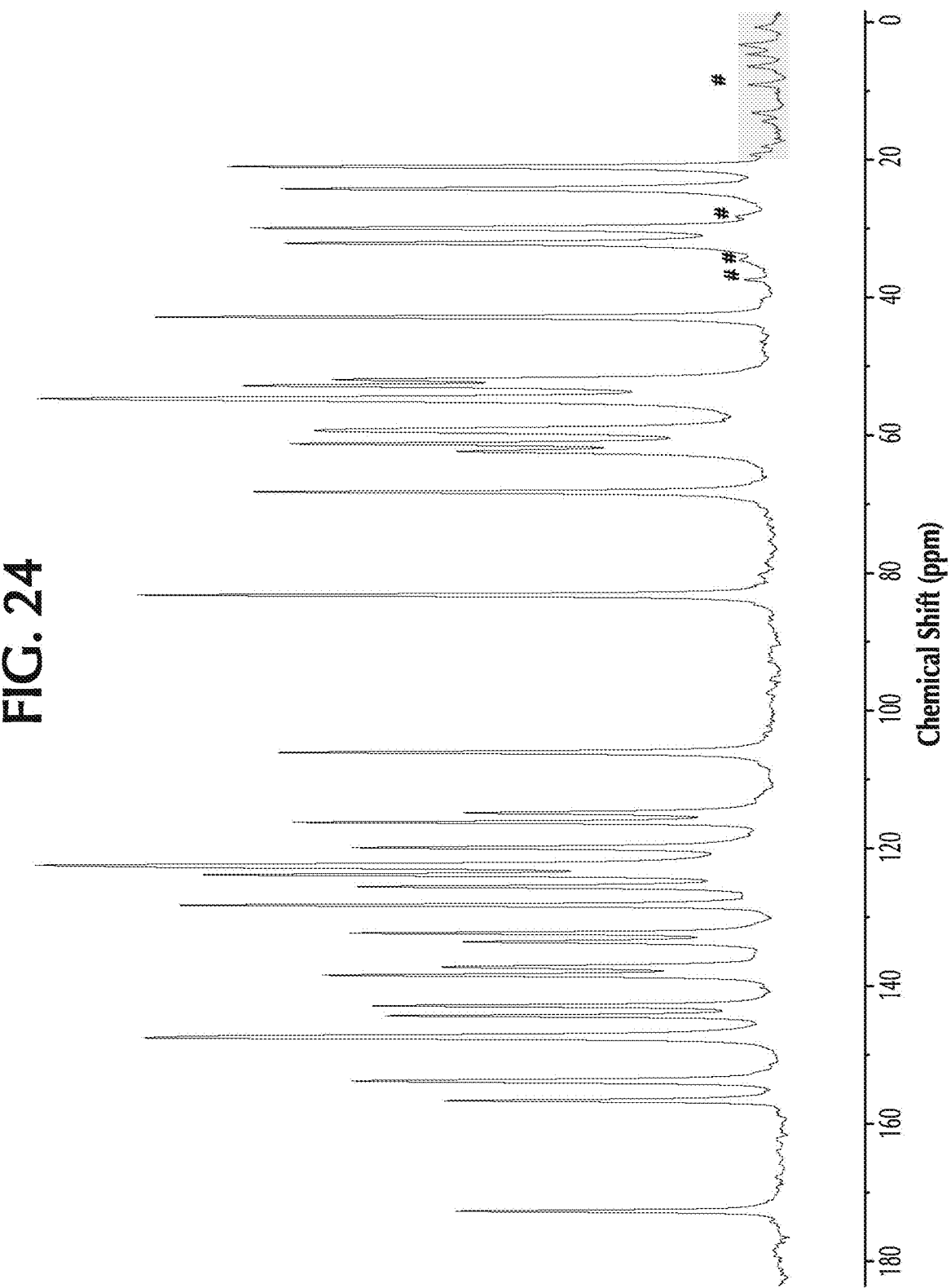
FIG. 24 shows an observed $^{13}$C ssNMR pattern of Form 3 of tris salt of Compound 2 conducted on a Bruker-BioSpin CPMAS probe positioned into a Bruker-BioSpin Avance III 500 MHz ($^1$H frequency) NMR spectrometer. The peaks marked by hashed marks and the gray shaded box are spinning sidebands.

Automatic peak picking was performed using Bruker-BioSpin TopSpin version 3.6 software. Generally, a threshold value of 3% relative intensity was used for preliminary peak selection. The output of the automated peak picking was visually checked to ensure validity and adjustments were manually made if necessary. Although specific solid state NMR peak values are reported herein there does exist a range for these peak values due to differences in instruments, samples, and sample preparation. This is common practice in the art of solid state NMR because of the variation inherent in peak positions. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample. The chemical shift data is dependent on the testing conditions (i.e. spinning speed and sample holder), reference material, and data processing parameters, among other factors. Typically, the ss-NMR results are accurate to within about ±0.2 ppm. FIG. 24 shows an observed $^{13}$C ssNMR pattern of Form 3 of tris salt of Compound 2.

TABLE E3-6

Carbon chemical shifts observed (Characteristic peaks are starred).

| $^{13}$C Chemical Shifts [ppm] ± 0.2 ppm | Relative Intensity |
|---|---|
| 21.0 | 75 |
| 24.2 | 67 |
| 29.9 | 71 |
| 32.1 | 67 |
| 42.8* | 85 |
| 51.9 | 59 |
| 52.8 | 72 |
| 547* | 100 |
| 59.3 | 62 |
| 61.2 | 66 |
| 62.3 | 44 |
| 68.2 | 72 |
| 83.2 | 87 |
| 106.0 | 67 |
| 114.8 | 41 |
| 116.2 | 65 |
| 119.9 | 56 |
| 122.4 | 99 |
| 122.7 | 88 |

TABLE E3-6-continued

Carbon chemical shifts observed
(Characteristic peaks are starred).

| $^{13}$C Chemical Shifts [ppm] ± 0.2 ppm | Relative Intensity |
|---|---|
| 123.8 | 80 |
| 125.5 | 58 |
| 128.2* | 83 |
| 132.3 | 58 |
| 133.5 | 43 |
| 137.2 | 45 |
| 138.4* | 63 |
| 142.8 | 55 |
| 144.3 | 54 |
| 147.2 | 79 |
| 147.5 | 89 |
| 153.7 | 58 |
| 156.6* | 46 |
| 172.6 | 44 |

Example A: Investigation of Metabolism of Compound 2 (in the Form of its Tris Salt) In-Vitro in Mouse, Rat, Rabbit, Monkey, and Human Hepatocytes, and in the Human Hepatopack System The metabolism of Compound 2 (in the form of its tris salt) was examined in-vitro in mouse, rat, rabbit, monkey, and human hepatocytes, and in the human Hepatopack system. Metabolism was examined in-vivo in rat plasma and bile from an exploratory pharmacokinetic study following a 1.0 mg/kg IV bolus dose of Compound 2. A total of 24 metabolites were detected in these matrices. These included glucuronidation, hydroxylation, piperidine desaturation and aromatization, and N-dealkylation of the piperidine ring, as well as several secondary metabolites. The glucuronide metabolite m/z 751b and the hydroxylated metabolite m/z 591c were the most abundant metabolites in the human in vitro systems. In rat plasma following a 1.0 mg/kg IV bolus dose, Compound 2 was detected, as well as metabolites m/z 751b, m/z 523, and m/z 331. In rat bile, metabolites m/z 751b, m/z 523, m/z 591c, m/z 767a and/or b, and m/z 331 were detected, as well as Compound 2.

Objectives

An objective of this study was to provide a qualitative assessment of the biotransformation of Compound 2 in hepatocytes from mouse, rat, rabbit, monkey, and human hepatocytes, as well as in rat plasma and bile samples.

Materials and Methods 1.1. Chemicals

Compound 2 and its tris salt [i.e. 1,3-dihydroxy-2-(hydroxymethyl)propan-2-aminium salt] can be prepared by the methods disclosed in U.S. Pat. No. 10,676,465 (see Example 10 therein). Metabolite 751b can be synthetically prepared by reacting Compound 2 with glucuronic acid. Male CD-1 mouse hepatocytes (lot YHL), male Wistar-Han rat hepatocytes (Celsius; product number: M000065; lot: SLA), female New Zealand rabbit hepatocytes (lot 1510147), male cryopreserved cynomolgus monkey hepatocytes (Celsius; product number: M00305; lot: DNB) and mixed-gender cryopreserved human hepatocytes (Bioreclamation; product number: S01988; lot: DCM) were obtained for the hepatocyte in-vitro assessments.

William's E Medium was obtained from Gibco. Acetonitrile (ACN), dimethyl sulfoxide (DMSO), methanol (MeOH), and all other reagents were of the highest grade commercially available.

1.2. Hepatocytes

Incubations with mouse, rat, rabbit, monkey, and human hepatocytes were conducted at a cell density of $7.5 \times 10^5$ cells/mL and 10 µM Compound 2. At time 0 hrs 550 µL aliquots were removed from incubations and quenched with 5 volumes of ACN containing 0.1% formic acid. At 1 and 4 hrs, 275 µL aliquots were removed and quenched as above; these were combined in the same tube to prepare a composite sample. For all hepatocyte experiments, samples were processed by centrifugation at 1900×g for 5 minutes, and then the supernatant was transferred to clean glass tubes and evaporated to dryness under a stream of $N_2$ using a Turbovap at 37° C. Sample residues were reconstituted in mobile phase prior to analysis by HPLC/UV/MS".

1.3. Incubation with Human Micropatterned Hepatocyte Co-Culture

Micro-patterned co-cultured (MPCC) hepatocyte 24-well plates containing human donors (16 wells each) were provided by Ascendance Biotechnology (formerly Hepregen Corp. (Medford, MA). [see Wang W W W, Khetani S R, Krzyzewski S, et al. Assessment of a Micropatterned Hepatocyte Coculture System to Generate Major Human Excretory and Circulating Drug Metabolites. Drug Metab Dispos 2010; 38(10):1900-5.] The MPCCs were created at Ascendance Biotechnology and maintained in serum containing medium for 5-6 days to allow for stabilization of the co-cultures prior to shipment. A mixed-gender cryopreserved pool of 10 human donors (X008001-P; lot YFA) was used to seed the plates and was purchased from BioreclamationIVT (Westbury, NY). MPCC hepatocytes are plated with fibroblasts in a 1:3 ratio with ~25,000 hepatocytes/well in a 24-well plate. 24-Well MPCC plates were shipped to Pfizer, fresh medium (400 µL/well) was applied and cultures were kept at 37° C. with 90% $O_2$/10% $CO_2$ and 95% relative humidity for two days. Micropatterned co-cultures containing pooled hepatocytes were allowed 7 days to fully stabilize with respect to liver-specific functions. Cultures were washed to remove serum, and Compound 2 (the tris salt, 20 µM in DMSO) in serum-free HCM (400 µL/well) was added to the human MPCC cells and the stromal controls. At respective time points (0, 2, and 7 days), the culture medium was removed and mixed with 4 volumes of ACN, then stored frozen at −40° C. until samples could be analyzed. Samples were subsequently processed by the addition of 2.5 mL of 1:1 ACN:MeOH containing 0.1% formic acid. After vortexing, the samples were centrifuged at 1900×g for 5 min, then the supernatant was transferred to 15 mL conical tubes and evaporated under $N_2$ using a Turbovap set at 37° C. The residues were reconstituted in mobile phase (5:95 v:v ACN: 0.1% aqueous formic acid) prior to analysis by HPLC/UV/MS".

1.4. Rat Plasma and Bile Preparation

Plasma and bile samples were obtained from a bile duct cannulated rat experiment (Study PK-0111) in which a 1.0 mg/kg IV bolus dose was administered to fed male rats (N=3). No control plasma was available from this experiment.

Plasma timepoint samples from individual animals were combined in a time-normalized manner (0.033-24 hrs) using the method of Hamilton [See Hamilton R A, Garnett W R, Kline B J. Determination of a mean valproic acid serum level by assay of a single pooled sample. Clin Pharmacol Ther 1981; 29(3):408-13]. The entire volume of each replicate Hamilton pool was combined to create a single pooled sample (576 µL) for analysis.

Bile samples (0-3, 3-7, and 7-24 hrs) from individual animals were pooled in proportion to the amount collect in each interval. Then 0.5 mL of each individual pool was combined to prepare a composite sample for analysis.

Pooled plasma and bile samples were extracted with ACN containing 0.1% formic acid, and after centrifugation at 1900×g, the supernatant was transferred to clean tubes and evaporated under $N_2$ in a Turbovap set at 37° C. Residues were reconstituted in mobile phase (5:95 v:v ACN:0.1% aqueous formic acid) prior to analysis by HPLC/UV/MS".

1.5. HPLC/UV/MS" Analysis

Samples were analyzed by HPLC/UV/MS" using a Thermo Orbitrap Elite mass spectrometer in conjunction with a Thermo Open Accela UHPLC system. A 3.0×150 mm, 2.5 μm Acquity CSH C18 HPLC column (Waters) was heated to 45° C. for separation of analytes. The mobile phase was a gradient of A): water containing 0.1% formic acid, and B): acetonitrile. The flow rate was 450 μL/min, and the following gradient program was utilized:

| Time (min) | Solvent A (%) | Solvent B (%) |
|---|---|---|
| 0.0 | 95 | 5 |
| 1.0 | 95 | 5 |
| 21.0 | 45 | 55 |
| 21.1 | 5 | 95 |
| 24.0 | 5 | 95 |
| 24.1 | 95 | 5 |
| 28.0 | 95 | 5 |

UV absorbance was monitored with a photo-diode array detector from 220-450 nm. The mass spectrometer was operated in positive-ion mode with a HESI ion source at a potential of 3.0 kV, and capillary and source heater temperatures of 380 and 300° C., respectively. Sheath, auxiliary, and sweep gas flows were set to 45, 10, and 2 units, respectively. Full scan mass spectra were acquired over the range 120-1200 m/z at a resolving power of 30,000 (specified at m/z 400). Data-dependent $MS^n$ spectra were acquired in an automated fashion at 15,000 resolving power using CID and HCD fragmentation with normalized collision energy settings of 28 and 65 V, respectively.

Metabolites were characterized by comparisons of mass spectral fragmentation patterns with that of a Compound 2 standard. All HPLC/UV/MS" data were processed using Xcalibur v. 2.2, and integrated UV peak areas were subjected to weighted UV binning procedures utilizing an Excel template.

Results & Analyses

Figure 25:
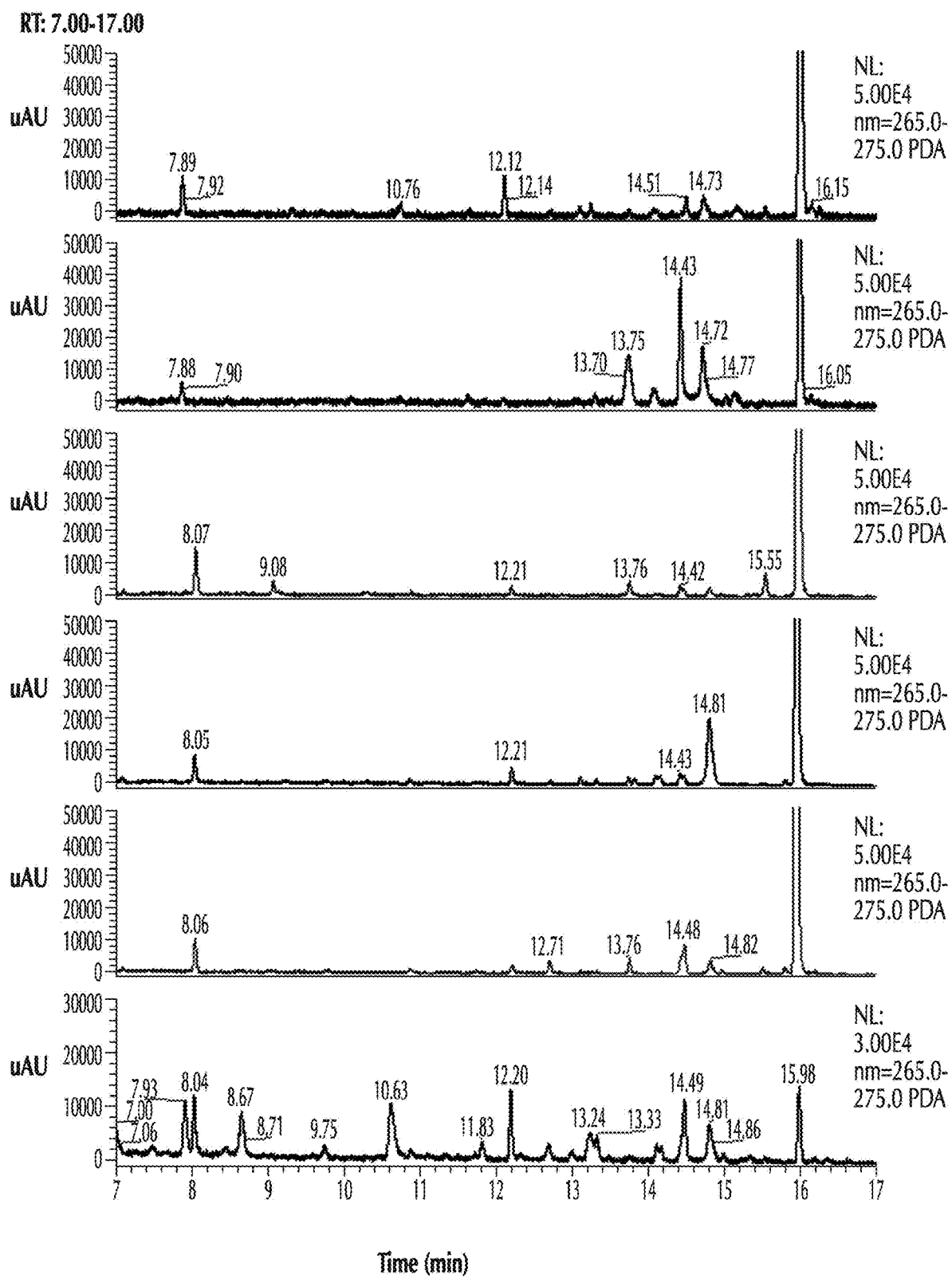
FIG. 25 shows HPLC-UV chromatograms for Compound 2 in mouse, rabbit, rat, monkey, and human Cryopreserved Hepatocytes (Time=4 hrs), and human co-cultured hepatocytes (Hepatopack, Time=7 days).
Figure 26:
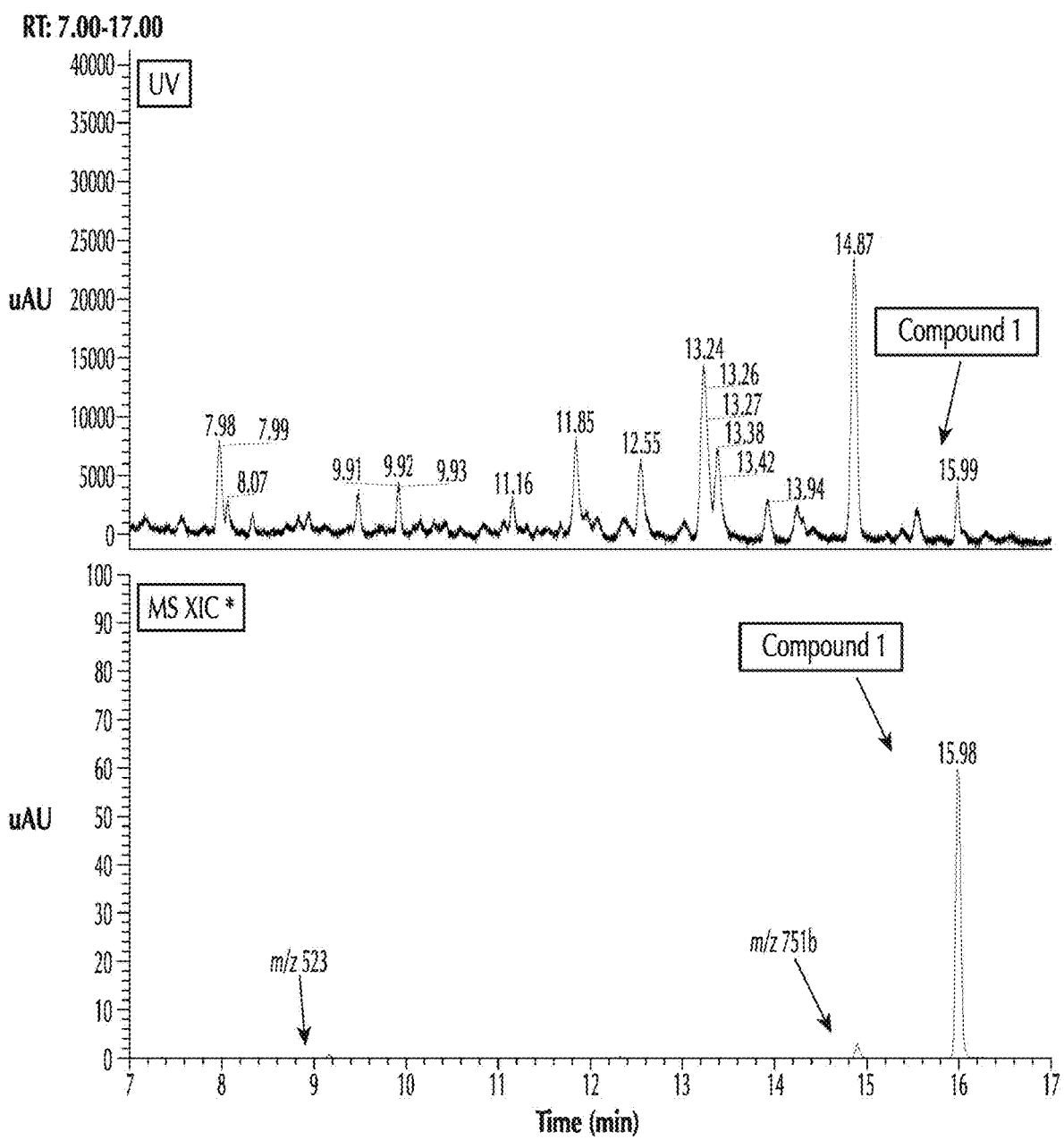
FIG. 26 shows HPLC/UV chromatogram (top) and HPLC/MS extracted-ion chromatogram (XIC, bottom) for Compound 2 in rat plasma following a 1.0 mg/kg IV bolus dose.
Figure 27:
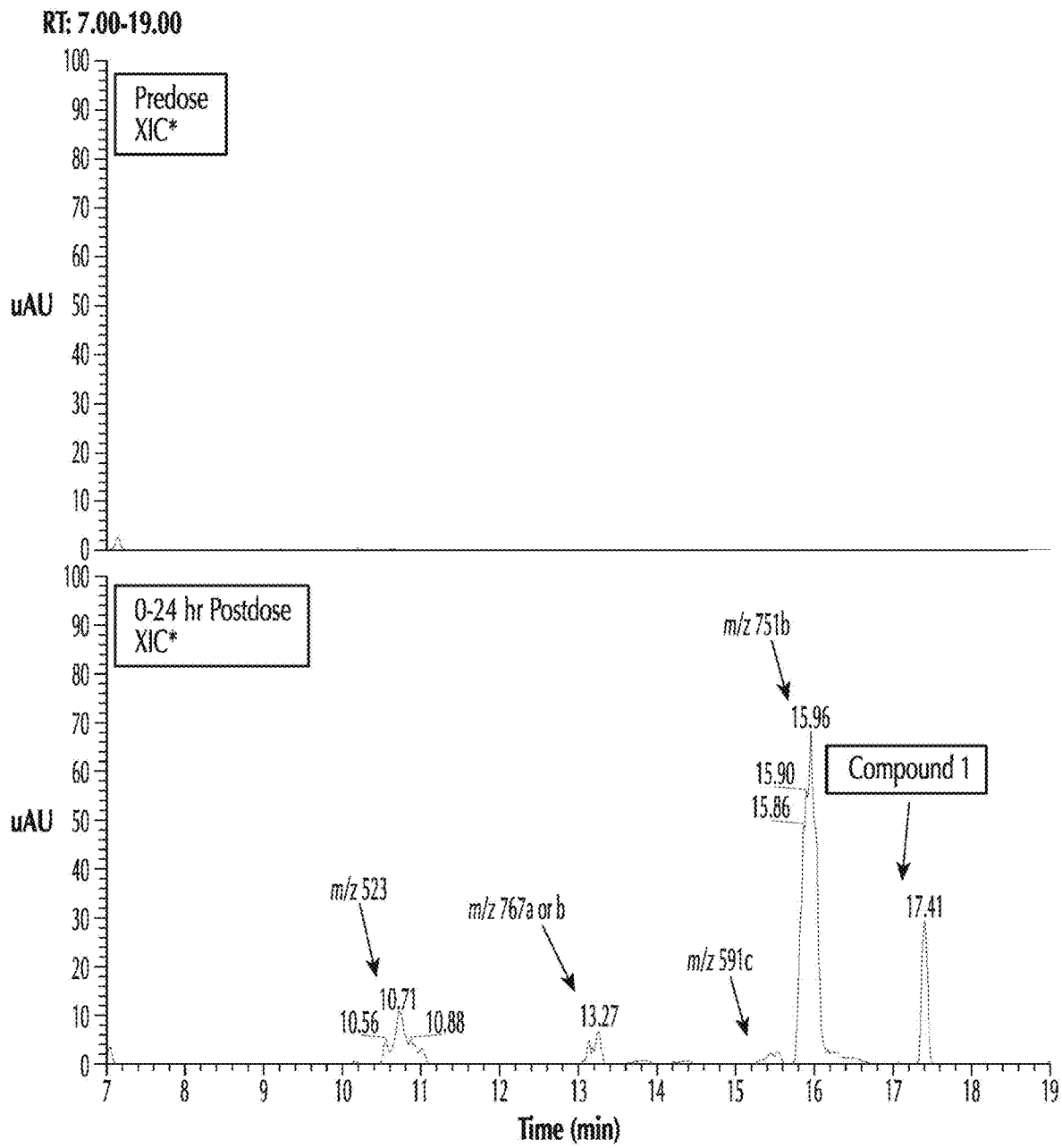
FIG. 27 shows HPLC/MS extracted-ion chromatogram (XIC) of pooled rat bile before (top) and after (bottom) a 1.0 mg/kg IV bolus dose of Compound 2.

A total of 24 metabolites of Compound 2 were detected in studies utilizing mouse, rat, rabbit, monkey and human hepatocyte preparations, as well as rat plasma and bile samples. A summary of all observed in vitro metabolites is provided in Table R-1, and circulating metabolites in rat plasma following a 1.0 mg/kg IV dose of Compound 2 are tabulated in Table R-2. HPLC/UV chromatograms showing the cross-species hepatocyte profiles for Compound 2 are provided in FIG. 25, and the rat plasma and bile HPLC/MS extracted-ion chromatograms (XIC) are shown in FIG. 26 and FIG. 2527. Because the HPLC/UV chromatogram of rat plasma contained many peaks which did not appear to be drug-related, relative abundances of metabolites were not tabulated. HPLC/MS interrogation/analysis was carried out on rat bile. The retention times of Compound 2 and all metabolites in rat bile were shifted relative to all other matrices due to interactions of the matrix with the HPLC column, and chromatographic peak shape was poor. Therefore, for metabolites with multiple isobaric species, exact correlations based upon retention times could not be made.

TABLE R-1

In Vitro Metabolism of Compound 2 in Mouse, Rat, Rabbit, Monkey, and Human Cryopreserved Hepatocytes, and in Human Co-Cultured Hepatocytes (Hepatopack).

| Metabolite | Description | $t_R$ (min) | m/z | Mouse | Rat | Rabbit | Monkey | Human | Hepatopack |
|---|---|---|---|---|---|---|---|---|---|
| 438 | Catechol | 8.18 | 438.202 | ND | trace | ND | trace | trace | ND |
| 523 | N-dealkylation (piperidine) + OH + gluc. | 9.11 | 523.148 | trace | ++ | trace | ND | ND | ND |
| 767 a | Hydroxylation + glucuronidation | 10.75 | 767.234 | + | ND | trace | ND | trace | + |
| 518 | Catechol sulfate | 10.80 | 518.159 | + | trace | ND | + | + | ND |
| 767 b | Hydroxylation + glucuronidation | 12.14 | 767.234 | ++ | + | + | + | + | ++ |
| 331 | N-dealkylation (piperidine) | 12.75 | 331.121 | + | trace | trace | + | + | trace |
| 591 a | Hydroxylation | 13.15 | 591.201 | + | trace | trace | + | + | trace |
| 767 c | Hydroxylation + glucuronidation | 13.28 | 767.234 | + | trace | ND | + | + | + |
| 882 a | Glutathione adduct (benzimidazole) | 13.35 | $441.647^{+2}$ | ND | ND | + | ND | ND | ND |
| 882 b | Glutathione adduct (benzimidazole) | 13.50 | $441.647^{+2}$ | ND | ND | + | ND | ND | ND |
| 694 | Cysteine adduct (benzimidazole) | 13.82 | $347.608^{+2}$ | ND | ND | +++ | ND | ND | ND |
| 591 b | Hydroxylation | 13.80 | 591.201 | + | ++ | trace | + | ++ | + |
| 751 a | Glucuronide conjugation | 14.15 | 751.238 | + | trace | + | trace | trace | + |
| 505 | N-dealkylation (benzimidazole) | 14.46 | 505.164 | trace | trace | * | ND | ND | ND |
| 593 | Oxetane hydrolysis | 14.46 | 593.216 | + | trace | +++ | + | ** | ** |
| 591 c | Hydroxylation | 14.53 | 591.201 | + | + | + | + | ++ | +++ |
| 751 b | Glucuronide conjugation | 14.65 | 751.238 | ++ | + | ++ | +++ | +++ | ++ |
| 607 | Bis-hydroxylation | 14.78 | 607.195 | ND | ND | *** | ND | ND | ND |
| 569 | Aromatization | 15.08 | 569.159 | + | trace | + | trace | + | + |
| 751 c | Glucuronide conjugation | 15.15 | 751.238 | trace | ND | trace | trace | ND | + |
| 573 a | Dehydrogenation | 15.58 | 573.190 | + | ++ | trace | + | + | + |

TABLE R-1-continued

In Vitro Metabolism of Compound 2 in Mouse, Rat, Rabbit, Monkey, and Human Cryopreserved Hepatocytes, and in Human Co-Cultured Hepatocytes (Hepatopack).

| Metabolite | Description | $t_R$ (min) | m/z | Mouse | Rat | Rabbit | Monkey | Human | Hepatopack |
|---|---|---|---|---|---|---|---|---|---|
| 573 b | Dehydrogenation | 16.20 | 573.190 | + | ND | + | ND | ND | trace |
| 671 | Hydroxylation + sulfation | 16.20 | 671.157 | ND | ++ | ND | ND | ND | ND |
| 591 d | N-oxidation | 16.26 | 591.201 | trace | trace | trace | trace | trace | + |

\* m/z 593 and m/z 505 co-eluted in rabbit hepatocytes.
\*\* m/z 591 c and m/z 593 were merged in human hepatocytes and Hepatopack.
\*\*\* m/z 607 and m/z 751 b were merged in rabbit hepatocytes.
ND Not detected.;
Trace: observed by HPLC/MS measurements only.
+ Minor as assessed by HPLC/UV measurements;
++ moderate as assessed by HPLC/UV measurements;
+++ major as assessed by HPLC/UV measurements.

TABLE R-2

Circulating Metabolites of Compound 2 in Rat Plasma following a 1.0 mg/kg IV Dose.

| Metabolite | Description | $t_R$ (min) | m/z |
|---|---|---|---|
| 523 | N-dealkylation (piperidine) + OH + Gluc. | 9.11 | 523.148 |
| 331 | N-dealkylation (piperidine) | 12.75 | 331.121 |
| 751 b | Glucuronide conjugation | 14.65 | 751.238 |
| Compound 2 | Parent | 15.98 | 575.206 |

R.1. Compound 2 (m/z 575)

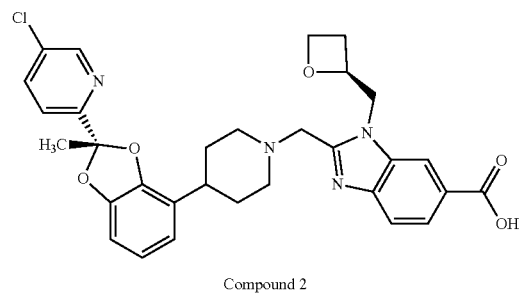 [SMILES: C[C@]1(c2ccc(Cl)cn2)Oc2cccc(C3CCN(Cc4nc5ccc(C(=O)O)cc5n4C[C@@H]4CCO4)CC3)c2O1]

Compound 2

Figure 28:
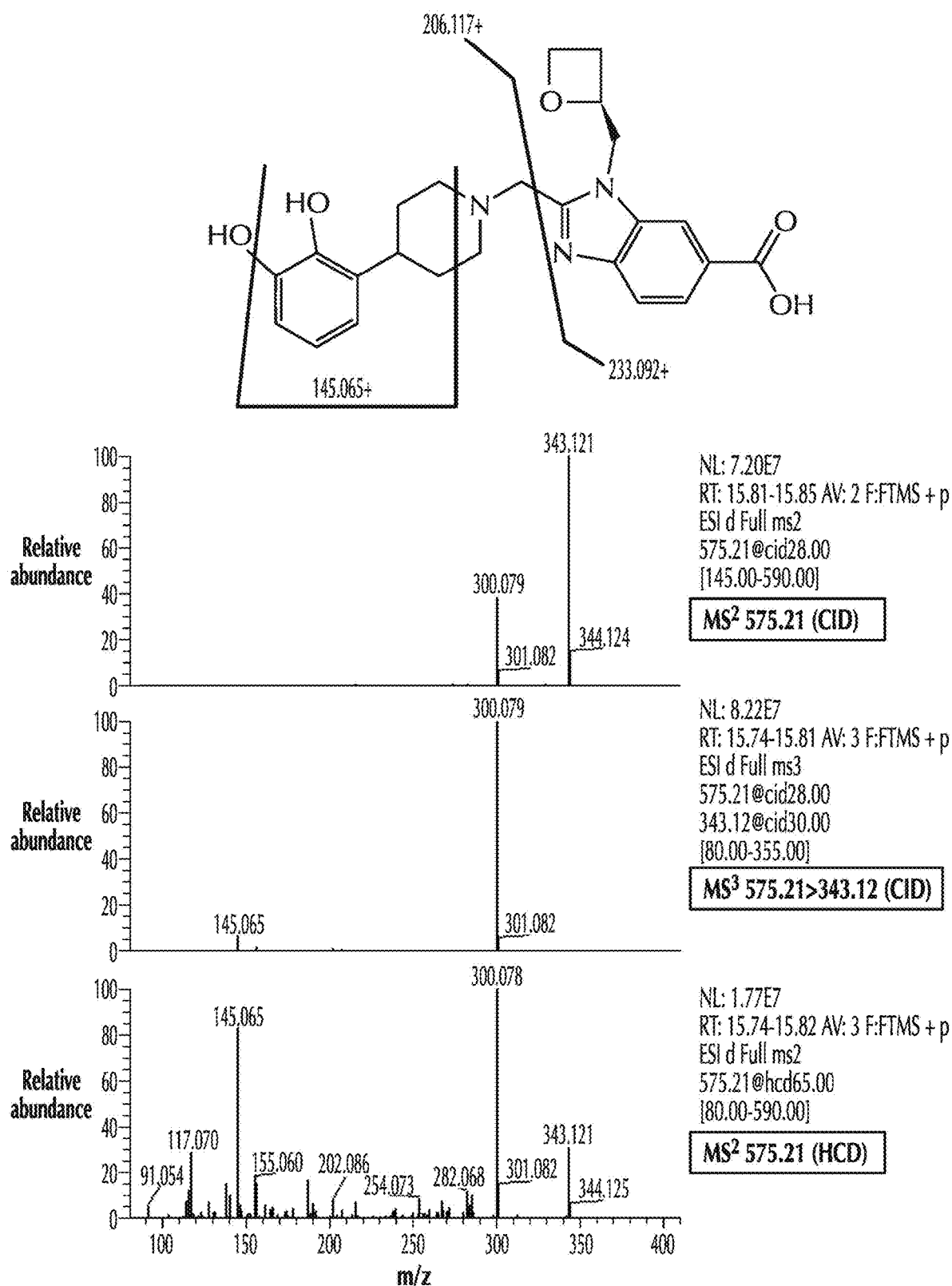
FIG. 28 shows mass spectra of Compound 2 (m/z 575).

Compound 2 eluted at approximately 15.98 min with m/z 575.206$^+$. The CID and HCD mass spectra and proposed fragmentation patterns are shown in FIG. 28. The fragment ion at m/z 343.121$^+$ results from loss of the substituted benzimidazole moiety, and the subsequent neutral loss of N-methylmethanimine (monoisotopic mass 43.042 Da) yields the m/z 300.079$^+$ ion. Loss of the substituted pyridine moiety and an oxygen atom from m/z 300.079$^+$ yields the m/z 145.065$^+$ ion.

R.2. Metabolite 438 (Metabolite M/Z 438)

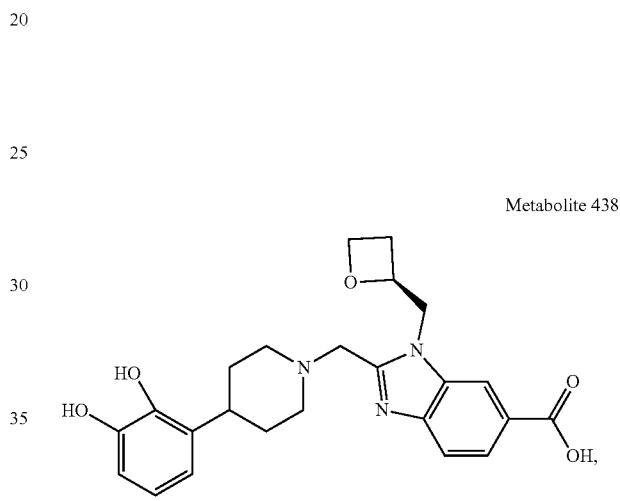

Metabolite 438

Figure 29:
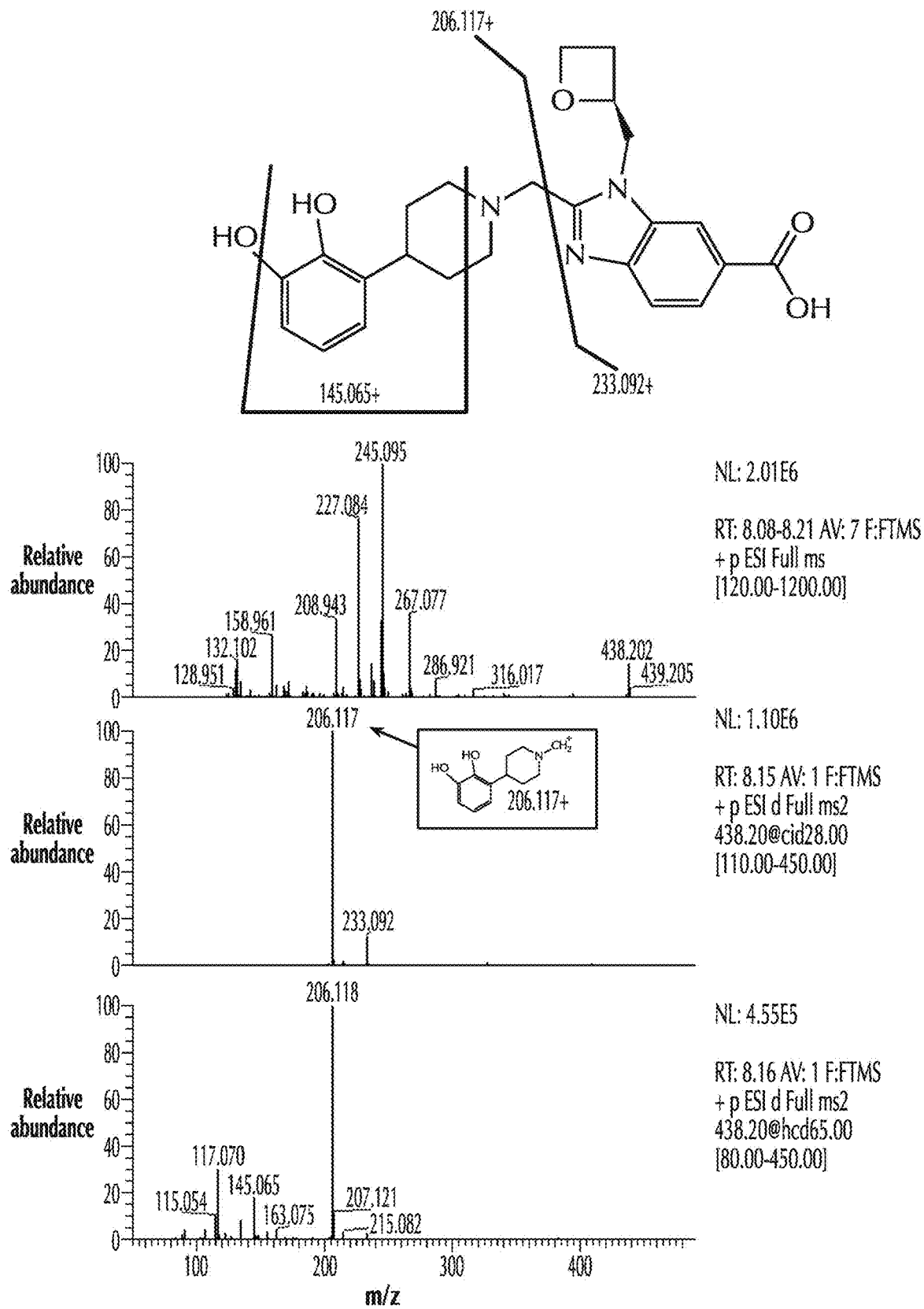
FIG. 29 shows mass spectra and proposed structure of Metabolite m/z 438 (of Compound 2).

Chemical name: (S)-2-((4-(2,3-dihydroxyphenyl)piperidin-1-yl)methyl)-1-(oxetan-2-ylmethyl)-1H-benzo[d]imidazole-6-carboxylic acid Metabolite m/z 438 was observed as a trace metabolite in rat, monkey, and human hepatocytes and eluted at approximately 8.18 min with m/z 438.202$^+$. This metabolite is a catechol formed from the benzdioxolone by loss of the methylchloropyridine moiety (mass calculated for $C_{24}H_{28}N_3O_5$ is 438.2023$^+$, observed m/z 438.2018$^+$, Δ=−1.2 ppm). The CID and HCD mass spectra and proposed fragmentation patterns are shown in FIG. 29. The fragment ion at m/z 206.117$^+$ results from cleavage of the piperidine-benzimidazole linkage, while the m/z 233.092$^+$ ion is due to charge retention on the substituted benzimidazole moiety, indicating that this is unchanged. Neutral loss of N-methylmethanimine (monoisotopic mass 43.042 Da) from m/z 206.117$^+$ yields m/z 163.075$^+$. Dehydration of m/z 163.075$^+$ yields the m/z 145.065$^+$ ion, which is also observed in the MS$^n$ spectra of Compound 2.

R.3. Metabolite 523 (Metabolite m/z 523)

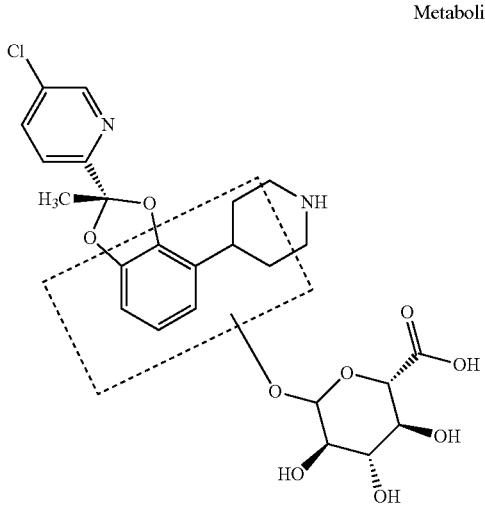

Metabolite 523

Figure 30:
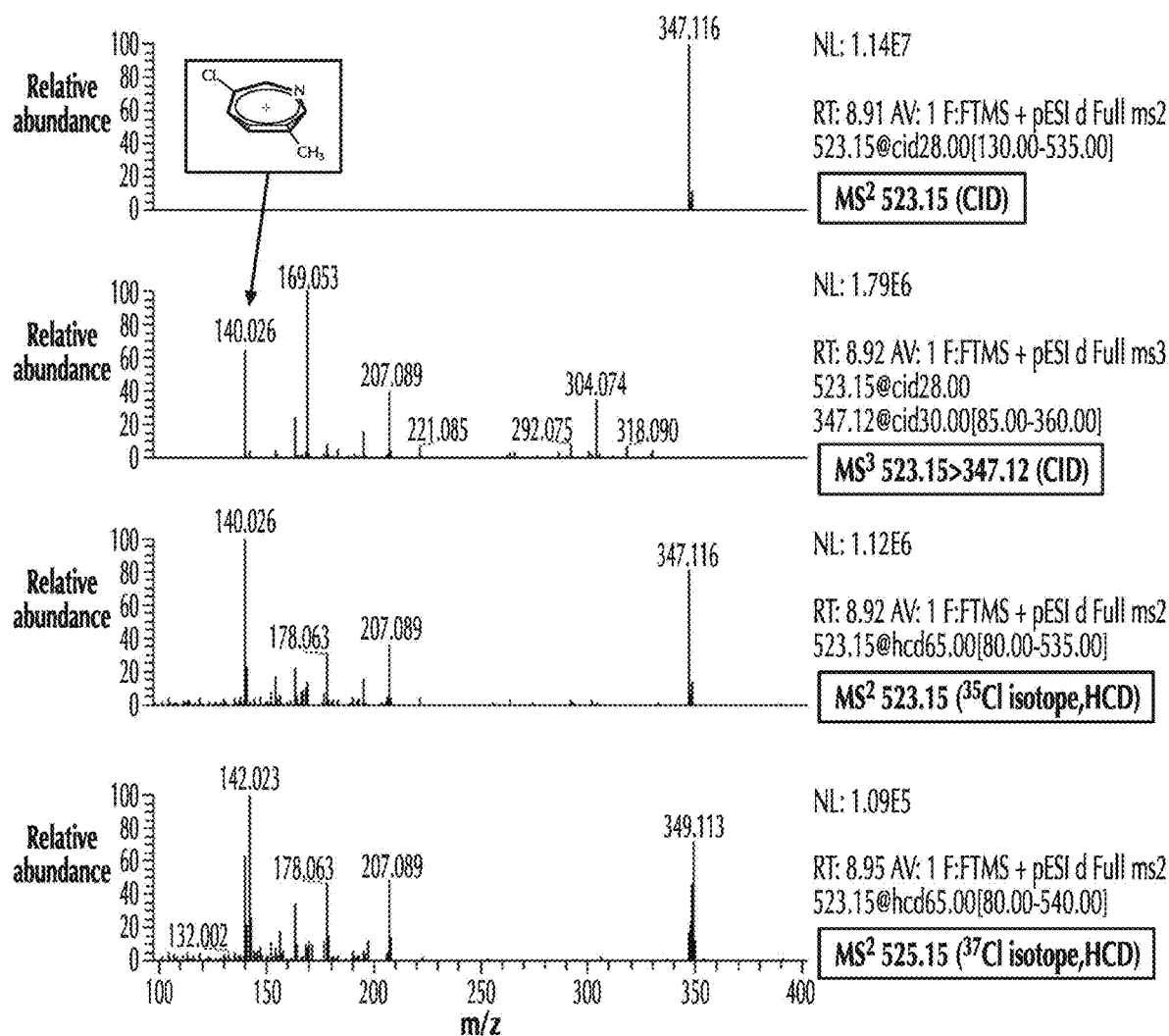
FIG. 30 shows mass spectra and proposed structure of Metabolite m/z 523 (of Compound 2).

Metabolite m/z 523 was observed in mouse, rat and rabbit hepatocytes and rat bile and plasma, and eluted at approximately 9.11 min with m/z 523.148$^+$. This metabolite is a glucuronide conjugate resulting from piperidine N-dealkylation and hydroxylation. The CID and HCD mass spectra and proposed fragmentation patterns are shown in FIG. 30. The fragment ion at m/z 347.116$^+$ in the MS$^2$ spectra of m/z 523 is the aglycone. Neutral loss of N-methylmethanimine (monoisotopic mass 43.042 Da) from the aglycone yields the m/z 304.074$^+$ ion. The m/z 140.026$^+$ ion can be rationalized as the methylated tropylium ion containing the Cl and pyridyl N atoms, which would result from cleavage of the C—O bonds of the quaternary C atom (calculated m/z for $C_7H_7NCl^+$ is 140.0262$^+$, observed m/z is 140.0263$^+$, Δ=1.1 ppm). The absence of an oxygen atom in this moiety suggests that the hydroxylation has occurred either on the phenyl ring or one of the piperidine carbon atoms, and likely not α to the piperidine N atom.

R.4. Metabolite 767a (Metabolite m/z 767a)

Figure 31:
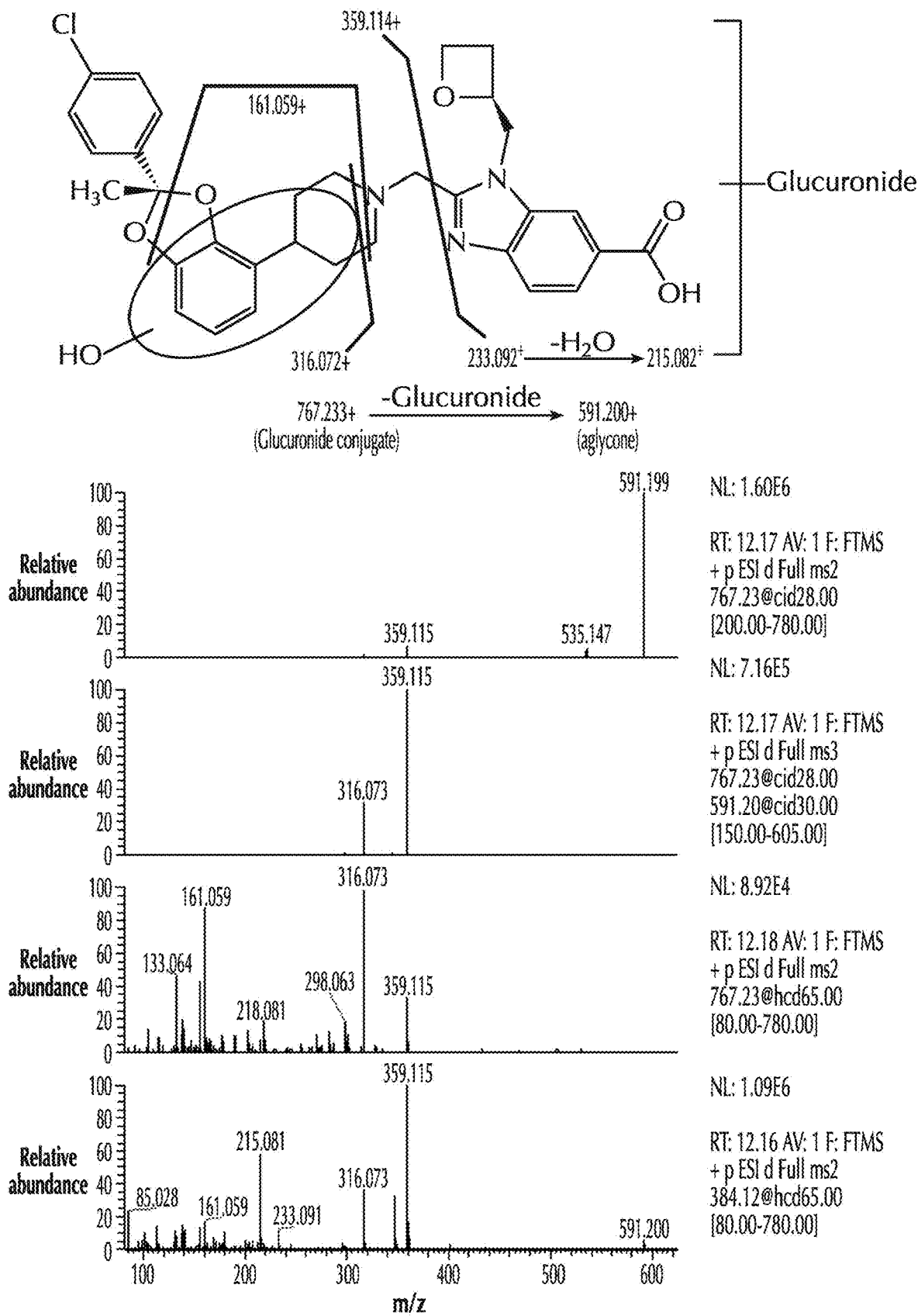
FIG. 31 shows mass spectra and proposed structure of Metabolite m/z 767a (of Compound 2).

Metabolite 767a eluted at approximately 10.75 min with observed masses m/z 384.119$^{+2}$ and 767.231$^+$ and was detected in mouse, rabbit, and human hepatocyte incubations. This metabolite is a glucuronide conjugate of a hydroxylated metabolite. The CID and HCD mass spectra and proposed fragmentation patterns are shown in FIG. 31. The aglycone is observed at m/z 591.199$^+$, while the fragment ion at m/z 359.115$^+$ results from loss of the substituted benzimidazole moiety from the aglycone and is + 16 Da relative to the corresponding ion of Compound 2. The m/z 233.092$^+$ ion is due to charge retention on the substituted benzimidazole moiety, and neutral loss of water from this ion results in the m/z 215.081$^+$ ion. The m/z 161.059$^+$ ion in the MS$^2$ HCD spectrum of m/z 767.23$^+$ (third pane) is + 16 Da relative to the m/z 145.065$^+$ ion of Compound 2, suggesting that the oxidation has occurred either on the phenyl ring or one of the piperidine carbon atoms, and likely not α to the piperidine N atom.

R.5. Metabolite 518 (Metabolite m/z 518)

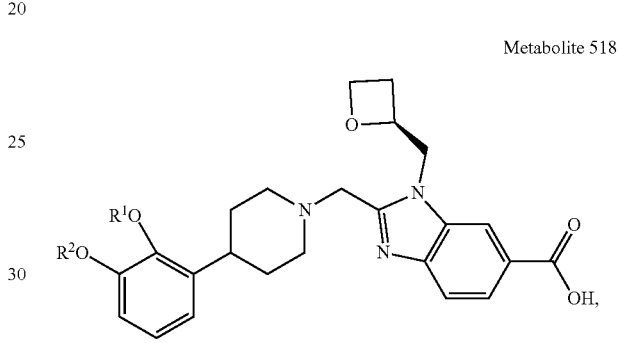

Metabolite 518 wherein one of R$^1$ and R$^2$ is H, and the other is —S(=O)$_2$OH.

Metabolite m/z 518 was observed as a trace metabolite in mouse, rat, monkey, and human hepatocytes and eluted at approximately 10.80 min with m/z 518.1587$^+$. This metabolite appears to be a sulfate conjugate of catechol metabolite m/z 438.202$^+$ (mass calculated for $C_{24}H_{28}N_3SO_8$ is 518.1592$^+$, observed m/z 518.1587$^+$, Δ=−0.9 ppm). No MS$^2$ spectra were obtained for this metabolite, but the full-scan MS spectrum and proposed structure are shown in FIG. 32.

R.6. Metabolite 767b (Metabolite m/z 767b)

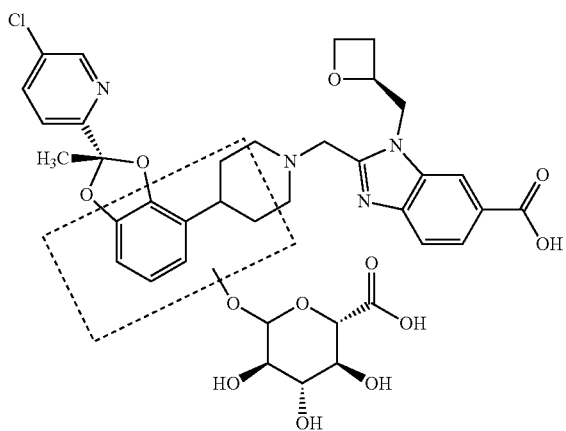

Metabolite 767a

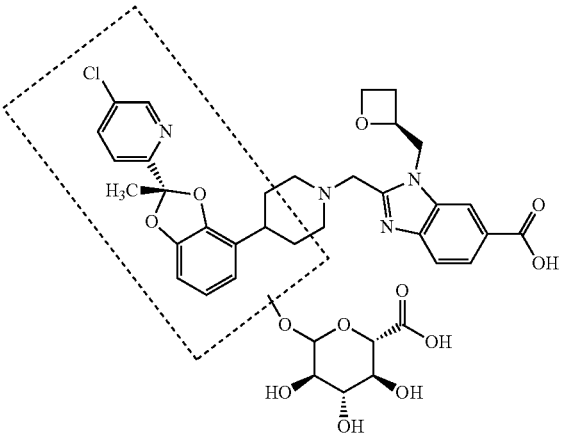

Metabolite 767b

Figure 33:
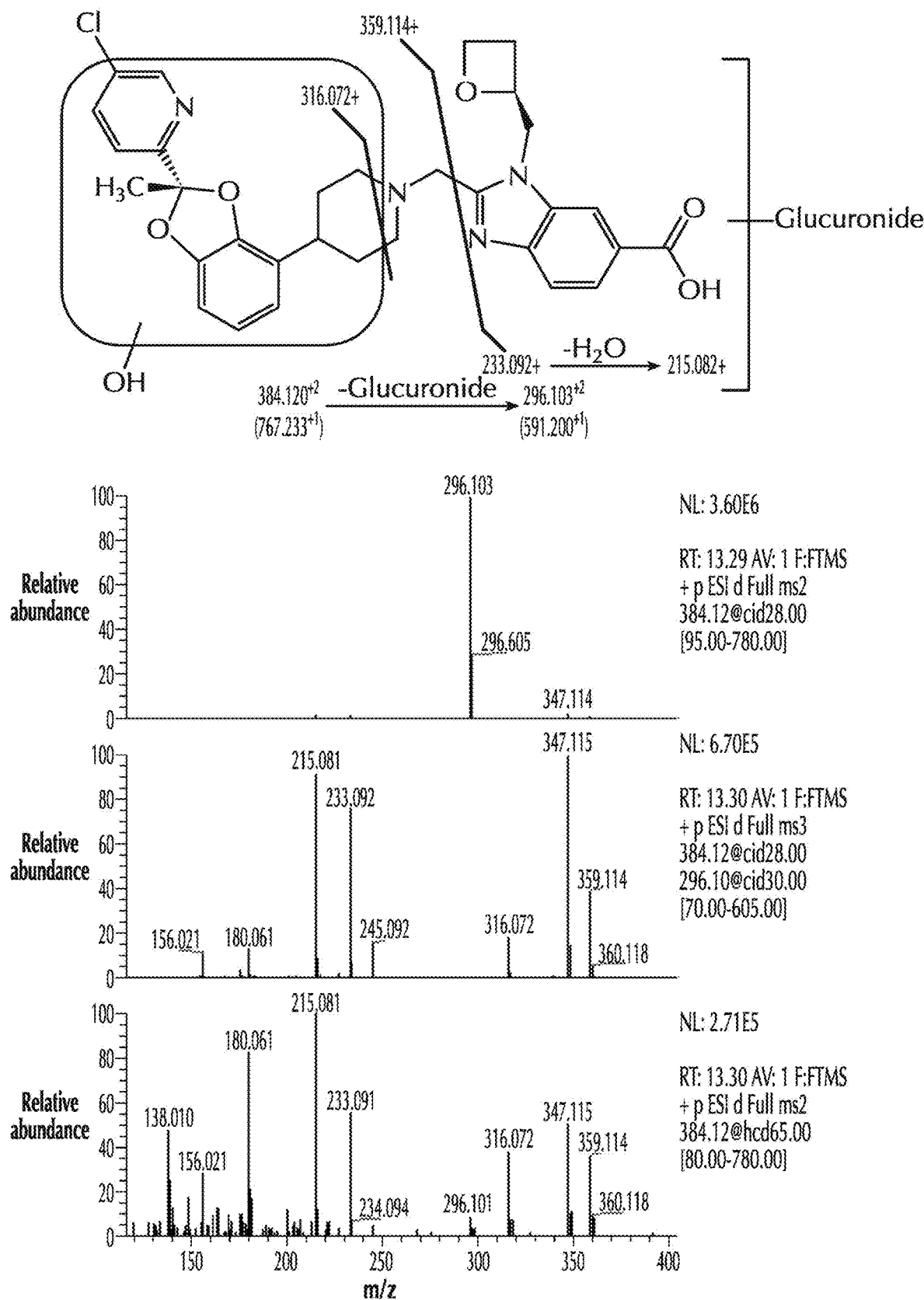
FIG. 33 shows mass spectra and proposed structure of Metabolite m/z 767b (of Compound 2).

Metabolite 767b eluted at approximately 12.14 min with observed masses m/z 384.119$^{+2}$ and 767.231$^+$ and was observed in all hepatocyte incubations. This metabolite is a glucuronide conjugate of a hydroxylated metabolite, where the oxidation occurs either on the pyridine moiety or the benzdioxolone-piperidine moiety. The CID and HCD mass spectra and proposed fragmentation patterns are shown in FIG. 33. Upon CID fragmentation of the m/z 384.119$^{+2}$ ion of metabolite 767b, the major fragment ion produced is m/z 296.103$^{+2}$, which is the doubly-charged aglycone (m/z 591.200$^+$). The fragment ion at m/z 359.114$^+$ results from loss of the substituted benzimidazole moiety from the aglycone and is +16 Da relative to the corresponding ion of Compound 2. Neutral loss of N-methylmethanimine (monoisotopic mass 43.042 Da) from m/z 359.114$^+$ yields the m/z 316.072$^+$ ion, which is also +16 Da relative to the corresponding ion of Compound 2. The m/z 233.092$^+$ ion is due to charge retention on the substituted benzimidazole moiety, and neutral loss of water from this ion results in the m/z 215.081$^+$ ion.

R.7. Metabolite 331 (Metabolite m/z 331)

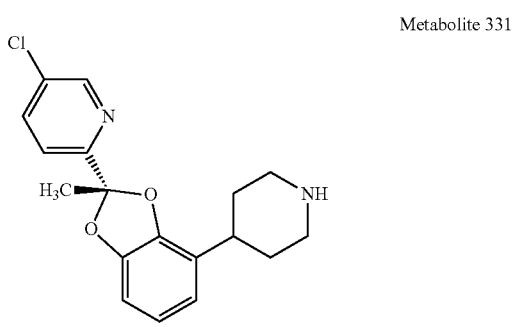 [SMILES: C[C@]1(c2ccc(Cl)cn2)Oc2cccc(C3CCNCC3)c2O1]

Metabolite 331

Figure 34:
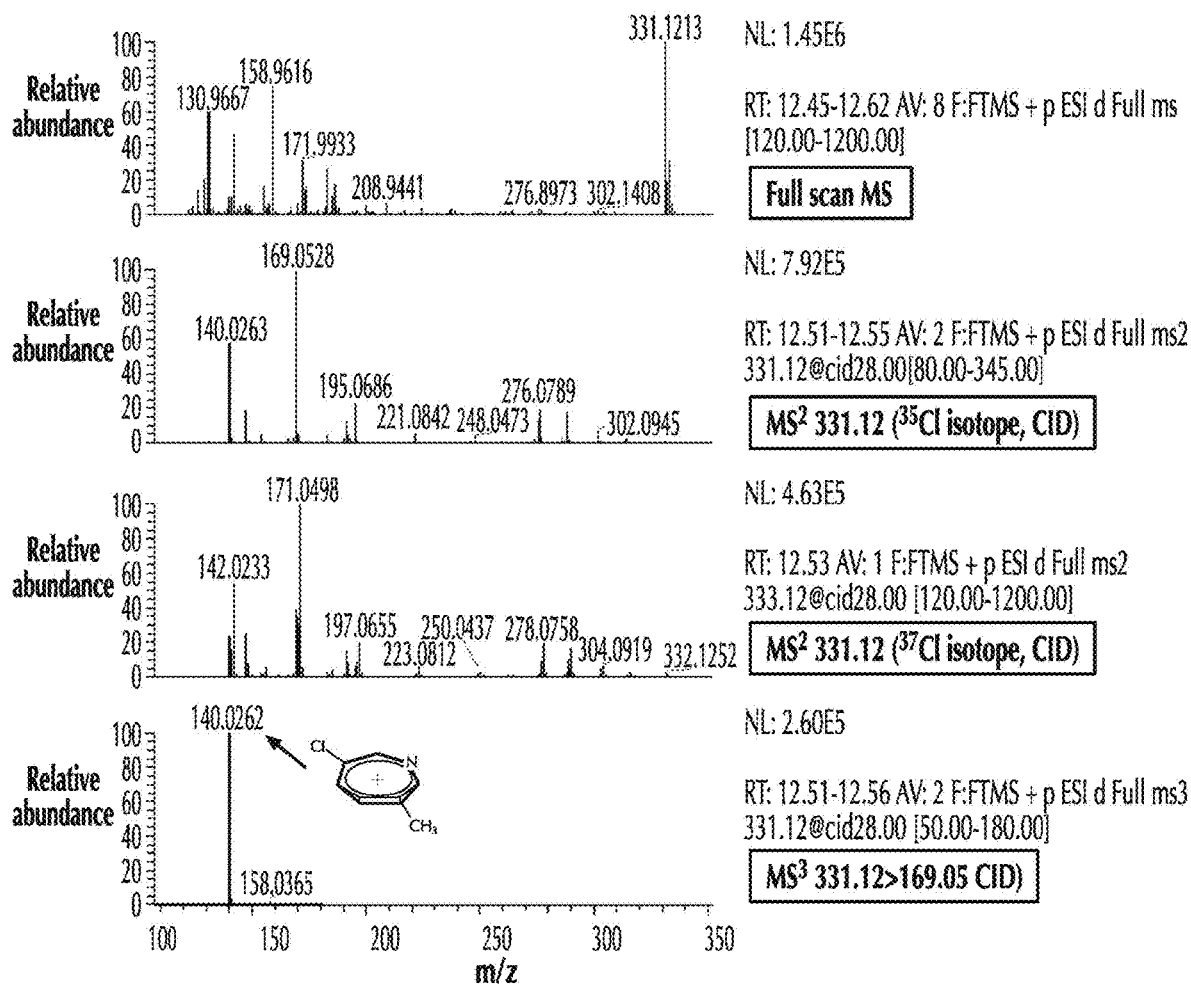
FIG. 34 shows mass spectra and proposed structure of Metabolite m/z 331 (of Compound 2).

Metabolite 331 eluted at approximately 12.75 min with m/z 331.1213$^+$ and was observed in all hepatocyte incubations and rat bile and plasma. The mass spectra and proposed fragmentation patterns are shown in FIG. 34. This metabolite is the product of N-dealkylation at the piperidine N atom and contains the benzdioxolone and chloro-pyridyl moieties (mass calculated for elemental formula $C_{18}H_{20}N_2O_2Cl^+$=m/z 331.1208$^+$, observed m/z 331.1213$^+$, Δ=1.6 ppm). The primary CID fragment was observed at m/z 169.0528$^+$ and appears to be a rearrangement product of uncertain structure. The m/z 140.026$^+$ ion can be rationalized as the methylated tropylium ion containing the $C_1$ and pyridyl N atoms, which would result from cleavage of the C—O bonds of the quaternary C atom (calculated m/z for $C_7H_7NCl^+$ is 140.0262, observed m/z is 140.0259, Δ=−1.8 ppm).

R.8. Metabolite 591a (Metabolite m/z 591a)

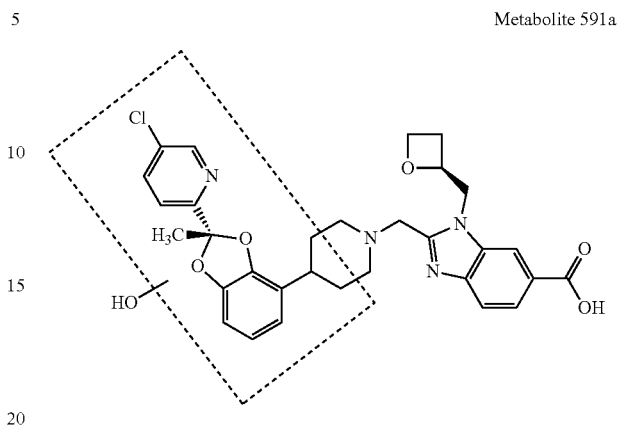

Metabolite 591a

Figure 35:
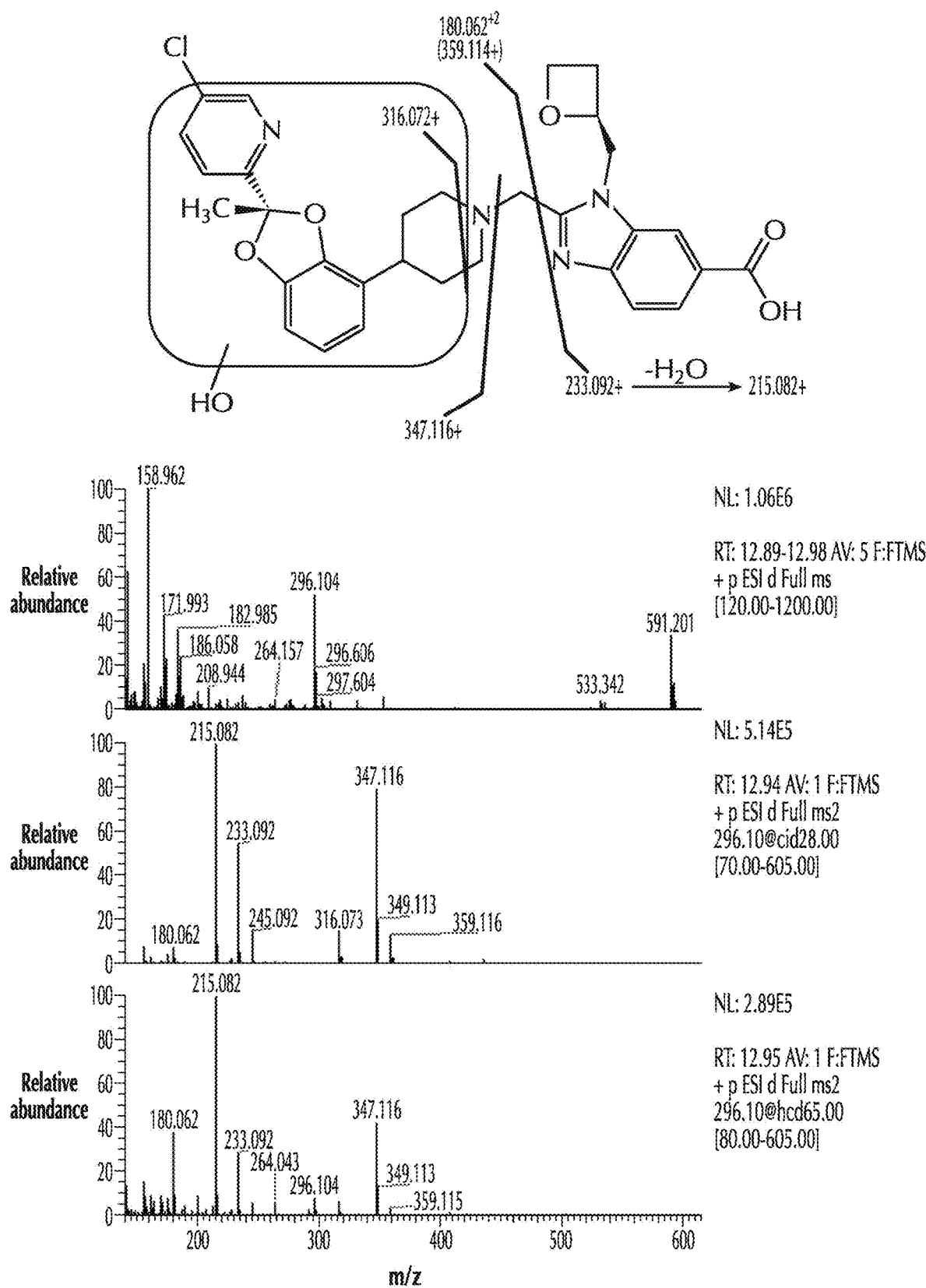
FIG. 35 shows mass spectra and proposed structure of Metabolite m/z 591a (of Compound 2).

Metabolite 591a eluted at approximately 13.15 min with masses m/z 296.104$^{+2}$ and 591.201$^+$ and was observed in all hepatocyte incubations. This metabolite is a hydroxylation of Compound 2. The CID and HCD mass spectra and proposed fragmentation patterns are shown in FIG. 35. The fragment ion at m/z 359.115$^+$ (180.062$^{+2}$) results from loss of the substituted benzimidazole moiety and is +16 Da relative to the corresponding ion of Compound 2. The m/z 233.092$^+$ ion is due to charge retention on the substituted benzimidazole moiety, and neutral loss of water from this ion results in the m/z 215.081$^+$ ion. The m/z 347.116$^+$ ion in the MS$^2$ spectra of m/z 296.104$^{+2}$ is +16 Da relative to metabolite m/z 331 (N-dealkylation of the piperidine N atom). This data indicates that the oxidation has occurred either on the piperidine or phenyl ring, or the pyridine moiety.

R.9. Metabolite 767c (Metabolite m/z 767c)

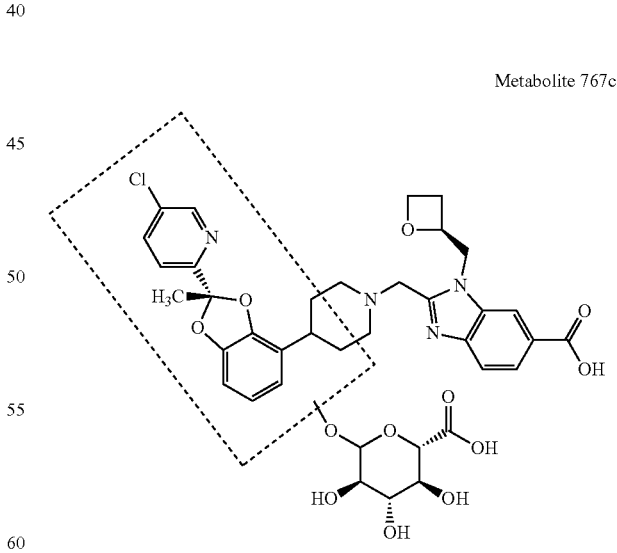

Metabolite 767c

Figure 36:
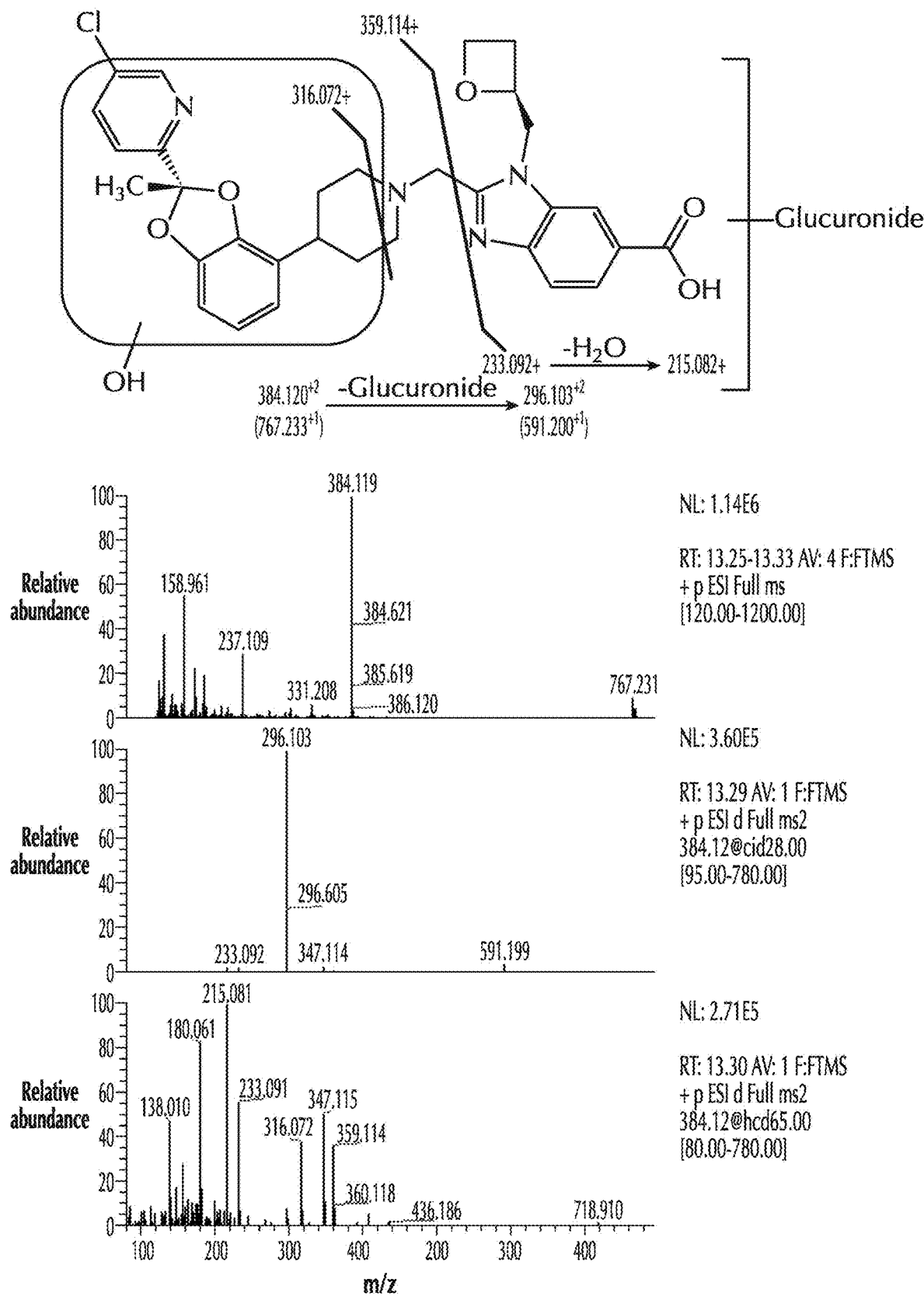
FIG. 36 shows mass spectra and proposed structure of Metabolite m/z 767c (of Compound 2).

Metabolite 767c eluted at approximately 13.28 min with observed masses m/z 384.119$^{+2}$ and 767.231$^+$ and was observed primarily in mouse and monkey hepatocyte incubations. This metabolite is a glucuronide conjugate of a hydroxylated metabolite, where the oxidation occurs either on the pyridine moiety or the benzdioxolone-piperidine moiety. The CID and HCD mass spectra and proposed fragmentation patterns are shown in FIG. 36. Upon CID fragmentation of the m/z 384.119$^{+2}$ ion of metabolite 767c, the major fragment ion produced is m/z 296.103$^{+2}$, which is the doubly-charged aglycone (observed m/z 591.199$^{+}$). The fragment ion at m/z 359.114$^{+}$ results from loss of the substituted benzimidazole moiety from the aglycone and is +16 Da relative to the corresponding ion of Compound 2. Neutral loss of N-methylmethanimine (monoisotopic mass 43.042 Da) from m/z 359.114$^{+}$ yields the m/z 316.072$^{+}$ ion, which is also +16 Da relative to the corresponding ion of Compound 2. The m/z 233.091$^{+}$ ion is due to charge retention on the substituted benzimidazole moiety, and neutral loss of water from this ion results in the m/z 215.081$^{+}$ ion. Together, this data supports the proposed structure.

R.10. Metabolites 882a and b (Metabolites m/z 882a and b)

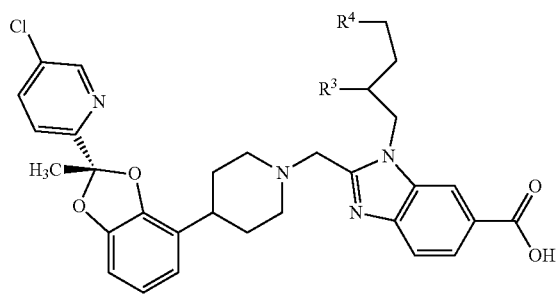

wherein one of $R^3$ and $R^4$ is OH, and the other is a moiety of

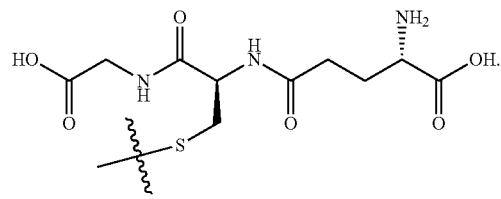 [SMILES: *SC[C@H](NC(=O)CC[C@H](N)C(=O)O)C(=O)NCC(=O)O]

Metabolites 882a and b

Figure 37:
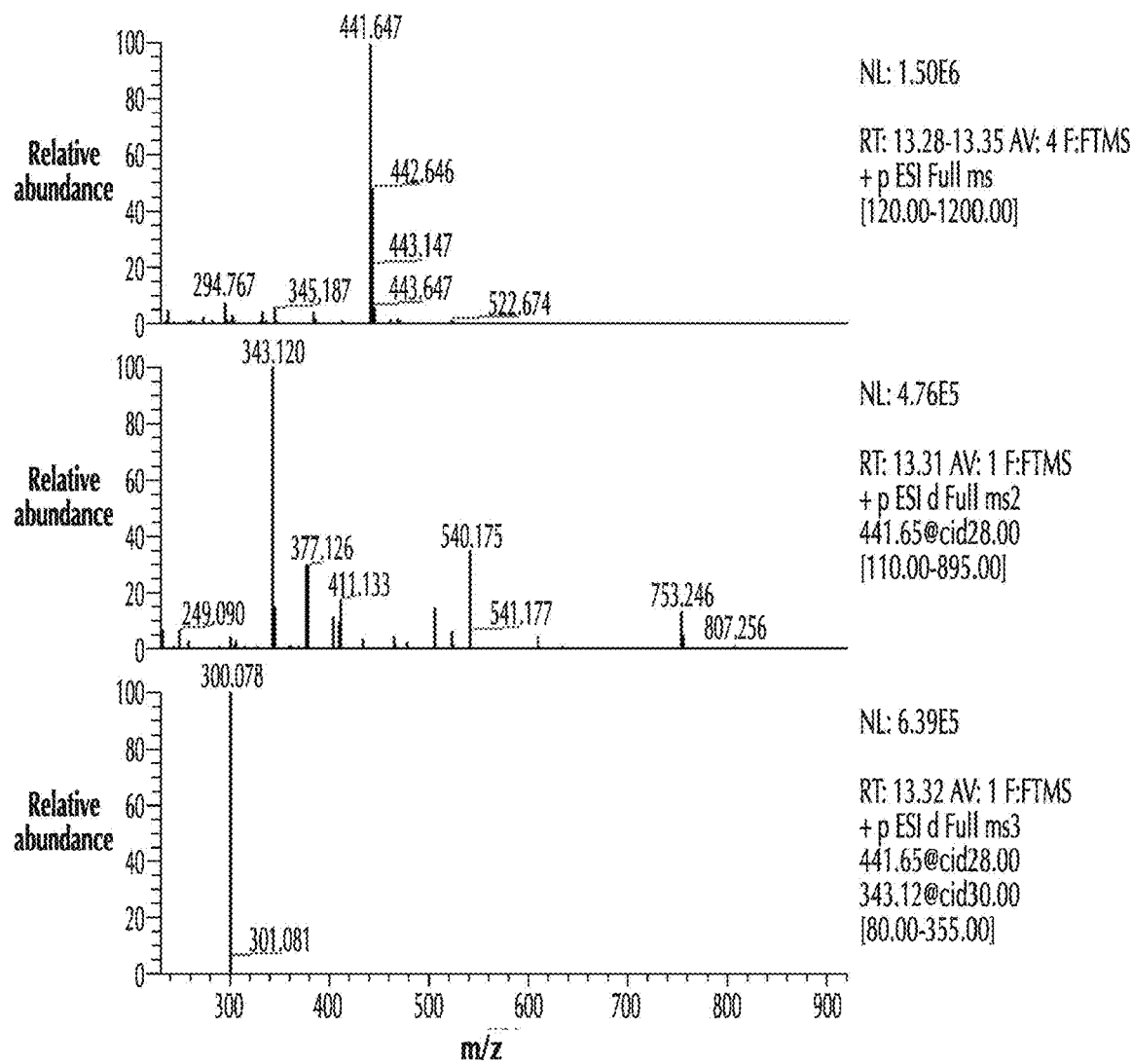
FIG. 37 shows mass spectra and proposed structure of Metabolite m/z 882a (of Compound 2).

Metabolites 882a and b eluted at approximately 13.31 and 13.49, min, respectively, with m/z 441.647$^{+2}$ (882.288$^{+}$) and are isomers with identical MS and MS$^n$ spectra. These metabolites were observed only in rabbit hepatocyte incubations. These metabolites appear to be glutathione conjugates+2H atoms relative to Compound 2, and this is supported by accurate mass measurements (mass calculated for $C_{41}H_{50}N_7O_{11}SCl$ is m/z 441.6483$^{+2}$ observed m/z 441.6473$^{+2}$, Δ=−2.3 ppm). CID mass spectra and proposed fragmentation patterns of m/z 882a are shown in FIG. 37. Upon CID fragmentation of the m/z 441.65$^{+2}$ ion of metabolites 882a or b, the major fragment ion produced is m/z 343.120$^{+}$, which results from cleavage of the piperidine-benzimidazole linkage and loss of the glutathione-conjugated moiety, and is identical to the ion observed in the CID spectra of Compound 2. Subsequent neutral loss of N-methylmethanimine (monoisotopic mass 43.042 Da) from m/z 343.120$^{+}$ yields the m/z 300.078 ion. Neutral loss of the glutamic acid residue from m/z 441.65$^{+2}$ yields the m/z 753.246$^{+}$ ion. The fragment ion at m/z 540.175$^{+}$ is the substituted benzimidazole moiety retaining GSH addition, and neutral loss of the glutamic acid residue from this yields the m/z 411.133$^{+}$ ion. The exact position of attachment of GSH is unknown.

R.11. Metabolite 694 (Metabolite m/z 694)

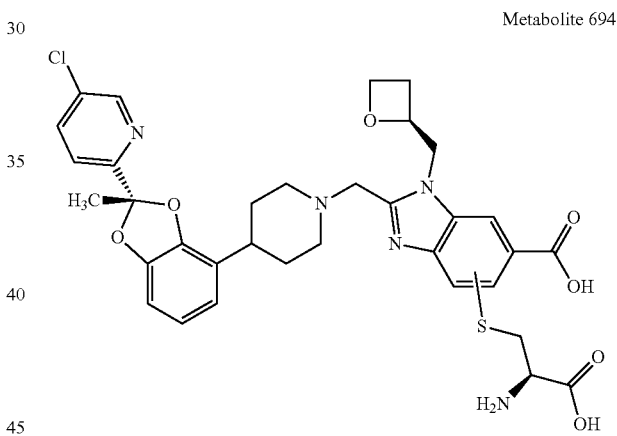

Metabolite 694

Figure 38:
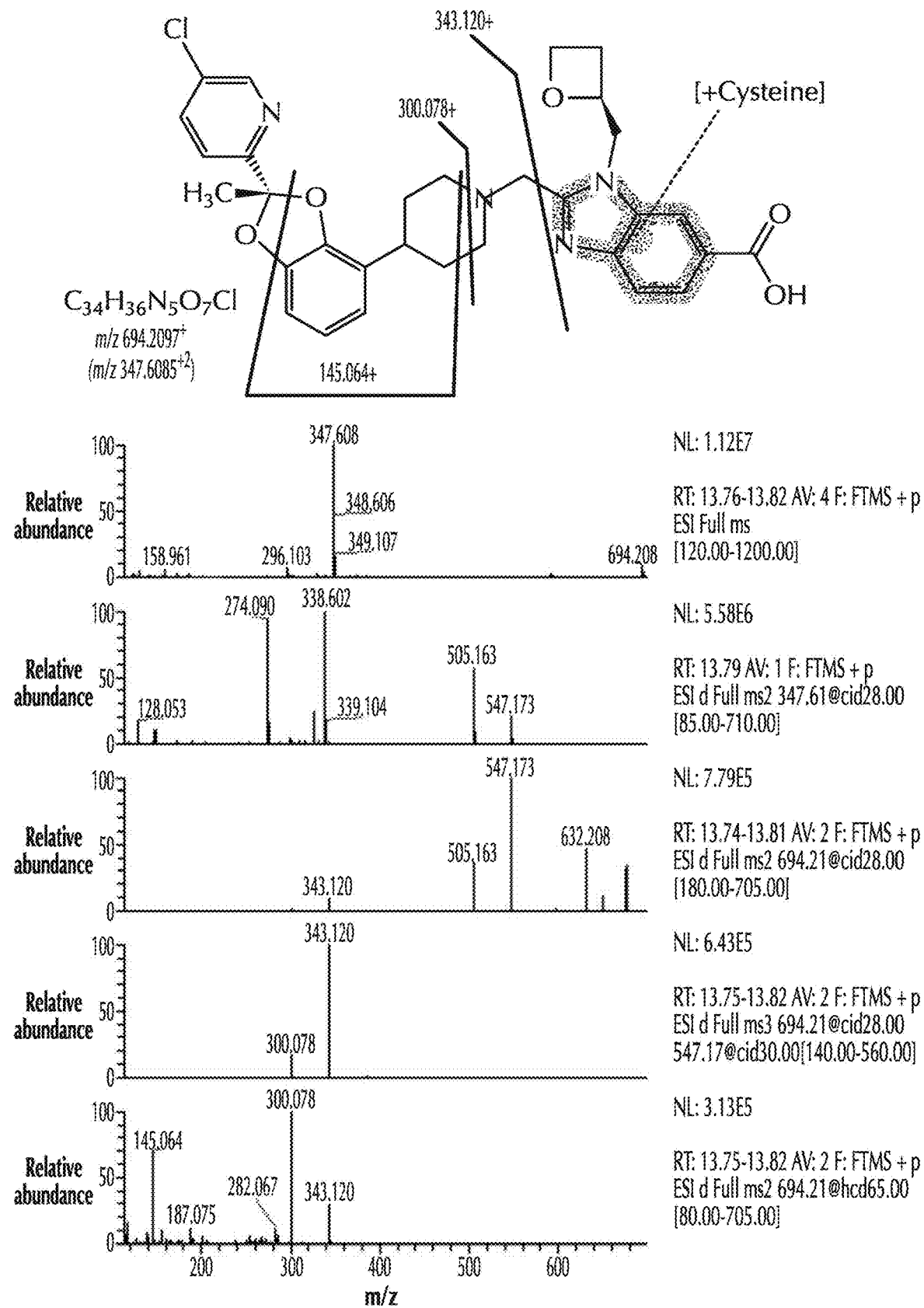
FIG. 38 shows mass spectra and proposed structure of Metabolite m/z 694 (of Compound 2).

Metabolite m/z 694 eluted at approximately 13.8 min with m/z 347.608$^{+2}$ (694.208$^{+}$). This metabolite was only observed in rabbit hepatocyte incubations. This metabolite appears to be a direct cysteine conjugate of Compound 2, and this is supported by accurate mass measurements (mass calculated for $C_{34}H_{38}N_5O_7SCl$ is m/z 347.6085$^{+2}$, observed m/z 347.6076$^{+2}$, Δ=−2.5 ppm). The CID mass spectra and proposed fragmentation patterns are shown in FIG. 38. Upon CID fragmentation of m/z 694.21$^{+}$ the major fragment ion produced is m/z 547.173$^{+}$, which subsequently yields m/z 343.120$^{+}$ and 300.078$^{+}$, resulting from cleavage of the piperidine-benzimidazole linkage and fragmentation of the piperidine ring, respectively. Both of these are observed in the CID spectra of Compound 2. These ions suggest that the cysteine adduction is not a modification to the piperidine, benzdioxolone, or chloropyridine moieties, but on the benzimidazole moiety. The exact nature of metabolite m/z 694 is not known.

R.12. Metabolite 591b (Metabolite m/z 591b)

Metabolite 591b

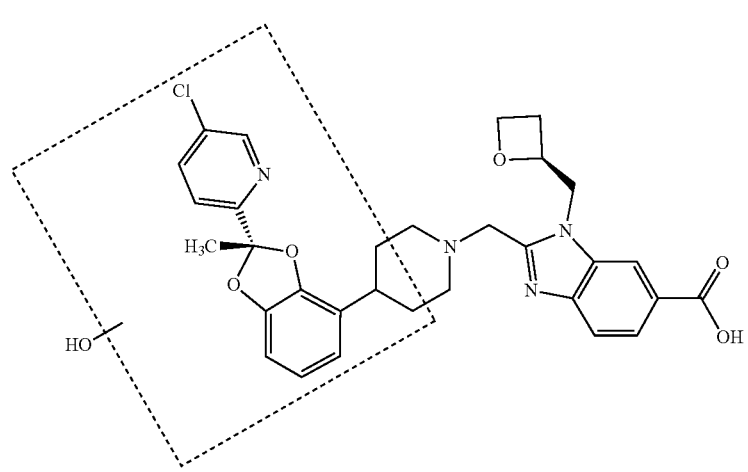

Figure 39:
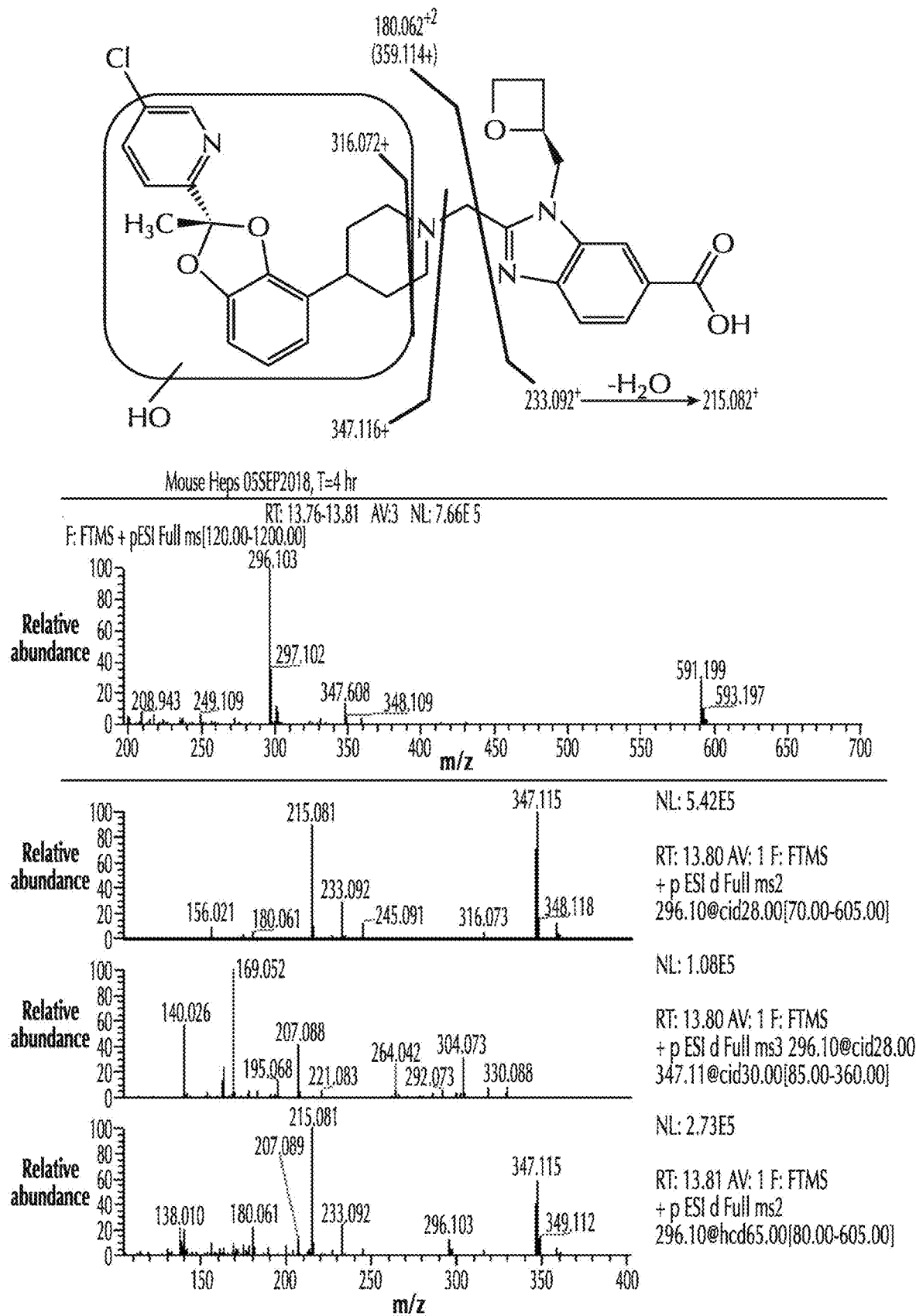
FIG. 39 shows mass spectra and proposed structure of Metabolite m/z 591b (of Compound 2).

Metabolite 591b is a hydroxylated metabolite which elutes at approximately 13.80 min and was observed with masses m/z 296.103$^{+2}$ and 591.199$^+$. This metabolite was observed in all hepatocyte incubations. The CID and HCD mass spectra and proposed fragmentation patterns are shown in FIG. 39. The m/z 347.115$^+$ ion in the MS$^2$ spectra of m/z 296.10$^{+2}$ is due to loss of the substitution on the piperidine N atom, and +16 Da relative to metabolite m/z 331 (N-dealkylation of the piperidine N atom). The m/z 233.092$^+$ ion is due to charge retention on the substituted benzimidazole moiety, and neutral loss of water from this ion results in the m/z 215.081$^+$ ion. This data indicates that the oxidation has occurred either on the piperidine or phenyl ring, or the pyridine moiety.

R.13. Metabolite 751a (Metabolite m/z 751a)

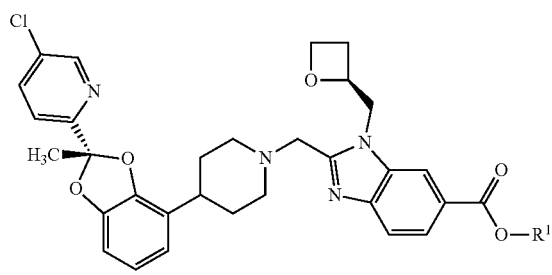

wherein R$^{10}$ is:

Metabolite 751a

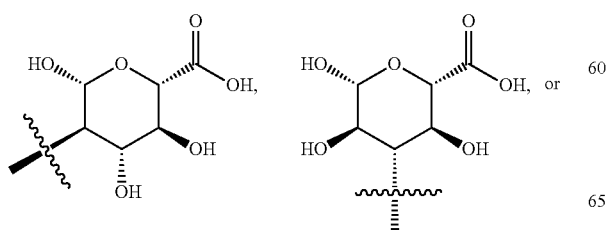

-continued

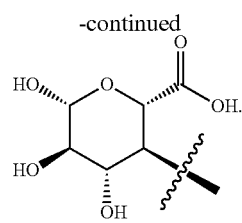

Figure 40:
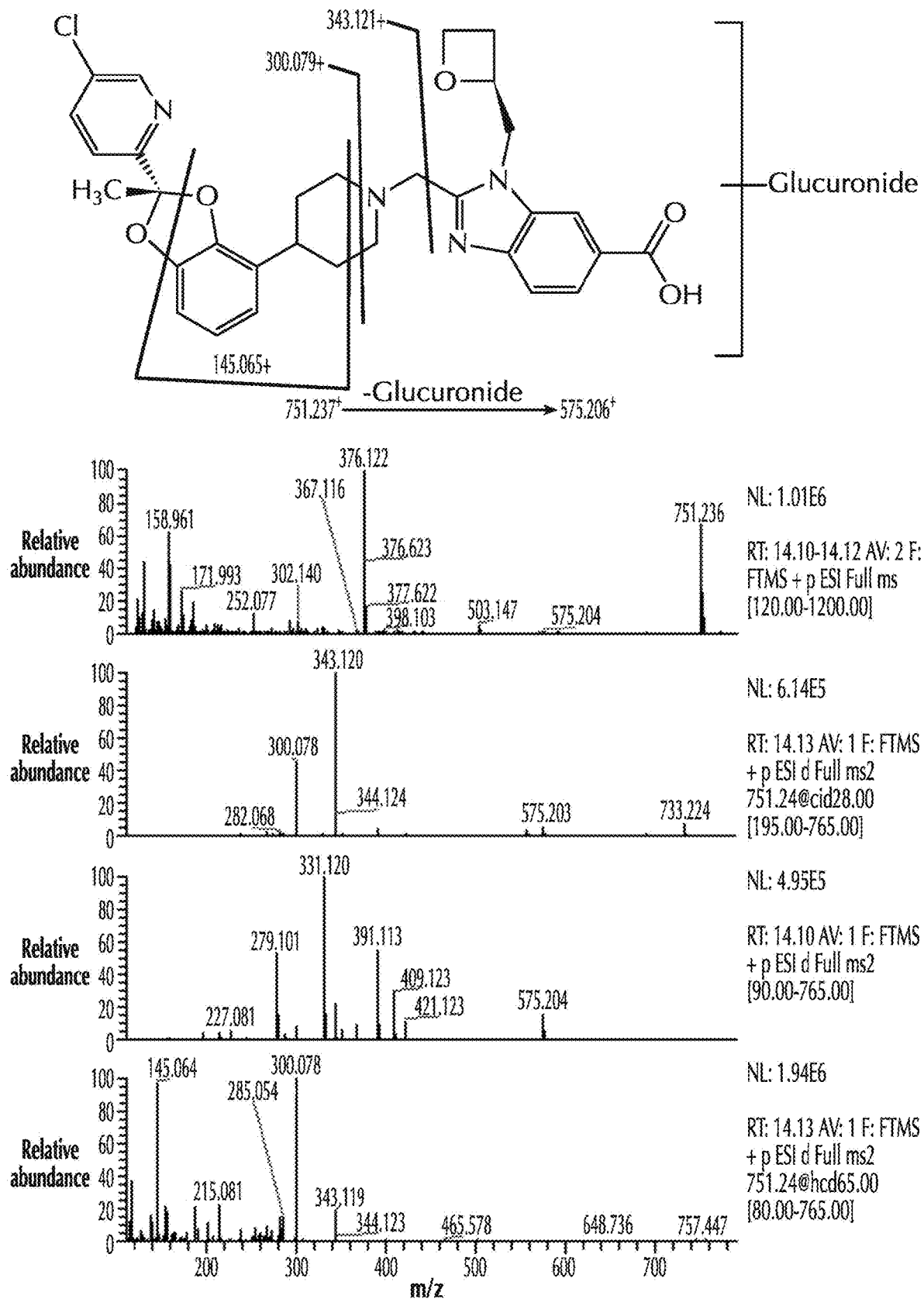
FIG. 40 shows mass spectra and proposed structure of Metabolite m/z 751a (of Compound 2).

Metabolite 751a eluted at approximately 14.15 min with masses m/z 376.122$^{+2}$ and 751.236$^+$ and was observed in all hepatocyte incubations. This metabolite is a glucuronide conjugate of Compound 2. The CID and HCD mass spectra and proposed fragmentation patterns are shown in FIG. 40. The fragment ion at m/z 575.203$^+$ is the aglycone. The fragment ions at m/z 343.120$^+$, 300.078$^+$, 215.081$^+$, and 145.064$^+$ are identical to those observed in the spectra of Compound 2. The exact position of glucuronidation could not be determined.

R.14. Metabolite 505 (Metabolite m/z 505)

Metabolite 505

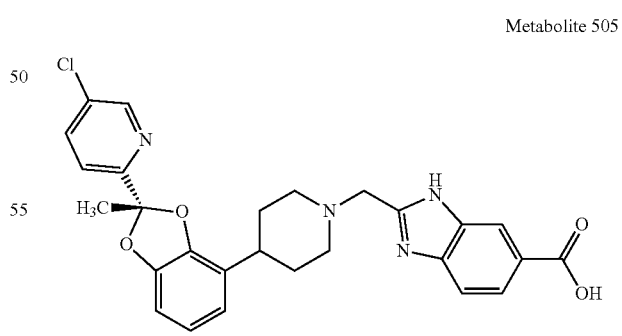

Chemical name: (S)-2-((4-(2-(5-chloropyridin-2-yl)-2-methylbenzo[d][1,3]dioxol-4-yl)piperidin-1-yl)methyl)-1H-benzo[d]imidazole-6-carboxylic acid Metabolite m/z 505 eluted at approximately 14.46 min with observed masses m/z 253.085$^{+2}$ and 505.163$^+$ and co-eluted with metabolite m/z 593. Metabolite m/z 505 was observed in mouse, rat, and rabbit hepatocyte incubations. This metabolite is formed by N-dealkylation of Compound 2 at the benzimidazole moiety. The CID and HCD mass spectra of metabolite m/z 505 and proposed fragmentation patterns are shown in FIG. 41. Cleavages around the piperidine-benzimidazole linkage dominated the spectra, producing the m/z 343.120$^+$/163.050$^+$ pair or the m/z 331.120$^+$/175.050$^+$ pair, depending upon which side of the methylene bridge the fragmentation occurred. The m/z 300.078$^+$ ion results from cleavage across the piperidine ring and was also observed in the spectrum of Compound 2.

R.15. Metabolite 593 (Metabolite m/z 593)

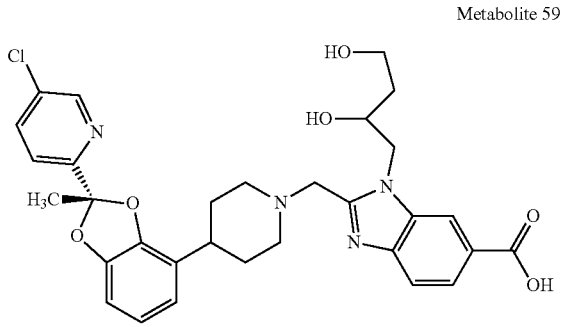

Metabolite 593

Not wishing to be bound by any particular theory, it is believed that Metabolite 593 has the following structure.

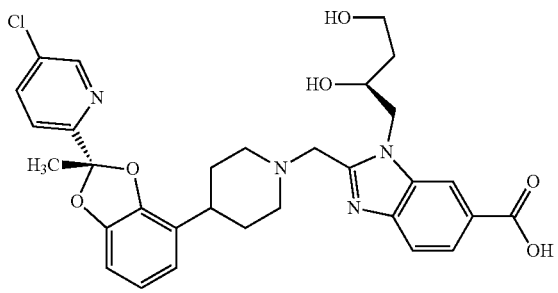 [SMILES: C[C@]1(c2ccc(Cl)cn2)Oc2cccc(C3CCN(Cc4nc5ccc(C(=O)O)cc5n4C[C@@H](O)CCO)CC3)c2O1]

Figure 42:
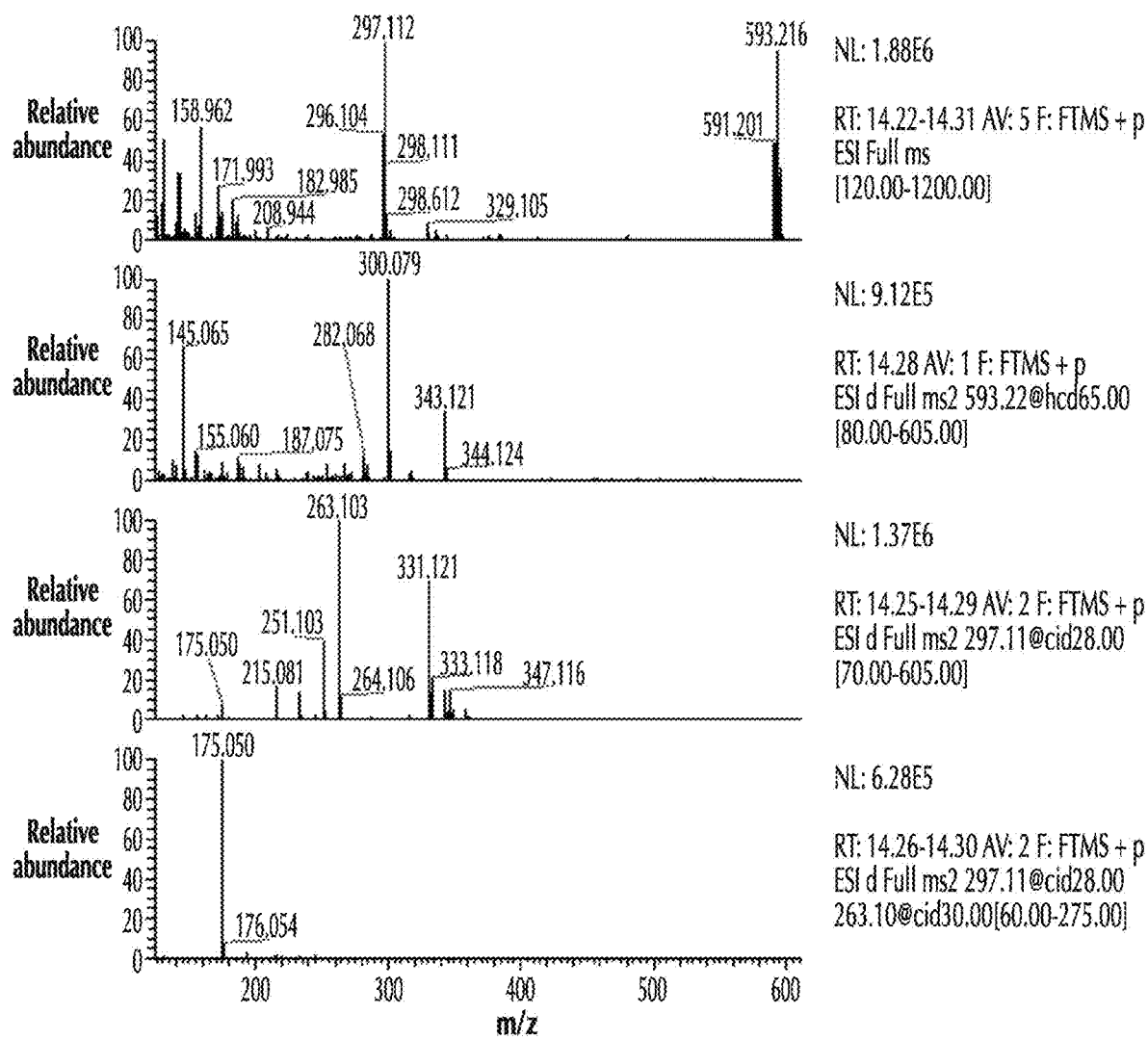
FIG. 42 shows mass spectra and proposed structure of Metabolite m/z 593 (of Compound 2).

Metabolite m/z 593 eluted at approximately 14.46 min with observed masses m/z 297.112$^{+2}$ and 593.216$^+$ and was observed in all hepatocyte incubations. This metabolite appears to be formed by hydrolysis of the oxetane ring of Compound 2. The CID and HCD mass spectra of metabolite m/z 593 and proposed fragmentation patterns are shown in FIG. 42. Cleavages around the piperidine-benzimidazole linkage dominated the spectra, producing the m/z 343.121$^+$/251.103$^+$ pair or the m/z 331.121$^+$/263.103$^+$ pair, depending upon which side of the methylene bridge is cleaved and where charge retention occurs. The m/z 300.079$^+$ ion in the MS$^2$ of m/z 593.22$^+$ results from cleavage across the piperidine ring and was also observed in the spectrum of Compound 2. The MS$^3$ 297.11$^{+2}$>263.10$^+$ spectrum (bottom pane) shows that loss of the hydrolyzed oxetane yields the m/z 175.050$^+$ ion, indicating that this moiety was not modified.

R.16. Metabolite 591c (Metabolite m/z 591c)

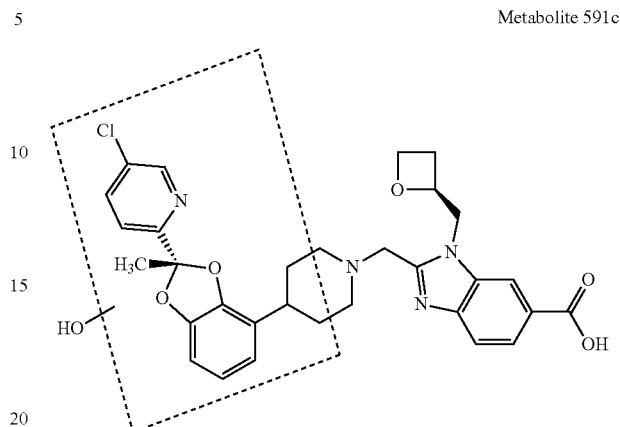

Metabolite 591c

Figure 43:
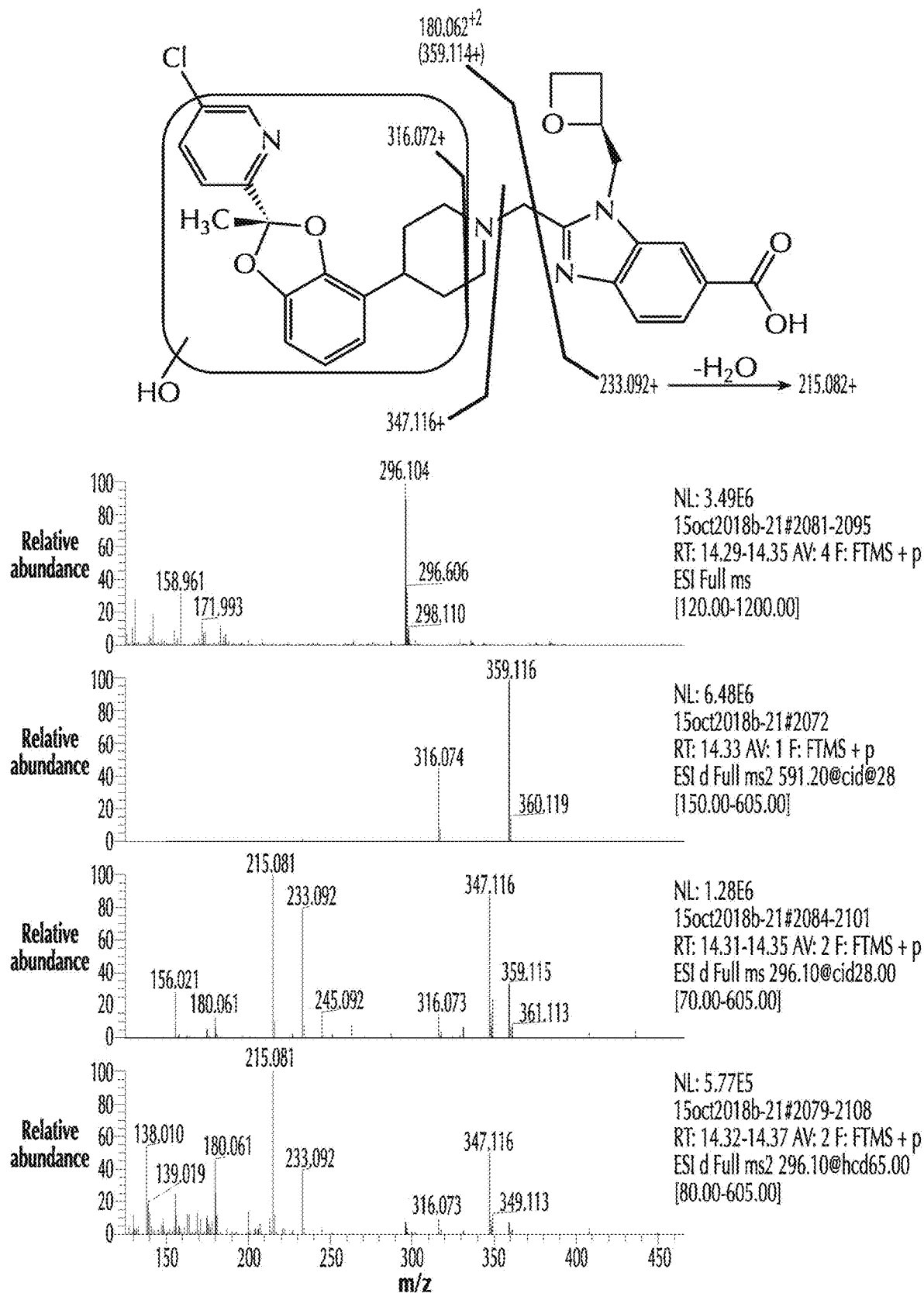
FIG. 43 shows mass spectra and proposed structure of Metabolite m/z 591c (of Compound 2).

Metabolite 591c eluted at approximately 14.53 min with observed masses m/z 296.104$^{+2}$ and 591.201$^+$ and was observed in all hepatocyte incubations. This metabolite is a hydroxylation of Compound 2. The CID and HCD mass spectra and proposed fragmentation patterns are shown in FIG. 43. The fragment ion at m/z 359.116$^+$ (180.061$^{+2}$) results from loss of the substituted benzimidazole moiety and is +16 Da relative to the corresponding ion of Compound 2. The m/z 347.116$^+$ ion in the MS$^2$ spectra of m/z 296.10$^{+2}$ is +16 Da relative to metabolite m/z 331 (N-dealkylation of the piperidine N atom). The m/z 233.092$^+$ ion is due to charge retention on the substituted benzimidazole moiety, and neutral loss of water from this ion results in the m/z 215.081$^+$ ion. This data indicates that the oxidation has occurred either on the piperidine or phenyl ring, or the pyridine moiety.

R.17. Metabolite 751b (Metabolite m/z 751b)

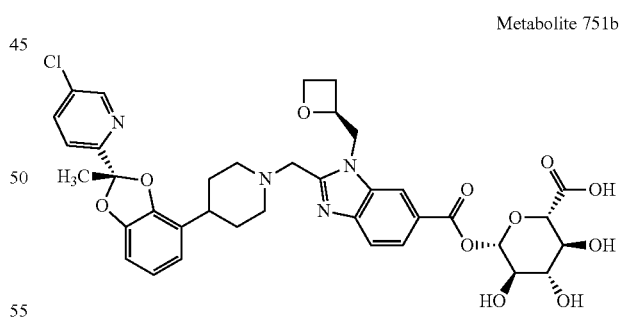

Metabolite 751b

Metabolite 751b eluted at approximately 14.65 min with 751.237$^+$ and was observed in all hepatocyte incubations and in rat bile and plasma. This metabolite is a glucuronide conjugate of Compound 2. By comparison of individual and co-injected samples of synthetically made Metabolite 751b with a Day 7 human Hepatopack incubation sample, the retention time and HCD mass spectra were observed to match. Chromatograms and HCD mass spectra are shown in FIG. 44. The aglycone (m/z 575.206$^+$) was not observed in the HCD spectra of either m/z 751b or synthetically made Metabolite 751b, but the fragment ions at m/z 343.120$^+$, 300.078⁺, and 145.065⁺ are identical and match those observed in the spectra of Compound 2.

R.18. Metabolite 607 (Metabolite m/z 607)

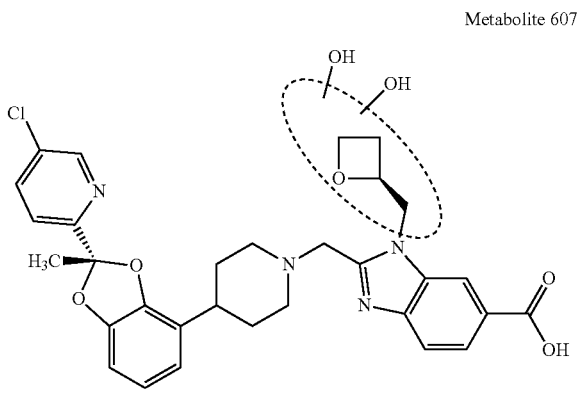

Metabolite 607

Metabolite m/z 607 eluted at approximately 14.78 min with observed masses m/z $304.101^{+2}$ and 607.194⁺ and co-eluted with metabolite m/z 751b. Metabolite m/z 607 was observed only in rabbit hepatocyte incubations. This metabolite appears to be formed by bis oxidation of Compound 2 at the oxetane moiety. The CID and HCD mass spectra of m/z $304.10^{+2}$ and proposed fragmentation patterns are shown in FIG. 45. Cleavages around the piperidine-benzimidazole linkage dominated the spectra, producing the m/z 343.120⁺/265.082⁺ pair or the m/z 331.120⁺/277.081⁺ pair, depending upon which side of the methylene bridge the fragmentation occurred. The m/z 300.078⁺ ion results from cleavage across the piperidine ring and was also observed in the spectrum of Compound 2. Fragment ion m/z 163.050⁺ results from charge retention on the unchanged 1H-benzo[d]imidazole-6-carboxylic acid moiety. This suggests that the bis-oxidation, which occurs on the portion of the molecule represented by the m/z 265.081⁺ fragment ion, must occur on the methyloxetane moiety.

R.19. Metabolite m/z 569 (Metabolite m/z 569)

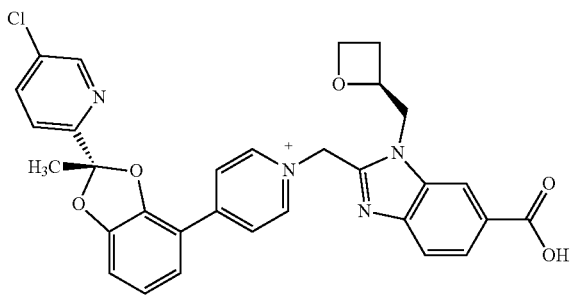

Metabolite 569

Figure 46:
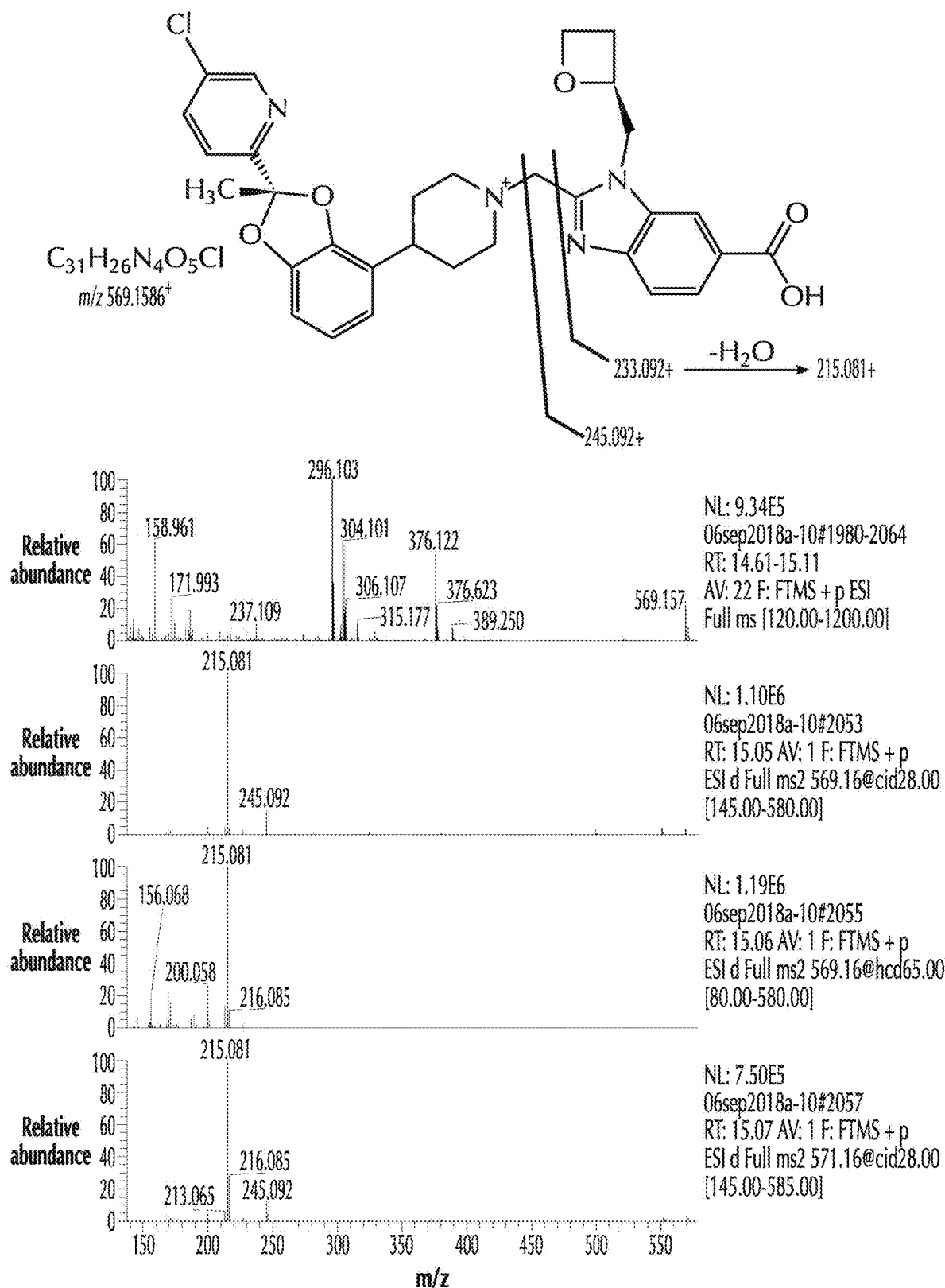
FIG. 46 shows mass spectra and proposed structure of Metabolite m/z 569 (of Compound 2).

Metabolite 569 eluted at approximately 15.08 min with m/z 569.157⁺ and was observed in all hepatocyte incubations. This metabolite is proposed to result from aromatization of the piperidine moiety in Compound 2 (mass calculated for $C_{31}H_{26}N_4O_5Cl^+$ is m/z 569.1586⁺, observed m/z 569.1572⁺, Δ=−2.5 ppm). The CID and HCD mass spectra and proposed fragmentation patterns are shown in FIG. 46. In the CID spectrum of m/z 569.16⁺ the major fragment ion at m/z 215.081⁺ is the dehydrated benzimidazole, which is also observed in the CID spectrum of Compound 2, while other ions resulting from cleavage around the piperidine-benzimidazole linkage are notably absent. Additionally, the m/z 245.092⁺ fragment ion is attributed to the unchanged 2-methyl-1-(oxetan-2-yl-methyl)-1H-benzo[d]imidazole-6-carboxylic acid moiety, all of which suggest that the piperidine is the site of aromatization.

R.20. Metabolite 751c (Metabolite m/z 751c)

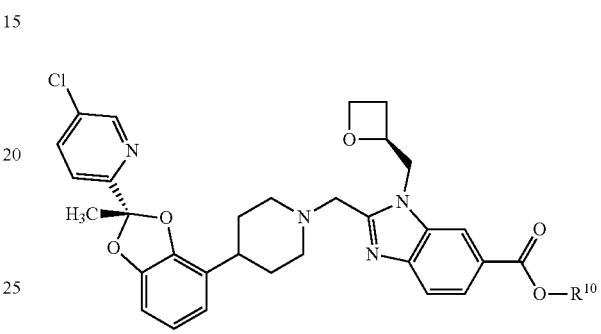

wherein $R^{10}$ is:

Metabolite 751c

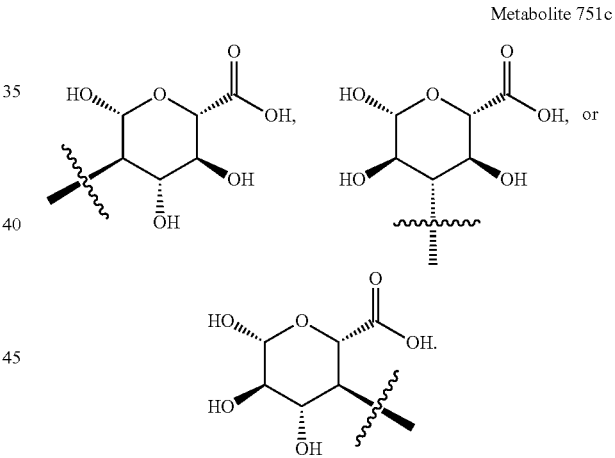

Metabolite 751c eluted at approximately 15.15 min with masses m/z $376.122^{+2}$ and 751.236⁺ and was observed as a trace metabolite in mouse, rabbit, and monkey hepatocyte incubations. This metabolite is a glucuronide conjugate of Compound 2. The CID and HCD mass spectra and proposed fragmentation patterns are shown in FIG. 47. In the CID spectrum of m/z $376.12^{+2}$ (center pane), the fragment ion at m/z 575.204⁺ is the aglycone, while the m/z $367.116^{+2}$ and $279.101^{+2}$ ions are dehydration products of the glucuronide and the aglycone, respectively. In the HCD spectrum of m/z $376.12^{+2}$ (bottom pane), the fragment ion at m/z 331.120⁺ results from cleavage of the bond between the piperidine N atom and the methyl benzimidazole moiety, while the 300.077⁺, 215.081⁺, and 140.026⁺ ions are observed in the spectra of Compound 2. The exact position of glucuronidation could not be determined.

R.21. Metabolite 573a (Metabolite m/z 573a)

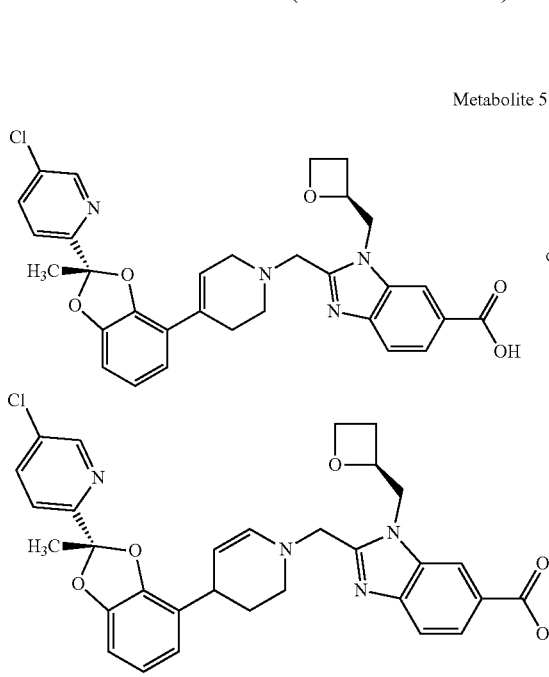

Metabolite 573a

Figure 48:
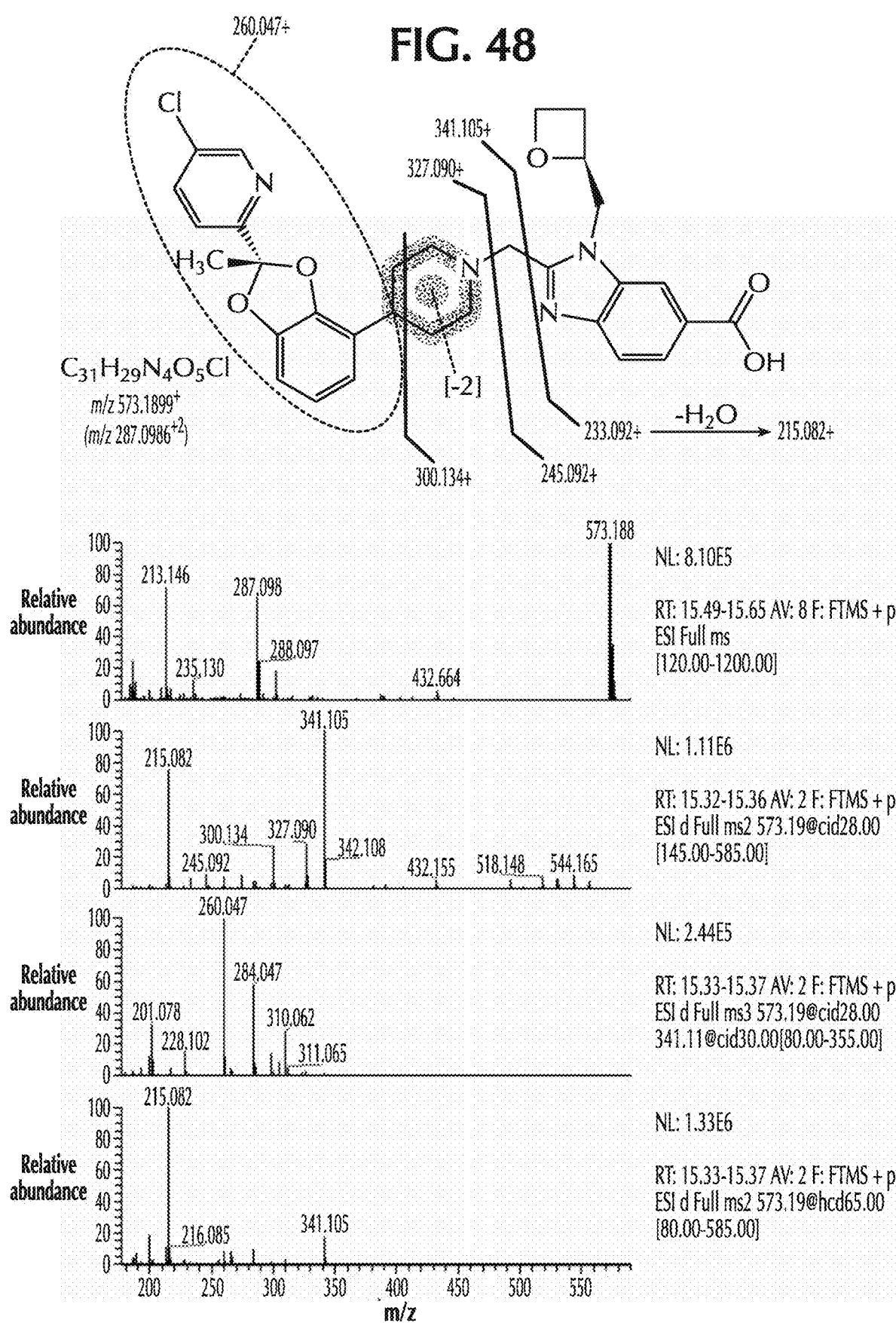
FIG. 48 shows mass spectra and proposed structure of Metabolite m/z 753a (of Compound 2).

Metabolite 573a eluted at approximately 15.58 min with masses m/z 287.098$^{+2}$ and 573.188$^+$ and was observed as a low-level metabolite in all hepatocyte incubations. This metabolite is proposed to result from desaturation of the piperidine moiety in Compound 2 (mass calculated for $C_{31}H_{30}N_4O_5Cl^+$ is m/z 573.1899$^+$, observed m/z 573.1885$^+$, Δ=−2.5 ppm). The CID and HCD mass spectra and proposed fragmentation patterns are shown in FIG. 48. In the CID spectrum of m/z 573.19$^+$ cleavages around the piperidine-benzimidazole linkage dominated the spectra, producing the m/z 341.105$^+$/233.092$^+$ pair or the m/z 327.090$^+$/245.092$^+$ pair, depending upon which side of the methylene bridge the fragmentation occurred. The m/z 300.134$^+$ ion results from cleavage across the piperidine ring, while the m/z 260.047$^+$ ion contains the unchanged chloropyridine and benzdioxolone moieties with the benzyl C atom from the piperidine ring. Additionally, the m/z 245.092$^+$ fragment ion is attributed to the unchanged 2-methyl-1-{[(2S)-oxetan-2-yl]methyl}-1H-benzimidazole-6-carboxylic acid moiety, which suggests that the piperidine is the site of dehydrogenation.

R.22. Metabolite 573b (Metabolite m/z 573b)

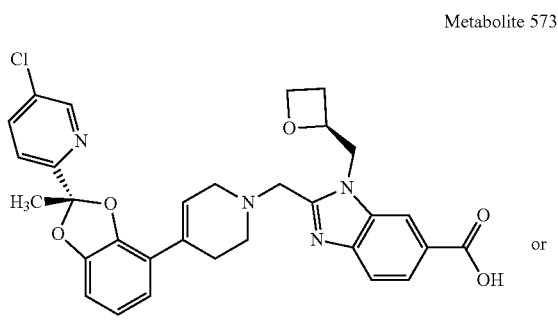

Metabolite 573b

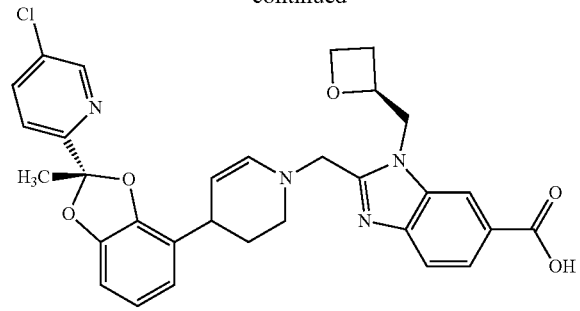

-continued

Figure 49:
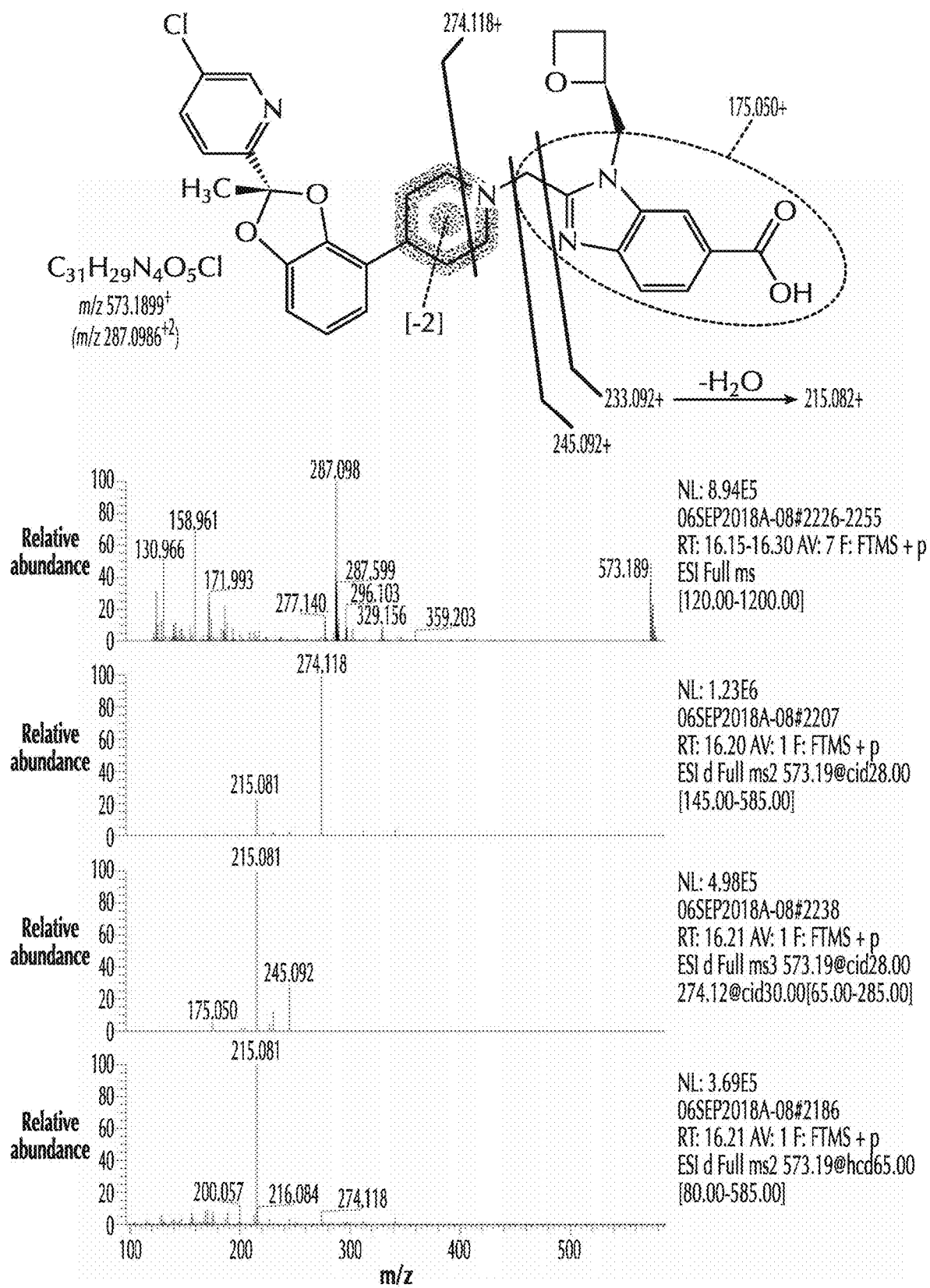
FIG. 49 shows mass spectra and proposed structure of Metabolite m/z 753b (of Compound 2).

Metabolite 573b eluted at approximately 16.20 min with observed masses m/z 287.098$^{+2}$ and 573.188$^+$ and was observed as a minor metabolite in mouse and rabbit hepatocyte incubations. This metabolite is proposed to result from desaturation of the piperidine moiety in Compound 2 (mass calculated for $C_{31}H_{30}N_4O_5Cl^+$ is m/z 573.1899$^+$, observed m/z 573.1888$^+$, Δ=−2.0 ppm). The CID and HCD mass spectra and proposed fragmentation patterns are shown in FIG. 49. In the spectra of m/z 573.19$^+$ the abundant fragment ions contain the unchanged 2-methyl-1-{[(2S)-oxetan-2-yl]methyl}-1H-benzimidazole-6-carboxylic acid moiety (m/z 175.050$^+$), which suggests that the desaturation has not occurred on the oxetane ring. The m/z 274.118$^+$ ion results from cleavage across the piperidine ring, while the m/z 245.092$^+$ and 233.092$^+$ ions are produced by cleavage of the piperidine-benzimidazole linkage and differ only by 1 C atom. Together these fragment ions suggest that the desaturation has occurred on the piperidine ring at a position different from metabolite m/z 573a.

R.23. Metabolite 671 (Metabolite m/z 671)

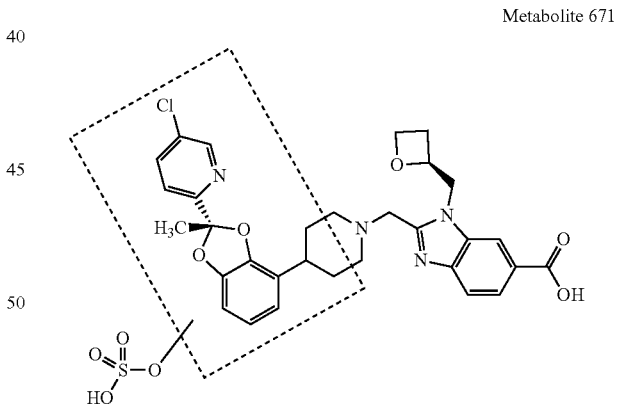

Metabolite 671

Figure 50:
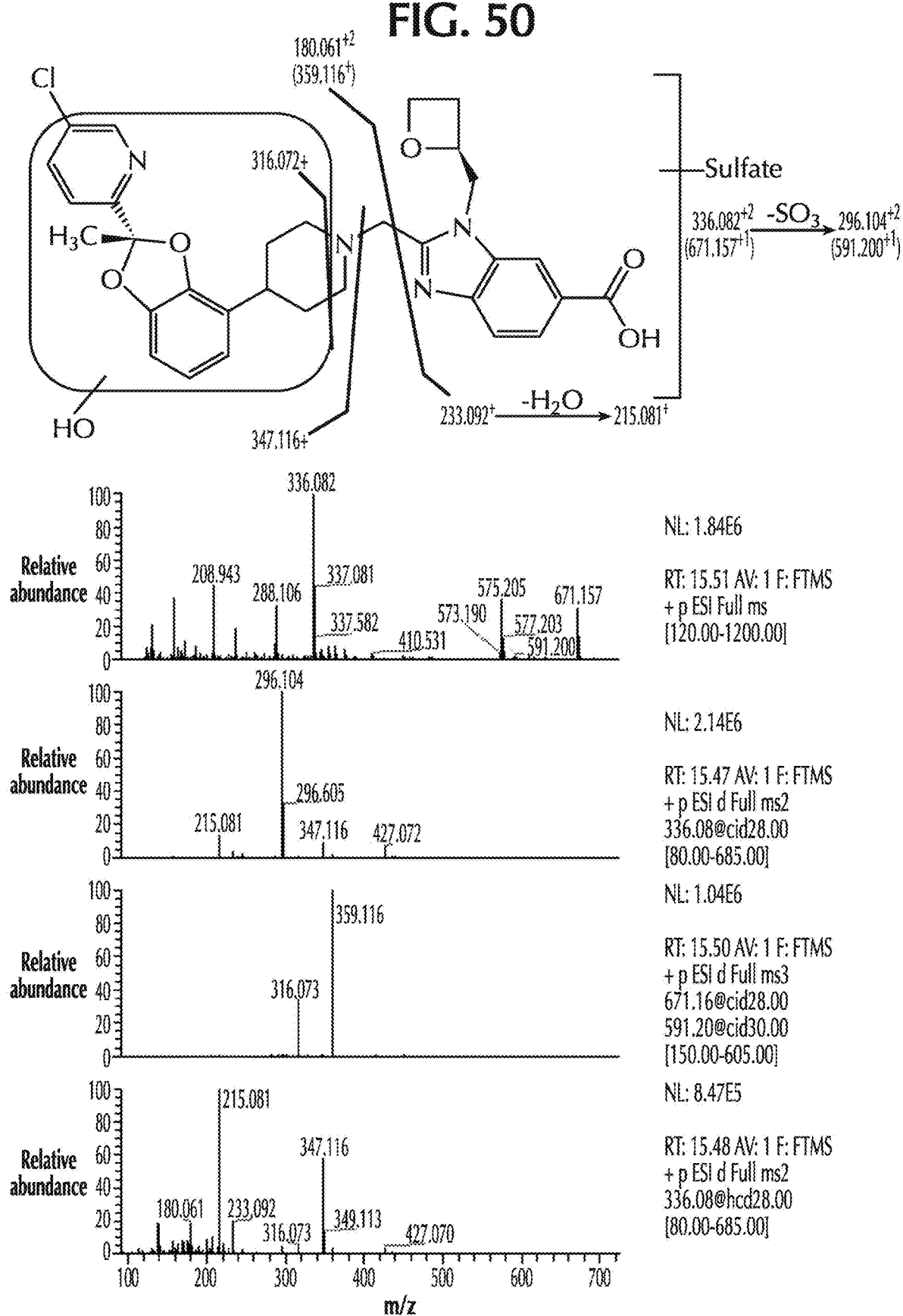
FIG. 50 shows mass spectra and proposed structure of Metabolite m/z 671 (of Compound 2).

Metabolite m/z 671 eluted later than Compound 2 at approximately 16.20 min with observed masses m/z 336.082$^{+2}$ and 671.156$^+$ and was observed in rat hepatocyte incubations. This metabolite is a sulfate conjugate of a single oxidation of Compound 2. The CID and HCD mass spectra and proposed fragmentation patterns are shown in FIG. 50. In the MS$^2$ spectrum of 336.08$^{+2}$ the fragment ion at m/z 296.104$^{+2}$ results from loss of sulfate conjugation. The fragment ion at m/z 359.116$^+$ (180.061$^{+2}$) in the MS$^3$ 671.16$^+$>591.20$^+$ CID spectrum results from loss of SO$_3$ and the substituted benzimidazole moiety, and is +16 Da relative to the corresponding ion of Compound 2. Neutral loss of N-methylmethanimine (monoisotopic mass 43.042 Da) from m/z 359.116$^+$ yields the m/z 316.073$^+$ ion, which is also +16 Da relative to the corresponding ion of Compound 2. The m/z 347.116$^+$ ion in the MS$^2$ spectra of m/z 336.08$^{+2}$ is +16 Da relative to metabolite m/z 331 (N-dealkylation of the piperidine N atom). The m/z 233.092$^+$ ion is due to charge retention on the substituted benzimidazole moiety, and neutral loss of water from this ion results in the m/z 215.081$^+$ ion. This data indicates that the oxidation has occurred either on the piperidine or phenyl ring, or the pyridine moiety, however, the precise location of sulfate conjugation cannot be determined.

R.24. Metabolite 591d (Metabolite m/z 591d)

Metabolite 591d

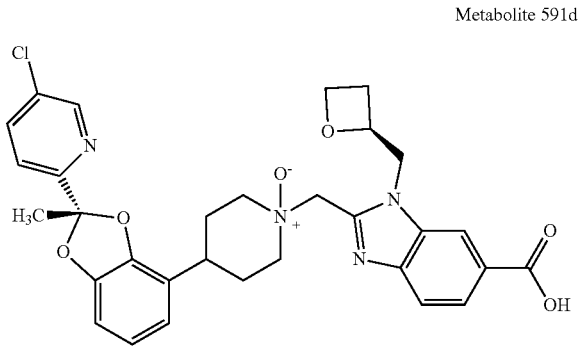

Figure 51:
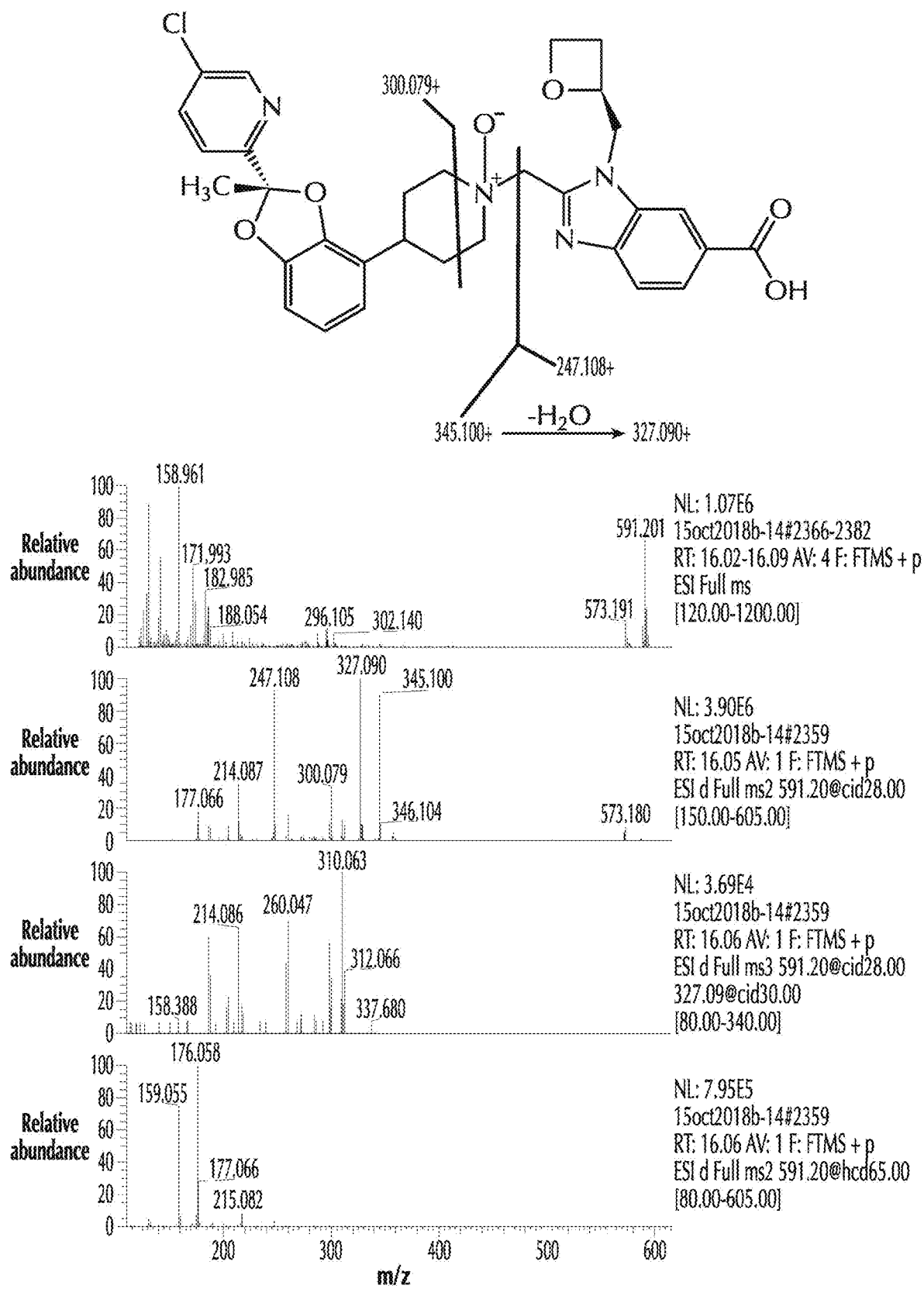
FIG. 51 shows mass spectra and proposed structure of Metabolite m/z 591d (of Compound 2).

Metabolite 591d eluted later than Compound 2 at approximately 16.26 min with observed masses m/z 296.104$^{+2}$ and 591.201$^+$ and was observed in all hepatocyte incubations. This metabolite is a single oxidation of Compound 2. The CID and HCD mass spectra and proposed fragmentation patterns are shown in FIG. 51. The fragment ion at m/z 345.100$^+$ results from loss of the substituted benzimidazole moiety (m/z 247.108$^+$ in the MS$^2$ spectra of m/z 591.20$^+$). Dehydration of m/z 345.100$^+$ yields the m/z 327.090$^+$ ion. The m/z 300.079$^+$ ion is also observed in Compound 2, suggesting that neither the chloropyridine moiety nor the benzdioxolone has been modified. Treatment of a rat hepatocyte sample with TiCl$_3$ for 2 hrs at room temperature caused the m/z 591d metabolite peak to disappear. Taken together, the data suggests that the oxidation has occurred on the piperidine ring system and is likely an N-oxide metabolite on the piperidine N atom.

Example AA. CHO GLP-1R Clone H6—Assay 1

GLP-1R-mediated agonist activity was determined with a cell-based functional assay utilizing an HTRF (Homogeneous Time-Resolved Fluorescence) cAMP detection kit (cAMP HI Range Assay Kit; CisBio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either standard or experimental sample.

The human GLP-1R coding sequence (NCBI Reference Sequence NP_002053.3, including naturally-occurring variant Gly168Ser) was subcloned into pcDNA3 (Invitrogen) and a cell line stably expressing the receptor was isolated (designated Clone H6). Saturation binding analyses (filtration assay procedure) using $^{125}$I-GLP-1$_{7-36}$ (Perkin Elmer) showed that plasma membranes derived from this cell line express a high GLP-1R density (K$_d$: 0.4 nM, B$_{max}$: 1900 fmol/mg protein).

Cells were removed from cryopreservation, re-suspended in 40 mL of Dulbecco's Phosphate Buffered Saline (DPBS—Lonza Cat #17-512Q) and centrifuged at 800×g for 5 minutes at 22° C. The cell pellet was then re-suspended in 10 mL of growth medium [DMEM/F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081) and 500 µg/mL Geneticin (G418) (Invitrogen #10131035)]. A 1 mL sample of the cell suspension in growth media was counted on a Becton Dickinson ViCell to determine cell viability and cell count per mL. The remaining cell suspension was then adjusted with growth media to deliver 2000 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment in 5% carbon dioxide.

Varying concentrations of each compound to be tested (in DMSO) were diluted in assay buffer (HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E) containing 100 µM 3-isobutyl-1-methylxanthin (IBMX; Sigma cat #15879). The final DMSO concentration is 1%.

After 48 hours, the growth media was removed from the assay plate wells, and the cells were treated with 20 µL of the serially diluted compound in assay buffer for 30 minutes at 37° C. in a humidified environment in 5% carbon dioxide. Following the 30 minute incubation, 10 µL of labeled d2 cAMP and 10 µL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1$_{7-36}$ (1 µM) included on each plate. EC$_{50}$ determinations were made from agonist dose-response curves analyzed with a curve fitting program using a 4-parameter logistic dose response equation.

Example BB. CHO GLP-1R Clone C6—Assay 2

GLP-1R-mediated agonist activity was determined with a cell-based functional assay utilizing an HTRF (Homogeneous Time-Resolved Fluorescence) cAMP detection kit (cAMP HI Range Assay Kit; Cis Bio cat #62AM6PEJ) that measures cAMP levels in the cell. The method is a competitive immunoassay between native cAMP produced by the cells and exogenous cAMP labeled with the dye d2. The tracer binding is visualized by a mAb anti-cAMP labeled with Cryptate. The specific signal (i.e. energy transfer) is inversely proportional to the concentration of cAMP in either a standard or an experimental sample.

The human GLP-1R coding sequence (NCBI Reference Sequence NP_002053.3, including naturally-occurring variant Leu260Phe) was subcloned into pcDNA5-FRT-TO and a clonal CHO cell line stably expressing a low receptor density was isolated using the Flp-In™ T-Rex™ System, as described by the manufacturer (ThermoFisher). Saturation binding analyses (filtration assay procedure) using $^{125}$I-GLP-1 (Perkin Elmer) showed that plasma membranes derived from this cell line (designated clone C6) express a low GLP-1R density ($K_d$: 0.3 nM, $B_{max}$: 240 fmol/mg protein), relative to the clone H6 cell line.

Cells were removed from cryopreservation, re-suspended in 40 mL of Dulbecco's Phosphate Buffered Saline (DPBS—Lonza Cat #17-512Q) and centrifuged at 800×g for 5 minutes at 22° C. The DPBS was aspirated, and the cell pellet was re-suspended in 10 mL of complete growth medium (DMEM:F12 1:1 Mixture with HEPES, L-Gln, 500 mL (DMEM/F12 Lonza Cat #12-719F), 10% heat inactivated fetal bovine serum (Gibco Cat #16140-071), 5 mL of 100× Pen-Strep (Gibco Cat #15140-122), 5 mL of 100× L-Glutamine (Gibco Cat #25030-081), 700 µg/mL Hygromycin (Invitrogen Cat #10687010) and 15 µg/mL Blasticidin (Gibco Cat #R21001). A 1 mL sample of the cell suspension in growth media was counted on a Becton Dickinson ViCell to determine cell viability and cell count per mL. The remaining cell suspension was then adjusted with growth media to deliver 1600 viable cells per well using a Matrix Combi Multidrop reagent dispenser, and the cells were dispensed into a white 384 well tissue culture treated assay plate (Corning 3570). The assay plate was then incubated for 48 hours at 37° C. in a humidified environment (95% $O_2$, 5% $CO_2$)

Varying concentrations of each compound to be tested (in DMSO) were diluted in assay buffer [HBSS with Calcium/Magnesium (Lonza/BioWhittaker cat #10-527F)/0.1% BSA (Sigma Aldrich cat #A7409-1L)/20 mM HEPES (Lonza/BioWhittaker cat #17-737E)] containing 100 µM 3-isobutyl-1-methylxanthin (IBMX; Sigma cat #15879). The final DMSO concentration in the compound/assay buffer mixture is 1%.

After 48 hours, the growth media was removed from the assay plate wells, and the cells were treated with 20 µL of the serially diluted compound in assay buffer for 30 minutes at 37° C. in a humidified environment (95% $O_2$, 5% $CO_2$). Following the 30 minute incubation, 10 µL of labeled d2 cAMP and 10 µL of anti-cAMP antibody (both diluted 1:20 in cell lysis buffer; as described in the manufacturer's assay protocol) were added to each well of the assay plate. The plates were then incubated at room temperature and after 60 minutes, changes in the HTRF signal were read with an Envision 2104 multi-label plate reader using excitation of 330 nm and emissions of 615 and 665 nm. Raw data were converted to nM cAMP by interpolation from a cAMP standard curve (as described in the manufacturer's assay protocol) and the percent effect was determined relative to a saturating concentration of the full agonist GLP-1 (1 µM) included on each plate. $EC_{50}$ determinations were made from agonist dose response curves analyzed with a curve fitting program using a 4-parameter logistic dose response equation.

In Table X-1, assay data are presented to two (2) significant figures as the geometric mean ($EC_{50}$s) and arithmetic mean (Emax) based on the number of replicates listed (Number). A blank cell means there was no data for that Example or the Emax was not calculated. Table X-1. Biological activity for Compounds 1 and 2 and some of their metabolites.

| Compound | Assay 1 $EC_{50}$ (nM) | Assay 1 Emax (%) | Assay 1 Number | Assay 2 $EC_{50}$ (nM) | Assay 2 Emax (%) | Assay 2 Number |
|---|---|---|---|---|---|---|
| Compound 1 | 1.1 | 79 | 5 | 13 | 100 | 18 |
| Compound M1 | 130 | 114 | 2 | 2500 | 98 | 2 |
| Compound M2 | >20,000 | 2 | 3 | >20,000 | 0 | 2 |
| Compound 2**** | 0.96 | 99 | 5 | 17 | 96 | 8 |
| Metabolite 751b (in Example A) | ND | ND | ND | 170 | 68 | 2 |

****Tested as formate salt and free acid
ND: Not determined

All references, including publications, patents, and patent documents are hereby incorporated by reference herein, as though individually incorporated by reference. The present disclosure provides reference to various embodiments and techniques. However, it should be understood that many variations and modifications may be made while remaining within the scope of the present disclosure.

What is claimed is:

1. A compound of Formula XA-1, XA-2, XA-3, XA-4, XA-5, or XA-6:

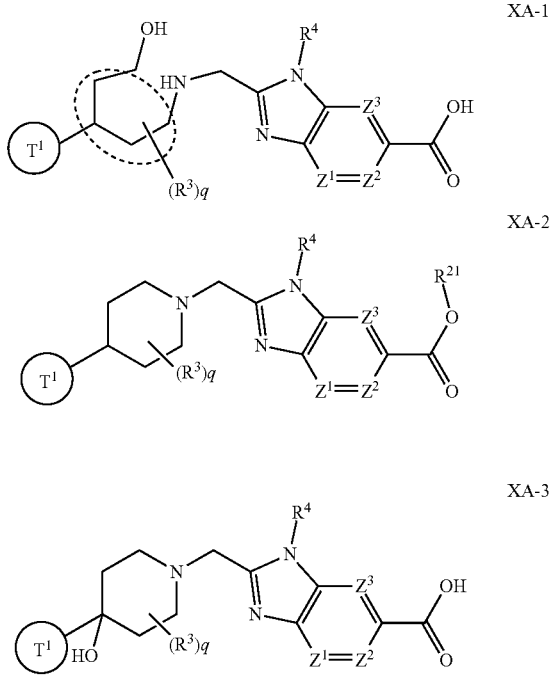

-continued

XA-4

XA-5

XA-6 or a pharmaceutically acceptable salt thereof, wherein:
Ring $T^1$ is phenyl or pyridinyl, wherein each of the phenyl or pyridinyl is substituted with 1, 2, 3, or 4 independently selected $R^{500}$, wherein each $R^{500}$ is independently F, Cl, —CN, or —$OR^{501}$, or two adjacent $R^{500}$ together form a moiety of —O—$CR^{502}R^{503}$—O— that is fused to the phenyl or pyridinyl of Ring $T^1$, and wherein when the phenyl or pyridinyl of ring $T^1$ is not substituted with a moiety of —O—$CR^{502}R^{503}$—O—, then it is at least substituted with one —$OR^{501}$;
each $R^{501}$ is independently —$C(R^{504}R^{505})R^{506}$;
$R^{502}$ is H or —$C_{1-3}$alkyl, wherein the —$C_{1-3}$alkyl is substituted with 0 to 1 OH;
$R^{503}$ is independently phenyl or a 6-membered heteroaryl, wherein each of the phenyl or pyridinyl is substituted with 0, 1, 2, or 3 independently selected $R^{507}$;
each of $R^{504}$ and $R^{505}$ is H or —$C_{1-3}$alkyl, wherein the —$C_{1-3}$alkyl is substituted with 0 to 1 OH;
each $R^{506}$ is independently phenyl or a 6-membered heteroaryl, wherein each of the phenyl or pyridinyl is substituted with 0, 1, 2, or 3 independently selected $R^{508}$;
each $R^{507}$ is independently halogen, —CN, —$C_{1-3}$alkyl, or —$OC_{1-3}$alkyl, wherein each of the $C_{1-3}$alkyl and $OC_{1-3}$alkyl is substituted with 0 to 3 F atoms;
each $R^{508}$ is independently halogen, —CN, —$C_{1-3}$alkyl, or —$OC_{1-3}$alkyl, wherein each of the $C_{1-3}$alkyl and $OC_{1-3}$alkyl is substituted with 0 to 3 F atoms;
each $R^3$ is independently F, —OH, —CN, —$C_{1-3}$alkyl, —$OC_{1-3}$alkyl, or —$C_{3-4}$cycloalkyl, or 2 $R^3$s may together cyclize to form —$C_{3-4}$spirocycloalkyl, wherein the alkyl of $C_{1-3}$alkyl and $OC_{1-3}$alkyl, cycloalkyl, or spirocycloalkyl may be substituted as valency allows with 0 to 3 F atoms and with 0 to 1 —OH;
q is 0, 1, or 2;
$R^4$ is —$C_{1-3}$alkyl, —$C_{0-3}$alkylene-$C_{3-6}$cycloalkyl, —$C_{0-3}$alkylene-$R^5$, or —$C_{1-3}$alkylene-$R^6$, wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, and —$N(R^N)_2$, and wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;
$R^5$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1 —CN, and
0 to 1 —$OR^O$;
$R^6$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;
each $R^O$ is independently H, or —$C_{1-3}$alkyl, wherein $C_{1-3}$alkyl may be substituted with 0 to 3 F atoms;
each $R^N$ is independently H, or —$C_{1-3}$alkyl;
$Z^1$ is CH or N;
$Z^2$ and $Z^3$ are each independently —$CR^Z$ or N, provided that when $Z^1$ or $Z^3$ is N, $Z^2$ is —$CR^Z$;
each $R^Z$ is independently H, F, Cl, or —$CH_3$; and
$R^{21}$ is glucuronidation,
wherein the compound of Formula XA-1, XA-2, XA-3, XA-4, XA-5, or XA-6, or pharmaceutically acceptable salt is substantially isolated.

2. A compound that is selected from:
a compound of Formula Mtblt-1

Mtblt-1

115 a compound of Formula Mtblt-2

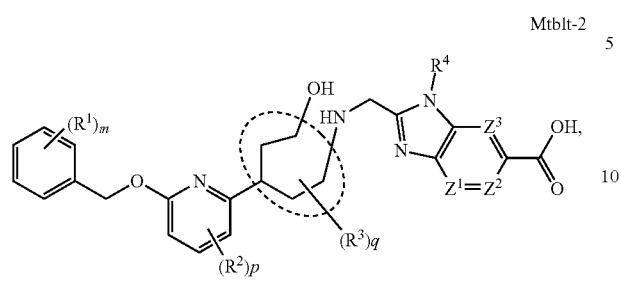

a compound of Formula Mtblt-3

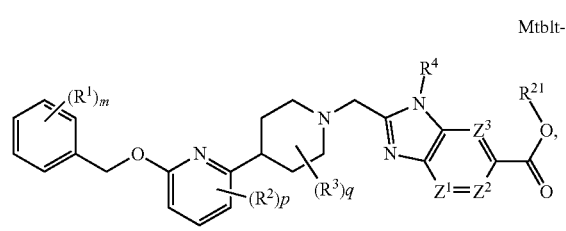

a compound of Formula Mtblt-4

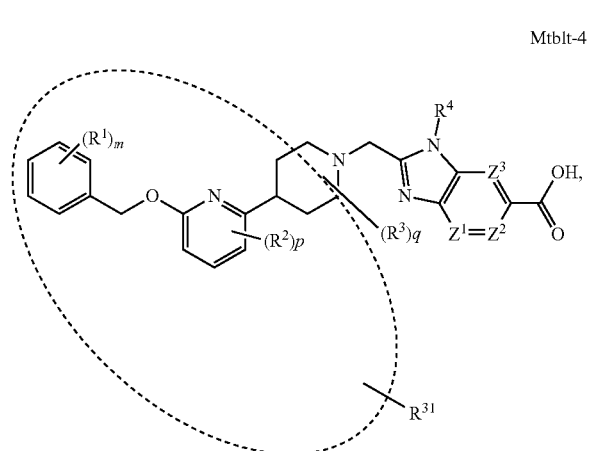

a compound of Formula Mtblt-5

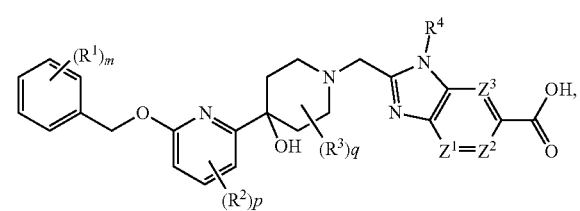

116 a compound of Formula Mtblt-6

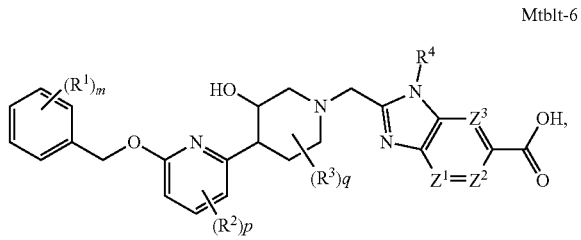

a compound of Formula Mtblt-7

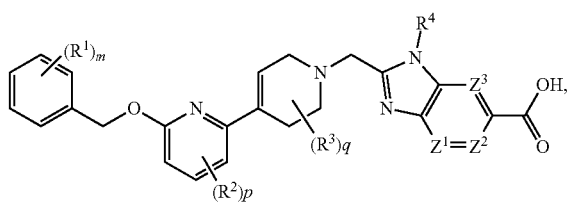

a compound of Formula Mtblt-8

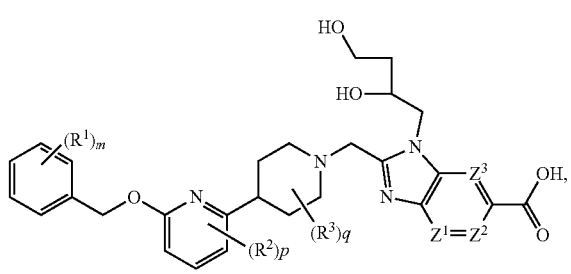

and
a compound of Formula Mtblt-9

Formula Mtblt-9 or a pharmaceutically acceptable salt thereof, wherein
each $R^1$ is independently halogen, —CN, —C$_{1-3}$alkyl, or —OC$_{1-3}$alkyl, wherein the alkyl of C$_{1-3}$alkyl and OC$_{1-3}$alkyl is substituted with 0 to 3 F atoms;
m is 0, 1, 2, or 3;
each $R^2$ is independently F, Cl, or —CN;
p is 0, 1 or 2;
each $R^3$ is independently F, —OH, —CN, —C$_{1-3}$alkyl, —OC$_{1-3}$alkyl, or —C$_{3-4}$cycloalkyl, or 2 R$^3$s may together cyclize to form —C$_{3-4}$spirocycloalkyl, wherein the alkyl of C$_{1-3}$alkyl and OC$_{1-3}$alkyl, cycloalkyl, or spirocycloalkyl may be substituted as valency allows with 0 to 3 F atoms and with 0 to 1 —OH;

q is 0, 1, or 2;

$R^4$ is —$C_{1-3}$alkyl, —$C_{0-3}$alkylene-$C_{3-6}$cycloalkyl, —$C_{0-3}$alkylene-$R^5$, or —$C_{1-3}$alkylene-$R^6$, wherein said alkyl may be substituted as valency allows with 0 to 3 substituents independently selected from 0 to 3 F atoms and 0 to 1 substituent selected from —$C_{0-1}$alkylene-CN, —$C_{0-1}$alkylene-$OR^O$, and —$N(R^N)_2$, and wherein said alkylene and cycloalkyl may be independently substituted as valency allows with 0 to 2 substituents independently selected from 0 to 2 F atoms and 0 to 1 substituent selected from —$C_{0-1}$alkylene-CN, —$C_{0-1}$alkylene-$OR^O$, and —$N(R^N)_2$;

$R^5$ is a 4- to 6-membered heterocycloalkyl, wherein said heterocycloalkyl may be substituted with 0 to 2 substituents as valency allows independently selected from:
0 to 1 oxo (=O),
0 to 1 —CN,
0 to 2 F atoms, and
0 to 2 substituents independently selected from —$C_{1-3}$alkyl and —$OC_{1-3}$alkyl, wherein the alkyl of $C_{1-3}$alkyl and $OC_{1-3}$alkyl may be substituted with 0 to 3 substituents as valency allows independently selected from:
0 to 3 F atoms,
0 to 1 —CN, and
0 to 1 —$OR^O$;

$R^6$ is a 5- to 6-membered heteroaryl, wherein said heteroaryl may be substituted with 0 to 2 substituents as valency allows independently selected from:
0 to 2 halogens,
0 to 1 substituent selected from —$OR^O$ and —$N(R^N)_2$, and
0 to 2 —$C_{1-3}$alkyl, wherein the alkyl may be substituted with 0 to 3 substituents as valency allows independently selected from:
0 to 3 F atoms, and
0 to 1 —$OR^O$;

each $R^O$ is independently H, or —$C_{1-3}$alkyl, wherein $C_{1-3}$alkyl may be substituted with 0 to 3 F atoms;

each $R^N$ is independently H, or —$C_{1-3}$alkyl;

$Z^1$ is CH or N;

$Z^2$ and $Z^3$ are each independently —$CR^Z$ or N, provided that when $Z^1$ or $Z^3$ is N, $Z^2$ is —$CR^Z$;

each $R^Z$ is independently H, F, Cl, or —$CH_3$;

$R^{21}$ is glucuronidation; and $R^{31}$ is —OH, —O—S(=O)$_2$OH, or —O-glucuronidation, wherein the compound of Formula Mtblt-1, Mtblt-2, Mtblt-3, Mtblt-4, Mtblt-5, Mtblt-6, Mtblt-7, Mtblt-8, or Mtblt-9, or pharmaceutically acceptable salt is substantially isolated.

3. A composition comprising the compound or pharmaceutically acceptable salt of claim 2, wherein the compound or pharmaceutically acceptable salt thereof is present in the composition in an amount greater than about 25% by weight.

4. The composition of claim 3 wherein the compound or pharmaceutically acceptable salt thereof is present in the composition in an amount greater than about 50% by weight.

5. The composition of claim 3 wherein the compound or pharmaceutically acceptable salt thereof is present in the composition in an amount greater than about 75% by weight.

6. A preparation of the compound or pharmaceutically acceptable salt of claim 1, which has greater than about 95% purity.

7. A pharmaceutical composition comprising the compound or pharmaceutically acceptable salt of claim 1, and a least one pharmaceutically acceptable carrier.

8. The pharmaceutical composition of claim 7, wherein the compound or pharmaceutically acceptable salt thereof is present in the composition in an amount greater than about 0.1% by weight.

9. A pharmaceutical combination comprising (1) the compound or pharmaceutically acceptable salt of claim 1, and (2) an additional therapeutic agent.

10. A compound selected from Compound M2, Compound 574a, Compound 574b, Compound M1, a compound of Formula X, and Compound M4:

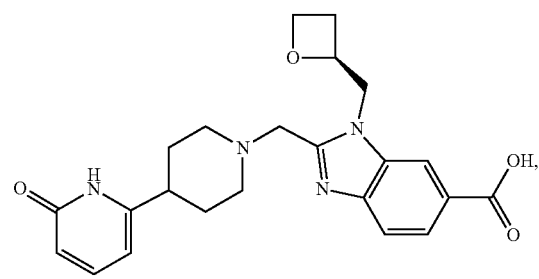

M2

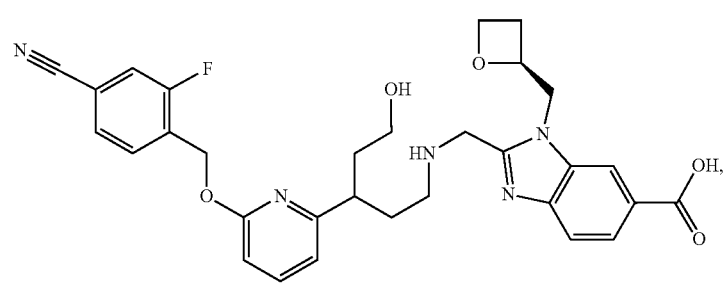

574a

-continued

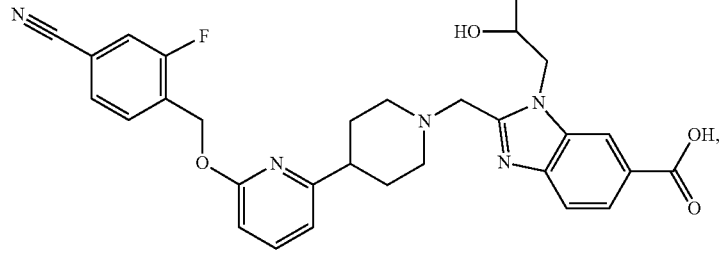
574b

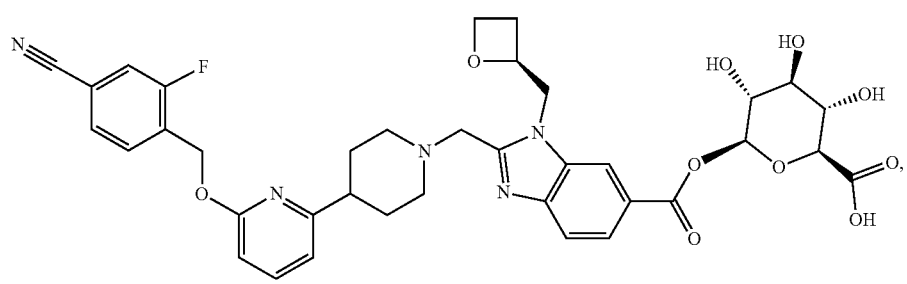
M1 a compound of Formula X

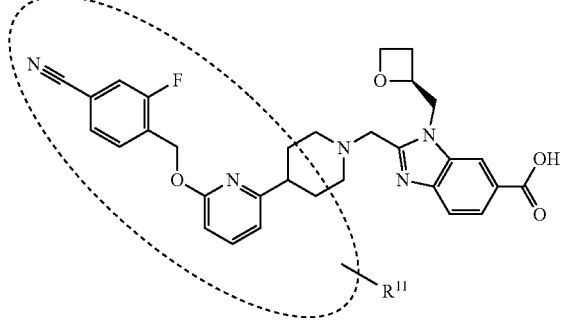

wherein R[11] is

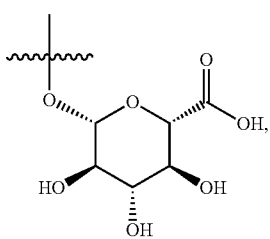 [SMILES: *O[C@@H]1O[C@H](C(=O)O)[C@@H](O)[C@H](O)[C@H]1O]

and wherein R[1] is substituted at the phenyl ring, the pyridine ring, or the part of the piperidine ring within the dotted oval shape; and or a pharmaceutically acceptable salt thereof, wherein the compound or pharmaceutically acceptable salt thereof is substantially isolated.

11. The compound or pharmaceutically acceptable salt of claim 10, wherein the compound or pharmaceutically acceptable salt is Compound M1, Compound M4, Compound 574a, Compound 574b, or a compound of Formula X, or a pharmaceutically acceptable salt thereof, and wherein the compound or pharmaceutically acceptable salt is substantially isolated.

12. A composition comprising a compound or pharmaceutically acceptable salt of claim 10, wherein the compound or pharmaceutically acceptable salt is selected from Compound M1, Compound M4, Compound 574a, Compound 574b, and a compound of Formula X, or a pharmaceutically acceptable salt thereof, wherein the compound or pharmaceutically acceptable salt thereof is present in the composition in an amount greater than about 25% by weight.

13. The composition of claim 12 wherein the compound or pharmaceutically acceptable salt thereof is present in the composition in an amount greater than about 50% by weight.

14. The composition of claim 12 wherein the compound or pharmaceutically acceptable salt thereof is present in the composition in an amount greater than about 75% by weight.

15. A preparation comprising a compound or pharmaceutically acceptable salt of claim 10, wherein the compound or pharmaceutically acceptable salt is selected from Compound M2, Compound M4, Compound 574a, Compound 574b, and a compound of Formula X, or a pharmaceutically acceptable salt thereof, which has greater than about 95% purity.

16. A pharmaceutical composition comprising a compound or pharmaceutically acceptable salt of claim 10 and a least one pharmaceutically acceptable carrier, wherein the compound or pharmaceutically acceptable salt is selected from Compound M1, Compound M4, Compound 574a, Compound 574b, and a compound of Formula X.

17. The pharmaceutical composition of claim 16, wherein the compound or pharmaceutically acceptable salt thereof is present in the composition in an amount greater than about 0.1% by weight.

18. A pharmaceutical combination comprising (1) a compound or pharmaceutically acceptable salt of claim 10, wherein the compound or pharmaceutically acceptable salt is selected from Compound M1, Compound M4, Compound 574a, Compound 574b, and a compound of Formula X, or a pharmaceutically acceptable salt thereof, and (2) an additional therapeutic agent.

19. The pharmaceutical combination of claim 9, wherein the additional therapeutic agent is a diacylglyceryl acyltransferase 2 inhibitor.

20. The pharmaceutical combination of claim 9, wherein the additional therapeutic agent is selected from:

(S)-2-(5-((3-Ethoxy-5-fluoropyridin-2-yl)oxy)pyridin-3-yl)-N-(tetrahydrofuran-3-yl)pyrimidine-5-carboxamide;

N-(2-cyanopropan-2-yl)-2-(5-((3-ethoxypyridin-2-yl)oxy)pyridin-3-yl)pyrimidine-5-carboxamide;

2-(5-((3-ethoxypyridin-2-yl)oxy)pyridin-3-yl)-N-(3-methyl-1,1-dioxidotetrahydrothiophen-3-yl)pyrimidine-5-carboxamide;

2-(5-((3-ethoxypyridin-2-yl)oxy)pyridin-3-yl)-N-(1-hydroxy-2-methylpropan-2-yl)pyrimidine-5-carboxamide;

(S)-2-(5-((3-ethoxypyridin-2-yl)oxy)pyridin-3-yl)-N-(tetrahydrofuran-3-yl)pyrimidine-5-carboxamide;

(S)-2-(5-((3-ethoxypyridin-2-yl)oxy)pyridin-3-yl)-N-(3-(hydroxymethyl)tetrahydrofuran-3-yl)pyrimidine-5-carboxamide;

(R)-2-(5-((3-ethoxypyridin-2-yl)oxy)pyridin-3-yl)-N-(3-(hydroxymethyl)tetrahydrofuran-3-yl)pyrimidine-5-carboxamide;

2-(5-((3-ethoxypyridin-2-yl)oxy)pyridin-3-yl)-N-(2-methyl-1-(methylsulfonyl)propan-2-yl)pyrimidine-5-carboxamide;

(S)-2-(5-((3-(2-fluoroethoxy)pyridin-2-yl)oxy)pyridin-3-yl)-N-(tetrahydrofuran-3-yl)pyrimidine-5-carboxamide;

3-(5-((3-ethoxypyridin-2-yl)oxy)pyridin-3-yl)-N-(1-hydroxy-2-methylpropan-2-yl)-1,2,4-triazine-6-carboxamide;

N-(1,3-dihydroxy-2-methylpropan-2-yl)-2-(5-((3-ethoxypyridin-2-yl)oxy)pyridin-3-yl)pyrimidine-5-carboxamide;

(S)-3-(5-((3-ethoxypyridin-2-yl)oxy)pyridin-3-yl)-N-(tetrahydrofuran-3-yl)-1,2,4-triazine-6-carboxamide;

N-(1,1-dioxidotetrahydrothiophen-3-yl)-2-(5-((3-ethoxypyridin-2-yl)oxy)pyridin-3-yl)pyrimidine-5-carboxamide;

(R)-2-(5-((3-ethoxypyridin-2-yl)oxy)pyridin-3-yl)-N-(tetrahydrofuran-3-yl)pyrimidine-5-carboxamide; and 2-(5-((3-ethoxypyrazin-2-yl)oxy)pyridin-3-yl)-N-(1-hydroxy-2-methylpropan-2-yl)pyrimidine-5-carboxamide, or a pharmaceutically acceptable salt thereof.

21. The pharmaceutical combination of claim 9, wherein the additional therapeutic agent is (S)-2-(5-((3-ethoxypyridin-2-yl)oxy)pyridin-3-yl)-N-(tetrahydrofuran-3-yl)pyrimidine-5-carboxamide, or a pharmaceutically acceptable salt thereof.

* * * * *